(12) United States Patent
Knutson et al.

(10) Patent No.: US 12,162,865 B2
(45) Date of Patent: *Dec. 10, 2024

(54) METHODS OF TREATING CANCER

(71) Applicant: Epizyme, Inc., Cambridge, MA (US)

(72) Inventors: Sarah K. Knutson, Lincoln, MA (US); Natalie Warholic, Cambridge, MA (US); Heike Keilhack, Belmont, MA (US)

(73) Assignee: Epizyme, Inc., Cambridge, MA (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/689,704

(22) Filed: Mar. 8, 2022

(65) Prior Publication Data

US 2022/0315566 A1 Oct. 6, 2022

Related U.S. Application Data

(63) Continuation of application No. 16/749,073, filed on Jan. 22, 2020, now abandoned, which is a continuation of application No. 15/979,916, filed on May 15, 2018, now abandoned, which is a continuation of application No. 15/598,262, filed on May 17, 2017, now abandoned, which is a continuation of application No. 14/054,646, filed on Oct. 15, 2013, now Pat. No. 9,688,665.

(60) Provisional application No. 61/786,277, filed on Mar. 14, 2013, provisional application No. 61/780,703, filed on Mar. 13, 2013, provisional application No. 61/758,972, filed on Jan. 31, 2013, provisional application No. 61/714,145, filed on Oct. 15, 2012, provisional application No. 61/714,140, filed on Oct. 15, 2012, provisional application No. 61/714,045, filed on Oct. 15, 2012.

(51) Int. Cl.

| | | |
|---|---|---|
| *C07D 405/14* | (2006.01) | |
| *A61K 31/4412* | (2006.01) | |
| *A61K 31/4545* | (2006.01) | |
| *A61K 31/5377* | (2006.01) | |
| *C07D 211/86* | (2006.01) | |
| *C07D 405/12* | (2006.01) | |
| *C12Q 1/6886* | (2018.01) | |

(52) U.S. Cl.
CPC ........ *C07D 405/14* (2013.01); *A61K 31/4412* (2013.01); *A61K 31/4545* (2013.01); *A61K 31/5377* (2013.01); *C07D 211/86* (2013.01); *C07D 405/12* (2013.01); *C12Q 1/6886* (2013.01)

(58) Field of Classification Search
CPC ............ A61K 31/4412; A61K 31/4545; A61K 31/5377; A61P 35/00; C07D 211/86; C07D 405/12; C07D 405/14

See application file for complete search history.

(56) References Cited

U.S. PATENT DOCUMENTS

| | | | |
|---|---|---|---|
| 4,522,811 A | 6/1985 | Eppstein et al. | |
| 5,455,044 A | 10/1995 | Kim et al. | |
| 5,763,263 A | 6/1998 | Dehlinger | |
| 8,410,088 B2 | 4/2013 | Kuntz et al. | |
| 8,536,179 B2 | 9/2013 | Miller et al. | |
| 8,598,167 B1 | 12/2013 | Kuntz et al. | |
| 8,691,507 B2 | 4/2014 | Copeland et al. | |
| 8,765,732 B2 | 7/2014 | Kuntz et al. | |
| 8,895,245 B2 | 11/2014 | Copeland et al. | |
| 8,962,620 B2 | 2/2015 | Kuntz et al. | |
| 9,006,242 B2 | 4/2015 | Kuntz et al. | |
| 9,045,477 B2 | 6/2015 | Campbell et al. | |
| 9,089,575 B2 | 7/2015 | Kuntz et al. | |
| 9,090,562 B2 | 7/2015 | Kuntz et al. | |
| 9,175,331 B2 | 11/2015 | Kuntz et al. | |
| 9,206,157 B2 | 12/2015 | Kuntz et al. | |
| 9,243,001 B2 | 1/2016 | Campbell et al. | |
| 9,333,217 B2 | 5/2016 | Copeland et al. | |
| 9,334,527 B2 | 5/2016 | Kuntz et al. | |
| 9,365,570 B2 | 6/2016 | Campbell et al. | |
| 9,376,422 B2 | 6/2016 | Kuntz et al. | |
| 9,394,283 B2 | 7/2016 | Kuntz et al. | |
| 9,469,646 B2 | 10/2016 | Albrecht et al. | |
| 9,522,152 B2 | 12/2016 | Kuntz et al. | |
| 9,532,992 B2 | 1/2017 | Kuntz et al. | |
| 9,549,931 B2 | 1/2017 | Kuntz et al. | |
| 9,624,205 B2 | 4/2017 | Campbell | |
| 9,637,472 B2 | 5/2017 | Kuntz et al. | |

(Continued)

FOREIGN PATENT DOCUMENTS

| | | |
|---|---|---|
| CN | 103261890 A | 8/2013 |
| CN | 103619337 A | 3/2014 |

(Continued)

OTHER PUBLICATIONS

"Myoepithelial carcinoma" [online]. Genetic and Rare Diseases Information Center (GARD). Retrieved from: https://rarediseases.info.nih.gov/diseases/10558/myoepithelial-carcinoma; downloaded Mar. 20, 2020, 4 pages.

(Continued)

*Primary Examiner* — Theodore R. Howell

(74) *Attorney, Agent, or Firm* — Dechert LLP; Andrea L. C. Reid; Nicholas J. Pace

(57) ABSTRACT

The present invention relates to methods of treating cancer by administering the EZH2 inhibitor compounds and pharmaceutical compositions to subjects in need thereof. The present invention also relates to the use of such compounds for research or other non-therapeutic purposes.

14 Claims, 29 Drawing Sheets

Specification includes a Sequence Listing.

(56) References Cited

U.S. PATENT DOCUMENTS

| | | | |
|---|---|---|---|
| 9,688,665 | B2 | 6/2017 | Knutson et al. |
| 9,701,666 | B2 | 7/2017 | Kuntz et al. |
| 9,776,996 | B2 | 10/2017 | Campbell et al. |
| 9,855,275 | B2 | 1/2018 | Kuntz et al. |
| 9,872,862 | B2 | 1/2018 | Kuntz et al. |
| 9,889,138 | B2 * | 2/2018 | Keilhack ............... A61K 31/45 |
| 9,949,999 | B2 | 4/2018 | Copeland et al. |
| 10,040,782 | B2 | 8/2018 | Kuntz et al. |
| 10,092,572 | B2 | 10/2018 | Kuntz et al. |
| 10,098,888 | B2 | 10/2018 | Kuntz et al. |
| 10,150,759 | B2 | 12/2018 | Kuntz et al. |
| 10,150,764 | B2 | 12/2018 | Campbell |
| 10,155,002 | B2 | 12/2018 | Kuntz et al. |
| 10,166,238 | B2 | 1/2019 | Keilhack et al. |
| 10,174,019 | B2 | 1/2019 | Campbell et al. |
| 10,245,269 | B2 | 4/2019 | Kuntz et al. |
| 10,273,223 | B2 | 4/2019 | Kuntz et al. |
| 10,301,290 | B2 | 5/2019 | Keilhack et al. |
| 10,369,155 | B2 * | 8/2019 | Keilhack ............ A61K 31/5377 |
| 10,420,775 | B2 | 9/2019 | Kuntz et al. |
| 10,456,407 | B2 | 10/2019 | Keilhack et al. |
| 10,463,671 | B2 | 11/2019 | Keilhack et al. |
| 10,493,076 | B2 | 12/2019 | Keilhack et al. |
| 10,710,987 | B2 | 7/2020 | Kuntz et al. |
| 10,786,511 | B2 | 9/2020 | Keilhack et al. |
| 10,787,440 | B2 | 9/2020 | Keilhack et al. |
| 10,821,113 | B2 | 11/2020 | Kuntz et al. |
| 10,898,490 | B2 | 1/2021 | Keilhack et al. |
| 10,946,024 | B2 | 3/2021 | Keilhack |
| 11,026,949 | B2 | 6/2021 | Keilhack et al. |
| 11,052,093 | B2 | 7/2021 | Kuntz et al. |
| 11,147,819 | B2 | 10/2021 | Ribich et al. |
| 11,202,781 | B2 | 12/2021 | Keilhack et al. |
| 11,370,781 | B2 | 6/2022 | Keilhack et al. |
| 11,452,727 | B2 | 9/2022 | Raimondi et al. |
| 11,491,163 | B2 | 11/2022 | Kuntz et al. |
| 11,602,529 | B2 | 3/2023 | Daigle et al. |
| 11,642,346 | B2 | 5/2023 | Klaus et al. |
| 11,642,347 | B2 | 5/2023 | Keilhack et al. |
| 11,642,348 | B2 | 5/2023 | Kuntz et al. |
| 11,642,349 | B2 | 5/2023 | Keilhack et al. |
| 11,786,533 | B2 | 10/2023 | Ribich et al. |
| 11,951,108 | B2 | 4/2024 | Raimondi |
| 11,951,109 | B2 | 4/2024 | Keilhack et al. |
| 2003/0175736 | A1 | 9/2003 | Chinnaiyan et al. |
| 2005/0107290 | A1 | 5/2005 | Ito et al. |
| 2009/0012031 | A1 | 1/2009 | Chinnaiyan et al. |
| 2011/0064664 | A1 | 3/2011 | Lopez-Berestein et al. |
| 2012/0071418 | A1 | 3/2012 | Copeland et al. |
| 2012/0114670 | A1 | 5/2012 | Land et al. |
| 2012/0264734 | A1 | 10/2012 | Kuntz et al. |
| 2013/0040906 | A1 | 2/2013 | Kuntz et al. |
| 2013/0053383 | A1 | 2/2013 | Duquenne et al. |
| 2014/0120083 | A1 | 5/2014 | Stern et al. |
| 2014/0128393 | A1 | 5/2014 | Knutson et al. |
| 2014/0296248 | A1 | 10/2014 | Bernards et al. |
| 2015/0065483 | A1 | 3/2015 | Kuntz et al. |
| 2015/0065503 | A1 | 3/2015 | Kuntz et al. |
| 2015/0352119 | A1 | 12/2015 | Kuntz et al. |
| 2015/0353494 | A1 | 12/2015 | Kuntz et al. |
| 2015/0368229 | A1 | 12/2015 | Albrecht et al. |
| 2016/0022693 | A1 | 1/2016 | Kuntz et al. |
| 2016/0067260 | A1 | 3/2016 | Dransfield et al. |
| 2016/0228447 | A1 | 8/2016 | Keilhack et al. |
| 2016/0326596 | A1 | 11/2016 | Levine et al. |
| 2017/0138946 | A1 | 5/2017 | Levine et al. |
| 2017/0305889 | A1 | 10/2017 | Knutson et al. |
| 2017/0305890 | A1 | 10/2017 | Knutson et al. |
| 2018/0071300 | A1 | 3/2018 | Keilhack et al. |
| 2018/0235975 | A1 | 8/2018 | Keilhack et al. |
| 2018/0296563 | A1 | 10/2018 | Keilhack |
| 2019/0038633 | A1 | 2/2019 | Smith et al. |
| 2019/0070188 | A1 | 3/2019 | Keilhack et al. |
| 2019/0083504 | A1 | 3/2019 | Keilhack et al. |
| 2019/0100514 | A1 | 4/2019 | Knutson et al. |
| 2019/0240230 | A1 | 8/2019 | Keilhack et al. |
| 2019/0255060 | A1 | 8/2019 | Keilhack et al. |
| 2019/0315725 | A1 | 10/2019 | Keilhack et al. |
| 2019/0350929 | A1 | 11/2019 | Ribich |
| 2020/0016162 | A1 | 1/2020 | Kuntz et al. |
| 2020/0022987 | A1 | 1/2020 | Keilhack et al. |
| 2020/0113911 | A1 | 4/2020 | Keilhack et al. |
| 2020/0138825 | A1 | 5/2020 | Keilhack et al. |
| 2020/0262823 | A1 | 8/2020 | Knutson et al. |
| 2020/0268765 | A1 | 8/2020 | Keilhack et al. |
| 2020/0323865 | A1 | 10/2020 | Smith et al. |
| 2020/0323866 | A1 | 10/2020 | Keilhack et al. |
| 2020/0330472 | A1 | 10/2020 | Keilhack et al. |
| 2020/0397812 | A1 | 12/2020 | Copeland et al. |
| 2021/0008075 | A1 | 1/2021 | Keilhack et al. |
| 2021/0017163 | A1 | 1/2021 | Kuntz et al. |
| 2021/0053948 | A1 | 2/2021 | Keilhack et al. |
| 2021/0060030 | A1 | 3/2021 | Keilhack et al. |
| 2021/0121470 | A1 | 4/2021 | Keilhack et al. |
| 2021/0213027 | A1 | 7/2021 | Keilhack et al. |
| 2021/0267990 | A1 | 9/2021 | Keilhack |
| 2021/0353632 | A1 | 11/2021 | Keilhack et al. |
| 2021/0379076 | A1 | 12/2021 | Kuntz et al. |
| 2022/0160721 | A1 | 5/2022 | Smith et al. |
| 2022/0175771 | A1 | 6/2022 | Ribich |
| 2022/0193084 | A1 | 6/2022 | Blakemore et al. |
| 2022/0218714 | A1 | 7/2022 | Keilhack et al. |
| 2022/0226336 | A1 | 7/2022 | Keilhack et al. |
| 2022/0281854 | A1 | 9/2022 | Keilhack et al. |
| 2023/0000877 | A1 | 1/2023 | Raimondi et al. |
| 2023/0140327 | A1 | 5/2023 | Kuntz et al. |
| 2023/0181549 | A1 | 6/2023 | Daigle et al. |
| 2023/0201212 | A1 | 6/2023 | Blakemore et al. |
| 2023/0201213 | A1 | 6/2023 | Campbell et al. |
| 2024/0024331 | A1 | 1/2024 | Keilhack et al. |
| 2024/0041895 | A1 | 2/2024 | Klaus et al. |
| 2024/0058348 | A1 | 2/2024 | Keilhack et al. |
| 2024/0139203 | A1 | 5/2024 | Ribich et al. |
| 2024/0165121 | A1 | 5/2024 | Kuntz et al. |
| 2024/0166636 | A1 | 5/2024 | Verwijs et al. |
| 2024/0180919 | A1 | 6/2024 | Ribich et al. |
| 2024/0245697 | A1 | 7/2024 | Kuntz et al. |
| 2024/0245698 | A1 | 7/2024 | Kuntz et al. |

FOREIGN PATENT DOCUMENTS

| | | |
|---|---|---|
| CN | 104540500 A | 4/2015 |
| CN | 104768555 A | 7/2015 |
| CN | 108349958 B | 2/2022 |
| WO | WO-2009006577 A2 | 1/2009 |
| WO | WO 2011/103016 A2 | 8/2011 |
| WO | WO 2011/140324 A1 | 11/2011 |
| WO | WO-2011140325 A1 | 11/2011 |
| WO | WO-2012005805 A1 | 1/2012 |
| WO | WO 2012/034132 A2 | 3/2012 |
| WO | WO 2012/068589 A2 | 5/2012 |
| WO | WO 2012/071096 A2 | 5/2012 |
| WO | WO 2012/075080 A1 | 6/2012 |
| WO | WO 2012/118812 A2 | 9/2012 |
| WO | WO 2012/138783 A2 | 10/2012 |
| WO | WO 2012/142504 A1 | 10/2012 |
| WO | WO 2012/142513 A1 | 10/2012 |
| WO | WO 2013/039988 A1 | 3/2013 |
| WO | WO 2013/049770 A2 | 4/2013 |
| WO | WO 2013/059944 A1 | 5/2013 |
| WO | WO 2013/120104 A2 | 8/2013 |
| WO | WO 2013/138361 A1 | 9/2013 |
| WO | WO 2013/140148 A1 | 9/2013 |
| WO | WO 2013/155317 A1 | 10/2013 |
| WO | WO 2013/155464 A1 | 10/2013 |
| WO | WO 2013/173441 A1 | 11/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO-2014092905 A1 | 6/2014 |
| WO | WO 2014/124418 A1 | 8/2014 |
| WO | WO 2014/144747 A1 | 9/2014 |

(56) References Cited

FOREIGN PATENT DOCUMENTS

| | | |
|---|---|---|
| WO | WO 2014/172044 A1 | 10/2014 |
| WO | WO 2014/176047 A1 | 10/2014 |
| WO | WO 2014/177982 A1 | 11/2014 |
| WO | WO 2014/195919 A1 | 12/2014 |
| WO | WO 2015/004618 A1 | 1/2015 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/103431 A1 | 7/2015 |
| WO | WO 2015/128837 A1 | 9/2015 |
| WO | WO 2015/132765 A1 | 9/2015 |
| WO | WO 2015/143012 A1 | 9/2015 |
| WO | WO 2015/193768 A1 | 12/2015 |
| WO | WO 2015/195848 A1 | 12/2015 |
| WO | WO 2015/196064 A1 | 12/2015 |
| WO | WO 2015/200650 A9 | 12/2015 |
| WO | WO 2016/061507 A1 | 4/2016 |
| WO | WO 2016/081523 A1 | 5/2016 |
| WO | WO 2016/172199 A1 | 10/2016 |
| WO | WO 2016/201328 A1 | 12/2016 |
| WO | WO 2017/035234 A1 | 3/2017 |
| WO | WO 2017/053930 A2 | 3/2017 |
| WO | WO 2017/062495 A2 | 4/2017 |
| WO | WO 2017/079757 A1 | 5/2017 |
| WO | WO 2017/100362 A2 | 6/2017 |
| WO | WO 2017/132518 A1 | 8/2017 |
| WO | WO 2017/139404 A1 | 8/2017 |
| WO | WO-2017214373 A1 | 12/2017 |
| WO | WO 2018/144798 A1 | 8/2018 |

OTHER PUBLICATIONS

Alarcon-Vargas, D. et al. (Feb. 2, 2006) "Targeting cyclin D1, a downstream effector of INI1/hSNF5, in rhabdoid tumors" Oncogene, 25(5):722-734 (Abstract only, retrieved from: https://www.ncbi.nlm.nih.gov/pubmed/16302003, 2 pages).
Alimova, I. et al. (2012) "Targeting the enhancer of zeste homologue 2 in medulloblastoma" Intl J Cancer, 131:1800-1809 [online]. Retrieved from the Internet: https://onlinelibrary.wiley.com/doi/full/10.1002/ijc.27455; 15 pages.
Alimova, I. et al. (2013) "Inhibition of EZH2 Suppresses Self-Renewal and Induces Radiation Sensitivity in Atypical Rhabdoid Teratoid Tumor Cells" Neuro-Oncology, 15(2):149-160.
Belikov, V.G. Pharmaceutical Chemistry. High School, 1993; pp. 43-47. Russian with English translation, 14 pages.
Betz, B.L. et al. (2002) "Re-expression of hSNF5/INI1/BAF47 in pediatric tumor cells leads to G1 arrest associated with induction of p16ink4a and activation of RB" Oncogene, 21:5193-5203.
Campbell, J.E. et al. (Mar. 4, 2015) "EPZ011989, A Potent, Orally-Available EZH2 Inhibitor with Robust in Vivo Activity" ACS Med Chem Lett, 6:491-495.
Cascio, M.J. et al. (2010) "Epithelioid sarcoma expresses epidermal growth factor receptor but gene amplification and kinase domain mutations are rare" Modern Pathology, 23:574-580.
CCLG—Chemotherapy Standardisation Group 2008, "Estimation of Body Surface Area in Infants and Children" [online]. Retrieved from: https://www.ouh.nhs.uk/oxparc/professionals/documents/BodysurfaceareaCCLGChart1.pdf; accessed May 8, 2021, 1 page.
Chang et al. (2012) "The role of EZH2 in tumour progression" Br J Cancer, 106:243-247.
Chan-Penebre, E. et al. (2017) "Selective Killing of SMARCA2- and SMARCA4-deficient Small Cell Carcinoma of the Ovary, Hypercalcemic Type Cells by Inhibition of EZH2: In Vitro and In Vivo Preclinical Models" Mol Cancer Ther, 16(5):850-860.
Chase, A. and N.C. Cross (2011) "Aberrations of EZH2 in cancer" Clin Cancer Res, 17(9):2613-2618.
Chen, H. et al. (1996) "Cloning of a Human Homolog of the Drosophila Enhancer of zeste Gene (EZH2) That Maps to Chromosome 21q22.2" Genomics, 38:30-37.

Cheng, S.-W. G. et al. (May 1999) "c-MYC interacts with INI1/hSNF5 and requires the SWI/SNF complex for transactivation function" Nat Genet, 22:102-105.
Ciarapica, R. et al. (2011) "Enhancer of zeste homolog 2 (EZH2) in pediatric soft tissue sarcomas: first implications" BMC Medicine, 9:63, 9 pages.
ClinicalTrials.Gov, "Open-Label, Multicenter, Phase 1/2 Study of Tazemetostat (EZH2 Histone Methyl Transferase [HMT] Inhibitor) as a Single Agent in Subjects With Adv. Solid Tumors or With B-cell Lymphomas and Tazemetostat in Combination With Prednisolone in Subjects With DLBCL" Clinical Trials Identifier: NCT01897571, first posted Jul. 12, 2013, last updated Dec. 10, 2021 [online]. Retrieved from: https://clinicaltrials.gov/ct2/show/NCT01897571; retrieved on May 31, 2022; 11 printed pages.
Copeland, R.A. (2013) "Molecular pathways: protein methyltransferases in cancer" Clin Cancer Res, 19(23):6344-6350.
Cortes-Dericks, L. et al. (2010) "Putative cancer stem cells in malignant pleural mesothelioma show resistance to cisplatin and pemetrexed" International Journal of Oncology, 37:437-444.
Danziger, D. J. and P.M. Dean (1989) "Automated site-directed drug design: a general algorithm for knowledge acquisition about hydrogen-bonding regions at protein surfaces" Proc Royal Soc London, 236:101-113.
Desouza, R-M. et al. (Jul. 2, 20142) "Pediatric medulloblastoma—update on molecular classification driving targeted therapies" Frontiers in Oncology, vol. 4, Article 176, 8 pages.
Dhanak, D. and P. Jackson (2014) "Development and classes of epigenetic drugs for cancer" Biochem Biophys Res Commun, 455:58-69.
Fillmore et al. (2015) "EZH2 inhibition sensitizes BRG1 and EGFR mutant lung tumors to TopoII inhibitors" Nature, 520(7546):239-242. HHS Public Access Author Manuscript; available in PMC Oct. 9, 2015, 21 pages.
Fiskus et al. (2009) "Combined epigenetic therapy with the histone methyltransferase EZH2 inhibitor 3-deazaneplanocin A and the histone deacetylase inhibitor panobinostat against human AML cells" Blood, 114(13):2733-2743.
Foulkes, W.D. et al. (2014) "No. small surprise—small cell carcinoma of the ovary, hypercalcaemic type, is a malignant rhabdoid tumour" J Pathol, 233:209-214.
Garapaty-Rao, S. et al. (Nov. 2013) "Identification of EZH2 and EZH1 Small Molecule Inhibitors with Selective Impact on Diffuse Large B Cell Lymphoma Cell Growth" Chem Biol, 20:1329-1339.
Genentech, Inc. (May 6, 2016) TECENTRIQ™: Highlights of Prescribing Information [online]. Retrieved from: https://www.accessdata.fda.gov/drugsatfda_docs/label/2016/761034s000lbl.pdf; retrieved on Nov. 12, 2019, 17 pages.
Gounder, M. et al. "Phase 2 Multicenter Study of the EZH2 Inhibitor Tazemetostat in Adults with INI1 Negative Epithelioid Sarcoma (ES) (NCT02601950)" Poster 381 presented at ASCO, Chicago, IL, on Jun. 4, 2017, 1 page.
Helming, K.C. et al. (Sep. 8, 2014) "Vulnerabilities of mutant SWI/SNF complexes in cancer" Cancer Cell, 26:309-317.
Hollmann, T.J. et al. (Oct. 2011) "INI1-Deficient Tumors: Diagnostic Features and Molecular Genetics" Am J Surg Pathol, 35(10):e47-e63.
Hornick, J.L. et al. (2009) "Loss of INI1 expression is characteristic of both conventional and proximal-type epithelioid sarcoma" Am J Surg Pathol, 33(4):542-550.
Italiano, A. et al. (Sep. 2015) "A phase 1 study of EPZ-6438 (E7438), an Enhancer of Zeste-Homolog 2 (EZH2) inhibitor: Preliminary activity in INI1-negative tumors" Eur J Cancer, 51(Suppl 3):S54-S55, Abstract 302.
Jagani, Z. et al. (2010) "Loss of the tumor suppressor Snf5 leads to aberrant activation of the Hedgehog-Gli pathway" Nat Med, 16:1429-1433. NIH Public Access Author Manuscript; available in PMC Dec. 11, 2013; 12 pages.
Januario, T. et al. (Nov. 14, 2017) "PRC2-mediated repression of SMARCA2 predicts EZH2 inhibitor activity in SWI/SNF mutant tumors" PNAS, 114(46):12249-12254.
Jelinic, P. et al. (2014) "Recurrent SMARCA4 mutations in small cell carcinoma of the ovary" Nat Genet, 46:424-426. HHS Public

(56) References Cited

OTHER PUBLICATIONS

Access Author Manuscript, retrieved from the Internet: https://www.ncbi.nlm.nih.gov/pmc/articles/PMC5699446/pdf/nihms920036.pdf, 10 pages.

Jo, V.Y. et al. (May 2015) "Epithelioid Malignant Peripheral Nerve Sheath Tumor" Am J Surg Pathol, 39(5):673-682.

Kadoch, C. et al. (2013) "Reversible Disruption of mSWI/SNF (BAF) Complexes by the SS18-SSX Oncogenic Fusion in Synovial Sarcoma" Cell, 153:71-85.

Kadoch, C. et al. (2016) "PRC2 and SWI/SNF Chromatin Remodeling Complexes in Health and Disease" Biochemistry, 55(11):1600-1614.

Karnezis, A.N. et al. (2016) "Dual loss of the SWI/SNF complex ATPases SMARCA4/BRG1 and SMARCA2/BRM is highly sensitive and specific for small cell carcinoma of the ovary, hypercalcaemic type" J Pathol, 238:389-400.

Kim, K.H. et al. (Sep. 2014) "Mechanisms by which SMARCB1 loss drives rhabdoid tumor growth" Cancer Genet, 207:365-372. NIH Public Access Author Manuscript; available in PMC Sep. 1, 2015; 15 pages.

Kleer, C.G. et al. (Sep. 30, 2003) "EZH2 is a marker of aggressive breast cancer and promotes neoplastic transformation of breast epithelial cells" Proc Natl Acad Sci USA, 100(20):11606-11611.

Knutson, S.K. et al. (2012) "A Selective Inhibitor of EZH2 Blocks H3K27 Methylation and Kills Mutant Lymphoma Cells" Nat Chem Biol, 8:890-896.

Knutson, S.K. et al. (2013) "Durable tumor regression in genetically altered malignant rhabdoid tumors by inhibition of methyltransferase EZH2" Proc Natl Acad Sci USA, 110(19):7922-7927.

Knutson, S.K. et al. (Apr. 2014) "Selective inhibition of EZH2 by EPZ-6438 leads to potent antitumor activity in EZH2-mutant non-Hodgkin lymphoma" Mol Cancer Ther, 13(4):842-854.

Knutson, S.K. et al. (Dec. 10, 2014) "Synergistic antitumor activity of EZH2 inhibitors and glucocorticoid receptor agonists in models of germinal center non-Hodgkin lymphomas" PLoS One, 9(12):e111840, 22 pages.

Kuntz, K.W. et al. (2016) "The Importance of Being Me: Magic Methyls, Methyltransferase Inhibitors, and the Discovery of Tazemetostat" J Med Chem, 59:1556-1564.

Kupryjanczyk, J. et al. (2013) "Ovarian small cell carcinoma of hypercalcemic type—evidence of germline origin and SMARCA4 gene inactivation. A pilot study" Pol J Pathol, 64:238-246.

Kurmasheva, R.T. et al. (Mar. 2017) "Initial testing (stage 1) of tazemetostat (EPZ-6438), a novel EZH2 inhibitor, by the Pediatric Preclinical Testing Program" Pediatric Blood & Cancer, 64(3):DOI: 10.1002/pbc.26218. HHS Public Access Author Manuscript, available in PMC Mar. 1, 2018, 17 pages.

Kuwahara, Y. et al. (Mar. 1, 2010) "Reexpression of hSNF5 in malignant rhabdoid tumor cell lines causes cell cycle arrest through a p21CIP1/WAF1-dependent mechanism" Cancer Res, 70(5):1854-1865. NIH Public Access Author Manuscript, available in PMC Mar. 1, 2011, 18 pages.

Li, Y. et al. (Mar. 4, 2003) "Selective killing of cancer cells by β-lapachone: Direct checkpoint activation as a strategy against cancer" PNAS, 100(5):2674-2678.

Margueron, R. and D. Reinberg (2011) "The Polycomb complex PRC2 and its mark in life" Nature, 469(7330):343-349.

Matsubara, D. et al. (2013) "Lung cancer with loss of BRG1/BRM, shows epithelial mesenchymal transition phenotype and distinct histologic and genetic features" Cancer Sci, 104(2):266-273.

McCabe, M.T. et al. (2012) "EZH2 inhibition as a therapeutic strategy for lymphoma with EZH2-activating mutations" Nature, 492:108-112.

McConechy, M.K. et al.(2012) "Use of mutation profiles to refine the classification of endometrial carcinomas" J Pathol, 228(1):20-30.

McKenna, E.S. et al. (2012) "Epigenetic inactivation of the tumor suppressor BIN1 drives proliferation of SNF5-deficient tumors" Cell Cycle, 11(10):1956-1965.

Medjkane, S. et al. (May 15, 2004) "The Tumor Suppressor hSNF5/INI1 Modulates Cell Growth and Actin Cytoskeleton Organization" Cancer Research, 64:3406-3413.

Mocellin, S. and D. Nitti (2013) "CTLA-4 blockade and the renaissance of cancer immunotherapy" Biochim Biophys Acta, 1836:187-196.

Oike, T. et al. (Sep. 1, 2013) "A Synthetic Lethality-Based Strategy to Treat Cancers Harboring a Genetic Deficiency in the Chromatin Remodeling Factor BRG1" Cancer Res, 73(17):5508-5518.

Oike, T. et al. (Feb. 11, 2014) "Chromatin-regulating proteins as targets for cancer therapy" J Radiation Res, 55:613-628.

Oruetxebarria, I. et al. (Jan. 30, 2004) "p16INK4a is Required for hSNF5 Chromatin Remodeler-induced Cellular Senescence in Malignant Rhabdoid Tumor Cells" J Biol Chem, 279(5):3807-3816.

Qi, W. et al. (2012) "Selective inhibition of Ezh2 by a small molecule inhibitor blocks tumor cells proliferation" Proc Natl Acad Sci USA, 109(52):21360-21365.

Rabinovich, A. et al. (2015) "Primary rhabdoid tumor of the ovary: When large cells become small cells" Gynecologic Oncology Reports, 12:64-66.

Ramli, R. et al. (Jun. 2018) "An Analysis of Putative Cells of Origin for Malignant Rhabdoid Tumours (MRT): A Frontier For Development of MRT Cancer Modelling and Identification of Potential Therapeutic Targets" Neuro-Oncol, 20(Suppl 2): i33, ATRT-26; 1 page.

Ramos, P. et al. (2014) "Small cell carcinoma of the ovary, hypercalcemic type, displays frequent inactivating germline and somatic mutations in SMARCA4" Nat Genet, 46: 427-429. NIH Public Access Author Manuscript, retrieved from the Internet: https://www.ncbi.nlm.nih.gov/pmc/articles/PMC4332808/, 9 pages.

Reisman, D. et al. (Apr. 9, 2009) "The SWI/SNF complex and cancer" Oncogene, 28(14): 1653-1668.

Reisman, D.N. et al. (2003) "Loss of BRG1/BRM in human lung cancer cell lines and primary lung cancers: correlation with poor prognosis" Cancer Res, 63(3):560-566.

Shain, A.H. et al. (Jan. 2013) "The spectrum of SWI/SNF mutations, ubiquitous in human cancers" PLOS One, 8(1):e55119, 11 pages.

Simone, J.V. (1996) "Introduction" in Cecil Textbook of Medicine. 20th Ed., vol. 1. J. Claude Bennet and F. Plum (Eds.) W.B. Sauders Co.; pp. 1004-1010.

Smith, M.E. et al. (Jan. 15, 2008) "Rhabdoid tumor growth is inhibited by flavopiridol" Clin Cancer Res, 14(2):523-532.

Srendi, S.T. et al. (Mar. 2010) "Upregulation of mir-221 and mir-222 in atypical teratoid/rhabdoid tumors: potential therapeutic targets" Childs Nerv Sys, 26(3):279-283. (Abstract only, retrieved from: https://www.ncbi.nlm.nih.gov/pubmed/20012062, 2 pages).

Sugimoto, T. et al. (1999) "Malignant Rhabdoid-Tumor Cell Line Showing Neural and Smooth-Muscle-Cell Phenotypes" Int J Cancer, 82:678-686, doi.org/10.1002/(SICI)1097-0215(19990827)82:5<678::AID-IJC10>3.0.CO;2-K [online]. Retrieved from: https://onlinelibrary.wiley.com/doi/full/10.1002/%28SICI%291097-0215%2819990827%2982%3A5%3C678%3A%3AAID-IJC10%3E3.0.CO%3B2-K?SID=nlm%3Apubmed; 27 printed pages.

Thomas, A. et al. (Sep. 2015) "Refining the treatment of NSCLC according to histological and molecular subtypes" Nat Rev Clin Oncol, 12(9):511-526.

Ting, N. (Ed.) Dose Finding in Drug Development. Statistics for Biology and Health. M. Gail et al. (Series Eds.) Springer Science + Business Media, Inc., 2006; 261 pages.

Tuma, R.S. et al. (2010) "Targeted Epigenetic Therapies: The Next Frontier?" Journal of the National Cancer Institute, 102(24):1824-1825.

UNIPROTKB/SWISS-PROT Accession No. Q15910 (Mar. 21, 2012) "EZH2 Human" [online]. Retrieved from the Internet: http://www.uniprot.org/uniprot/Q15910.txt?version=113; retrieved on Jul. 23, 2012, 10 pages.

Varambally, S. et al. (2002) "The Polycomb Group Protein EZH2 is Involved in Progression of Prostate Cancer" Nature, 419:624-629.

Verbraecken, J. et al. (2006) "Body surface area in normal-weight, overweight, and obese adults. A comparison study" Metabolism Clinical and Experimental, 55:515-524.

Wilson, B.G. and C.W.M. Roberts (2011) "SWI/SNF nucleosome remodellers and cancer" Nat Rev Cancer, 11:481-492.

(56) References Cited

OTHER PUBLICATIONS

Wilson, B.G. et al. (Oct. 2010) "Epigenetic Antagonism between Polycomb and SWI/SNF Complexes during Oncogenic Transformation" Cancer Cell, 18(4):316-328.
Witkowski, L. et al. (May 2014) "Germline and somatic SMARCA4 mutations characterize small cell carcinoma of the ovary, hypercalcemic type" Nat Genet, 46(5):438-443, including "Methods", 2 pages.
Zhang, P. et al. (Mar. 7, 2015) "Antitumor effects of pharmacological EZH2 inhibition on malignant peripheral nerve sheath tumor through the miR-30a and KPNB1 pathway" Mol Cancer, 14:55, 17 pages.
GENBANK Accession No. CAB02546 (Apr. 18, 2005) "histone H3 [*Homo sapiens*]" National Center for Biotechnology Information (NCBI) [online]. Retrieved from: http://www.ncbi.nlm.nih.gov/protein/CAB02546; retrieved on Jul. 23, 2012, 2 pages.
GENBANK Accession No. NM_004447 (Jun. 2, 20126) "*Homo sapiens* epidermal growth factor receptor pathway substrate 8 (EPS8), mRNA" National Center for Biotechnology Information (NCBI) [online]. Retrieved from: http://www.ncbi.nlm.nih.gov/nuccore/NM_004447; retrieved on Jul. 23, 2012, 5 pages.
GENBANK Accession No. NM_004456 (Jun. 2, 20126) "*Homo sapiens* enhancer of zeste homolog 2 (*Drosophila*) (EZH2), transcript variant 1, mRNA" National Center for Biotechnology Information (NCBI) [online]. Retrieved from: http://www.ncbi.nlm.nih.gov/nuccore/NM_004456; retrieved on Jul. 23, 2012, 6 pages.
GENBANK Accession No. NM_152998 (Jun. 2, 20126) "*Homo sapiens* enhancer of zeste homolog 2 (*Drosophila*) (EZH2), transcript variant 2, mRNA" National Center for Biotechnology Information (NCBI) [online]. Retrieved from: http://www.ncbi.nlm.nih.gov/nuccore/NM_152998; retrieved on Jul. 23, 2012, 5 pages.
GENBANK Accession No. NP_694543 (Jun. 2, 20126) "histone-lysine N-methyltransferase EZH2 isoform b [*Homo sapiens*]" National Center for Biotechnology Information (NCBI) [online]. Retrieved from: http://www.ncbi.nlm.nih.gov/protein/NP_694543; retrieved on Jul. 23, 2012, 3 pages.
Callegaro-Filho, et al. (2015) "Radiotherapy for recurrent small cell carcinoma of the ovary: a case report and review of the literature" Gynecologic Oncology Reports, 11: 23-25.
Gail, M. et al. (2006) "Dose Finding in Drug Development: Statistics for Biology and Health" Springer Science+Business Media, Inc. 261 pages.
Daigle, S.R. et al. (Aug. 8, 2013) "Potent inhibition of DOT1L as treatment of MLL-fusion leukemia" Blood, 122:1017-1025.
GENBANK Accession No. NM_000489.3 (Jul. 28, 2013) "*Homo sapiens* alpha thalassemia/mental retardation syndrome X-linked (ATRX), transcript variant 1, mRNA" National Center for Biotechnology Information (NCBI) [online]; retrieved on Nov. 18, 2022, 10 pages.
GENBANK Accession No. NM_001007468.1 (Mar. 15, 2015) "*Homo sapiens* SWI/SNF related, matrix associated, actin dependent regulator of chromatin, subfamily b, member 1 (SMARCB1), transcript variant 2, mRNA" National Center for Biotechnology Information (NCBI) [online]; retrieved on Nov. 18, 2022, 4 pages.
GENBANK Accession No. NM_003073.3 (Mar. 15, 2015) "*Homo sapiens* SWI/SNF related, matrix associated, actin dependent regulator of chromatin, subfamily b, member 1 (SMARCB1), transcript variant 1, mRNA" National Center for Biotechnology Information (NCBI) [online]; retrieved on Nov. 18, 2022, 5 pages.
GENBANK Accession No. NM_003797.3 (Jun. 27, 2012) "*Homo sapiens* embryonic ectoderm development (EED), transcript variant 1, mRNA" National Center for Biotechnology Information (NCBI) [online]; retrieved on Jul. 23, 2012, 5 pages.
GENBANK Accession No. NM_005610.2 (Jun. 27, 2012) "*Homo sapiens* RB binding protein 4, chromatin remodeling factor (RBBP4), transcript variant 1, mRNA" National Center for Biotechnology Information (NCBI) [online]; retrieved on Jul. 23, 2012, 7 pages.
GENBANK Accession No. NM_006015.4 (May 20, 2017) "*Homo sapiens* AT-rich interaction domain 1A (ARID1A), transcript variant 1, mRNA" National Center for Biotechnology Information (NCBI) [online]; retrieved on Nov. 18, 2022, 10 pages.
GENBANK Accession No. NM_015355.2 (Jun. 28, 2012) "*Homo sapiens* SUZ12 polycomb repressive complex 2 subunit (SUZ12), mRNA" National Center for Biotechnology Information (NCBI) [online]; retrieved on Jul. 23, 2012, 6 pages.
GENBANK Accession No. NM_138270.2 (Jul. 28, 2013) "*Homo sapiens* alpha thalassemia/mental retardation syndrome X-linked (ATRX), transcript variant 2, mRNA" National Center for Biotechnology Information (NCBI) [online]; retrieved on Nov. 18, 2022, 10 pages.
GENBANK Accession No. NM_139135.2 (May 20, 2017) "*Homo sapiens* AT-rich interaction domain 1A (ARID1A), transcript variant 2, mRNA" National Center for Biotechnology Information (NCBI) [online]; retrieved on Nov. 18, 2022, 6 pages.
GENEPEPT Accession No. NP_000480.2 (Jul. 28, 2013) "transcriptional regulator ATRX isoform 1 [*Homo sapiens*]" National Center for Biotechnology Information (NCBI) [online]; retrieved on Nov. 18, 2022, 6 pages.
GENEPEPT Accession No. NP_001007469.1 (Nov. 13, 2022) "SWI/SNF-related matrix- associated actin-dependent regulator of chromatin subfamily B member 1 isoform b [*Homo sapiens*]" National Center for Biotechnology Information (NCBI) [online]; retrieved on Nov. 18, 2022, 3 pages.
GENEPEPT Accession No. NP_003064.2 (Nov. 13, 2022) "SWI/SNF-related matrix-associated actin-dependent regulator of chromatin subfamily B member 1 isoform a [*Homo sapiens*]" National Center for Biotechnology Information (NCBI) [online]; retrieved on Nov. 18, 2022, 3 pages.
GENEPEPT Accession No. NP_006006.3 (Oct. 22, 2022) "AT-rich interactive domain-containing protein 1A isoform a [*Homo sapiens*]" National Center for Biotechnology Information (NCBI) [online]; retrieved on Nov. 18, 2022, 7 pages.
GENEPEPT Accession No. NP_612114.1 (Jul. 28, 2013) "transcriptional regulator ATRX isoform 2 [*Homo sapiens*]" National Center for Biotechnology Information (NCBI) [online]; retrieved on Nov. 18, 2022, 6 pages.
GENEPEPT Accession No. NP_624361.1 (Oct. 22, 2022) "AT-rich interactive domain-containing protein 1A isoform b [*Homo sapiens*]" National Center for Biotechnology Information (NCBI) [online]; retrieved on Nov. 18, 2022, 4 pages.
Knutson, S.K. et al. (2015) "Abstract C87: EZH2 inhibition leads to decreased proliferation in SMARCA4-deleted ovarian cancer cell lines." Molecular Cancer Therapeutics 14(12_Supplement_2):C87-C87.
Mahmoud, F. et al. (Apr. 22, 2016) "Role of EZH2 histone methyl transferase in melanoma progression and metastasis" Cancer Biol Ther, 17(6): 579-591.
Sevenet, N. et al. (1999) "Spectrum of hSNF5IINI1 somatic mutations in human cancer and genotype-phenotype correlations." Human Molecular Genetics 8(13):2359-2368.
Su, L. et al. (2012) "Deconstruction of the SS18-SSX fusion oncoprotein complex: insights into disease etiology and therapeutics." Cancer Cell 21(3): 333-347.
Gadd, S. et al.(2010) "Rhabdoid tumor: gene expression clues to pathogenesis and potential therapeutic targets". Laboratory Investigation, 90(5): 724-738.
U.S. Appl. No. 15/987,000—filed May 23, 2018.
U.S. Appl. No. 18/478,483—filed Sep. 29, 2023.
U.S. Appl. No. 18/606,925—filed Mar. 15, 2024.
U.S. Appl. No. 18/606,903—filed Mar. 15, 2024.
U.S. Appl. No. 18/606,946—filed Mar. 15, 2024.
U.S. Appl. No. 18/734,942 of Keilhack et al., filed on Jun. 5, 2024.
U.S. Appl. No. 18/601,604 of Keilhack et al., filed on Mar. 11, 2024.
U.S. Appl. No. 18/595,993 of Raimondi, filed on Mar. 5, 2024.
U.S. Appl. No. 18/411,139 of Raimondi, filed on Jan. 12, 2024.
U.S. Appl. No. 18/431,262 of Raimondi et al., filed on Feb. 2, 2024.
U.S. Appl. No. 16/749,073 (Abandoned).
U.S. Appl. No. 15/979,916 (Abandoned).
U.S. Appl. No. 15/598,262 (Abandoned).
U.S. Appl. No. 14/054,646 (U.S. Pat. No. 9,688,665).

\* cited by examiner

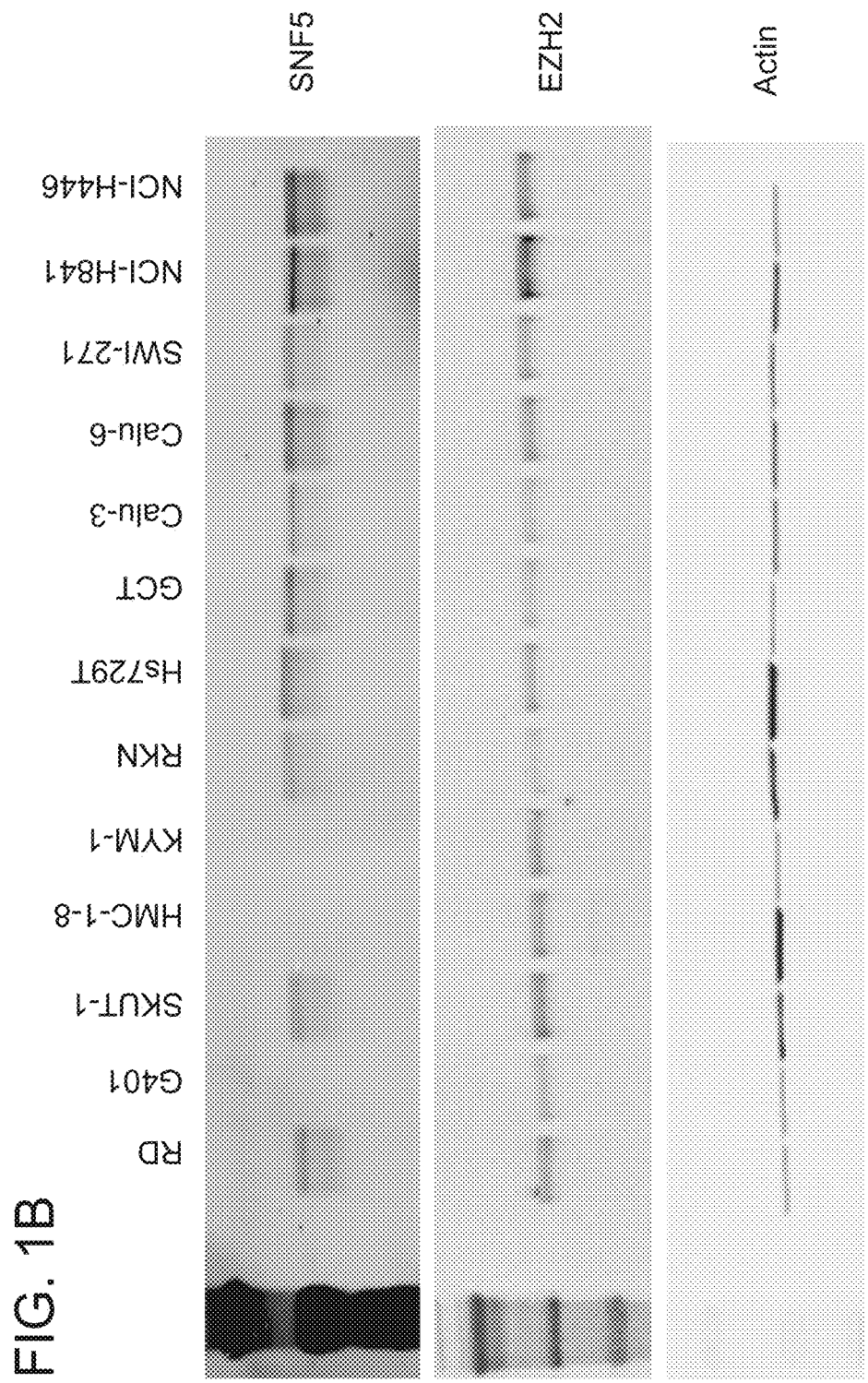

*SNF5 Mutant*

FIG. 3A   RD (5,000 cells/well)
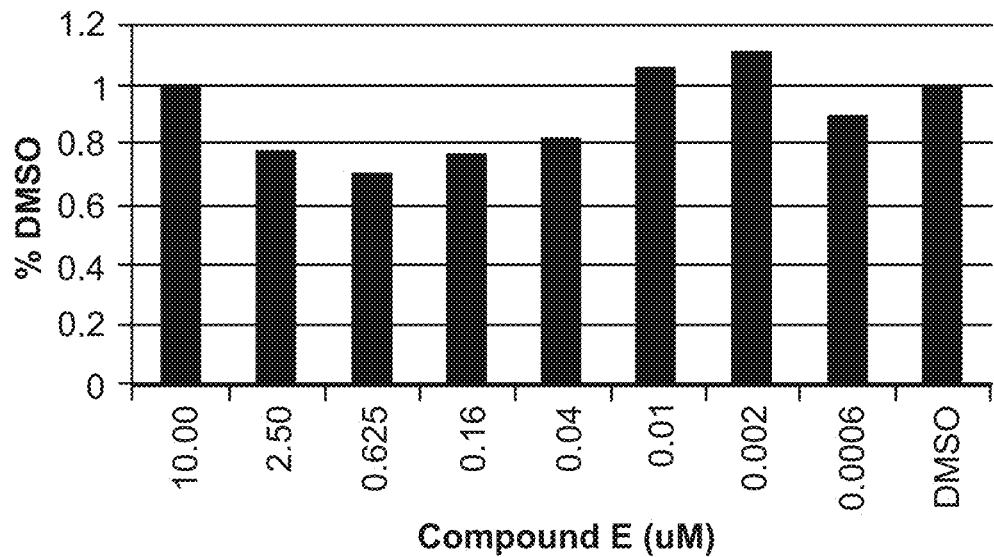
FIG. 3B   G401 (5,000 cells/well)
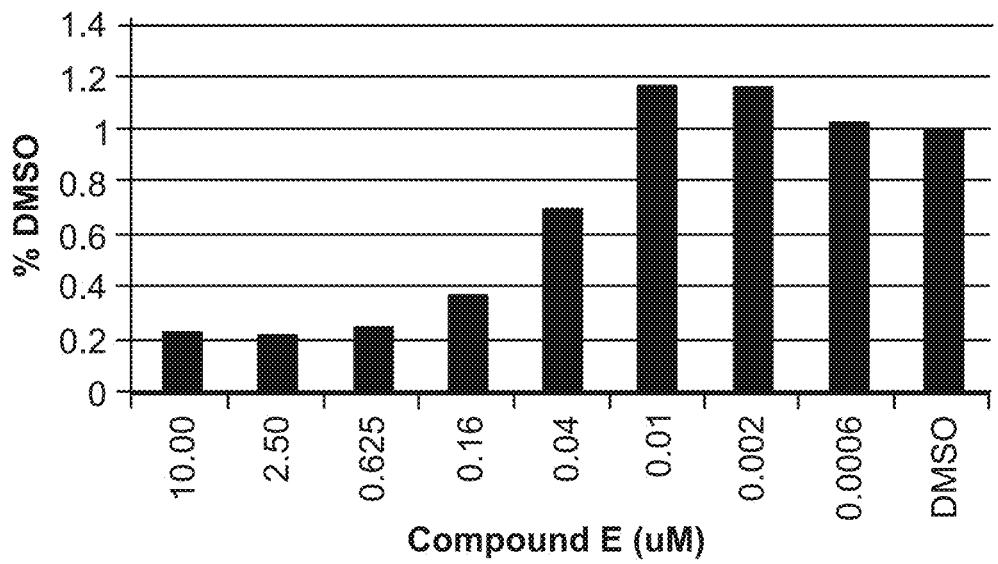

8 mice for PK/PD

Compound A

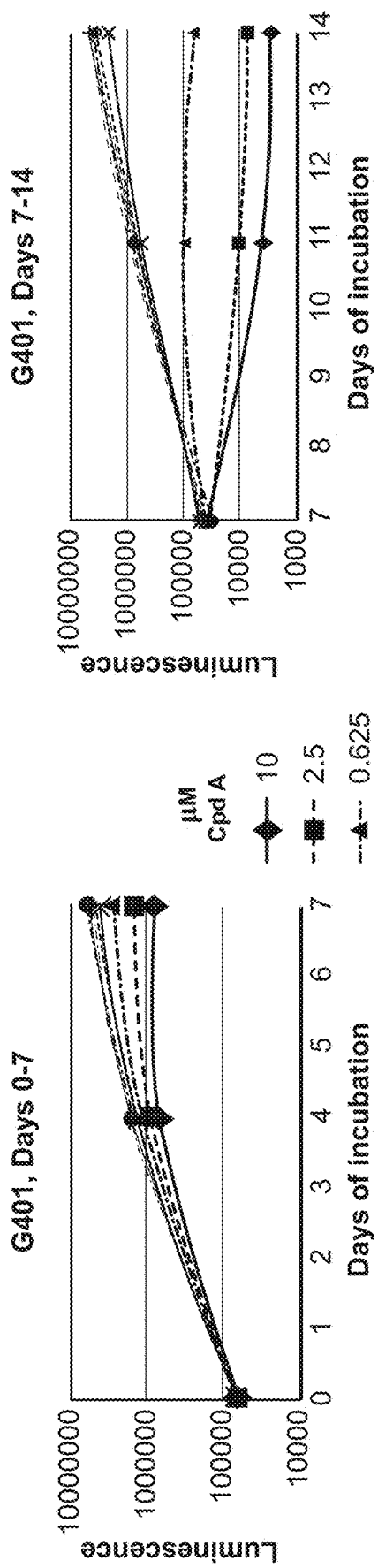
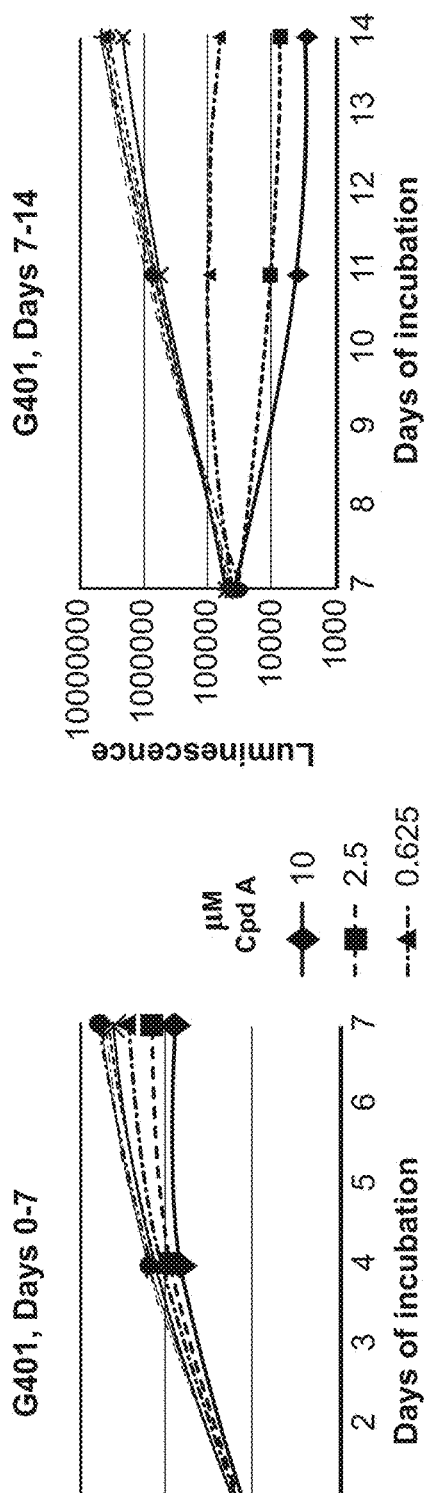
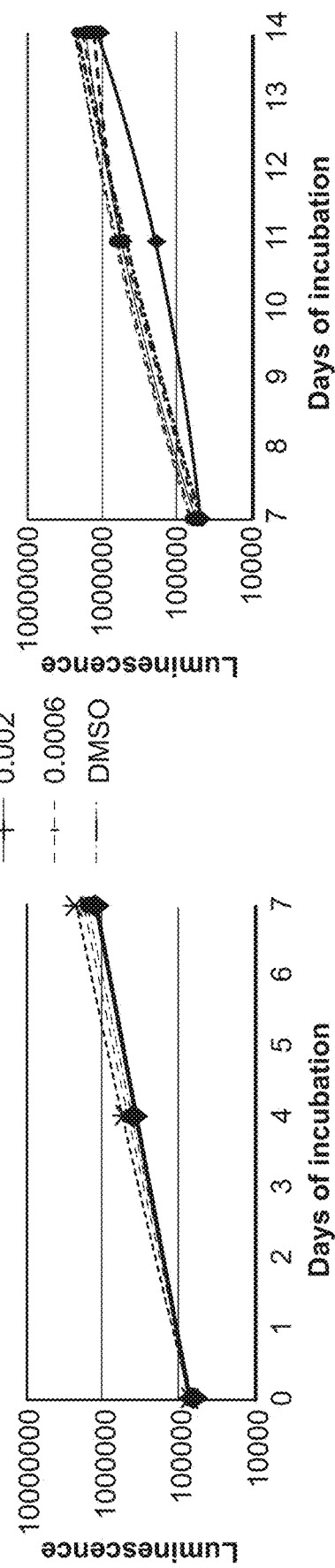
FIG. 10C
FIG. 10D
FIG. 10E
FIG. 10F

METHODS OF TREATING CANCER

RELATED APPLICATIONS

This application is a continuation of U.S. application Ser. No. 16/749,073, filed Jan. 22, 2020, which is a continuation of U.S. application Ser. No. 15/979,916, filed May 15, 2018, which is a continuation application of U.S. application Ser. No. 15/598,262, filed May 17, 2017, which is a continuation application of U.S. application Ser. No. 14/054,646, filed Oct. 15, 2013 (now U.S. Pat. No. 9,688,665), which claims priority to, and the benefit of U.S. Provisional Application Nos. 61/714,045, filed Oct. 15, 2012, 61/758,972, filed Jan. 31, 2013, 61/714,140, filed Oct. 15, 2012, 61/714,145, filed Oct. 15, 2012, 61/780,703, filed Mar. 13, 2013, and 61/786,277, filed Mar. 14, 2013. The contents of each of these provisional applications are incorporated herein by reference in their entireties.

INCORPORATION-BY-REFERENCE OF SEQUENCE LISTING

The contents of the text file named "41478-513001US_ST25.txt", which was created on Jan. 10, 2014 and is 141 KB in size, are hereby incorporated by reference in their entireties.

FIELD OF INVENTION

The present invention relates generally to the field of cancer treatment, and in particular, the treatment of cancer associated with the SWI/SNF complex (i.e., SWI/SNF mediated cancer). More particularly, the present invention provides methods and compositions which treat, alleviate, prevent, diminish or otherwise ameliorate the symptoms of cancer associated with the SWI/SNF complex.

BACKGROUND OF THE INVENTION

Disease-associated chromatin-modifying enzymes (e.g., EZH2) play a role in diseases such as proliferative disorders, metabolic disorders, and blood disorders. Thus, there is a need for the development of small molecules that are capable of modulating the activity of EZH2.

SUMMARY OF THE INVENTION

The present invention provides a method for treating or alleviating a symptom of a SWI/SNF-associated cancer in a subject by administering to a subject in need thereof a therapeutically effective amount of an EZH2 inhibitor, where the subject has a cancer selected from the group consisting of brain and central nervous system cancer, head and neck cancer, kidney cancer, ovarian cancer, pancreatic cancer, leukemia, lung cancer, lymphoma, myeloma, sarcoma, breast cancer, and prostate cancer. For example, the SWI/SNF-associated cancer is characterized by reduced expression and/or loss of function of the SWI/SNF complex or one or more components of the SWI/SNF complex.

For example, the subject has a cancer selected from the group consisting of medulloblastoma, malignant rhabdoid tumor, and atypical teratoid/rhabdoid tumor.

For example, the one or more components are selected from the group consisting of SNF5, ATRX, and ARID1A.

For example, the loss of function is caused by a loss of function mutation resulting from a point mutation, a deletion, and/or an insertion.

For example, the subject has a deletion of SNF5.

For example, the subject has a mutation of ATRX selected from the group consisting of a substitution of asparagine (N) for the wild type residue lysine (K) at amino acid position 688 of SEQ ID NO: 5 (K688N), and a substitution of isoleucine (I) for the wild type residue methionine (M) at amino acid position 366 of SEQ ID NO: 5 (M366I).

For example, subject has a mutation of ARID1A selected from the group consisting of a nonsense mutation for the wild type residue cysteine (C) at amino acid position 884 of SEQ ID NO: 11 (C884*), a substitution of lysine (K) for the wild type residue glutamic acid (E) at amino acid position 966 (E966K), a nonsense mutation for the wild type residue glutamine (Q) at amino acid position 1411 of SEQ ID NO: 11 (Q1411*), a frame shift mutation at the wild type residue phenylalanine (F) at amino acid position 1720 of SEQ ID NO: 11 (F1720fs), a frame shift mutation after the wild type residue glycine (G) at amino acid position 1847 of SEQ ID NO: 11 (G1847fs), a frame shift mutation at the wild type residue cysteine (C) at amino acid position 1874 of SEQ ID NO: 11 (C1874fs), a substitution of glutamic acid (E) for the wild type residue aspartic acid (D) at amino acid position 1957 (D1957E), a nonsense mutation for the wild type residue glutamine (Q) at amino acid position 1430 of SEQ ID NO: 11 (Q1430*), a frame shift mutation at the wild type residue arginine (R) at amino acid position 1721 of SEQ ID NO: 11 (R1721fs), a substitution of glutamic acid (E) for the wild type residue glycine (G) at amino acid position 1255 (G1255E), a frame shift mutation at the wild type residue glycine (G) at amino acid position 284 of SEQ ID NO: 11 (G284fs), a nonsense mutation for the wild type residue arginine (R) at amino acid position 1722 of SEQ ID NO: 11 (R1722*), a frame shift mutation at the wild type residue methionine (M) at amino acid position 274 of SEQ ID NO: 11 (M274fs), a frame shift mutation at the wild type residue glycine (G) at amino acid position 1847 of SEQ ID NO: 11 (G1847fs), a frame shift mutation at the wild type residue P at amino acid position 559 of SEQ ID NO: 11 (P559fs), a nonsense mutation for the wild type residue arginine (R) at amino acid position 1276 of SEQ ID NO: 11 (R1276*), a frame shift mutation at the wild type residue glutamine (Q) at amino acid position 2176 of SEQ ID NO: 11 (Q2176fs), a frame shift mutation at the wild type residue histidine (H) at amino acid position 203 of SEQ ID NO: 11 (H203fs), a frame shift mutation at the wild type residue alanine (A) at amino acid position 591 of SEQ ID NO: 11 (A591fs), a nonsense mutation for the wild type residue glutamine (Q) at amino acid position 1322 of SEQ ID NO: 11 (Q1322*), a nonsense mutation for the wild type residue serine (S) at amino acid position 2264 of SEQ ID NO: 11 (S2264*), a nonsense mutation for the wild type residue glutamine (Q) at amino acid position 586 of SEQ ID NO: 11 (Q586*), a frame shift mutation at the wild type residue glutamine (Q) at amino acid position 548 of SEQ ID NO: 11 (Q548fs), and a frame shift mutation at the wild type residue asparagine (N) at amino acid position 756 of SEQ ID NO: 11 (N756fs).

The present invention also provides a method of treating or alleviating a symptom of a SWI/SNF-associated cancer in a subject in need thereof by (a) determining the expression level of at least one gene selected from the group consisting of neuronal differentiation genes, cell cycle inhibition genes and tumor suppressor genes in a sample obtained from the subject; (b) selecting the subject having a decreased expression level of at least one gene in step a; and (c) administering to the subject selected in step b an effective amount of an EZH2 inhibitor, thereby treating or alleviating a symptom of cancer in the subject.

The present invention further provides a method of treating or alleviating a symptom of a SWI/SNF-associated cancer in a subject in need thereof by (a) determining the expression level of at least one gene selected from the group consisting of hedgehog pathway genes, myc pathway genes and histone methyltransferase genesin a sample obtained from the subject; (b) selecting the subject having an increased expression level of at least one gene in step a; and (c) administering to the subject selected in step b an effective amount of an EZH2 inhibitor, thereby treating or alleviating a symptom of cancer in the subject.

For example, the cancer can be medulloblastoma, malignant rhabdoid tumor or atypical teratoid rhabdoid tumor.

For example, the neuronal differentiation gene is CD133, DOCK4, or PTPRK.

For example, the cell cycle inhibition gene is CKDN1A or CDKN2A.

For example, the tumor suppressor gene is BIN1.

For example, the hedgehog pathway gene is GLI1 or PTCH1.

For example, the myc pathway gene is MYC.

For example, the histone methyltransferase gene is EZH2.

The present invention also provides a method of inducing neuronal differentiation, cell cycle inhibition or tumor suppression by contacting a cell with an EZH2 inhibitor. The EZH2 inhibitor may be in an amount sufficient to increase expression of at least one gene selected from the group consisting of CD133, DOCK4, PTPRK, CKDN1A, CDKN2A and BIN1.

The present invention also provides a method of inhibiting hedgehog signaling by contacting a cell with an EZH2 inhibitor. The EZH2 inhibitor can be in an amount sufficient to reduce expression of GLI1 and/or PTCH1.

The present invention also provides a method of inducing gene expression by contacting a cell with an EZH2 inhibitor. The EZH2 inhibitor can be in an amount sufficient to induce neuronal differentiation, cell cycle inhibition and/or tumor suppression. For example, the gene can be CD133, DOCK4, PTPRK, CKDN1A, CDKN2A or BIN1.

The present invention also provides a method of inhibiting gene expression by contacting a cell with an EZH2 inhibitor. The EZH2 inhibitor is in an amount sufficient to inhibit hedgehog signaling. For example, the gene can be GLI1 or PTCH1.

For example, the cell may have loss of function of SNF5, ARID1A, ATRX, and/or a component of the SWI/SNF complex.

For example, the loss of function is caused by a deletion of SNF5.

For example, the cell is a cancer cell. The cancer can be medulloblastoma, malignant rhabdoid tumor or atypical teratoid rhabdoid tumor.

For example, the EZH2 inhibitor is Compound A having the following formula:

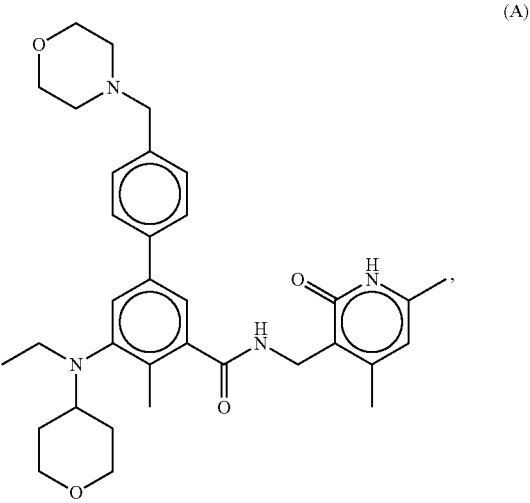

(A)

stereoisomers thereof, or pharmaceutically acceptable salts or solvates thereof.

For example, the EZH2 inhibitor is Compound B having the following formula:

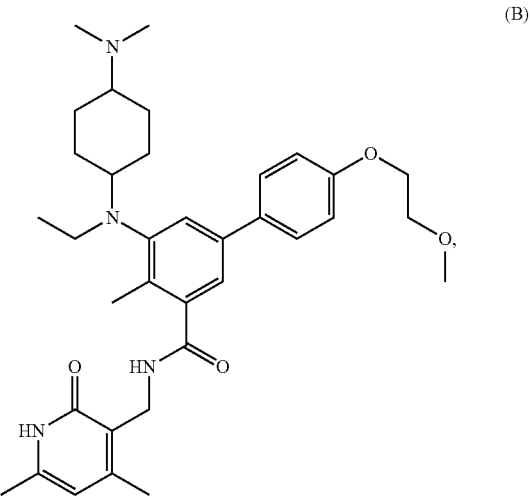

(B)

stereoisomers thereof, or pharmaceutically acceptable salts or solvates thereof.

For example, the EZH2 inhibitor is Compound C having the following formula:

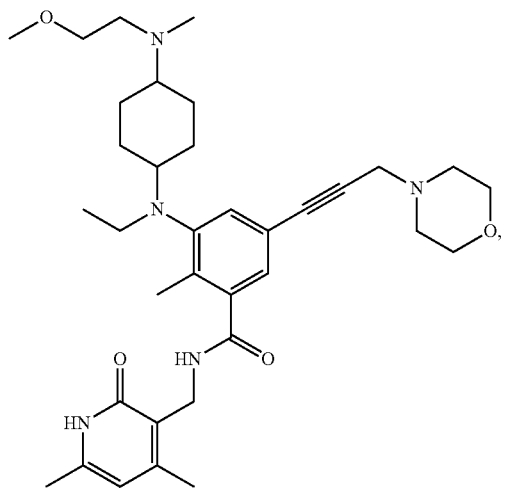

(C)

stereoisomers thereof, or pharmaceutically acceptable salts or solvates thereof.

For example, the EZH2 inhibitor is Compound D having the following formula:

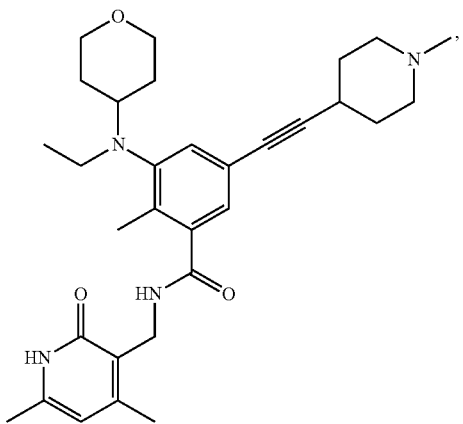

(D)

stereoisomers thereof, or pharmaceutically acceptable salts or solvates thereof.

For example, the EZH2 inhibitor is Compound E having the following formula:

(E)

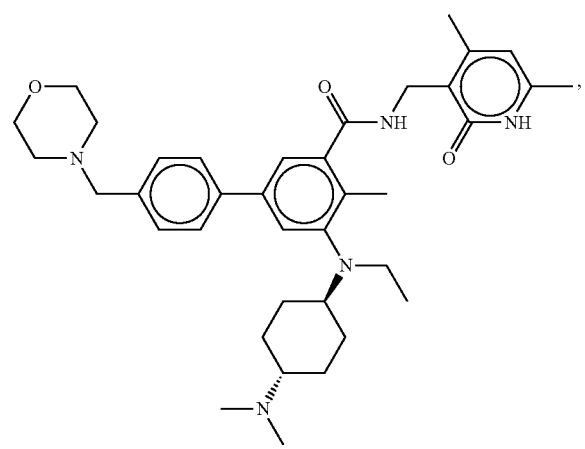

stereoisomers thereof, or pharmaceutically acceptable salts or solvates thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTIONS OF FIGURES

FIGS. 1A and 1B are a series of Western blot analyses of cell lines with wild type (RD and SJCRH30) and mutant SNF5.

Figure 1A:
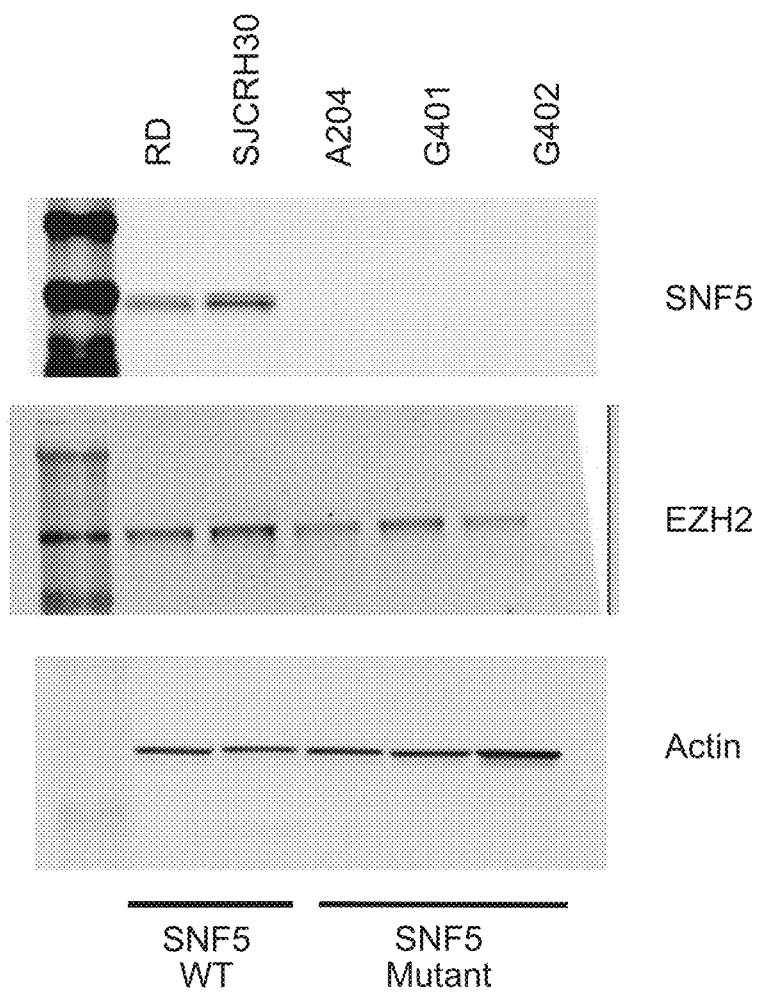
Figure 2A:
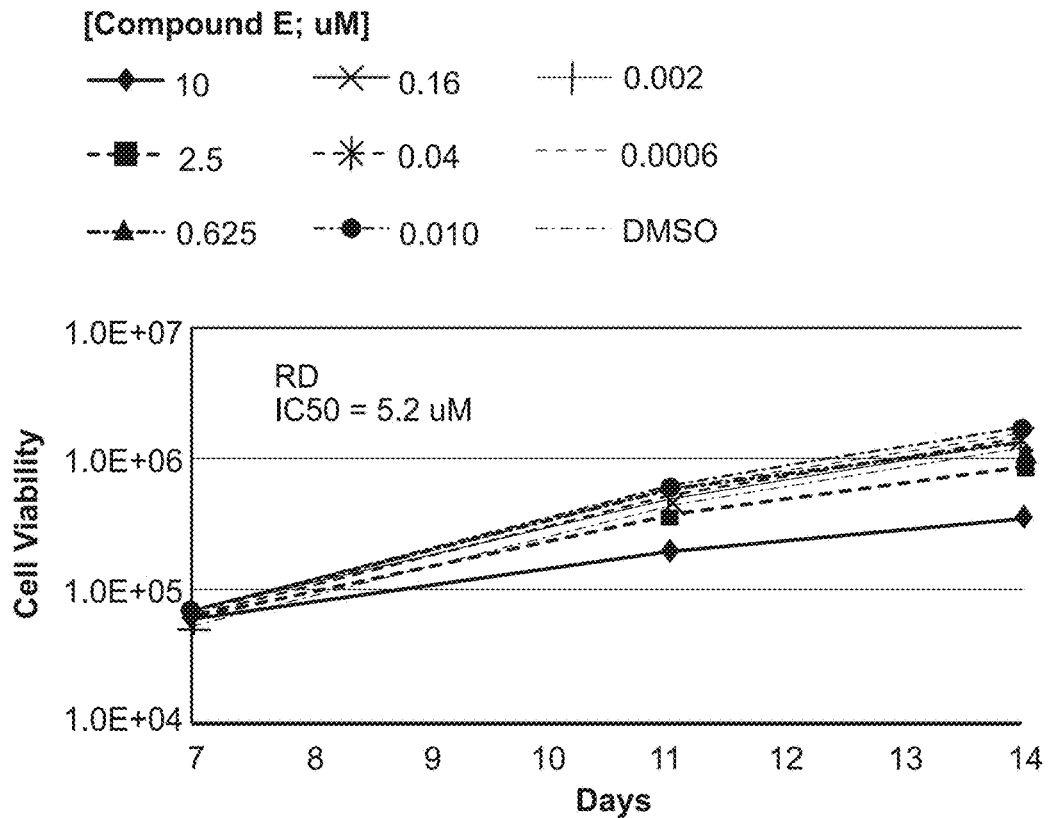
FIGS. 2A-2E are a series of graphs establishing that SNF5 mutant cell lines A204 (FIG. 2C), G401 (FIG. 2D) and G402 (FIG. 2E) selectively respond to EZH2 compound (Compound E) compared to wild type cell lines RD (FIG. 2A) and SJCRH30 (FIG. 2B).
Figure 2B:
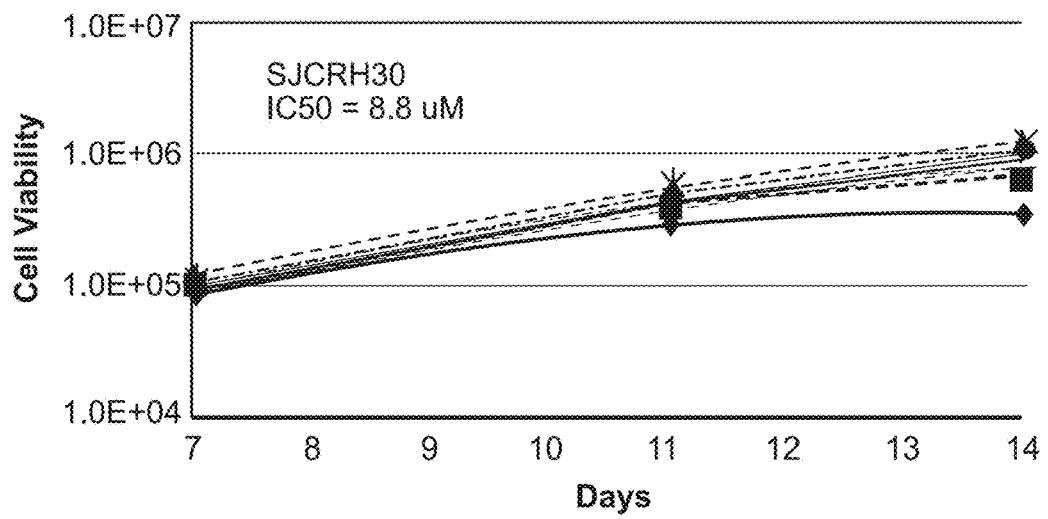
Figure 2C:
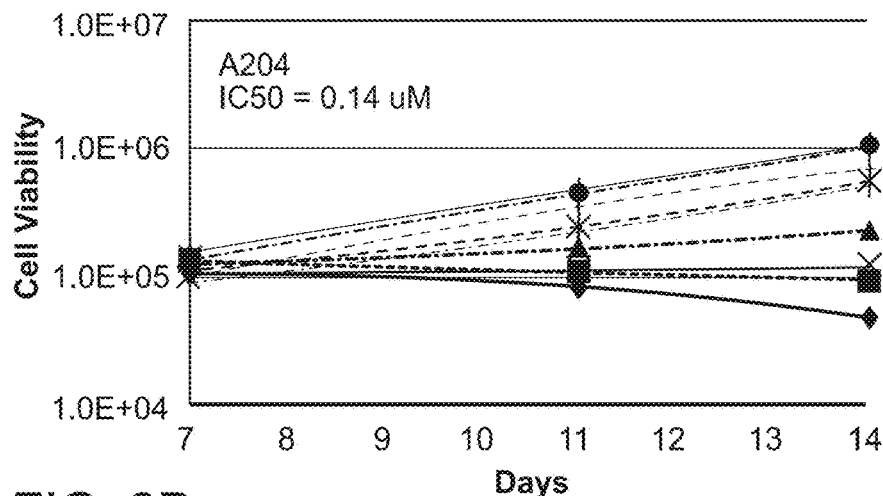
Figure 2D:
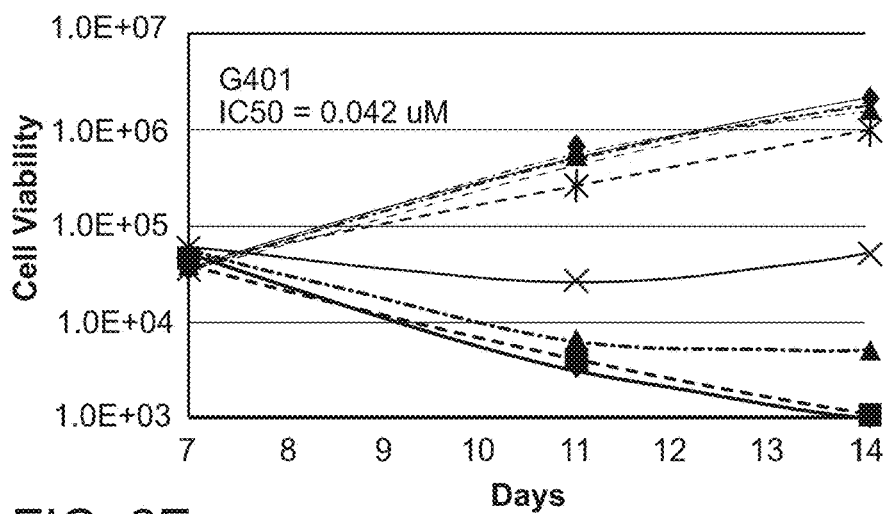
Figure 2E:
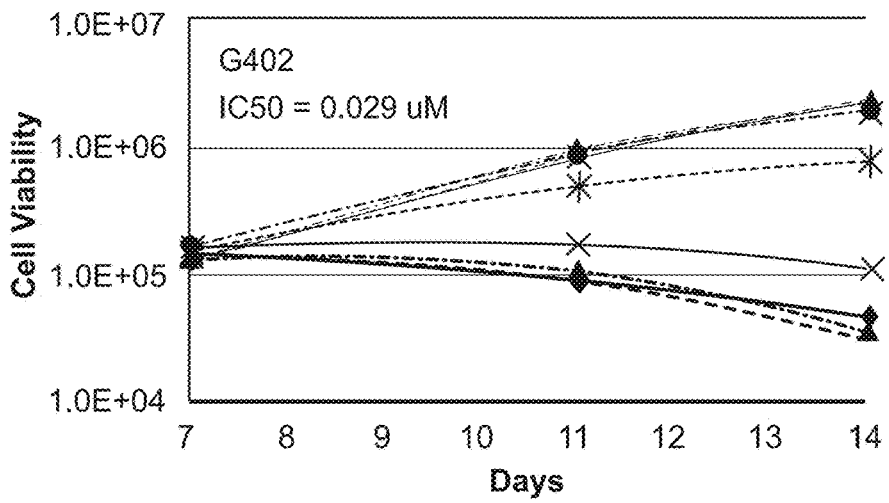
Figure 3C:
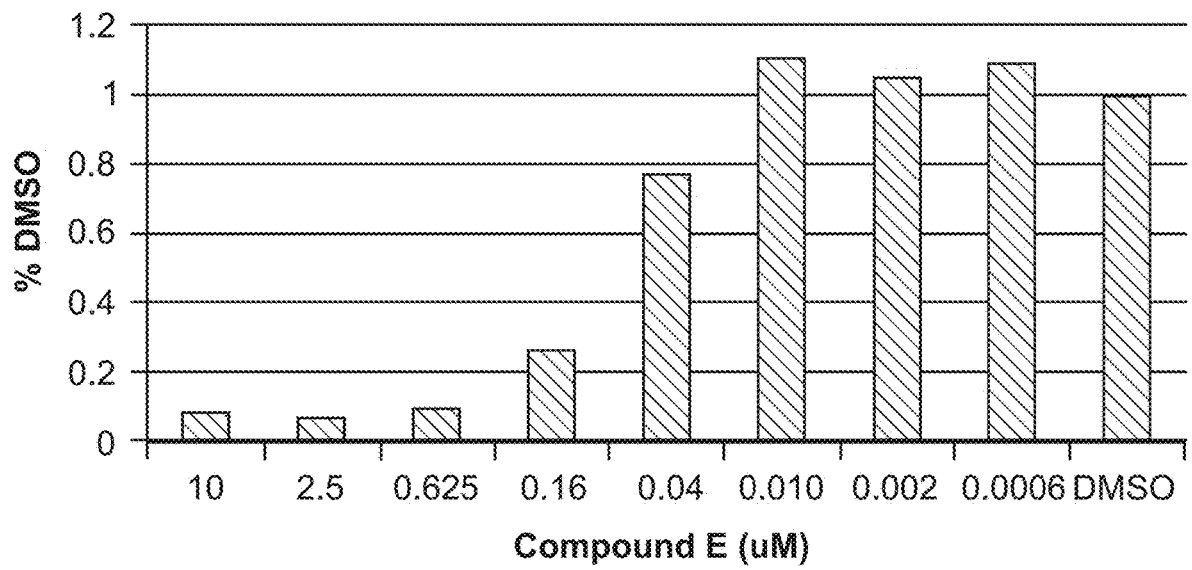
Figure 3D:
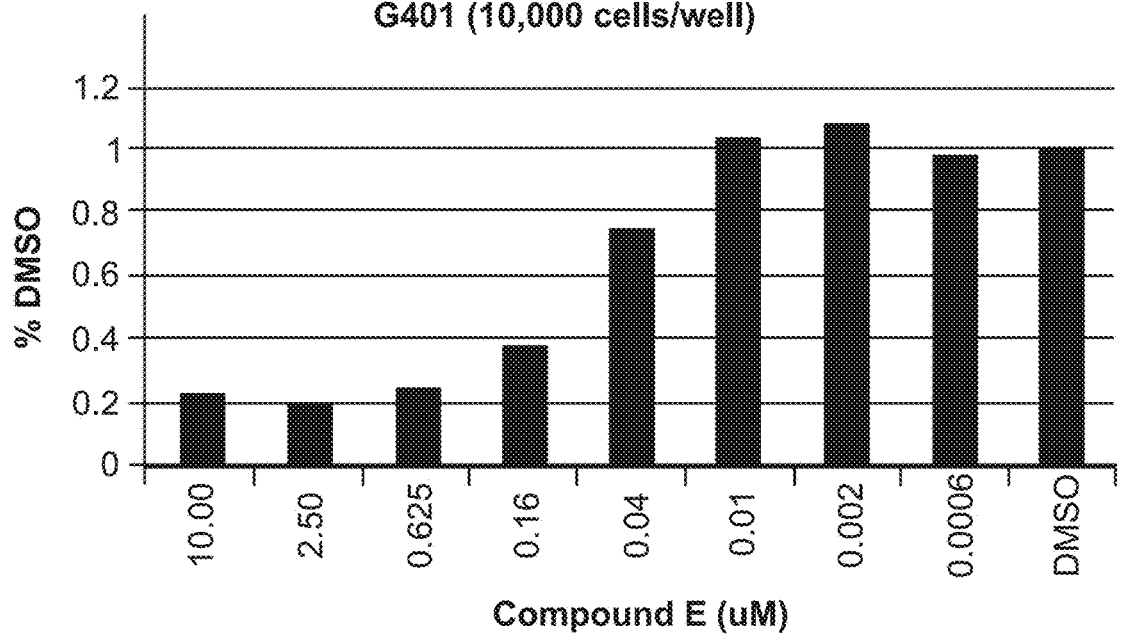
Figure 4A:
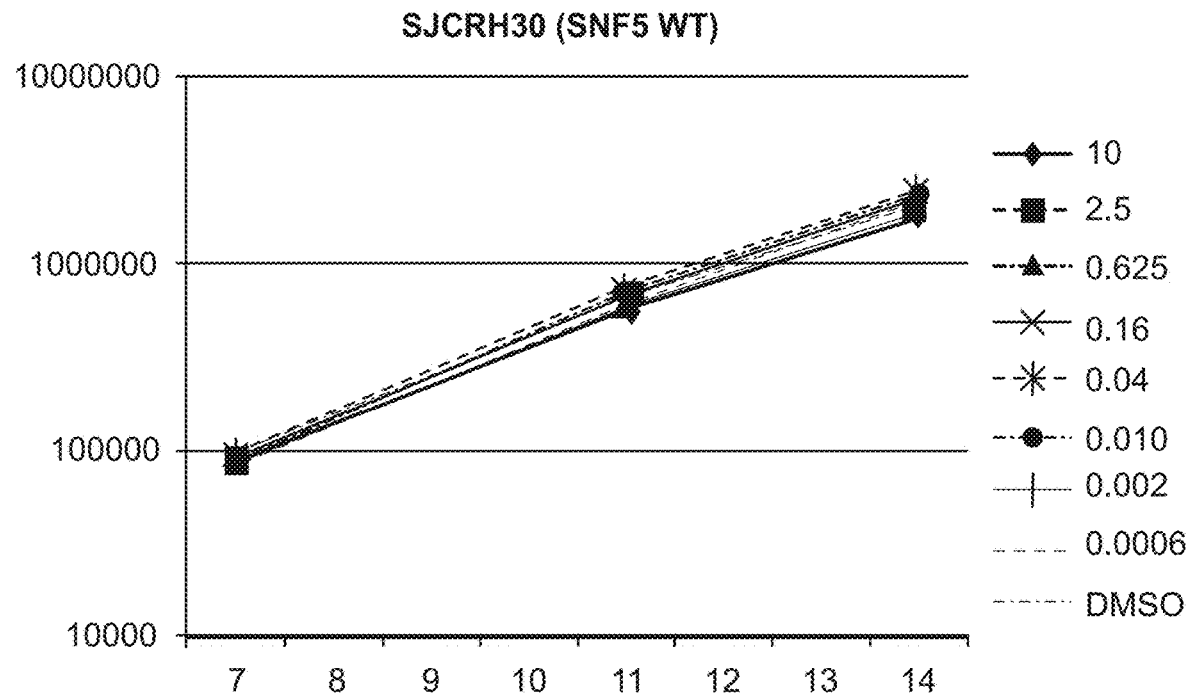
Figure 4B:
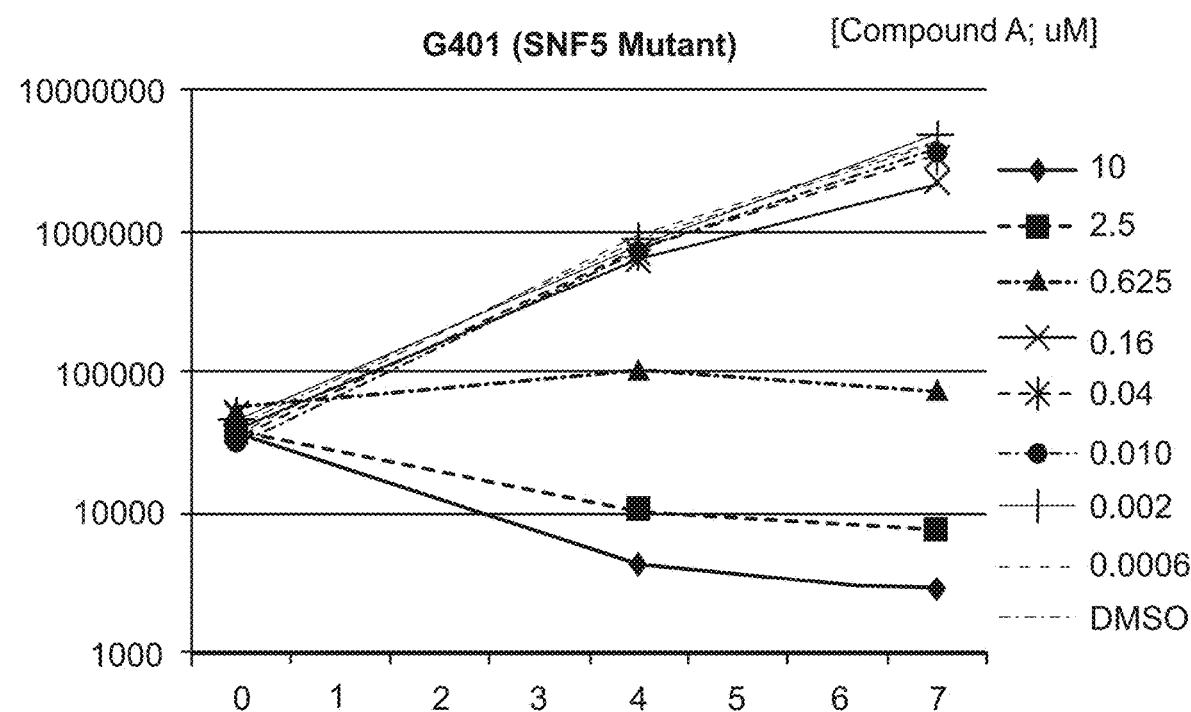
Figure 4C:
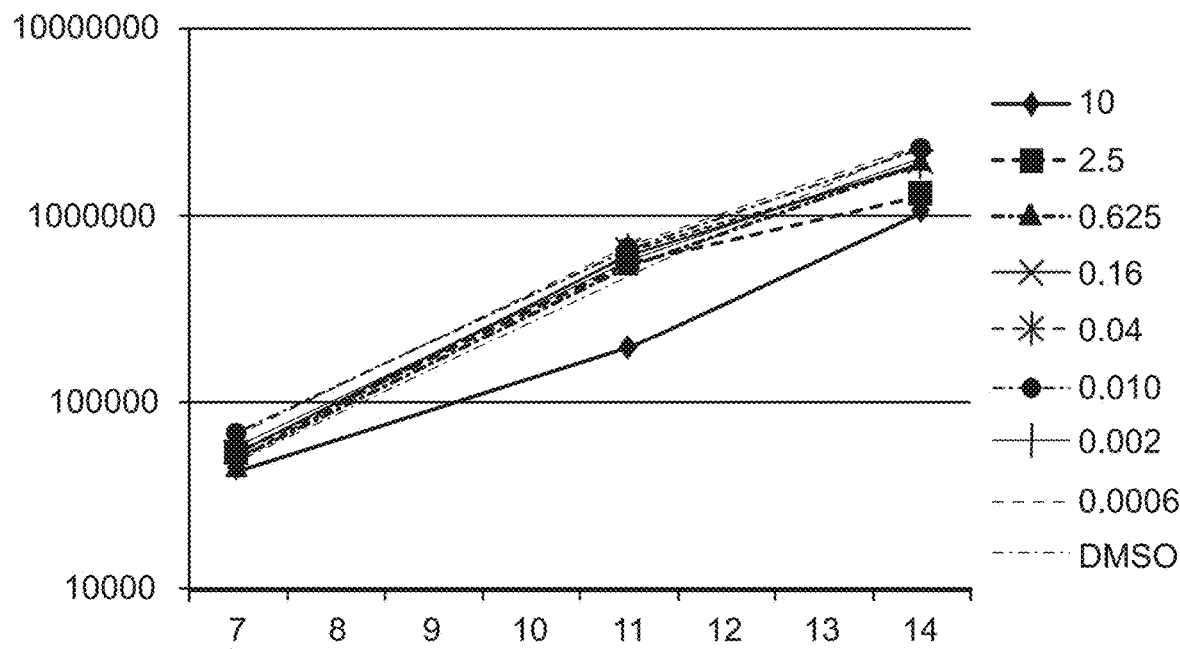
Figure 4D:
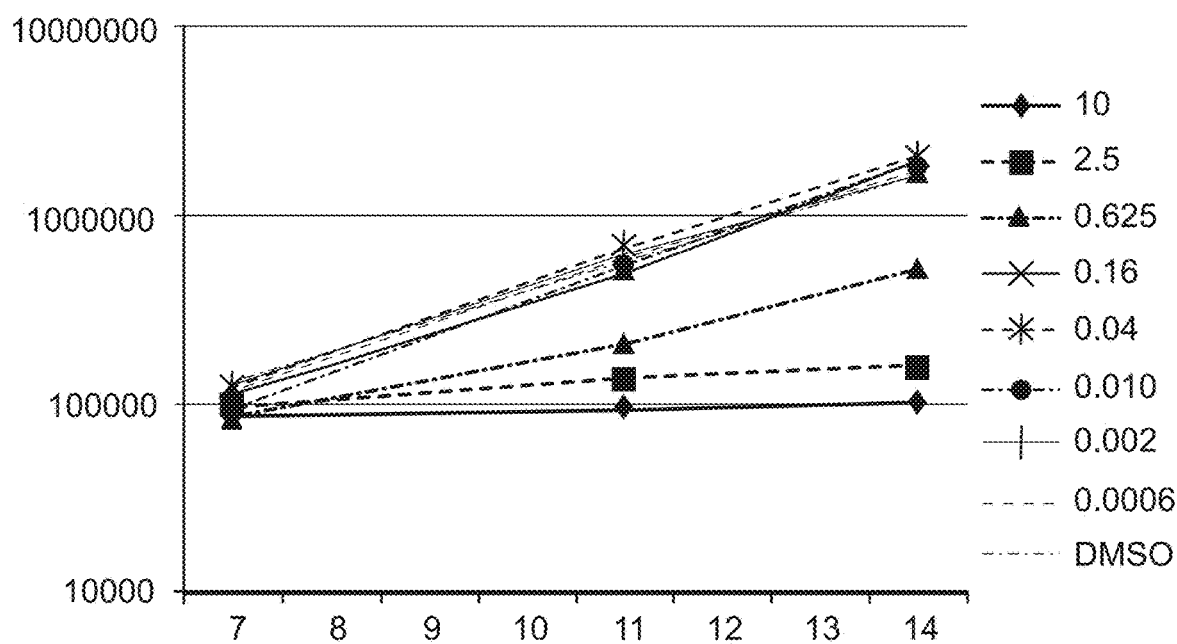

FIGS. 3A-3D are a series of bar graphs showing that G401 SNF mutant cell line is responding to Compound E after 7 days in soft agar compared to wild type cells RD. FIG. 3A shows cell line RD (5,000 cells/well). FIG. 3B shows G401 cells (5,000 cells/well). FIG. 3C shows G401 cells in 2D growth. FIG. 3D shows G401 cells (10,000 cells/well).

FIGS. 4A-4D are four graphs showing that G401 SNF5 mutant cell line is sensitive to Compound A in vitro. Wild type cell lines SJCRH30 (FIG. 4A) and RD (FIG. 4C) and SNF5 mutant cell lines G401 (FIG. 4B) and A204 (FIG. 4D) were pretreated for 7 days with indicated concentrations of Compound A and replated on day 0. Cell viability was determined by CellTiter-Glo® Luminescent Cell Viability Assay.

Figure 5A:
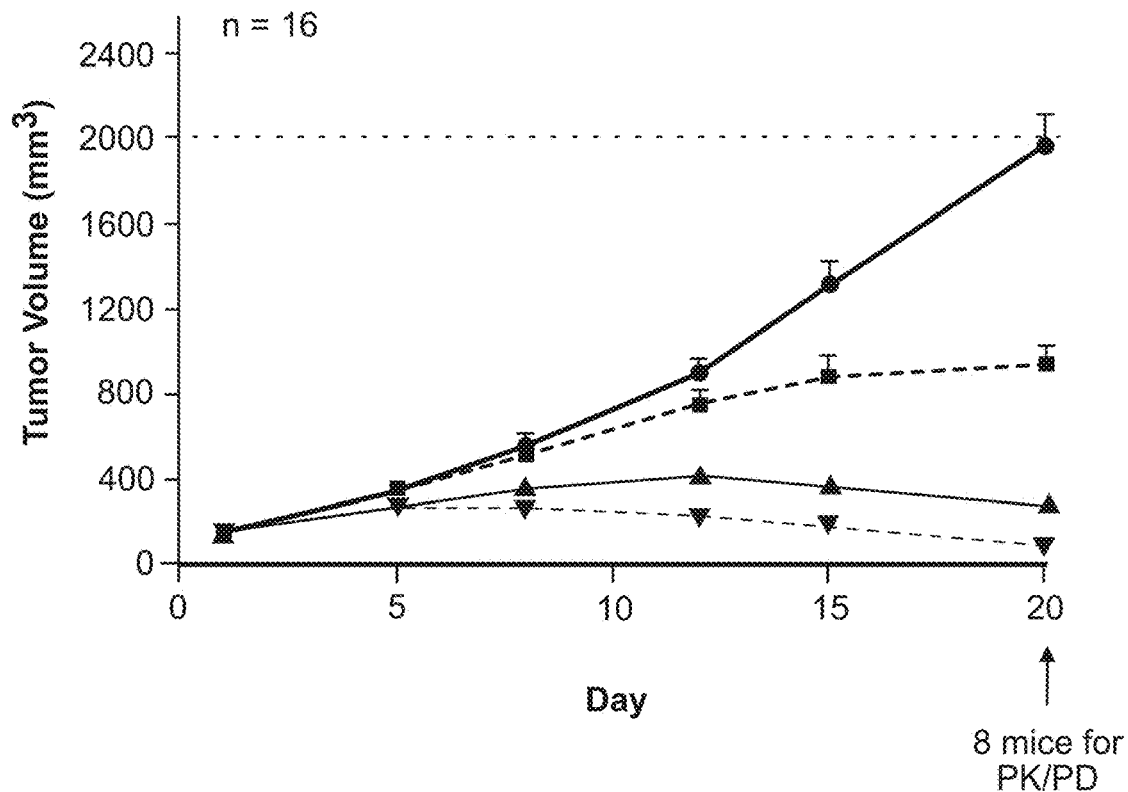
Figure 5B:
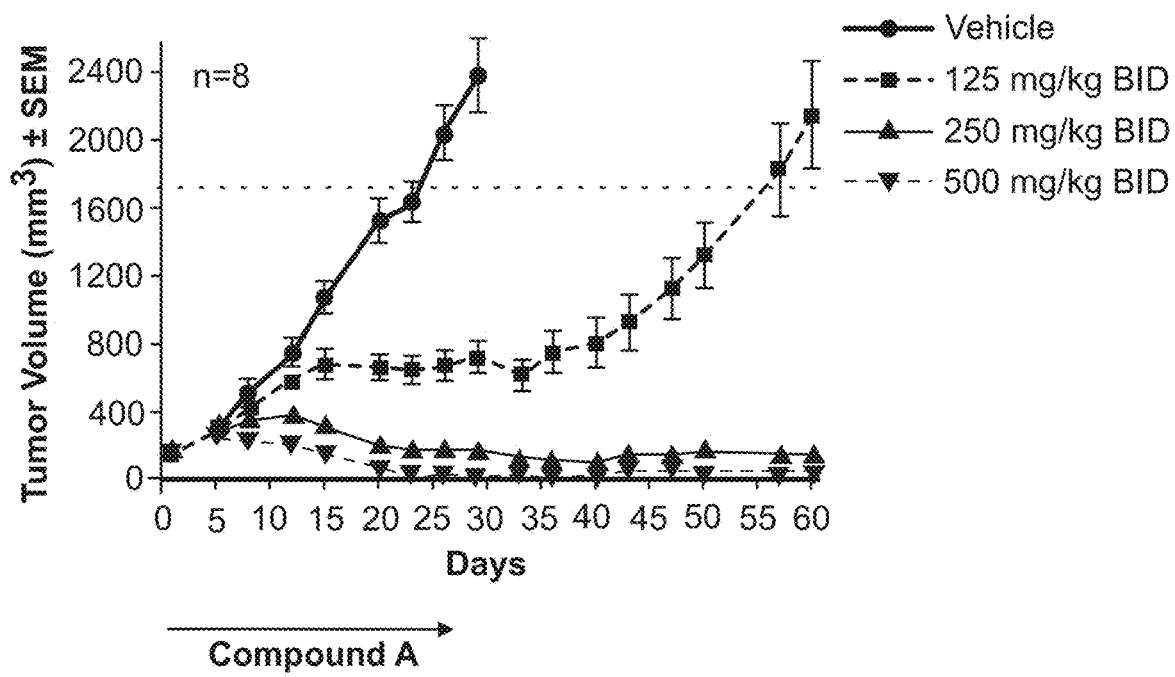

FIGS. 5A-5E are a series of graphs showing durable regressions in G401 xenografts (malignant rhabdoid tumor model) with Compound A treatment. FIG. 5A shows tumor regressions induced by Compound A at the indicated doses. FIG. 5B shows tumor regressions induced by twice daily administration of Compound A at the indicated doses. Data represent the mean values±SEM (n=8). Compound administration was stopped on day 28.

Figure 5C:
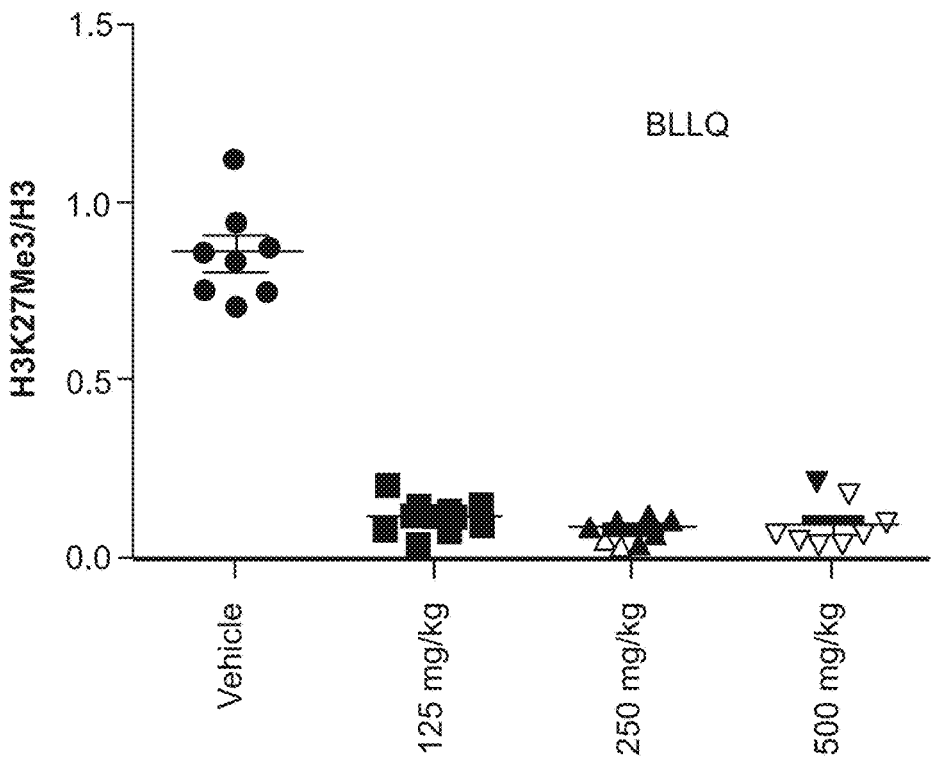
Figure 5D:
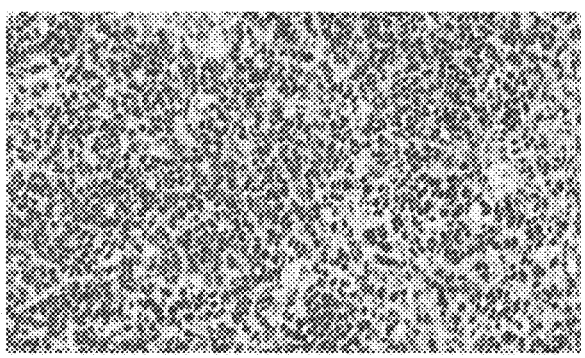
Figure 5E:
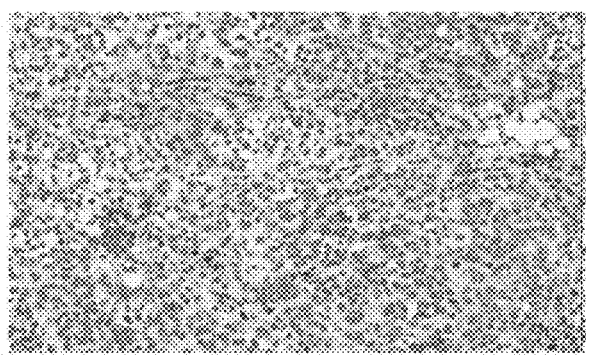

FIG. 5C shows the EZH2 target inhibition in G401 xenograft tumor tissue collected from a parallel cohort of mice on day 21. Each point shows the ratio of H3K27Me3 to total H3. Horizontal lines represent group mean values. BLLQ=below lower limit of quantification. FIGS. 5D and 5E show immunohistochemical staining of tumor histone methylation of tumor samples from the vehicle treated (FIG. 5D) and Compound A treated (FIG. 5E) (at 125 mg/kg) mice.

Figure 6:
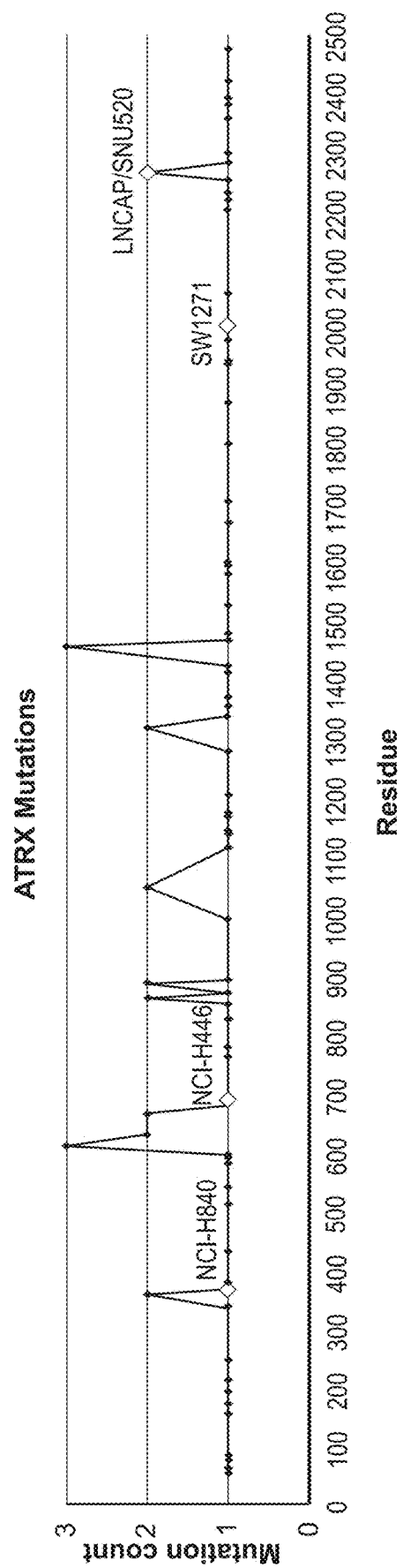

FIG. 6 is a graph showing the locations of ATRX mutations identified in SCLC cell lines.

Figures 7A, 7B:
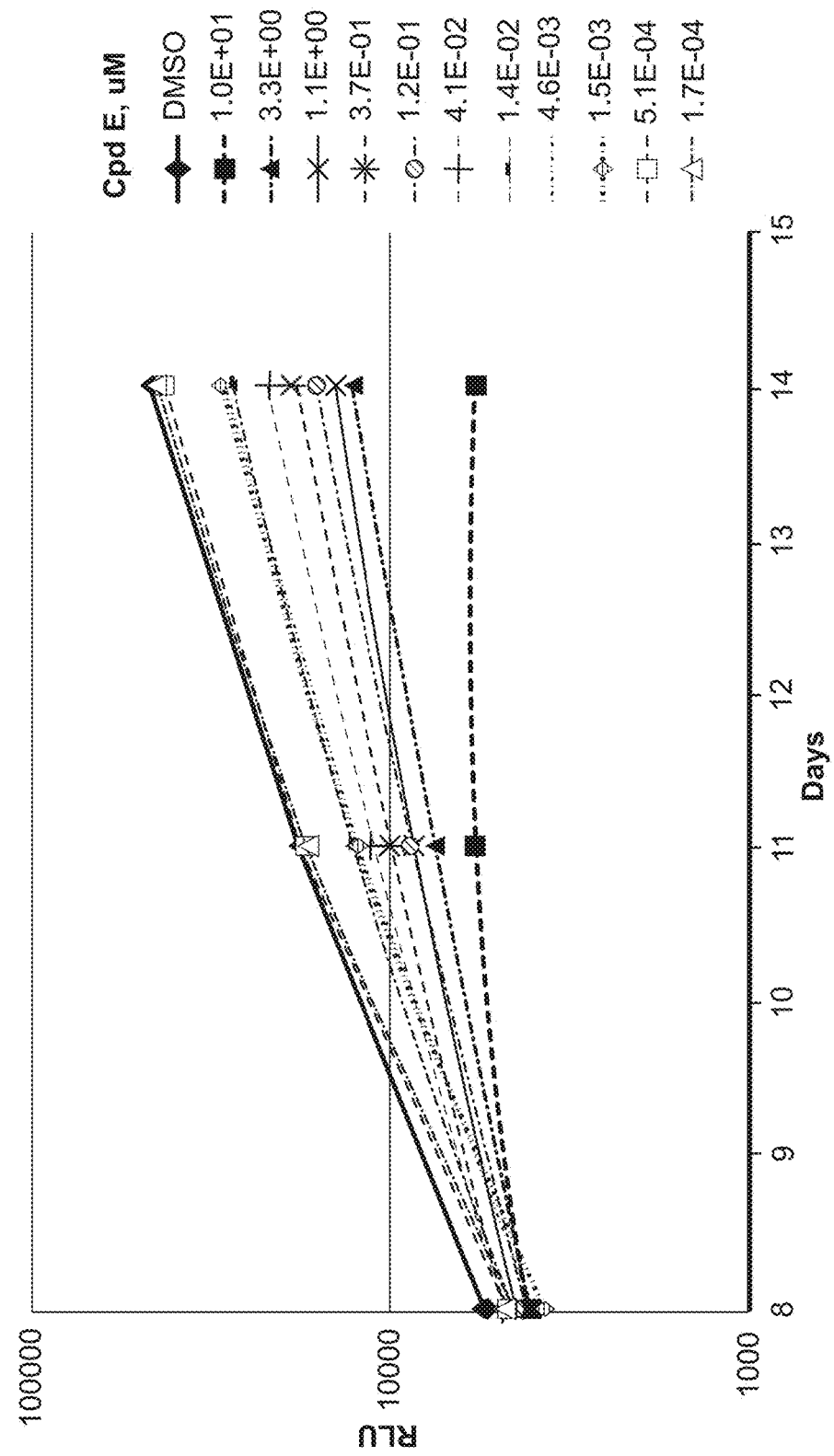

FIG. 7A is a graph showing that LNCAP prostate cancer cells display dose-dependent cell growth inhibition with Compound E treatment in vitro.

FIG. 7B is a graph showing IC50 value of Compound E at day 11 and day 14 for WSU-DLCL2 and LNCAP cells.

Figure 8A:
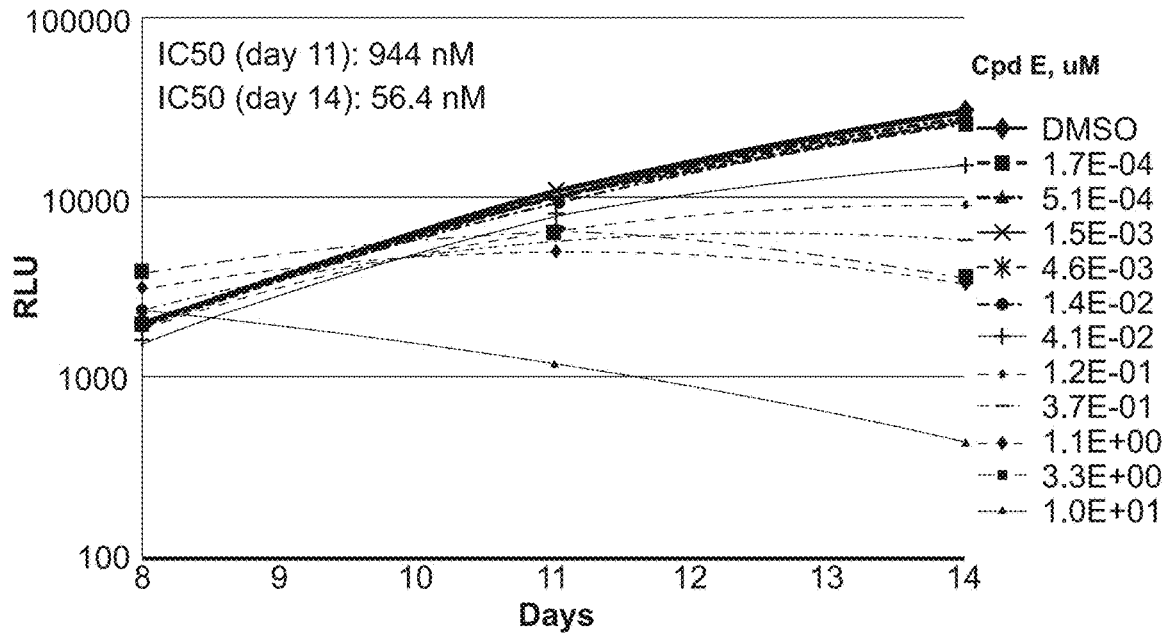
Figure 8B:
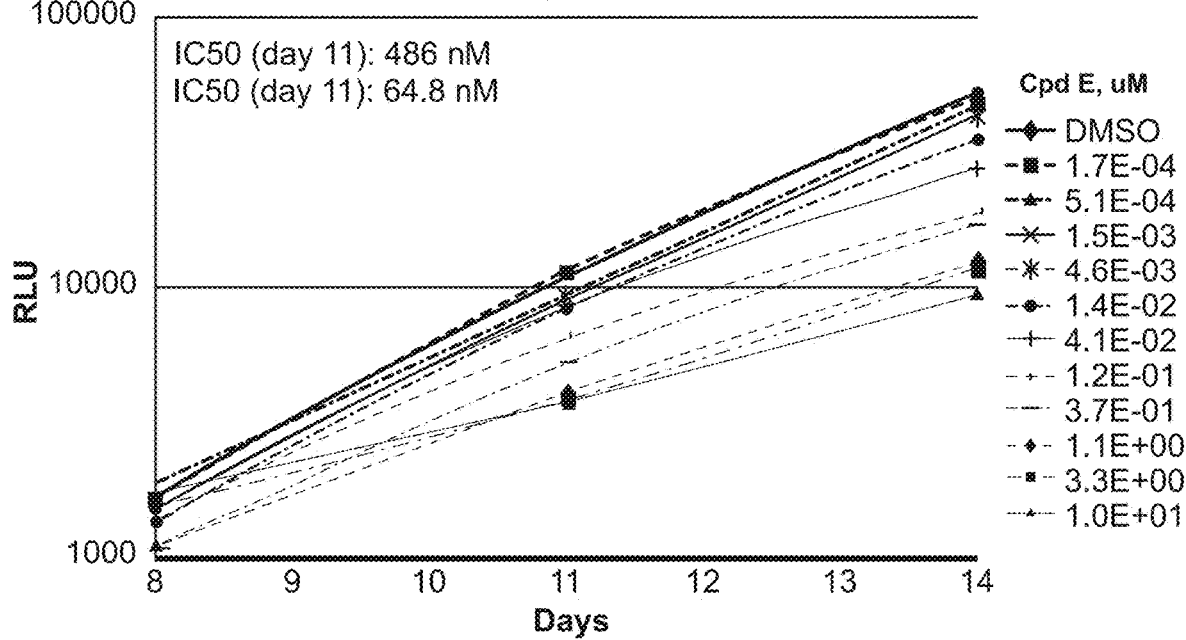
Figure 8C:
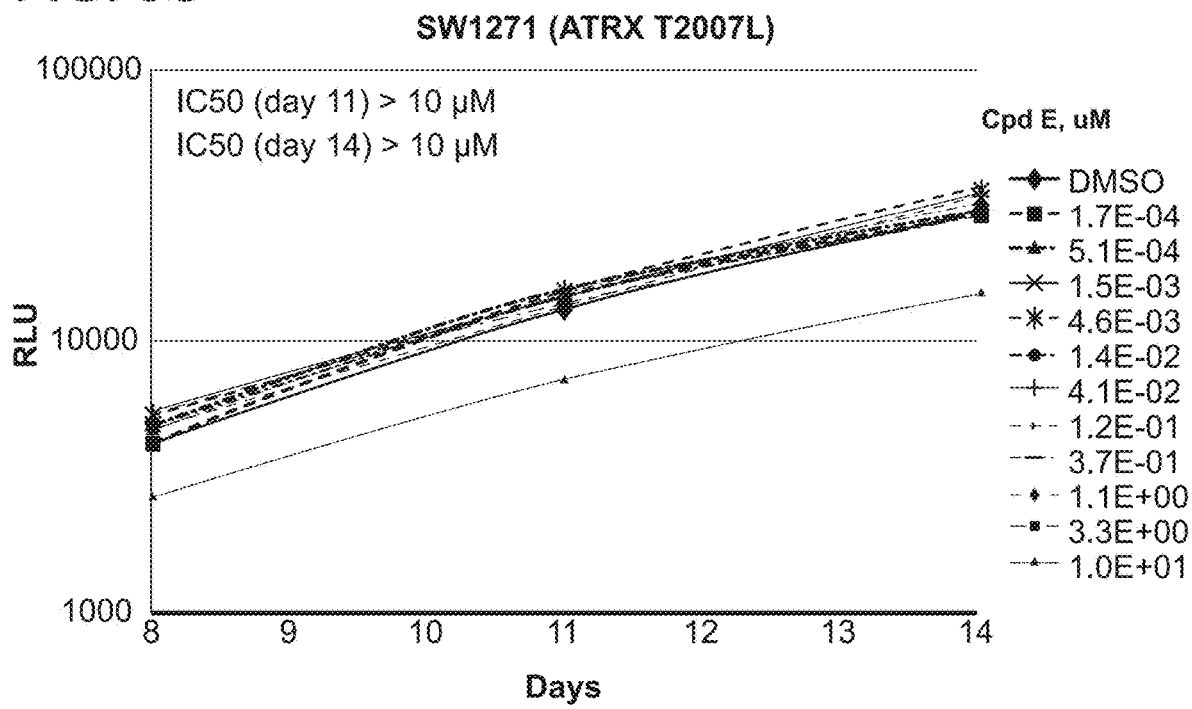

FIGS. 8A-8C are three graphs establishing that ATRX mutant SCLC lines NCI-H446 (FIG. 8A), SW1271 (FIG. 8B) and NCI-H841 (FIG. 8C) are responding to Compound E.

Figure 9A:
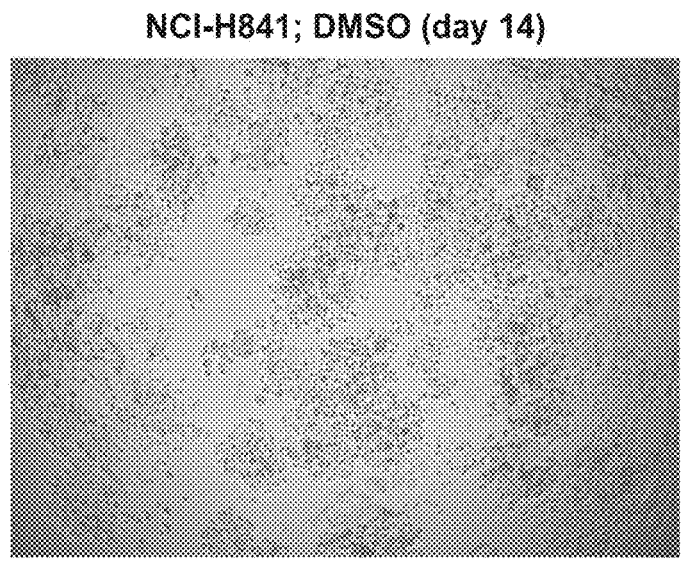
Figure 9B:
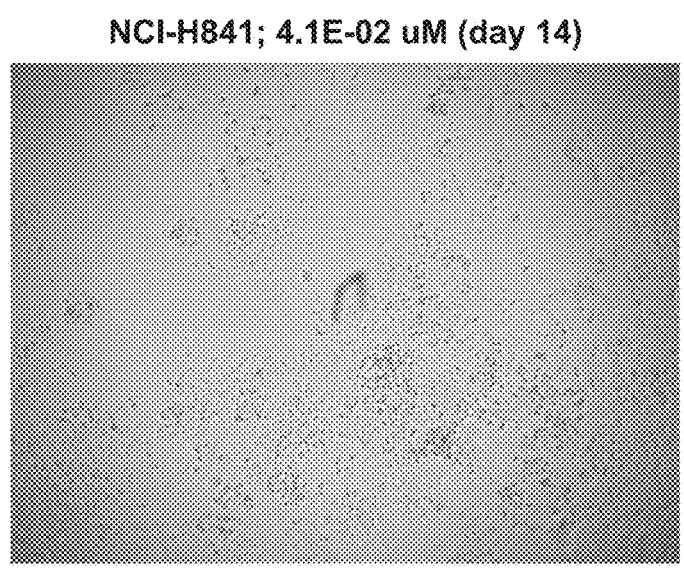
Figure 9C:
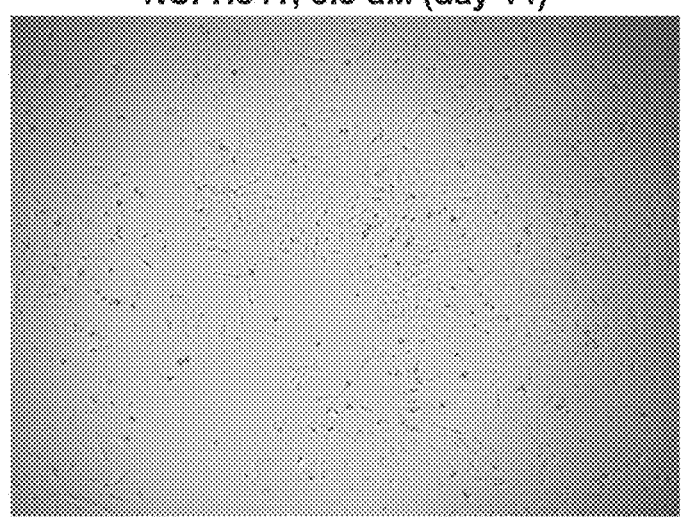

FIGS. 9A-9C are three microscopy images showing that SCLC line NCI-H841 changes morphology after treatment with vehicle (FIG. 9A) or Compound E at concentration of 4.1E-02 uM (FIG. 9B) or 3.3 uM (FIG. 9C).

Figure 10A:
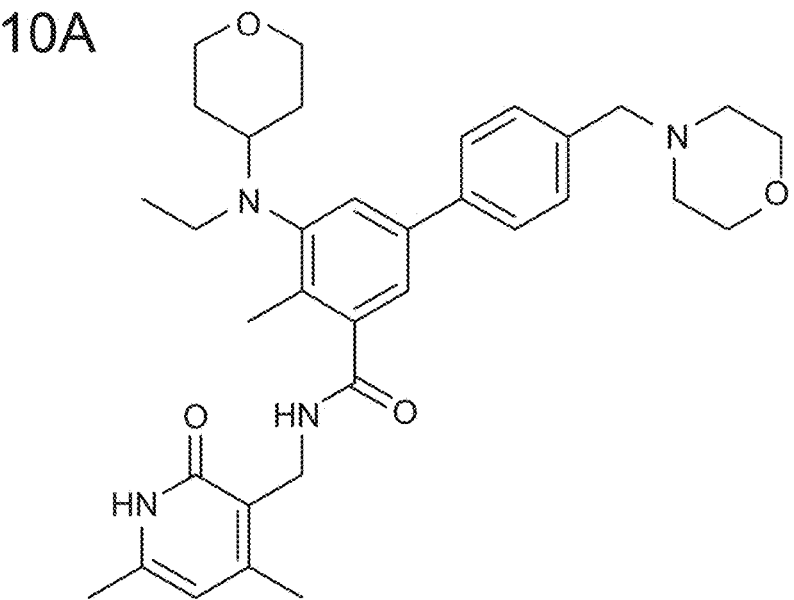
Figure 10B:
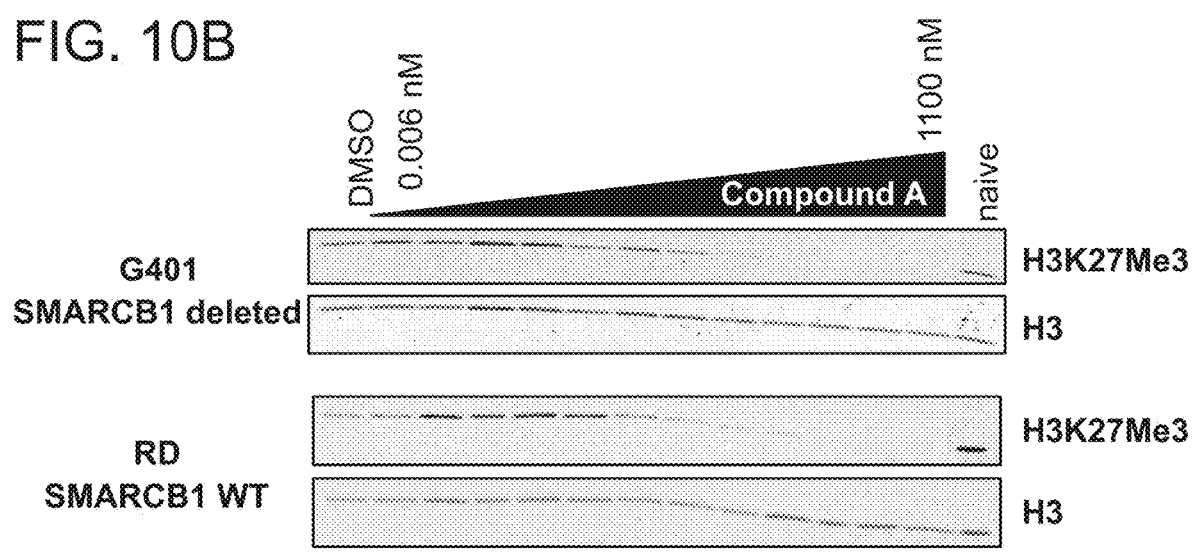

FIGS. 10A-10F are a series of graphs showing effects of Compound A on cellular global histone methylation and cell viability. FIG. 10A shows the chemical structure of Compound A. FIG. 10B illustrates the concentration-dependent inhibition of cellular H3K27Me3 levels in G401 and RD cells. FIGS. 10C through 10F illustrate the selective inhibition of proliferation of SMARCB1-deleted G401 cells by Compound A in vitro (measured by ATP content). G401 (FIGS. 10C and 10D) and RD cells (FIGS. 10E and 10F) were re-plated at the original seeding densities on day 7. Each point represents the mean for each concentration (n=3).

Figure 11A:
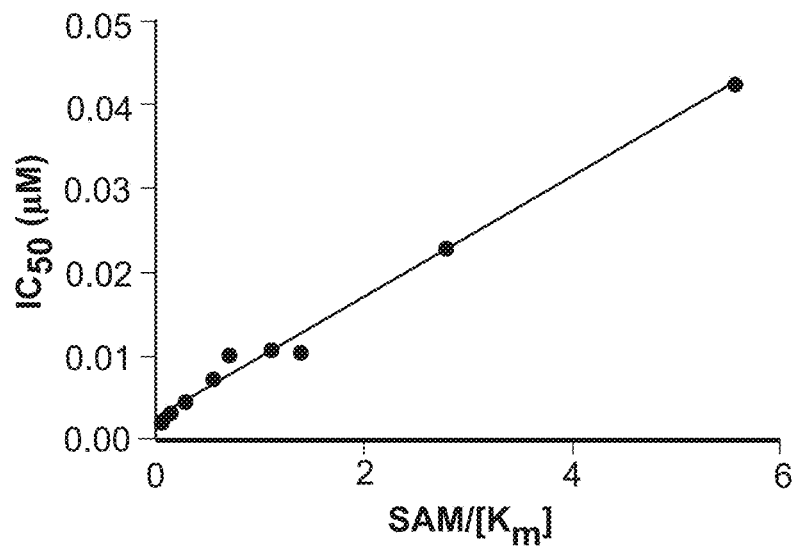
Figure 11B:
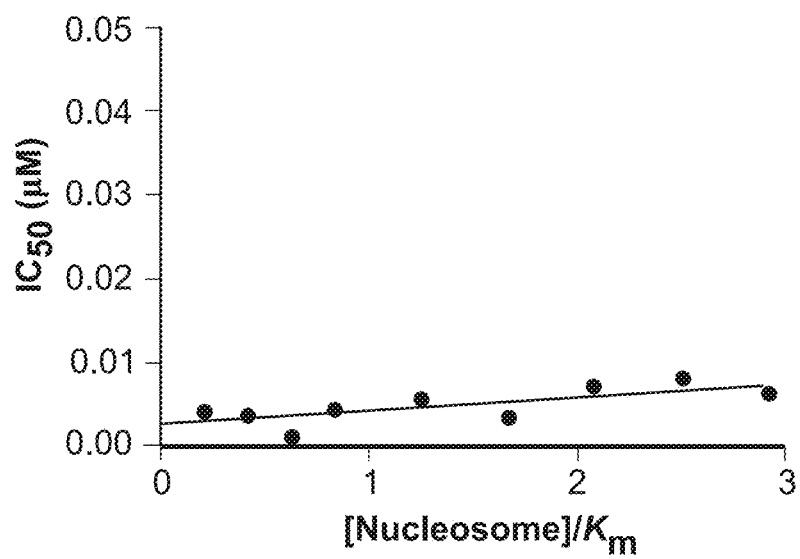

FIGS. 11A and 11B are a series of graphs showing biochemical mechanism of action studies. The $IC_{50}$ value of Compound A increases with increasing SAM concentration (FIG. 11A) and is minimally affected by increasing oligonucleosome concentration (FIG. 11B), indicating SAM-competitive and nucleosome-noncompetitive mechanism of action.

Figure 12A:
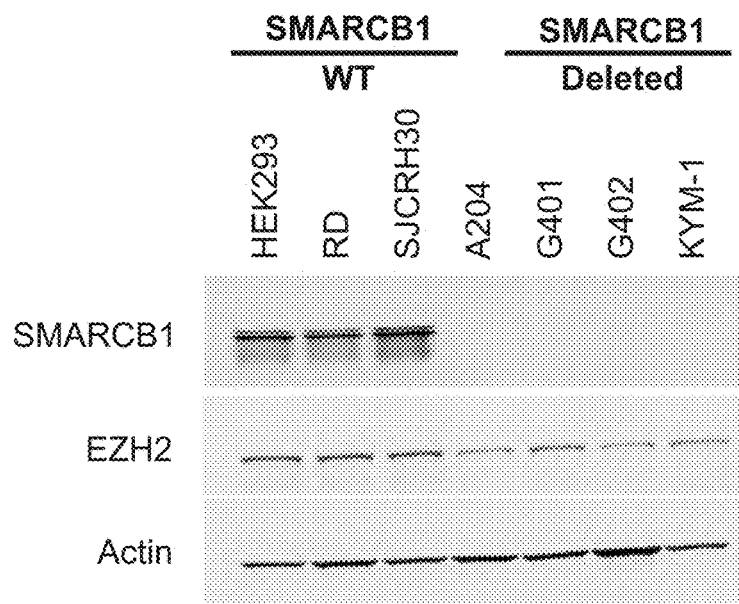
Figure 12B:
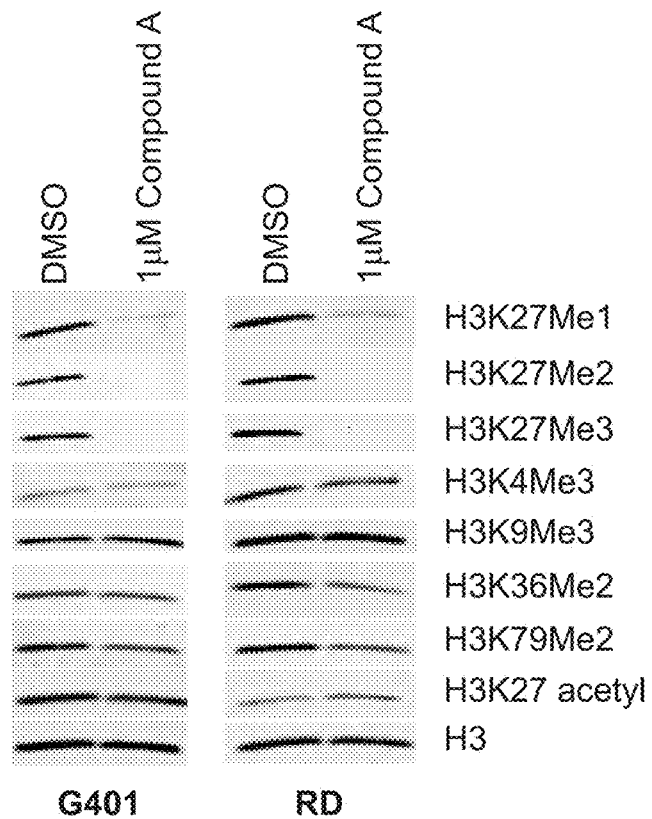

FIGS. 12A and 12B are a series of immunoblots demonstrating verification of SMARCB1 and EZH2 expression in cell lines and specificity of Compound A for inhibition of cellular histone methylation. FIG. 12A shows cell lysates analyzed by immunoblot with antibodies specific to SMARCB1, EZH2 and Actin (loading control). FIG. 12B illustrates selective inhibition of cellular H3K27 methylation in G401 and RD cells. Cells were incubated with Compound A for 4 days, and acid-extracted histones were analyzed by immunoblot.

Figure 13A:
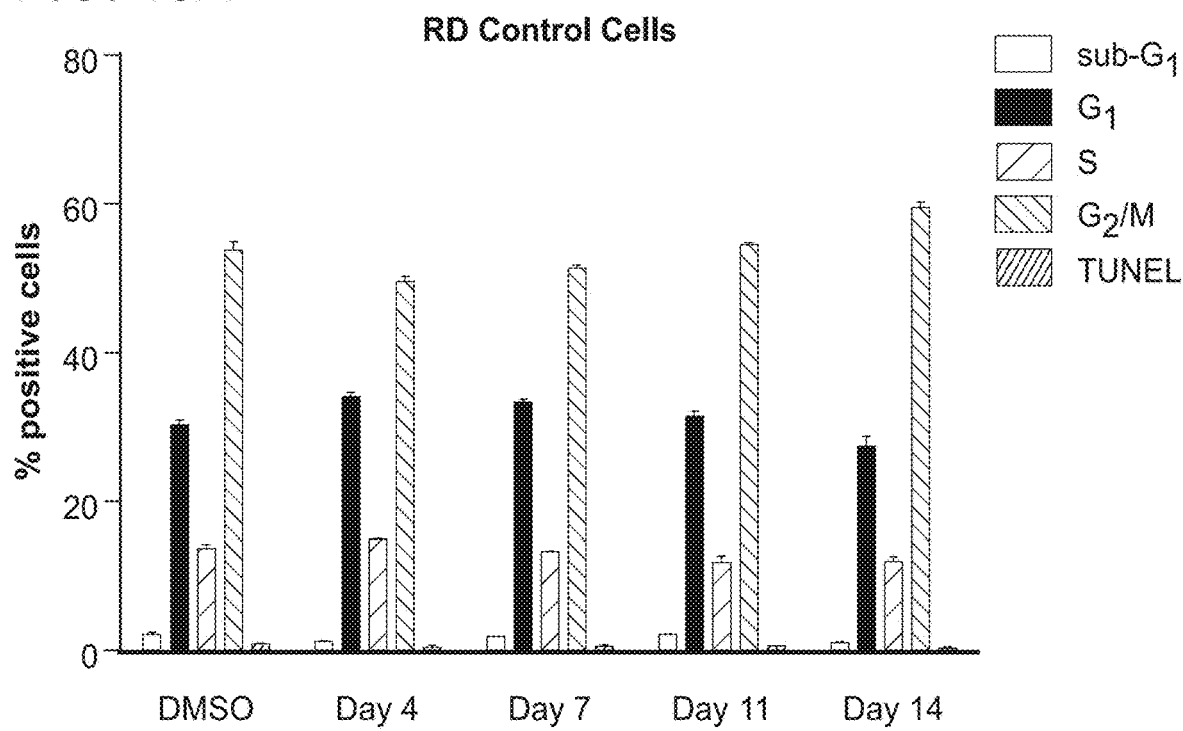
Figure 13B:
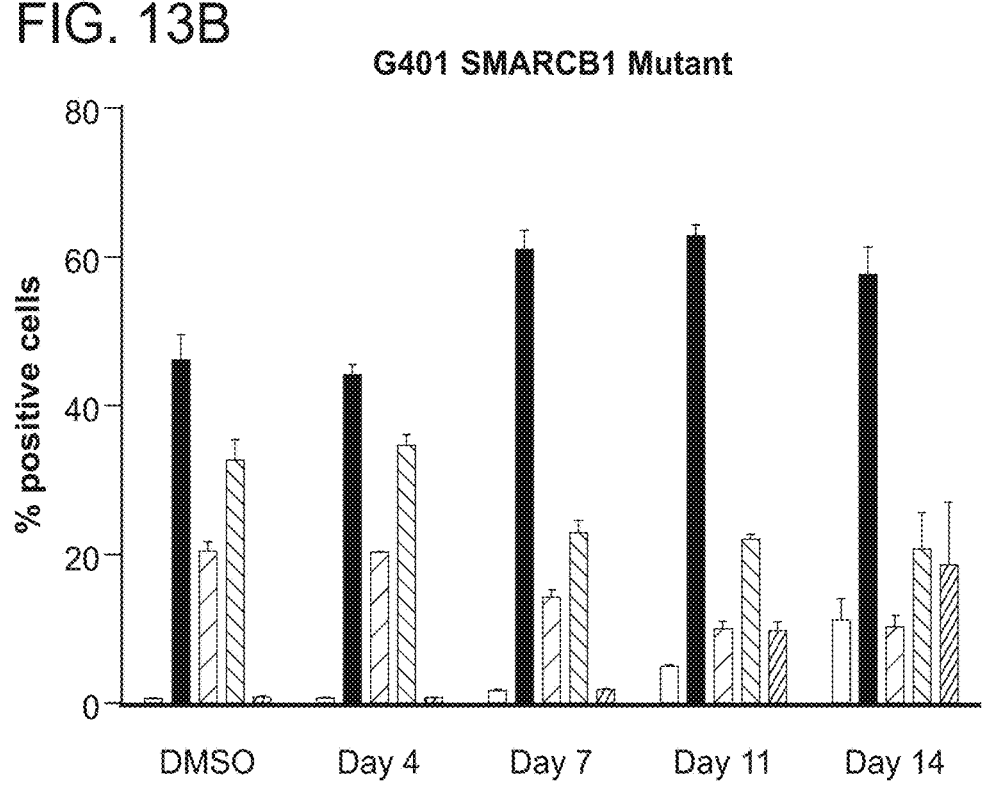

FIGS. 13A and 13B are a series of bar graphs demonstrating that Compound A induces $G_1$ arrest and apoptosis in SMARCB1-deleted MRT cells. Cell cycle analysis (by flow cytometry) and determination of apoptosis (by TUNEL assay) in RD (FIG. 13A) or G401 cells (FIG. 13B) during incubation with either vehicle or 1 µM Compound A for up to 14 days. $G_1$ arrest was observed as of day 7 and apoptosis was induced as of day 11. Data are represented as mean values±SEM (n=2). The DMSO control values shown are the average SEM from each time point. Cells were split and re-plated on days 4, 7 and 11 at the original seeding density.

Figure 14A:
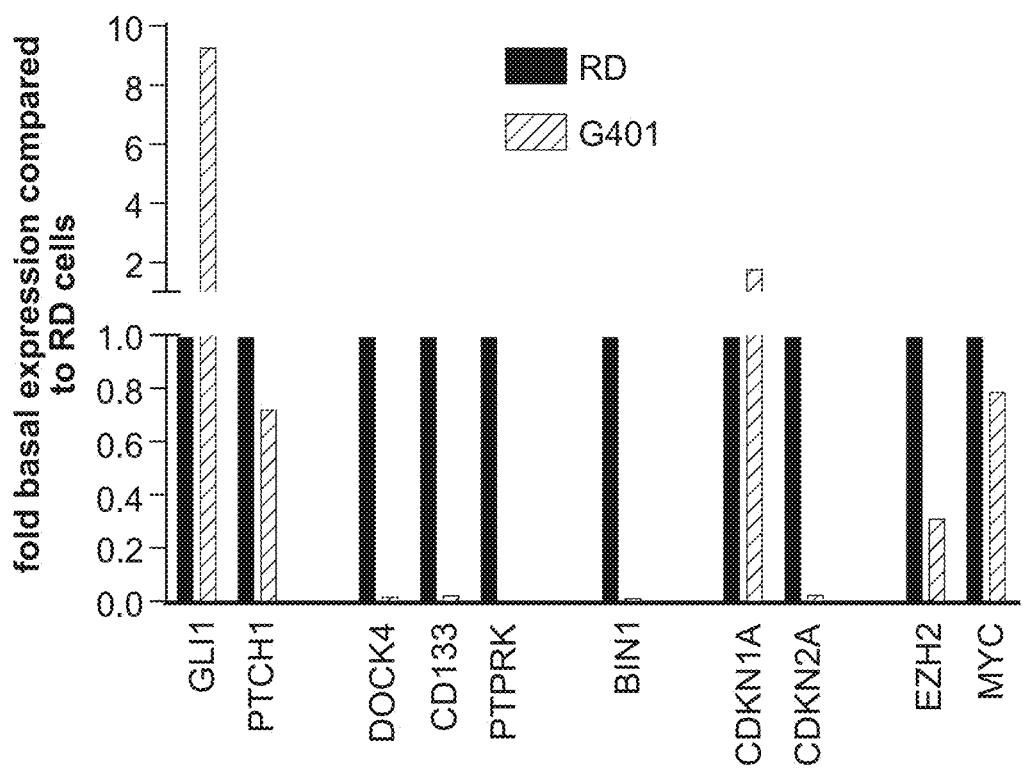
Figure 14C:
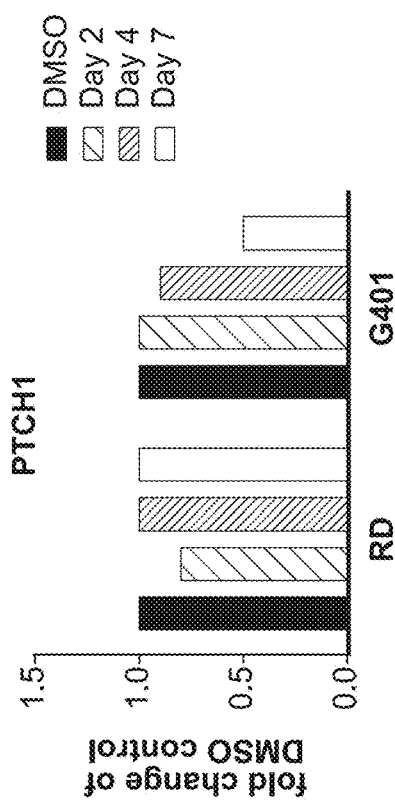
Figure 14B:
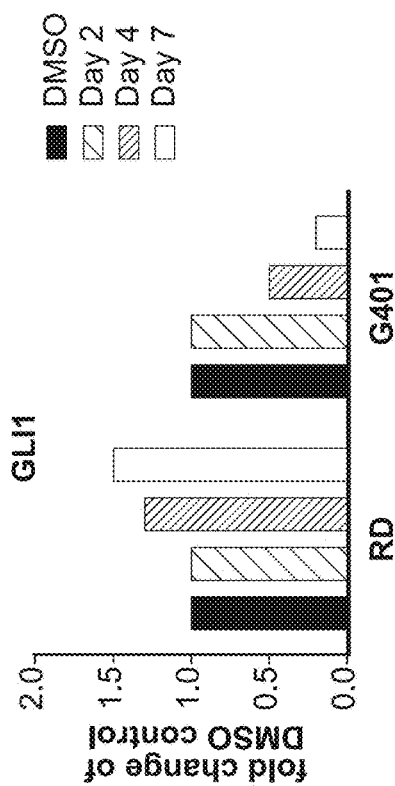
Figure 14E:
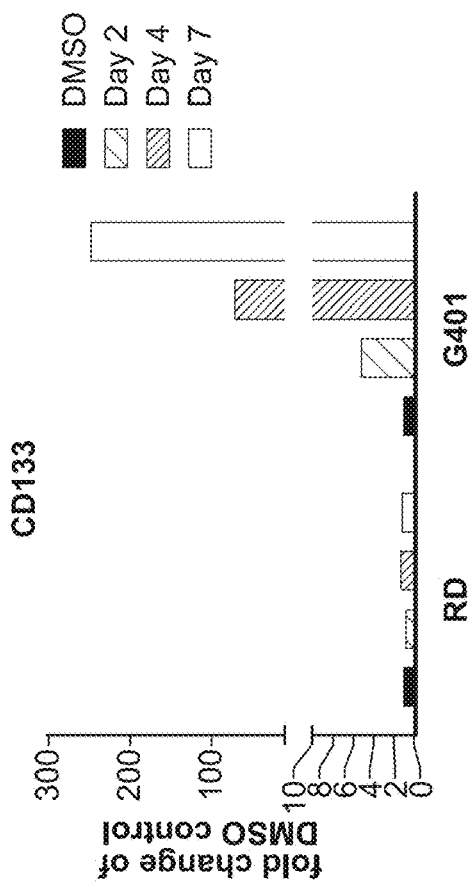
Figure 14D:
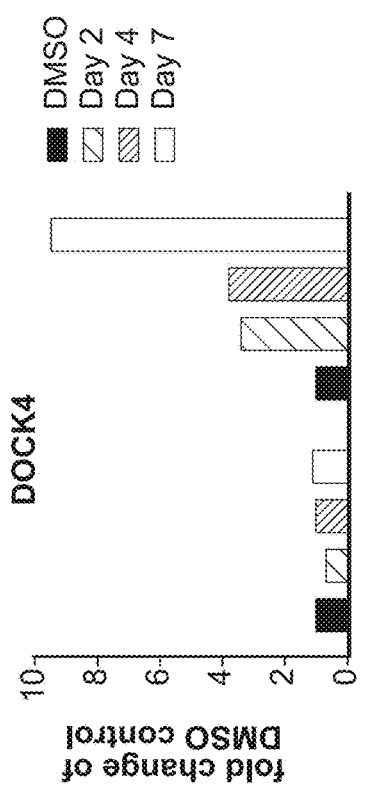
Figure 14F:
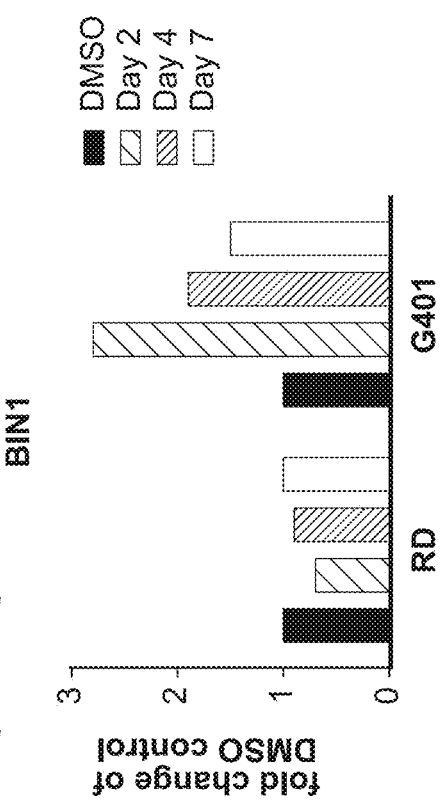
Figure 14G:
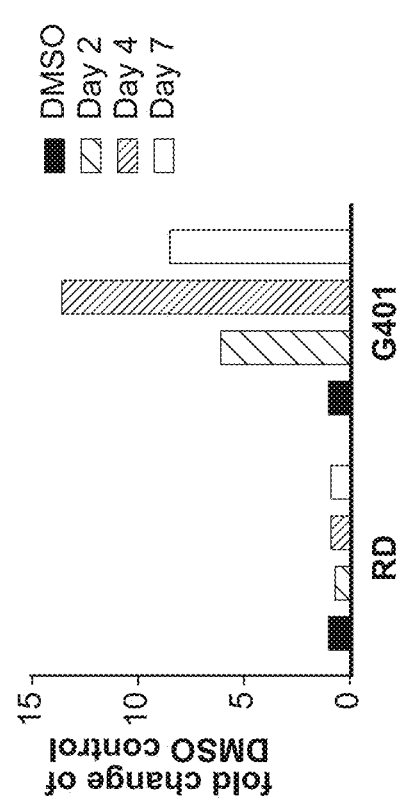
Figure 14H:
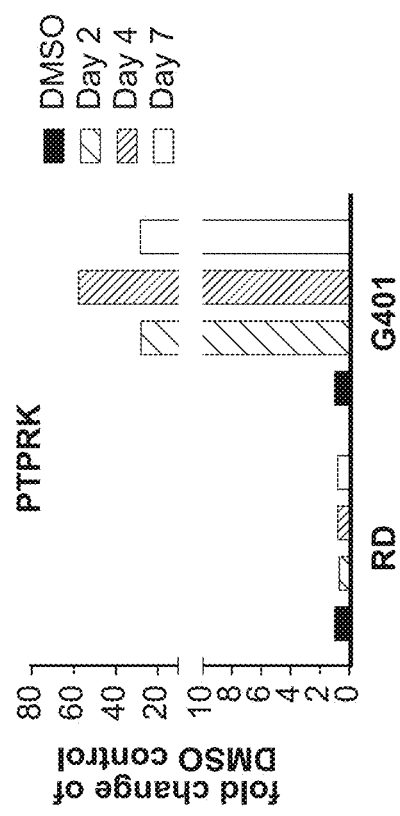
Figure 14I:
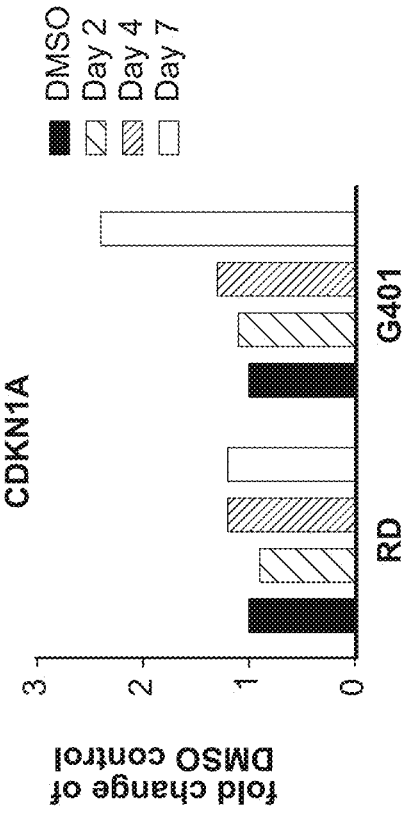
Figure 14K:
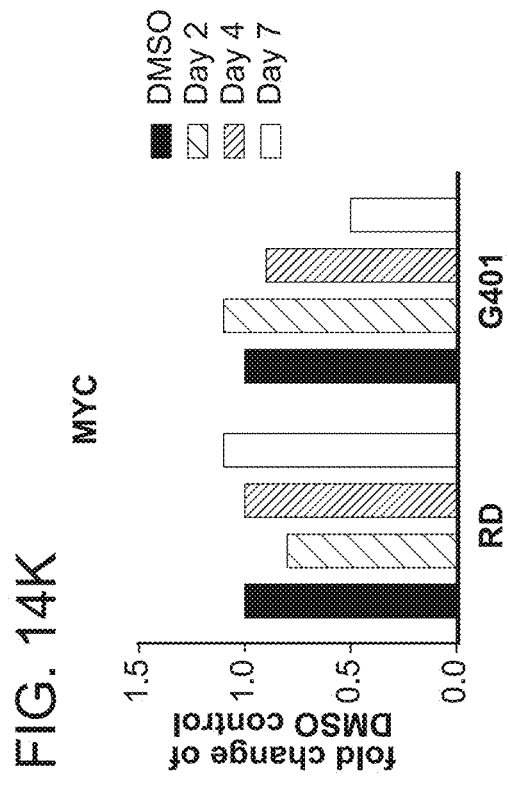
Figure 14J:
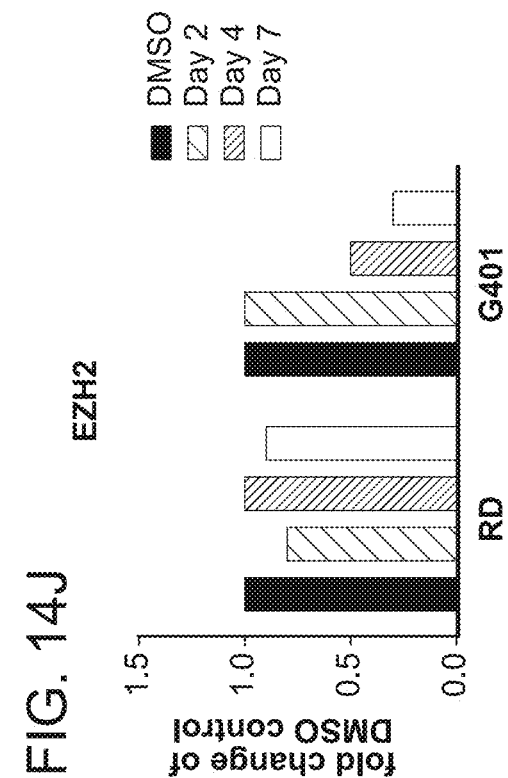
Figure 14L:
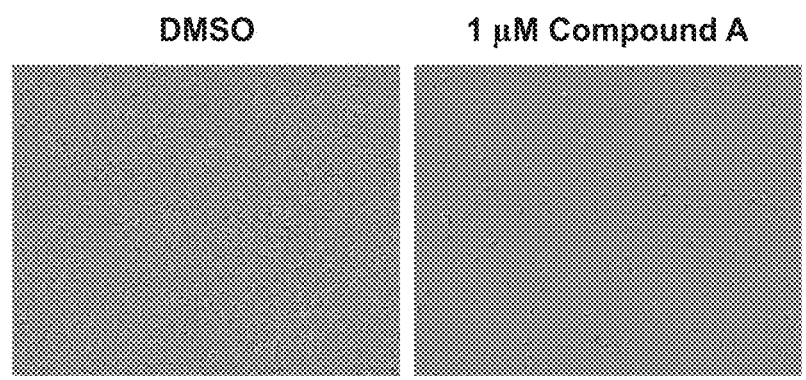

FIGS. 14A-14L are a series of graphs showing that Compound A induces changes in expression of SMARCB1 regulated genes and cell morphology. FIG. 14A shows the basal expression of SMARCB1 regulated genes in G401 SMARCB1-deleted cells, relative to RD control cells (measured by qPCR, n=2). FIGS. 14B-14K show the expression of GLI1 (FIG. 14B), PTCh1 (FIG. 14C), DOCK4 (FIG. 14D), CD133 (FIG. 14E), PTPRK (FIG. 14F), BIN1 (FIG. 14G), CDKN1A (FIG. 14H), CDKN2A (FIG. 14I), EZH2 (FIG. 14J), and MYC (FIG. 14K) genes in G401 and RD cells. The cells were incubated with either DMSO or 1 µM Compound A for 2, 4 and 7 days. Gene expression was determined by qPCR (n=2) and is expressed relative to the DMSO control of each time point. FIG. 14L illustrates the morphology of G402 cells that were incubated with either DMSO (left panel) or 1 µM Compound A (right panel) for 14 days. Cells were split and re-plated to the original seeding density on day 7.

Figure 15A:
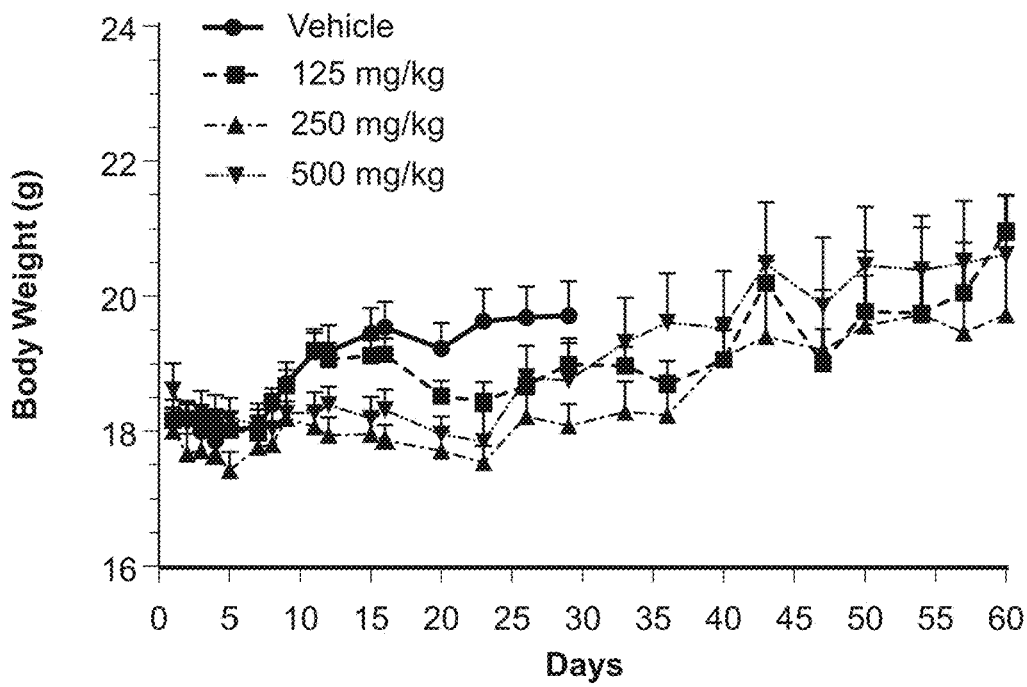
Figure 15B:
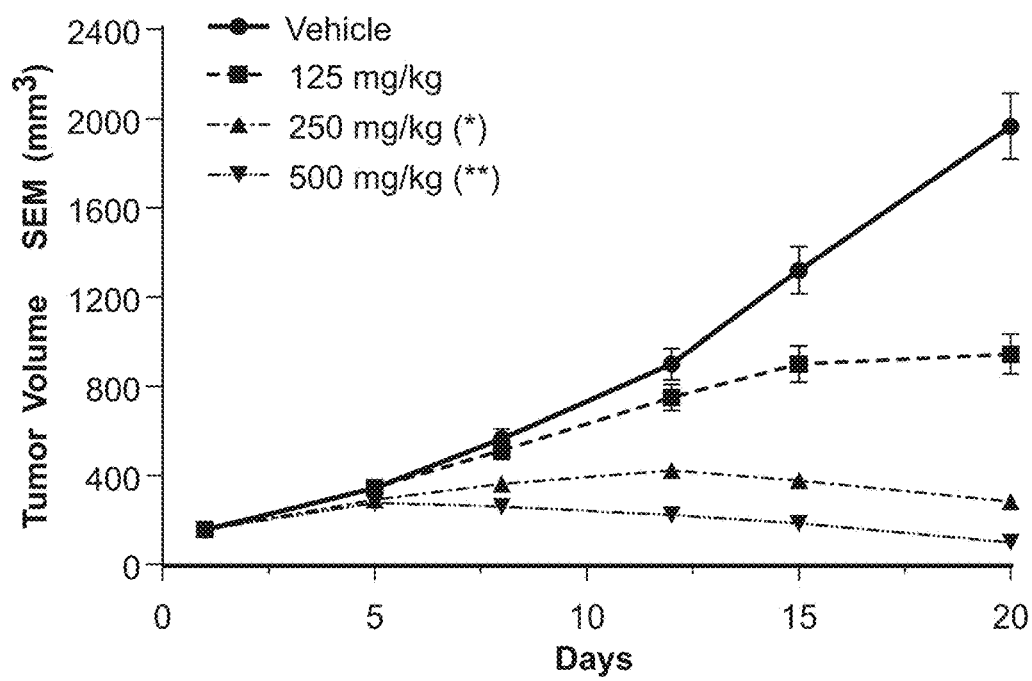
Figure 15C:
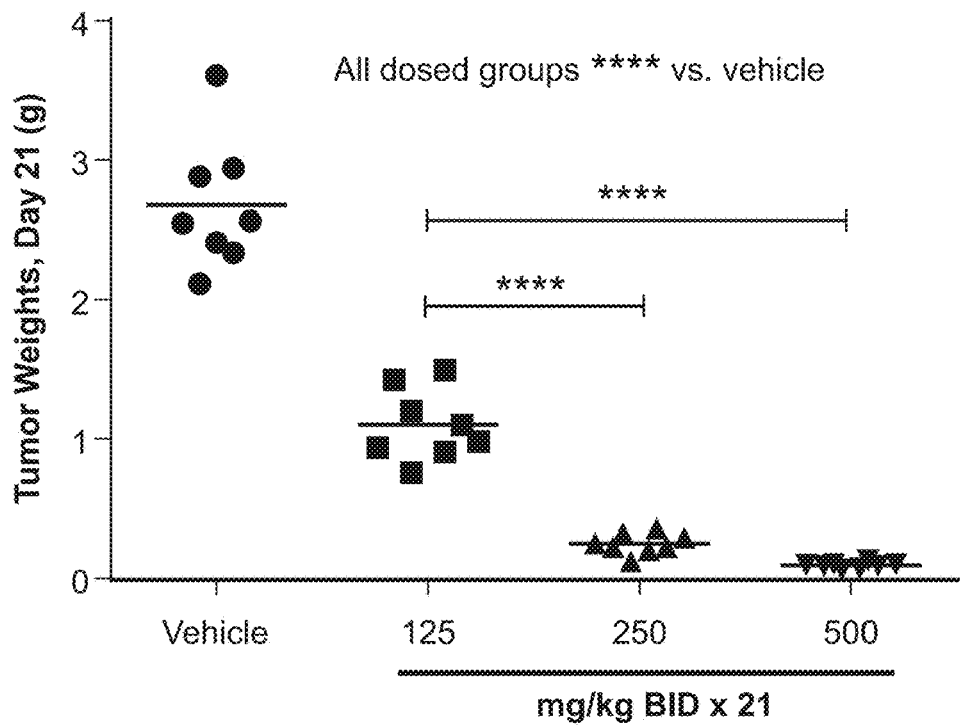
Figure 15D:
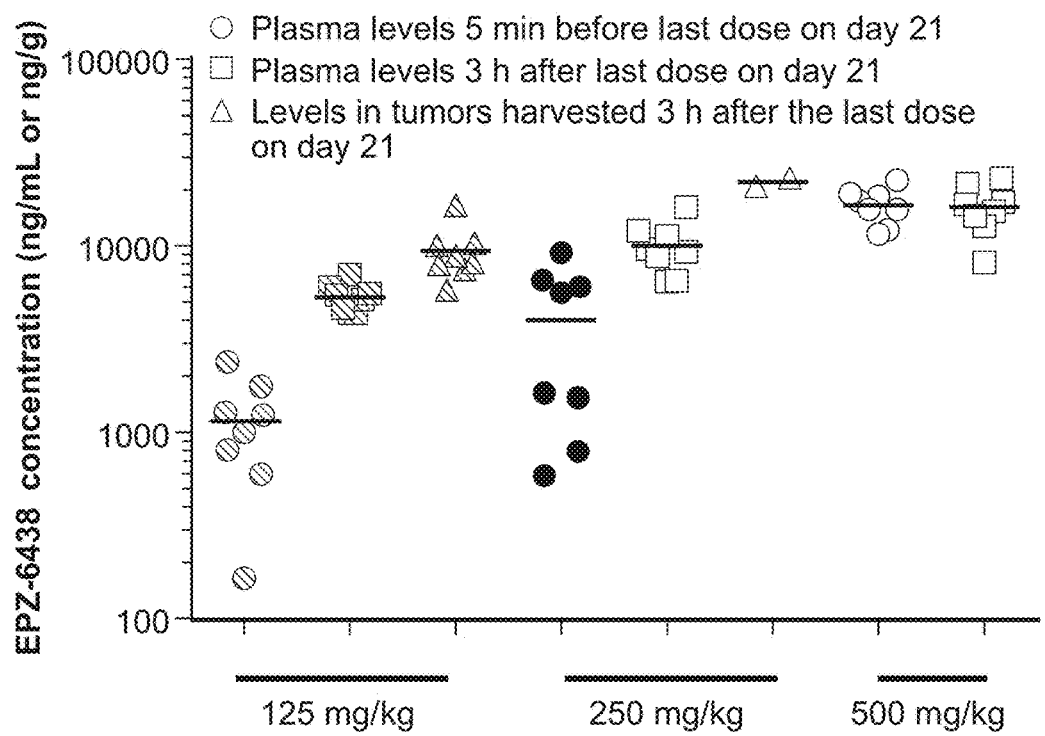

FIGS. 15A-15D are a series of graphs demonstrating body weights, tumor regressions and plasma levels in G401 xenograft bearing mice treated with Compound A. FIG. 15A shows body weights that were determined twice a week for animals treated with Compound A on a BID schedule for 28 days. Data are presented as mean values±SEM (n=16 until day 21, n=8 from day 22 to 60). FIG. 15B shows tumor regressions induced by twice daily (BID) administration of Compound A for 21 days at the indicated doses (mean values SEM, n=16). *p<0.05, p<0.01, repeated measures ANOVA, Dunnett's post-test vs. vehicle. FIG. 15C shows the tumor weights of 8 mice euthanized on day 21. **p<0.0001, Fisher's exact test. FIG. 15D shows plasma levels of Compound A. Plasma was collected 5 min before and 3 h after dosing of Compound A on day 21, and compound levels were measured by LC-MS/MS. Animals were euthanized, and tumors were collected 3 h after dosing on day 21. Tumor homogenates were generated and subjected to LC-MS/MS analysis to determine Compound A concentrations. Note that tumor compound levels could not be determined from all animals especially in the higher dose groups because the xenografts were too small on day 21. Dots represent values for the individual animals; horizontal lines represent group mean values.

Figure 16A:
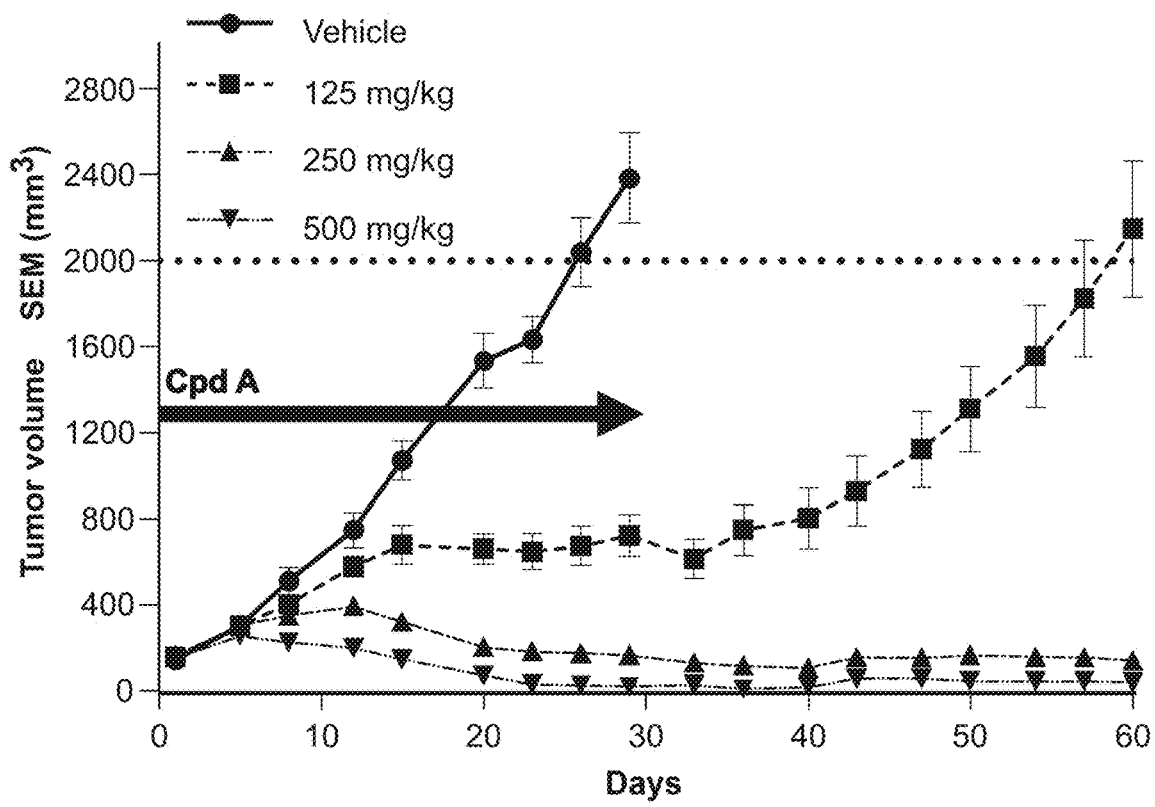
Figure 16B:
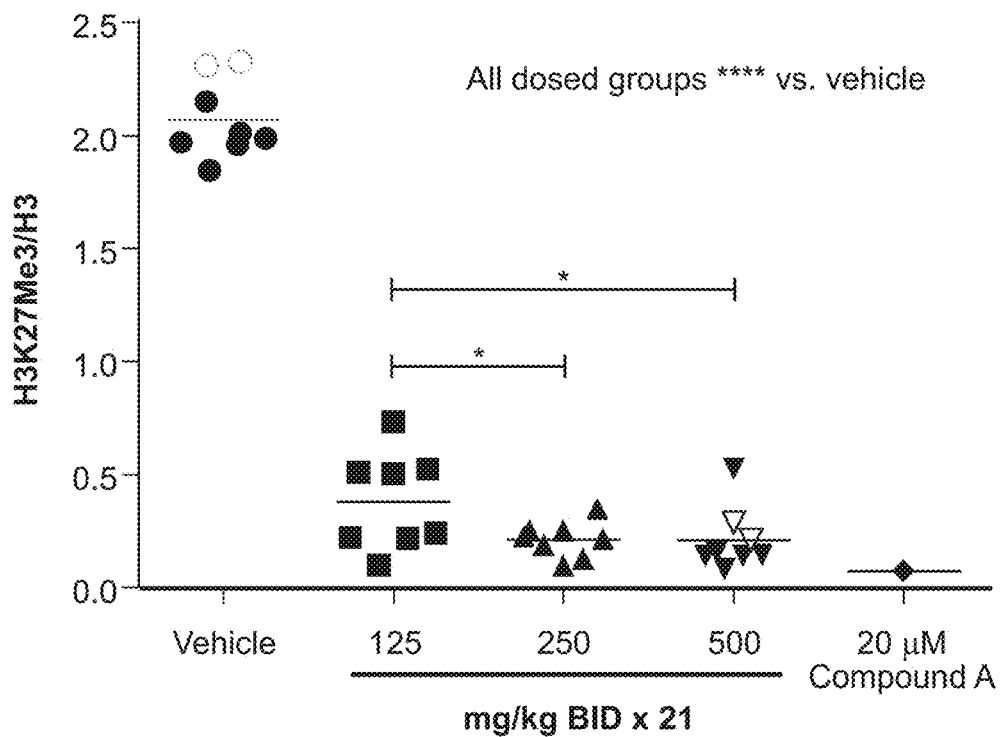
Figure 16D:
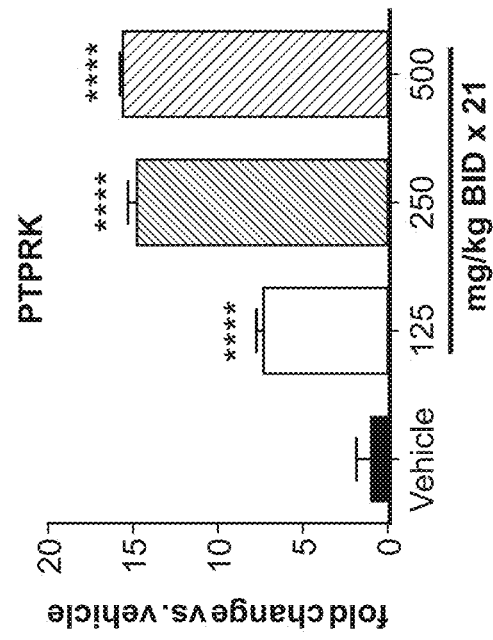
Figure 16F:
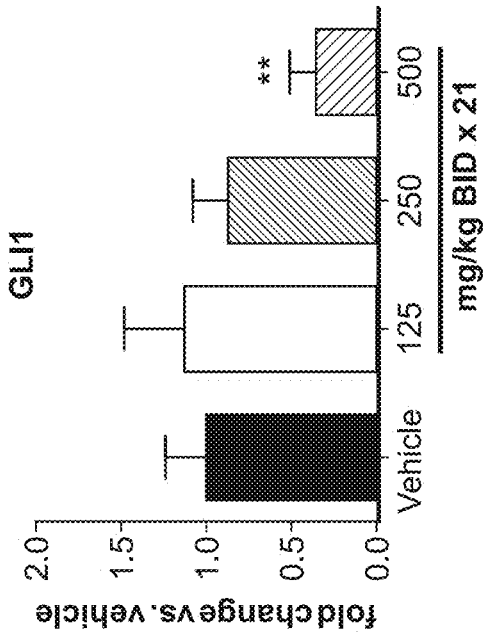

FIGS. 16A-16F are a series of graphs showing that Compound A eradicates SMARCB1-deleted MRT xenografts in SCID mice. FIG. 16A illustrates tumor regressions induced by twice daily (BID) administration of Compound A for 28 days at the indicated doses. Compound administration was stopped on day 28 and tumors were allowed to re-grow until they reached 2000 $mm^3$ (data shown as mean values±SEM, n=8). FIG. 16B shows the EZH2 target inhibition in G401 xenograft tumor tissue collected from mice euthanized on day 21. Each point shows the ratio of H3K27Me3 to total H3, measured by ELISA. Horizontal lines represent group mean values; grey symbols are values outside of the ELISA standard curve. FIGS. 16C-16F summarize the change in gene expression in G401 xenograft tumor tissue collected from mice treated with Compound A for 21 days. The graphs correspond to genes CD133 (FIG. 16C), PTPRK (FIG. 16D), DOCK4 (FIG. 16E), and GLI1 (FIG. 16F), respectively. Data are presented as fold change compared to vehicle±SEM (n=6, n=4 for 500 mg/kg group). *p<0.05, p<0.01, **p<0.0001, vs. vehicle, Fisher's exact test.

DETAILED DESCRIPTION OF THE INVENTION

The present invention is based in part upon the discovery that EZH2 inhibitors can effectively treat SWI/SNF-associated cancers that are characterized by altered expressions and/or loss of function of certain biomarkers or genes. Specifically, tumors or tumor cells having altered expressions and/or loss of function of selected biomarkers or genes are sensitive to the EZH2 inhibitors of the present invention. Accordingly, the present invention provides methods of treating or alleviating a symptom of cancers in a subject by administering a therapeutically effective amount of an EZH2 inhibitor to the subject, particular treating cancers associated with altered expression and/or loss of function of certain biomarkers or genes. For example, the biomarker is one component of the SWI/SNF complex. For example, the gene is selected from the group consisting of neuronal differentiation genes, cell cycle gene inhibition genes, tumor suppressor genes, hedgehog pathway genes, myc pathway genes and histone methyltransferase genes.

The SWI/SNF complex in human includes at least evolutionarily conserved core subunits and variant subunits. Evolutionarily conserved core subunits include SNF5 (also called SMARCB1, INI1 or BAF47), SMARCA4 (also known as BRM/SWI2-related gene 1, BRG1), BAF155, and BAF170. Variant subunits include BAF53 (A or B), BAF60 (A, B or C), BAF 57, BAF45 (A, B, C, or D). Other subunits include ARIDI1A (also known as SMARCF1), ARID1B, SMARCA2 (also known as brahma homologue, BRM), ATRX, BAF200, BAF180 (also known as PBRM1), and bromodomain-containing 7 (BRD7). The at least one component of the SWI/SNF complex can by any component of the complex, for example, the component/subunit described herein or known in the art.

In any methods presented herein, neuronal differentiation gene may be, but is not limited to, CD133 (also called PROM1), DOCK4, PTPRK, PROM2, LHX1, LHX6, LHX9, PAX6, PAX7, VEFGA, FZD3B, FYN, HIF1A, HTRA2, EVX1, CCDC64, or GFAP.

In any methods presented herein, cell cycle inhibition gene may be, but is not limited to, CKDN1A, CDKN2A, MEN1, CHEK1, IRF6, ALOX15B, CYP27B1, DBC1, NME6, GMNN, HEXIM1, LATS1, MYC, HRAS, TGFB1, IFNG, WNT1, TP53, THBS1, INHBA, IL8, IRF1, TPR, BMP2, BMP4, ETS1, HPGD, BMP7, GATA3, NR2F2, APC, PTPN3, CALR, IL12A, IL12B, PML, CDKN2B, CDKN2C, CDKN1B, SOX2, TAF6, DNA2, PLK1, TERF1, GAS1, CDKN2D, MLF1, PTEN, TGFB2, SMAD3, FOXO4, CDK6, TFAP4, MAP2K1, NOTCH2, FOXC1, DLG1, MAD2L1, ATM, NAE1, DGKZ, FHL1, SCRIB, BTG3, PTPRK, RPS6KA2, STK11, CDKN3, TBRG1, CDC73, THAP5, CRLF3, DCUN1D3, MYOCD, PAF1, LILRB1, UHMK1, PNPT1, USP47, HEXIM2, CDK5RAP1, NKX3-1, TIPIN, PCBP4, USP44, RBM38, CDT1, RGCC, RNF167, CLSPN, CHMP1A, WDR6, TCF7L2, LATS2, RASSF1, MLTK, MAD2L2, FBX05, ING4, or TRIM35.

In any methods presented herein, tumor suppressor gene may be, but is not limited to, BIN1. As used herein, the term "tumor suppressor gene" has its commonly understood meaning in the art, i.e. a gene whose expression and normal function act to suppress the neoplastic phenotype or induce apoptosis, or both. In some embodiments, tumor suppressor genes include cell cycle inhibition genes. Exemplary categories of tumor suppressors based on their functions include, but not limited to:
(1) genes that inhibit cell cycles;
(2) genes that are coupling the cell cycle to DNA damage. When there is damaged DNA in the cell, the cell should not divide. If the damage can be repaired, the cell cycle can continue. If the damage cannot be repaired, the cell should initiate apoptosis (programmed cell death);
(3) genes that prevent tumor cells from dispersing, block loss of contact inhibition, and inhibit metastasis. These genes and their encoded proteins are also known as metastasis suppressors; and
(4) DNA repair proteins. Mutations in these genes increase the risk of cancer.

In any methods presented herein, hedgehog signaling pathway gene may be, but is not limited to, GLI1, PTCH1, SUFU, KIF7, GLI2, BMP4, MAP3K10, SHH, TCTN3, DYRK2, PTCHD1, or SMO.

In any methods presented herein, myc pathway gene may be, but is not limited to, MYC NMI, NFYC, NFYB, Cyclin T1, RuvB-like 1, GTF2I, BRCA1, T-cell lymphoma invasion and metastasis-inducing protein 1, ACTL6A, PCAF, MYCBP2, MAPK8, Bcl-2, Transcription initiation protein SPT3 homolog, SAP130, DNMT3A, mothers against decapentaplegic homolog 3, MAX, mothers against decapentaplegic homolog 2, MYCBP, HTATIP, ZBTB17, Transformation/transcription domain-associated protein, TADA2L, PFDN5, MAPK1, TFAP2A, P73, TAF9, YY1, SMARCB1, SMARCA4, MLH1, EP400 or let-7.

In any methods presented herein, histone methyltransferase gene may be, but is not limited to, EZH2.

Compounds of the present invention inhibit the histone methyltransferase activity of EZH2 or a mutant thereof and, accordingly, in one aspect of the invention, compounds disclosed herein are candidates for treating or preventing certain conditions and diseases. The present invention provides methods for treating, preventing or alleviating a symptom of cancer or a precancerous condition. The method includes administering to a subject in need thereof, a therapeutically effective amount of a compound of the present invention, or a pharmaceutically acceptable salt, polymorph, solvate, or stereoisomer or thereof. Exemplary cancers that may be treated include medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullo carcinoma, diffuse large B-cell lymphoma, follicular lymphoma and not otherwise specified (NOS) sarcoma. Alternatively, cancers to be treated by the compounds of the present invention are non NHL cancers.

The present invention further provides the use of a compound of the present invention, or a pharmaceutically acceptable salt, polymorph or solvate thereof in the treatment of cancer or precancer, or, for the preparation of a medicament useful for the treatment of such cancer or pre-cancer. Exemplary cancers that may be treated include medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullo carcinoma, diffuse large B-cell lymphoma, follicular lymphoma and not otherwise specified (NOS) sarcoma. Alternatively, the compound of the present invention can be used for the treatment of non NHL cancers, or, for the preparation of a medicament useful for the treatment of non NHL cancers.

The compounds of this invention can be used to modulate protein (e.g., histone) methylation, e.g., to modulate histone methyltransferase or histone demethylase enzyme activity. The compounds of the invention can be used in vivo or in vitro for modulating protein methylation. Based upon the surprising discovery that methylation regulation by EZH2 involves in tumor formation, particular tumors bearing altered expression and/or loss of function of selected biomarkers/genes, the compounds described herein are suitable candidates for treating these diseases, i.e., to decrease methylation or restore methylation to roughly its level in counterpart normal cells.

In some embodiments, compounds of the present invention can selectively inhibit proliferation of the SWI/SNF complex associated tumor or tumor cells (as shown in FIGS. 1-9). Accordingly, the present invention provides methods for treating, preventing or alleviating a symptom of the SWI/SNF complex associated cancer or a precancerous condition by a compound of the present invention, or a pharmaceutically acceptable salt, polymorph or solvate thereof. The present invention further provides the use of a compound of the present invention, or a pharmaceutically acceptable salt, polymorph or solvate thereof in the treatment of the SWI/SNF complex associated cancer or a precancer condition, or, for the preparation of a medicament useful for the treatment of such cancer or pre-cancer.

Also provided in the present invention are methods for determining responsiveness of a subject having a cancer to an EZH2 inhibitor. The method includes the steps of obtaining a sample (a nucleic acid sample or a protein sample) from the subject and detecting reduced expression, haploinsufficiency, and/or loss of function of at least one component of the SWI/SNF complex, detecting the expression and/or function of this component, and the presence of such reduced expression, haploinsufficiency, and/or loss of function indicates that the subject is responsive to the EZH2 inhibitor. The term "sample" means any biological sample derived from the subject, includes but is not limited to, cells, tissues samples, body fluids (including, but not limited to, mucus, blood, plasma, serum, urine, saliva, and semen), tumor cells, and tumor tissues. Samples can be provided by the subject under treatment or testing. Alternatively samples can be obtained by the physician according to routine practice in the art.

The present invention also provides methods for determining predisposition of a subject to a cancer or a precancerous condition by obtaining a sample from the subject and detecting reduced expression, haploinsufficiency, and/or loss of function of at least one component of the SWI/SNF complex, and the presence of such reduced expression, haploinsufficiency, and/or loss of function indicates that the subject is predisposed to (i.e., having higher risk of) developing the cancer or the precancerous condition compared to a subject without such loss of function of the at least one component of the SWI/SNF complex.

The term "predisposed" as used herein in relation to cancer or a precancerous condition is to be understood to mean the increased probability (e.g., at least 1%, 5%, 10%, 20%, 30%, 40%, 50%, 60%, 70%, 80%, 90%, 100%, 150%, 200%, or more increase in probability) that a subject with reduced expression, haploinsufficiency, and/or loss of function of at least one component of the SWI/SNF complex, will suffer cancer or a precancerous condition, as compared to the probability that another subject not having reduced expression, haploinsufficiency, and/or loss of function of at least one component of the SWI/SNF complex, will suffer cancer or a precancerous condition, under circumstances where other risk factors (e.g., chemical/environment, food, and smoking history, etc.) for having cancer or a precancerous condition between the subjects are the same.

"Risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion.

Accordingly, the present invention provides personalized medicine, treatment and/or cancer management for a subject by genetic screening of reduced expression, haploinsufficiency, and/or loss of function of at least one component of the SWI/SNF complex in the subject. For example, the present invention provides methods for treating, preventing or alleviating a symptom of cancer or a precancerous condition by determining responsiveness of the subject to an EZH2 inhibitor and when the subject is responsive to the EZH2 inhibitor, administering to the subject a therapeutically effective amount of the EZH2 inhibitor, or a pharmaceutically acceptable salt, solvate, or stereoisomer or thereof. The responsiveness is determined by obtaining a sample from the subject and detecting reduced expression, haploinsufficiency, and/or loss of function of at least one component of the SWI/SNF complex (such as SNF5, ARID1A or ATRX), and the presence of such loss of function indicates that the subject is responsive to the EZH2 inhibitor.

In other example, the present invention provides methods of cancer management in a subject by determining predisposition of the subject to a cancer or a precancerous condition periodically. The methods include steps of obtaining a sample from the subject and detecting reduced expression, haploinsufficiency, and/or loss of function of at least one component of the SWI/SNF complex, and the presence of such reduced expression, haploinsufficiency, and/or loss of function indicates that the subject is predisposed to developing the cancer or the precancerous condition compared to a subject without such reduced expression, haploinsufficiency, and/or loss of function of the at least one component of the SWI/SNF complex.

In merely illustrative embodiments, the methods of treatment presented herein include steps of (a) collecting a nucleic acid sample or a protein sample from a biological sample obtained from a subject, (b) measuring the expression level or function level of a component of the SWI/SNF complex in the sample, (c) measuring the expression level or function level of the component of the SWI/SNF in a control sample; (d) comparing the expression level or the function level of the component measured in step (b) in the tested sample to the expression level or the function level of the component measured in step (c) in the control sample (or a reference value); (e) identifying the subject as a candidate for treatment when the expression level or the function level of the component measured in step (b) is reduced or lost (e.g., haploinsufficiency or loss of function) compared to the expression level or the function level of the component measured in step (c); and (f) administering a therapeutically effective amount of an EZH2 inhibitor to the subject identified in step (e) or selecting a treatment regimen for the subject identified in step (e). The expression level or the function level of component in the subject sample is reduced, for example, 10%, 25%, 50% or 1-, 2-, 5- or more fold compared to the expression level or the function level of the component in the control sample. Any suitable methods known in the art can be utilized to measure the expression level or the function level of the component of the SWI/SNF complex. In some embodiments, the subject has malignant rhabdoid tumor, medulloblastoma or atypical teratoid rhabdoid tumor. In some embodiments, the component is SNF5, ARID1A or ATRX.

For example, the identified subject can be treated with the standard of care treatment as described in the most current National Comprehensive Cancer Network (NCCN) guidelines.

For example, a control sample is obtained from a healthy, normal subject. Alternatively, a control sample is obtained from a subject who is not suffering, has not been diagnosed, or is not at risk of developing cancer associated with the SWI/SNF complex.

In one preferred aspect, the present invention provides a method for treating or alleviating a symptom of cancer in a subject by determining responsiveness of the subject to an EZH2 inhibitor and administering to the subject a therapeutically effective amount of the EZH2 inhibitor if the subject is responsive to the EZH2 inhibitor and the subject has a cancer selected from the group consisting of brain and CNS cancer, kidney cancer, ovarian cancer, pancreatic cancer, leukemia, lymphoma, myeloma, and/or sarcoma. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

In another preferred aspect, the present invention provides a method for treating or alleviating a symptom of malignant rhabdoid tumor in a subject by determining responsiveness of the subject to an EZH2 inhibitor and administering to the subject a therapeutically effective amount of the EZH2 inhibitor if the subject is responsive to the EZH2 inhibitor. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

In another preferred aspect, the present invention provides a method for treating or alleviating a symptom of medulloblastoma in a subject by determining responsiveness of the subject to an EZH2 inhibitor and administering to the subject a therapeutically effective amount of the EZH2 inhibitor if the subject is responsive to the EZH2 inhibitor. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

In another preferred aspect, the present invention provides a method for treating or alleviating a symptom of atypical teratoid rhabdoid tumor in a subject by determining responsiveness of the subject to an EZH2 inhibitor and administering to the subject a therapeutically effective amount of the EZH2 inhibitor if the subject is responsive to the EZH2 inhibitor. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

Malignant rhabdoid tumors (MRTs) and atypical teratoid rhabdoid tumors (ATRTs) are extremely aggressive pediatric cancers of the brain, kidney, and soft tissues that are highly malignant, locally invasive, frequently metastatic, and particularly lethal. They are typically diploid and lack genomic aberrations; however, they are characterized by an almost complete penetrance of loss of SMARCB1 (also called SNF5, INI1 or BAF47), a core component of the SWI/SNF chromatin remodeling complex. The biallelic inactivation of SMARCB1 is in essence the sole genetic event in MRTs and ATRTs which suggests a driver role for this genetic aberration.

Without being bound by any theory, a compound of the present invention specifically inhibits cellular H3K27 methylation leading to selective apoptotic killing of SMARCB1 mutant MRT cells. For example, in vitro treatment of SMARCB1-deleted MRT cell lines with Compound A induced strong anti-proliferative effects with $IC_{50}$ values in the nM range; while the control (wild-type) cell lines were minimally affected (FIG. 10C and table 6). Furthermore, the compound of the present invention induces genes of neuronal differentiation, cell cycle inhibition and tumor suppression while suppressing expression of hedgehog pathway genes, MYC and EZH2. For example, Compound A treatment of G401 SMARCB1-deleted cells for up to 7 days strongly induced expression of CD133, DOCK4 and PTPRK and up-regulated cell cycle inhibitors CDKN1A and CDKN2A and tumor suppressor BIN1, all in a time-dependent manner (FIG. 14B). Simultaneously, the expression of hedgehog pathway genes, MYC and EZH2 were reduced. Notably, G402 SMARCB1-deleted cells exposed to Compound A for 14 days assumed a neuron-like morphology (FIG. 14C).

Accordingly, the present invention further provides methods of treating or alleviating a symptom of cancer in a subject in need thereof by (a) determining the expression level of at least one gene selected from the group consisting of neuronal differentiation genes, cell cycle inhibition genes and tumor suppressor genes in a sample obtained from the subject; (b) selecting a subject having a decreased expression level of at least one gene in step (a); and (c) administering to the subject selected in step (b) an effective amount of a compound of the invention, thus treating or alleviating a symptom of cancer in the subject.

The present invention also provides methods of treating or alleviating a symptom of cancer in a subject in need thereof by (a) determining the expression level of at least one gene selected from the group consisting of hedgehog pathway genes, myc pathway genes and histone methyltransferase genes in a sample obtained from the subject; (b) selecting a subject having an increased expression level of at least one gene in step (a); and (c) administering to the subject selected in step (b) an effective amount of a compound of the invention, thus treating or alleviating a symptom of cancer in the subject.

Also provided herein are methods of selecting a cancer therapy for a subject in need thereof by (a) determining the expression level of at least one gene selected from the group consisting of neuronal differentiation genes, cell cycle inhibition genes, and tumor suppressor genes in a sample obtained from the subject, and (b) selecting a cancer therapy when the subject has a decreased expression level of at least one gene in step (a), where the cancer therapy includes the administration of an effective amount of a compound of the invention to the subject.

The present invention further provides methods of selecting a cancer therapy for a subject in need thereof by (a) determining the expression level of at least one gene selected from the group consisting of hedgehog pathway genes, myc pathway genes and histone methyltransferase genes in a sample obtained from the subject, and (b) selecting a cancer therapy when the subject has an increased expression level of at least one gene in step (a), where the cancer therapy includes the administration of an effective amount of a compound of the invention to the subject.

In merely illustrative embodiments, the methods presented herein may include the steps of (a) collecting a nucleic acid or a protein sample from a biological sample obtained from a subject, (b) measuring the expression level of at least one gene selected from the group consisting of neuronal differentiation genes, cell cycle inhibition genes, and tumor suppressor genes in the sample, (c) measuring the expression level of the same gene(s) in a control sample; (d) comparing the expression level of the gene measured in step (b) in the tested sample to the expression level of the gene measured in step (c) in the control sample (or to a reference value); (e) identifying the subject as a candidate for treatment when the expression level of the component measured in step (b) is reduced compared to the expression level of the gene measured in step (c); and (f) administering a therapeutically effective amount of an EZH2 inhibitor to the subject identified in step (e) or selecting a treatment regimen for the subject identified in step (e). The expression level of the gene in the tested subject is reduced, for example, 10%, 25%, 50% or 1-, 2-, 5- or more fold compared to the expression level of the gene in the control sample.

In merely illustrative embodiments, the methods presented herein may include the steps of (a) collecting a nucleic acid or a protein sample from a biological sample obtained from a subject, (b) measuring the expression level of at least one gene selected from the group consisting of hedgehog pathway genes, myc pathway genes and histone methyltransferase genes in the sample, (c) measuring the expression level of the same gene(s) in a control sample; (d) comparing the expression level of the gene measured in step (b) in the tested sample to the expression level of the gene measured in step (c) in the control sample (or to a reference value); (e) identifying the subject as a candidate for treatment when the expression level of the component measured in step (b) is increased compared to the expression level of the gene measured in step (c); and (f) administering a therapeutically effective amount of an EZH2 inhibitor to the subject identified in step (e) or selecting a treatment regimen for the subject identified in step (e). The expression level of the gene in the tested subject is increased, for example, 10%, 25%, 50% or 1-, 2-, 5- or more fold compared to the expression level of the gene in the control sample.

The term "expression level" refers to protein, RNA, or mRNA level of a particular gene of interest. Any methods known in the art can be utilized to determine the expression level of a particular gene of interest. Examples include, but are not limited to, reverse transcription and amplification assays (such as PCR, ligation RT-PCR or quantitative RT-PCT), hybridization assays, Northern blotting, dot blotting, in situ hybridization, gel electrophoresis, capillary electrophoresis, column chromatography, Western blotting, immunohistochemistry, immunostaining, or mass spectrometry.

Assays can be performed directly on biological samples or on protein/nucleic acids isolated from the samples. It is routine practice in the relevant art to carry out these assays. For example, the measuring step in any method described herein includes contacting the nucleic acid sample from the biological sample obtained from the subject with one or more primers that specifically hybridize to the gene of interest presented herein. Alternatively, the measuring step of any method described herein includes contacting the protein sample from the biological sample obtained from the subject with one or more antibodies that bind to the biomarker of the interest presented herein.

A decreased expression level of a particular gene means a decrease in its expression level by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level of this gene measured in a different (or previous) sample obtained from the same subject.

An increased expression level of a particular gene means an increase in its expression level by at least 5% 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000% 1500%, or more compared to a reference value or the expression level of this gene measured in a different (or previous) sample obtained from the same subject.

A "reference or baseline level/value" as used herein can be used interchangeably and is meant to be relative to a number or value derived from population studies, including without limitation, such subjects having similar age range, disease status (e.g., stage), subjects in the same or similar ethnic group, or relative to the starting sample of a subject undergoing treatment for cancer. Such reference values can be derived from statistical analyses and/or risk prediction data of populations obtained from mathematical algorithms and computed indices of cancer. Reference indices can also be constructed and used using algorithms and other methods of statistical and structural classification.

In some embodiments of the present invention, the reference or baseline value is the expression level of a particular gene of interest in a control sample derived from one or more healthy subjects or subjects who have not been diagnosed with any cancer.

In some embodiments of the present invention, the reference or baseline value is the expression level of a particular gene of interest in a sample obtained from the same subject prior to any cancer treatment. In other embodiments of the present invention, the reference or baseline value is the expression level of a particular gene of interest in a sample obtained from the same subject during a cancer treatment. Alternatively, the reference or baseline value is a prior measurement of the expression level of a particular gene of interest in a previously obtained sample from the same subject or from a subject having similar age range, disease status (e.g., stage) to the tested subject.

In some embodiments, an effective amount means an amount sufficient to increase the expression level of at least one gene which is decreased in the subject prior to the treatment or an amount sufficient to alleviate one or more symptoms of cancer. For example, an effective amount is an amount sufficient to increase the expression level of at least one gene selected from the group consisting of neuronal differentiation genes, cell cycle inhibition genes, and tumor suppressor genes by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level without the treatment of any compound.

In some embodiments, an effective amount means an amount sufficient to decrease the expression level of at least one gene which is increased in the subject prior to the treatment or an amount sufficient to alleviate one or more symptoms of cancer. For example, an effective amount is an amount sufficient to decrease the expression level of at least one gene selected from the group consisting of hedgehog pathway genes, MYC and EZH2 by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level without the treatment of any compound.

The precise effective amount for a subject will depend upon the subject's body weight, size, and health; the nature and extent of the condition; and the therapeutic selected for administration. An effective amount for a given situation can be determined by routine experimentation that is within the skill and judgment of the clinician.

The present invention further provides a method of determining efficacy of a cancer treatment in a subject in need thereof by (a) measuring the expression level of at least one gene selected from the group consisting of neuronal differentiation genes, cell cycle inhibition genes, and tumor suppressor genes in a sample obtained from the subject, (b) comparing the expression level of at least one gene in step (a) to a reference value or a prior measurement, and (c) determining the efficacy of the cancer treatment based on the comparison step. An exemplary cancer treatment is administering a compound of the invention to the tested subject.

The treatment is effective when the tested subject has an increased expression of at least one gene selected from the group consisting of neuronal differentiation genes, cell cycle inhibition genes and tumor suppressor genes 1) compared to a reference value or a prior measurement; or 2) over the period of time being monitored, such as 1, 2, 3, 4, 5, 6, or 7 days, or 1, 2, 3, 4, 5, 6, 7, 8, 9, 10 weeks, or 1, 2, 3, 4, 5, 6, 7, 8, 9, 10, 11, 12 months or longer. When the existing treatment is not effective, a new treatment or an increased dosage of the existing treatment (for example, increasing the dosage of the compound administered to the subject) should be sought for the tested subject.

The present invention also provides a method of determining efficacy of a cancer treatment in a subject in need thereof by (a) measuring the expression level of at least one gene selected from the group consisting of hedgehog pathway genes, myc pathway genes and histone methyltransferase genes in a sample obtained from the subject, (b) comparing the expression level of at least one gene in step (a) to a reference value or a prior measurement, and (c) determining the efficacy of the cancer treatment based on the comparison step. An exemplary cancer treatment is administering an EZH2 inhibitor of the invention to the tested subject.

For example, the treatment is effective when the tested subject has a decreased expression of at least one gene selected from the group consisting of hedgehog pathway genes, myc pathway genes and histone methyltransferase genes 1) compared to a reference value or a prior measurement; or 2) over the period of time being monitored, such as 1, 2, 3, 4, 5, 6, or 7 days, or 1, 2, 3, 4, 5, 6, 7, 8, 9, 10 weeks, or 1, 2, 3, 4, 5, 6, 7, 8, 9, 10, 11, 12 months or longer. When the existing treatment is not effective, a new treatment or an increased dosage of the existing treatment (for example, increasing the dosage of the compound administered to the subject) should be sought for the tested subject.

In any methods presented herein, cancer is selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullo carcinoma, diffuse large B-cell lymphoma, follicular lymphoma and not otherwise specified (NOS) sarcoma. More preferably, cancer is medulloblastoma, malignant rhabdoid tumor, or atypical teratoid rhabdoid tumor.

As used herein, the term "responsiveness" is interchangeable with terms "responsive", "sensitive", and "sensitivity", and it is meant that a subject is showing therapeutic responses when administered an EZH inhibitor, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered an EZH inhibitor, e.g., tumor cells or tumor tissues of the subject undergo apoptosis and/or necrosis, and/or display reduced growing, dividing, or proliferation.

As used herein, a "subject" is interchangeable with a "subject in need thereof", both of which refer to a subject having a disorder in which EZH2-mediated protein methylation plays a part, or a subject having an increased risk of developing such disorder relative to the population at large. A subject in need thereof may be a subject having a disorder associated with SWI/SNF complex. A subject in need thereof can have a precancerous condition. Preferably, a subject in need thereof has cancer. A subject in need thereof can have cancer associated with SWI/SNF complex. A subject in need thereof can have cancer associated with loss of function in at least one component of SWI/SNF complex. In a preferred aspect, a subject in need thereof has one or more cancers selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof has medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullo carcinoma, diffuse large B-cell lymphoma, follicular lymphoma and not otherwise specified (NOS) sarcoma. Alternatively, a subject in need thereof has a non NHL cancer.

As used herein, a "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject can be male or female.

A subject in need thereof can be one who has not been previously diagnosed or identified as having cancer or a precancerous condition. A subject in need thereof can be one who has been previously diagnosed or identified as having cancer or a precancerous condition. A subject in need thereof can also be one who is having (suffering from) cancer or a precancerous condition. Alternatively, a subject in need thereof can be one who has a risk of developing such disorder relative to the population at large (i.e., a subject who is predisposed to developing such disorder relative to the population at large).

Optionally a subject in need thereof has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

A subject in need thereof may be one who had, is having or is predisposed to developing a cancer or a precancerous condition associated with the SWI/SNF complex. A subject in need thereof may be one who had, is having or is predisposed to developing cancer or a precancerous condition associated with loss of function of at least one component of the SWI/SNF complex. In a preferred aspect, a subject in need thereof is one who had, is having or is predisposed to developing one or more cancers selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof is one who had, is having or is predisposed to developing brain and CNS cancer, kidney cancer, ovarian cancer, pancreatic cancer, leukemia, lymphoma, myeloma, and/or sarcoma. Exemplary brain and central CNS cancer includes medulloblastoma, oligodendroglioma, atypical teratoid rhabdoid tumor, choroid plexus carcinoma, choroid plexus papilloma, ependymoma, glioblastoma, meningioma, neuroglial tumor, oligoastrocytoma, oligodendroglioma, and pineoblastoma. Exemplary ovarian cancer includes ovarian clear cell adenocarcinoma, ovarian endomethrioid adenocarcinoma, and ovarian serous adenocarcinoma. Exemplary pancreatic cancer includes pancreatic ductal adenocarcinoma and pancreatic endocrine tumor. Exemplary sarcoma includes chondrosarcoma, clear cell sarcoma of soft tissue, ewing sarcoma, gastrointestinal stromal tumor, osteosarcoma, rhabdomyosarcoma, and not otherwise specified (NOS) sarcoma. Alternatively, cancers to be treated by the compounds of the present invention are non NHL cancers.

Alternatively, a subject in need thereof is one who had, is having or is predisposed to developing one or more cancers selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, and not otherwise specified (NOS) sarcoma. Preferably, a subject is one who had, is having or is predisposed to developing medulloblastoma, ovarian clear cell adenocarcinoma, ovarian endomethrioid adenocarcinoma, pancreatic ductal adenocarcinoma, malignant rhabdoid tumor, atypical teratoid rhabdoid tumor, choroid plexus carcinoma, choroid plexus papilloma, glioblastoma, meningioma, pineoblastoma, carcinosarcoma, extrarenal rhabdoid tumor, schwannoma, skin squamous cell carcinoma, chondrosarcoma, ewing sarcoma, epithelioid sarcoma, renal medullo carcinoma, diffuse large B-cell lymphoma, follicular lymphoma and/or NOS sarcoma. More preferably, a subject in need thereof is one who had, is having or is predisposed to developing malignant rhabdoid tumor, medulloblastoma and/or atypical teratoid rhabdoid tumor.

In some embodiments of the present invention, a subject in need thereof has a decreased expression level of at least one gene selected from the group consisting of neuronal differentiation genes, cell cycle inhibition genes, and tumor suppressor genes.

In some embodiments, a subject in need thereof has an increased expression level of at least one gene selected from the group consisting of hedgehog pathway genes, myc pathway genes and histone methyltransferase genes.

In some embodiments of the present invention, a subject in need thereof has loss of function of at least one component/subunit of the SWI/SNF complex. Alternatively, a subject in need thereof has reduced expression or haploinsufficiency of at least one component/subunit of the SWI/SNF complex. In certain embodiments, a subject in need thereof has loss of function of SNF5 subunit.

In any method of the present invention, a subject in need thereof may have reduced expression, haploinsufficiency or loss of function of at least one signaling component downstream of SWI/SNF complex. Such downstream component includes, but is not limited to, polycomb complex (PcG) and its targets.

As used herein, the term "loss of function" refers to less or no function of a gene product/protein compared to the wild type. Loss of function of a SWI/SNF complex component means the component/subunit or the entire SWI/SNF complex has less or no biological function compared to the wild type component/subunit or the entire SWI/SNF complex, respectively. Loss of function can be caused by transcriptional, post-transcription, or post translational mechanisms. In one aspect of the present invention, loss of function is caused by loss of function mutation resulted from a point mutation (e.g., a substitution, a missense mutation, or a nonsense mutation), an insertion, and/or a deletion in a polypeptide of a SWI/SNF complex component or a nucleic acid sequence encoding a polypeptide of a SWI/SNF complex component. The mutations referred herein are somatic mutations. The term "somatic mutation" refers to a deleterious alteration in at least one gene allele that is not found in every cell of the body, but is found only in isolated cells. A characteristic of the somatic mutations as used herein is, that they are restricted to particular tissues or even parts of tissues or cells within a tissue and are not present in the whole organism harboring the tissues or cells. The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene.

Accordingly, a loss of function mutation or a reduced expression can be detected using any suitable method available in the art. For example, a loss of function mutation can be detected by measuring the biological function of a gene product, such as the ATP-dependent chromatin remodeling activity of the SWI/SNF complex. Alternatively, a loss of function mutation can be determined by detecting any alternation in a nucleic acid sequence encoding a component of the SWI/SNF complex. For example, a nucleic acid sequence encoding a component of the SWI/SNF complex having a loss of function mutation can be detected by whole-genome resequencing or target region resequencing (the latter also known as targeted resequencing) using suitably selected sources of DNA and polymerase chain reaction (PCR) primers in accordance with methods well known in the art. The method typically and generally entails the steps of genomic DNA purification, PCR amplification to amplify the region of interest, cycle sequencing, sequencing reaction cleanup, capillary electrophoresis, and/or data analysis. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Alternatively or in addition, a nucleic acid sequence encoding a SWI/SNF polypeptide having a loss of function mutation may be detected using a Southern blot in accordance with methods well known in the art. Optionally, a loss of function mutation can be detected by measuring the absence of the expression of a component polypeptide or by measuring the expression of the mutant component polypeptide. Detection of (mutant) polypeptide expression can be carried out with any suitable immunoassay in the art, such as Western blot analysis.

Human nucleic acid and amino acid sequence of components of the SWI/SNF complex have previously been described. See, e.g., GenBank Accession Nos NP_003064.2, NM_003073.3, NP_001007469.1, and NM_001007468.1 for SNF5, GenBank Accession Nos NM_000489.3, NP_000480.2, NM_138270.2, and NP_612114.1 for ATRX, GenBank Accession Nos NP_006006.3, NM_006015.4, NP_624361.1, and NM_139135.2 for ARID1A, each of which is incorporated herein by reference in its entirety.

Spectrum of hSNF5 somatic mutations in human has also been described in Sevenet et al., Human Molecular Genetics, 8: 2359-2368, 1999, which is incorporated herein by reference in its entirety.

A subject in need thereof may have reduced expression, haploinsufficiency, and/or loss of function of SNF5. For example, a subject can comprise a deletion of SNF5 in SNF5 polypeptide or a nucleic acid sequence encoding a SNF5 polypeptide.

```
SWI/SNF-related matrix-associated actin-dependent regulator of chromatin subfamily B
member 1 isoform a (SMARCB1, also called SNF5)[Homo sapiens]
                                                                    (SEQ ID NO: 1)
    1 mmmmalsktf gqkpvkfqle ddgefymigs evgnylrmfr gslykrypsl
      wrrlatveer
   61 kkivasshgk ktkpntkdhg yttlatsvtl lkaseveeil dgndekykav
      sistepptyl
  121 reqkakrnsq wvptlpnssh hldavpcstt inrnrmgrdk krtfplcfdd
      hdpavihena
  181 sqpevlvpir ldmeidgqkl rdaftwnmne klmtpemfse ilcddldlnp
      ltfvpaiasa
  241 irqqiesypt dsiledqsdq rviiklnihv gnislvdqfe wdmsekensp
      ekfalklcse
  301 lglggefvtt iaysirgqls whqktyafse nplptveiai rntgdadqwc
      plletltdae
  361 mekkirdqdr ntrrmrrlan tapaw Homo sapiens SWI/SNF related, matrix associated, actin dependent regulator of chromatin,
subfamily b, member 1 (SMARCB1, also called SNF5), transcript variant 1, mRNA
                                                                    (SEQ ID NO: 2)
    1 aacgccagcg cctgcgcact gagggcggcc tggtcgtcgt ctgcggcggc
      ggcggcggct
   61 gaggagcccg gctgaggcgc cagtacccgg cccggtccgc atttcgcctt
      ccggcttcgg
```

-continued

```
 121 tttccctcgg cccagcacgc cccggccccg ccccagccct cctgatccct
     cgcagcccgg 181 ctccggccgc ccgcctctgc cgccgcaatg atgatgatgg cgctgagcaa
     gaccttcggg 241 cagaagcccg tgaagttcca gctggaggac gacggcgagt tctacatgat
     cggctccgag 301 gtgggaaact acctccgtat gttccgaggt tctctgtaca agagataccc
     ctcactctgg 361 aggcgactag ccactgtgga agagaggaag aaaatagttg catcgtcaca
     tggtaaaaaa 421 acaaaaccta acactaagga tcacggatac acgactctag ccaccagtgt
     gaccctgtta 481 aaagcctcgg aagtggaaga gattctggat ggcaacgatg agaagtacaa
     ggctgtgtcc 541 atcagcacag agcccccccac ctacctcagg gaacagaagg ccaagaggaa
     cagccagtgg 601 gtacccaccc tgcccaacag ctcccaccac ttagatgccg tgccatgctc
     cacaaccatc 661 aacaggaacc gcatgggccg agacaagaag agaaccttcc ccctttgctt
     tgatgaccat 721 gacccagctg tgatccatga aacgcatct cagcccgagg tgctggtccc
     catccggctg 781 gacatggaga tcgatgggca aagctgcga gacgccttca cctggaacat
     gaatgagaag 841 ttgatgacgc ctgagatgtt ttcagaaatc ctctgtgacg atctggattt
     gaacccgctg 901 acgtttgtgc cagccatcgc ctctgccatc agacagcaga tcgagtccta
     ccccacggac 961 agcatcctgg aggaccagtc agaccagcgc gtcatcatca agctgaacat
     ccatgtggga 1021 aacatttccc tggtggacca gtttgagtgg gacatgtcag agaaggagaa
     ctcaccagag 1081 aagtttgccc tgaagctgtg ctcggagctg gggttgggcg gggagtttgt
     caccaccatc 1141 gcatacagca tccggggaca gctgagctgg catcagaaga cctacgcctt
     cagcgagaac 1201 cctctgccca cagtggagat tgccatccgg aacacgggcg atgcggacca
     gtggtgccca 1261 ctgctggaga ctctgacaga cgctgagatg gagaagaaga tccgcgacca
     ggacaggaac
```

-continued

```
1321 acgaggcgga tgaggcgtct tgccaacacg gccccggcct ggtaaccagc
     ccatcagcac
1381 acggctccca cggagcatct cagaagattg gccgcctct cctccatctt
     ctggcaagga
1441 cagaggcgag gggacagccc agcgccatcc tgaggatcgg gtggggtgg
     agtgggggct
1501 tccaggtggc ccttcccggc acacattcca tttgttgagc cccagtcctg
     ccccccaccc
1561 caccctccct accctcccc agtctctggg gtcaggaaga aaccttattt
     taggttgtgt
1621 tttgtttttg tataggagcc ccaggcaggg ctagtaacag tttttaaata
     aaaggcaaca
1681 ggtcatgttc aatttcttca acaaaaaaaa aaaaaaa
```

SWI/SNF-related matrix-associated actin-dependent regulator of chromatin subfamily B member 1 isoform b [*Homo sapiens*] (SMARCB1, also called SNF5)

(SEQ ID NO: 3)

```
  1 mmmmalsktf gqkpvkfqle ddgefymigs evgnylrmfr gslykrypsl
    wrrlatveer
 61 kkivasshdh gyttlatsvt llkaseveei ldgndekyka vsisteppty
    lreqkakrns
121 qwvptlpnss hhldavpcst tinrnrmgrd kkrtfplcfd dhdpavihen
    asqpevlvpi
181 rldmeidgqk lrdaftwnmn eklmtpemfs eilcddldln pltfvpaias
    airgqiesyp
241 tdsiledqsd qrviiklnih vgnislvdqf ewdmsekens pekfalklcs
    elglggefvt
301 tiaysirgql swhqktyafs enplptveia irntgdadqw cplletltda
    emekkirdqd
361 rntrrmrrla ntapaw
```

*Homo sapiens* SWI/SNF related, matrix associated, actin dependent regulator of chromatin, subfamily b, member 1 (SMARCB1, also called SNF5), transcript variant 2, mRNA (SEQ ID NO: 4)

```
  1 aacgccagcg cctgcgcact gagggcggcc tggtcgtcgt ctgcggcggc
    ggcggcggct
 61 gaggagcccg gctgaggcgc cagtacccgg cccggtccgc atttcgcctt
    ccggcttcgg
121 tttccctcgg cccagcacgc cccggccccg ccccagccct cctgatccct
    cgcagcccgg
181 ctccggccgc ccgcctctgc cgccgcaatg atgatgatgg cgctgagcaa
    gaccttcggg
241 cagaagcccg tgaagttcca gctggaggac gacggcgagt tctacatgat
    cggctccgag
301 gtgggaaact acctccgtat gttccgaggt tctctgtaca agagataccc
    ctcactctgg
```

-continued

```
 361 aggcgactag ccactgtgga agagaggaag aaaatagttg catcgtcaca
     tgatcacgga
 421 tacacgactc tagccaccag tgtgaccctg ttaaaagcct cggaagtgga
     agagattctg
 481 gatggcaacg atgagaagta caaggctgtg tccatcagca cagagccccc
     cacctacctc
 541 agggaacaga aggccaagag gaacagccag tgggtaccca ccctgcccaa
     cagctcccac
 601 cacttagatg ccgtgccatg ctccacaacc atcaacagga accgcatggg
     ccgagacaag
 661 aagagaacct tcccccttttg ctttgatgac catgacccag ctgtgatcca
     tgagaacgca
 721 tctcagcccg aggtgctggt ccccatccgg ctggacatgg agatcgatgg
     gcagaagctg
 781 cgagacgcct tcacctggaa catgaatgag aagttgatga cgcctgagat
     gttttcagaa
 841 atcctctgtg acgatctgga tttgaacccg ctgacgtttg tgccagccat
     cgcctctgcc
 901 atcagacagc agatcgagtc ctaccccacg gacagcatcc tggaggacca
     gtcagaccag
 961 cgcgtcatca tcaagctgaa catccatgtg ggaaacattt ccctggtgga
     ccagtttgag
1021 tgggacatgt cagagaagga gaactcacca gagaagtttg ccctgaagct
     gtgctcggag
1081 ctggggttgg gcggggagtt tgtcaccacc atcgcataca gcatccgggg
     acagctgagc
1141 tggcatcaga agacctacgc cttcagcgag aaccctctgc ccacagtgga
     gattgccatc
1201 cggaacacgg gcgatgcgga ccagtggtgc ccactgctgg agactctgac
     agacgctgag
1261 atggagaaga agatccgcga ccaggacagg aacacgaggc ggatgaggcg
     tcttgccaac
1321 acggccccgg cctggtaacc agcccatcag cacacggctc ccacggagca
     tctcagaaga
1381 ttgggccgcc tctcctccat cttctggcaa ggacagaggc gagggacag
     cccagcgcca
1441 tcctgaggat cgggtggggg tggagtgggg gcttccaggt ggcccttccc
     ggcacacatt
1501 ccatttgttg agccccagtc ctgcccccca ccccaccctc cctacccctc
     cccagtctct
```

```
1561 ggggtcagga agaaacctta ttttaggttg tgttttgttt ttgtatagga gccccaggca 1621 gggctagtaa cagtttttaa ataaaaggca acaggtcatg ttcaatttct tcaacaaaaa 1681 aaaaaaaaaa
```

A subject in need thereof may have reduced expression, haploinsufficiency, and/or loss of function of ATRX. For example, a subject can comprise a mutation selected from the group consisting of a substitution of asparagine (N) for the wild type residue lysine (K) at amino acid position 688 of SEQ ID NO: 5 (K688N), and a substitution of isoleucine (I) for the wild type residue methionine (M) at amino acid position 366 of SEQ TD NO: 5 (M366I).

```
                Homo sapiens alpha thalassemia/mental retardation syndrome X-linked (ATRX) isoform 1
                                                                                    (SEQ ID NO: 5)
   1 mtaepmsesk lntlvqklhd flahsseese etsspprlam nqntdkisgs gsnsdmmens 61 keegtsssek skssgssrsk rkpsivtkyv esddekpldd etvnedasne nsenditmqs 121 lpkgtvivqp epvlnedkdd fkgpefrsrs kmktenlkkr gedglhgivs ctacgqqvnh 181 fqkdsiyrhp slqvlicknc fkyymsddis rdsdgmdeqc rwcaeggnli ccdfchnafc 241 kkcilrnlgr kelstimden nqwycyichp eplldlvtac nsvfenleql lqqnkkkikv 301 dseksnkvye htsrfspkkt ssncngeekk lddscsgsvt ysysalivpk emikkakkli 361 ettanmnssy vkflkqatdn seissatklr qlkafksvla dikkahlale edlnsefram 421 davnkekntk ehkvidakfe tkarkgekpc alekkdisks eaklsrkqvd sehmhqnvpt 481 eeqrtnkstg gehkksdrke epqyepants edldmdivsv pssvpedife nletamevqs 541 svdhqgdgss gteqevesss vklnisskdn rggiksktta kvtkelyvkl tpvslsnspi 601 kgadcqevpq dkdgykscgl npklekcglg qensdnehlv enevslllee sdlrrsprvk 661 ttplrrptet npvtsnsdee cnetvkekqk lsvpvrkkdk rnssdsaidn pkpnklpksk 721 qsetvdqnsd sdemlailke vsrmshssss dtdineihtn hktlydlktq agkddkgkrk 781 rksstsgsdf dtkkgksaks siiskkkrqt qsessnydse lekeiksmsk igaarttkkr 841 ipntkdfdss edekhskkgm dnqghknlkt sqegssddae rkqeretfss aegtvdkdtt
```

```
 901  imelrdrlpk kqqasastdg vdklsgkeqs ftslevrkva etkekskhlk
      tktckkvqdg
 961  lsdiaekflk kdqsdetsed dkkqskkgte ekkkpsdfkk kvikmeqqye
      sssdgteklp
1021  ereeichfpk gikqikngtt dgekkskkir dktskkkdel sdyaekstgk
      gdscdssedk
1081  kskngaygre kkrckllgks srkrqdcsss dtekysmked gcnssdkrlk
      rielrerrnl
1141  sskrntkeiq sgssssdaee ssednkkkkq rtsskkkavi vkekkrnslr
      tstkrkqadi
1201  tsssssdied ddqnsigegs sdeqkikpvt enlvlsshtg fcqssgdeal
      sksvpvtvdd
1261  ddddndpenr iakkmlleei kanlssdedg ssddepeegk krtgkqneen
      pgdeeaknqv
1321  nsesdsdsee skkpryrhrl lrhkltvsdg esgeekktkp kehkevkgrn
      rrkvssedse
1381  dsdfqesgvs eevsesedeq rprtrsakka eleenqrsyk qkkkrrrikv
      qedsssenks
1441  nseeeeeeke eeeeeeeee eeeedendds kspgkgrkki rkilkddklr
      tetqnalkee
1501  eerrkriaer erereklrev ieiedasptk cpittklvld edeetkeplv
      qvhrnmvikl
1561  kphqvdgvqf mwdcccesvk ktkkspgsgc ilahcmglgk tlqvvsflht
      vllcdkldfs
1621  talvvcplnt alnwmnefek wqeglkddek levselatvk rpgersymlq
      rwqedggvmi
1681  igyemyrnla qgrnvksrkl keifnkalvd pgpdfvvcde ghilkneasa
      vskamnsirs
1741  rrriiltgtp lqnnlieyhc mvnfikenll gsikefrnrf inpiqngqca
      dstmvdvrvm
1801  kkrahilyem lagcvqrkdy taltkflppk heyvlavrmt siqcklyqyy
      ldhltgvgnn
1861  seggrgkaga klfqdfqmls riwthpwclq ldyiskenkg yfdedsmdef
      iasdsdetsm
1921  slssddytkk kkkgkkgkkd ssssgsgsdn dvevikvwns rsrgggegnv
      detgnnpsvs
1981  lkleeskats ssnpsspapd wykdfvtdad aevlehsgkm vllfeilrma
      eeigdkvlvf
2041  sqslisldli edflelasre ktedkdkpli ykgegkwlrn idyyrldgst
      taqsrkkwae
```

```
2101  efndetnvrg  rlfiiistkag  slginlvaan  rviifdaswn  psydiqsifr
      vyrfgqtkpv 2161  yvyrflaqgt  medkiydrqv  tkqslsfrvv  dqqqverhft  mneltelytf
      epdllddpns 2221  ekkkkrdtpm  lpkdtilael  lqihkehivg  yhehdslldh  keeeelteee
      rkaawaeyea 2281  ekkgltmrfn  iptgtnlppv  sfnsqtpyip  fnlgalsams  nqqledlinq
      grekvveatn 2341  svtavriqpl  ediisavwke  nmnlseaqvg  alalsrqasq  eldvkrreai
      yndvltkqqm 2401  liscvqrilm  nrrlqqqynq  qqqqmtyqg   atlghlmmpk  ppnlimnpsn
      yqqidmrgmy 2461  qpvaggmqpp  plqrapppmr  sknpgpsqgk  sm
```

Homo sapiens alpha thalassemia/mental retardation syndrome X-linked (ATRX), transcript variant 1, mRNA (SEQ ID NO: 6)

```
   1  aattctcctg  cctgagcctc  ggcccaacaa  aatggcggcg  gcagcggtgt
      cgctttgttt 61  ccgcggctcc  tgcggcggtg  gcagtggtag  cggcctttga  gctgtgggga
      ggttccagca 121  gcagctacag  tgacgactaa  gactccagtg  catttctatc  gtaaccgggc
      gcggggagc 181  gcagatcggc  gcccagcaat  cacagaagcc  gacaaggcgt  tcaagcgaaa
      acatgaccgc 241  tgagcccatg  agtgaaagca  agttgaatac  attggtgcag  aagcttcatg
      acttccttgc 301  acactcatca  gaagaatctg  aagaaacaag  ttctcctcca  cgacttgcaa
      tgaatcaaaa 361  cacagataaa  atcagtggtt  ctggaagtaa  ctctgatatg  atgaaaaaca
      gcaaggaaga 421  gggaactagc  tcttcagaaa  aatccaagtc  ttcaggatcg  tcacgatcaa
      agaggaaacc 481  ttcaattgta  acaaagtatg  tagaatcaga  tgatgaaaaa  cctttggatg
      atgaaactgt 541  aaatgaagat  gcgtctaatg  aaaattcaga  aaatgatatt  actatgcaga
      gcttgccaaa 601  aggtacagtg  attgtacagc  cagagccagt  gctgaatgaa  gacaaagatg
      attttaaagg 661  gcctgaattt  agaagcagaa  gtaaaatgaa  aactgaaaat  ctcaaaaaac
      gcggagaaga 721  tgggcttcat  gggattgtga  gctgcactgc  ttgtggacaa  caggtcaatc
      attttcaaaa
```

-continued

```
 781 agattccatt tatagacacc cttcattgca agttcttatt tgtaagaatt
     gctttaagta 841 ttacatgagt gatgatatta gccgtgactc agatggaatg gatgaacaat
     gtaggtggtg 901 tgcggaaggt ggaaacttga tttgttgtga cttttgccat aatgctttct
     gcaagaaatg 961 cattctacgc aaccttggtc gaaaggagtt gtccacaata atggatgaaa
     acaaccaatg 1021 gtattgctac atttgtcacc cagagccttt gttggacttg gtcactgcat
     gtaacagcgt 1081 atttgagaat ttagaacagt tgttgcagca aaataagaag aagataaaag
     ttgacagtga 1141 aaagagtaat aaagtatatg aacatacatc cagattttct ccaaagaaga
     ctagttcaaa 1201 ttgtaatgga gaagaaaaga aattagatga ttcctgttct ggctctgtaa
     cctactctta 1261 ttccgcacta attgtgccca aagagatgat taagaaggca aaaaaactga
     ttgagaccac 1321 agccaacatg aactccagtt atgttaaatt tttaaagcag gcaacagata
     attcagaaat 1381 cagttctgct acaaaattac gtcagcttaa ggcttttaag tctgtgttgg
     ctgatattaa 1441 gaaggctcat cttgcattgg aagaagactt aaattccgag tttcgagcga
     tggatgctgt 1501 aaacaaagag aaaaatacca aagagcataa agtcatagat gctaagtttg
     aaacaaaagc 1561 acgaaaagga gaaaaacctt gtgctttgga aagaaggat atttcaaagt
     cagaagctaa 1621 actttcaaga aaacaggtag atagtgagca catgcatcag aatgttccaa
     cagaggaaca 1681 aagaacaaat aaaagtaccg gtggtgaaca taagaaatct gatagaaaag
     aagaacctca 1741 atatgaacct gccaacactt ctgaagattt agacatggat attgtgtctg
     ttccttcctc 1801 agttccagaa gacattttg agaatcttga gactgctatg gaagttcaga
     gttcagttga 1861 tcatcaaggg gatggcagca gtggaactga acaagaagtg gagagttcat
     ctgtaaaatt 1921 aaatatttct tcaaaagaca acagaggagg tattaaatca aaaactacag
     ctaaagtaac
```

-continued

```
1981  aaaagaatta tatgttaaac tcactcctgt ttcccttttct aattccccaa
      ttaaaggtgc
2041  tgattgtcag gaagttccac aagataaaga tggctataaa agttgtggtc
      tgaaccccaa
2101  gttagagaaa tgtggacttg gacaggaaaa cagtgataat gagcatttgg
      ttgaaaatga
2161  agtttcatta cttttagagg aatctgatct tcgaagatcc ccacgtgtaa
      agactacacc
2221  cttgaggcga ccgacagaaa ctaaccctgt aacatctaat tcagatgaag
      aatgtaatga
2281  aacagttaag gagaaacaaa aactatcagt tccagtgaga aaaaggata
      agcgtaattc
2341  ttctgacagt gctatagata atcctaagcc taataaattg ccaaaatcta
      agcaatcaga
2401  gactgtggat caaaattcag attctgatga aatgctagca atcctcaaag
      aggtgagcag
2461  gatgagtcac agttcttctt cagatactga tattaatgaa attcatacaa
      accataagac
2521  tttgtatgat ttaaagactc aggcggggaa agatgataaa ggaaaaagga
      aacgaaaaag
2581  ttctacatct ggctcagatt ttgatactaa aaagggcaaa tcagctaaga
      gctctataat
2641  ttctaaaaag aaacgacaaa cccagtctga gtcttctaat tatgactcag
      aattagaaaa
2701  agagataaag agcatgagta aaattggtgc tgccagaacc accaaaaaa
      gaattccaaa
2761  tacaaaagat tttgactctt ctgaagatga gaaacacagc aaaaaaggaa
      tggataatca
2821  agggcacaaa aatttgaaga cctcacaaga aggatcatct gatgatgctg
      aaagaaaaca
2881  agagagagag actttctctt cagcagaagg cacagttgat aaagacacga
      ccatcatgga
2941  attaagagat cgacttccta agaagcagca agcaagtgct tccactgatg
      gtgtcgataa
3001  gctttctggg aaagagcaga gttttacttc tttggaagtt agaaaagttg
      ctgaaactaa
3061  agaaaagagc aagcatctca aaccaaaac atgtaaaaaa gtacaggatg
      gcttatctga
3121  tattgcagag aaattcctaa agaaagacca gagcgatgaa acttctgaag
      atgataaaaa
```

-continued

```
3181  gcagagcaaa aagggaactg aagaaaaaaa gaaaccttca gactttaaga
      aaaaagtaat 3241  taaaatggaa caacagtatg aatcttcatc tgatggcact gaaaagttac
      ctgagcgaga 3301  agaaatttgt cattttccta agggcataaa acaaattaag aatggaacaa
      ctgatggaga 3361  aaagaaaagt aaaaaaataa gagataaaac ttctaaaaag aaggatgaat
      tatctgatta 3421  tgctgagaag tcaacaggga aaggagatag ttgtgactct tcagaggata
      aaaagagtaa 3481  gaatggagca tatggtagag agaagaaaag gtgcaagttg cttggaaaga
      gttcaaggaa 3541  gagacaagat tgttcatcat ctgatactga aaatattcc atgaagaag
      atggttgtaa 3601  ctcttctgat aagagactga aaagaataga attgagggaa agaagaaatt
      taagttcaaa 3661  gagaaatact aaggaaatac aaagtggctc atcatcatct gatgctgagg
      aaagttctga 3721  agataataaa agaagaagc aaagaacttc atctaaaaag aaggcagtca
      ttgtcaagga 3781  gaaaagaga aactccctaa gaacaagcac taaaaggaag caagctgaca
      ttacatcctc 3841  atcttcttct gatatagaag atgatgatca gaattctata ggtgagggaa
      gcagcgatga 3901  acagaaaatt aagcctgtga ctgaaaattt agtgctgtct tcacatactg
      gattttgcca 3961  atcttcagga gatgaagcct tatctaaatc agtgcctgtc acagtggatg
      atgatgatga 4021  cgacaatgat cctgagaata gaattgccaa gaagatgctt ttagaagaaa
      ttaaagccaa 4081  tctttcctct gatgaggatg gatcttcaga tgatgagcca gaagaaggga
      aaaaaagaac 4141  tggaaaacaa aatgaagaaa acccaggaga tgaggaagca aaaaatcaag
      tcaattctga 4201  atcagattca gattctgaag aatctaagaa gccaagatac agacataggc
      ttttgcggca 4261  caaattgact gtgagtgacg gagaatctgg agaagaaaaa aagacaaagc
      ctaaagagca 4321  taaagaagtc aaaggcagaa acagaagaaa ggtgagcagt gaagattcag
      aagattctga
```

```
4381  ttttcaggaa tcaggagtta gtgaagaagt tagtgaatcc gaagatgaac
      agcggcccag
4441  aacaaggtct gcaaagaaag cagagttgga agaaaatcag cggagctata
      aacagaaaaa
4501  gaaaaggcga cgtattaagg ttcaagaaga ttcatccagt gaaaacaaga
      gtaattctga
4561  ggaagaagag gaggaaaaag aagaggagga ggaagaggag gaggaggagg
      aagaggagga
4621  ggaagatgaa aatgatgatt ccaagtctcc tggaaaaggc agaaagaaaa
      ttcggaagat
4681  tcttaaagat gataaactga gaacagaaac acaaaatgct cttaaggaag
      aggaagagag
4741  acgaaaacgt attgctgaga gggagcgtga gcgagaaaaa ttgagagagg
      tgatagaaat
4801  tgaagatgct tcacccacca agtgtccaat aacaaccaag ttggttttag
      atgaagatga
4861  agaaaccaaa gaacctttag tgcaggttca tagaaatatg gttatcaaat
      tgaaacccca
4921  tcaagtagat ggtgttcagt ttatgtggga ttgctgctgt gagtctgtga
      aaaaaacaaa
4981  gaaatctcca ggttcaggat gcattcttgc ccactgtatg ggccttggta
      agactttaca
5041  ggtggtaagt tttcttcata cagttctttt gtgtgacaaa ctggatttca
      gcacggcgtt
5101  agtggtttgt cctcttaata ctgctttgaa ttggatgaat gaatttgaga
      agtggcaaga
5161  gggattaaaa gatgatgaga agcttgaggt ttctgaatta gcaactgtga
      aacgtcctca
5221  ggagagaagc tacatgctgc agaggtggca agaagatggt ggtgttatga
      tcataggcta
5281  tgagatgtat agaaatcttg ctcaaggaag gaatgtgaag agtcggaaac
      ttaaagaaat
5341  atttaacaaa gctttggttg atccaggccc tgattttgtt gtttgtgatg
      aaggccatat
5401  tctaaaaaat gaagcatctg ctgtttctaa agctatgaat tctatacgat
      caaggaggag
5461  gattatttta acaggaacac cacttcaaaa taacctaatt gagtatcatt
      gtatggttaa
5521  ttttatcaag gaaaatttac ttggatccat taaggagttc aggaatagat
      ttataaatcc
```

-continued

```
5581  aattcaaaat ggtcagtgtg cagattctac catggtagat gtcagagtga
      tgaaaaaacg 5641  tgctcacatt ctctatgaga tgttagctgg atgtgttcag aggaaagatt
      atacagcatt 5701  aacaaaattc ttgcctccaa aacacgaata tgtgttagct gtgagaatga
      cttctattca 5761  gtgcaagctc tatcagtact acttagatca cttaacaggt gtgggcaata
      atagtgaagg 5821  tggaagagga aaggcaggtg caaagctttt ccaagatttt cagatgttaa
      gtagaatatg 5881  gactcatcct tggtgtttgc agctagacta cattagcaaa gaaaataagg
      gttattttga 5941  tgaagacagt atggatgaat ttatagcctc agattctgat gaaacctcca
      tgagtttaag 6001  ctccgatgat tatacaaaaa agaagaaaaa agggaaaaag gggaaaaaag
      atagtagctc 6061  aagtggaagt ggcagtgaca atgatgttga agtgattaag gtctggaatt
      caagatctcg 6121  gggaggtggt gaaggaaatg tggatgaaac aggaaacaat ccttctgttt
      ctttaaaact 6181  ggaagaaagt aaagctactt cttcttctaa tccaagcagc ccagctccag
      actggtacaa 6241  agattttgtt acagatgctg atgctgaggt tttagagcat tctgggaaaa
      tggtacttct 6301  ctttgaaatt cttcgaatgg cagaggaaat tggggataaa gtccttgttt
      tcagccagtc 6361  cctcatatct ctggacttga ttgaagattt tcttgaatta gctagtaggg
      agaagacaga 6421  agataaagat aaaccccttaa tttataaagg tgaggggaag tggcttcgaa
      acattgacta 6481  ttaccgttta gatggttcca ctactgcaca gtcaaggaag aagtgggctg
      aagaatttaa 6541  tgatgaaact aatgtgagag gacgattatt tatcatttct actaaagcag
      gatctctagg 6601  aattaatctg gtagctgcta atcgagtaat tatattcgac gcttcttgga
      atccatctta 6661  tgacatccag agtatattca gagtttatcg ctttggacaa actaagcctg
      tttatgtata 6721  taggttctta gctcagggaa ccatggaaga taagatttat gatcggcaag
      taactaagca
```

-continued

```
6781  gtcactgtct tttcgagttg ttgatcagca gcaggtggag cgtcatttta
      ctatgaatga
6841  gcttactgaa ctttatactt ttgagccaga cttattagat gaccctaatt
      cagaaaagaa
6901  gaagaagagg gatactccca tgctgccaaa ggataccata cttgcagagc
      tccttcagat
6961  acataaagaa cacattgtag gataccatga acatgattct cttttggacc
      acaaagaaga
7021  agaagagttg actgaagaag aaagaaaagc agcttgggct gagtatgaag
      cagagaagaa
7081  gggactgacc atgcgtttca ataccaac tgggaccaat ttaccccctg
      tcagtttcaa
7141  ctctcaaact ccttatattc ctttcaattt gggagccctg tcagcaatga
      gtaatcaaca
7201  gctggaggac ctcattaatc aaggaagaga aaaagttgta gaagcaacaa
      acagtgtgac
7261  agcagtgagg attcaacctc ttgaggatat aatttcagct gtatggaagg
      agaacatgaa
7321  tctctcagag gcccaagtac aggcgttagc attaagtaga caagccagcc
      aggagcttga
7381  tgttaaacga agagaagcaa tctacaatga tgtattgaca aaacaacaga
      tgttaatcag
7441  ctgtgttcag cgaatactta tgaacagaag gctccagcag cagtacaatc
      agcagcaaca
7501  gcaacaaatg acttatcaac aagcaacact gggtcacctc atgatgccaa
      agcccccaaa
7561  tttgatcatg aatccttcta actaccagca gattgatatg agaggaatgt
      atcagccagt
7621  ggctggtggt atgcagccac caccattaca gcgtgcacca cccccaatga
      gaagcaaaaa
7681  tccaggacct tcccaaggga atcaatgtg attttgcact aaaagcttaa
      tggattgtta
7741  aaatcataga aagatctttt attttttag gaatcaatga cttaacagaa
      ctcaactgta
7801  taaatagttt ggtcccctta aatgccaatc ttccatatta gttttacttt
      tttttttttt
7861  aaatagggca taccatttct tcctgacatt tgtcagtgat gttgcctaga
      atcttcttac
7921  acacgctgag tacagaagat atttcaaatt gttttcagtg aaaacaagtc
      cttccataat
```

```
7981  agtaacaact ccacagattt cctctctaaa tttttatgcc tgcttttagc
      aaccataaaa 8041  ttgtcataaa attaataaat ttaggaaaga ataaagattt atatattcat
      tctttacata 8101  taaaaacaca cagctgagtt cttagagttg attcctcaag ttatgaaata
      cttttgtact 8161  taatccattt cttgattaaa gtgattgaaa tggtttaat gttcttttga
      ctgaagtctg 8221  aaactgggct cctgctttat tgtctctgtg actgaaagtt agaaactgag
      ggttatcttt 8281  gacacagaat tgtgtgcaat attcttaaat actactgctc taaaagttgg
      agaagtcttg 8341  cagttatctt agcattgtat aaacagcctt aagtatagcc taagaagaga
      attcctttt 8401  cttctttagt ccttctgcca ttttttattt tcagttatat gtgctgaaat
      aattactggt 8461  aaaatttcag ggttgtggat tatcttccac acatgaattt tctctctcct
      ggcacgaata 8521  taaagcacat ctcttaactg catggtgcca gtgctaatgc ttcatcctgt
      tgctggcagt 8581  gggatgtgga cttagaaaat caagttctag cattttagta ggttaacact
      gaagttgtgg 8641  ttgttaggtt cacaccctgt tttataaaca acatcaaaat ggcagaacca
      ttgctgactt 8701  taggttcaca tgaggaatgt acttttaaca attcccagta ctatcagtat
      tgtgaaataa 8761  ttcctctgaa agataagaat cactggcttc tatgcgcttc ttttctctca
      tcatcatgtt 8821  cttttacccc agtttcctta catttttta aattgtttca gagtttgttt
      ttttttagt 8881  ttagattgtg aggcaattat taaatcaaaa ttaattcatc caatacccct
      ttactagaag 8941  ttttactaga aaatgtatta cattttattt tttcttaatc cagttctgca
      aaaatgacct 9001  ataaatttat tcatgtacaa ttttggttac ttgaattgtt aagaaaaca
      ttgttttga 9061  ctatgggagt caactcaaca tggcagaacc attttgaga tgatgataca
      acaggtagtg 9121  aaacagctta agaattccaa aaaaaaaaa aaaaaaaaa aaagaaaac
      tgggtttggg
```

-continued

```
 9181 ctttgcttta ggtatcactg gattagaatg agtttaacat tagctaaaac
      tgctttgagt
 9241 tgtttggatg attaagagat tgccattttt atcttggaag aactagtggt
      aaaacatcca
 9301 agagcactag gattgtgata cagaatttgt gaggtttggt ggatccacgc
      ccctctcccc
 9361 cactttccca tgatgaaata tcactaataa atcctgtata tttagatatt
      atgctagcca
 9421 tgtaatcaga tttatttaat tgggtggggc aggtgtgtat ttactttaga
      aaaaatgaaa
 9481 aagacaagat ttatgagaaa tatttgaagg cagtacactc tggccaactg
      ttaccagttg
 9541 gtatttctac aagttcagaa tattttaaac ctgatttact agacctggga
      attttcaaca
 9601 tggtctaatt atttactcaa agacatagat gtgaaatttt taggcaacct
      tctaaatctt
 9661 tttcaccatg gatgaaacta taacttaaag aataatactt agaagggtta
      attggaaatc
 9721 agagtttgaa ataaaacttg gaccactttg tatacactct tctcacttga
      cattttagct
 9781 atataatatg tactttgagt ataacatcaa gctttaacaa atatttaaag
      acaaaaaaat
 9841 cacgtcagta aaatactaaa aggctcattt ttatatttgt tttagatgtt
      ttaaatagtt
 9901 gcaatggatt aaaaatgatg atttaaaatg ttgcttgtaa tacagttttg
      cctgctaaat
 9961 tctccacatt ttgtaacctg ttttatttct ttgggtgtaa agcgtttttg
      cttagtattg
10021 tgatattgta tatgttttgt cccagttgta tagtaatgtt tcagtccatc
      atccagcttt
10081 ggctgctgaa atcatacagc tgtgaagact tgcctttgtt tctgttagac
      tgcttttcag
10141 ttctgtattg agtatcttaa gtactgtaga aaagatgtca cttcttcctt
      taaggctgtt
10201 ttgtaatata tataaggact ggaattgtgt ttttaaagaa aagcattcaa
      gtatgacaat
10261 atactatctg tgttttcacc attcaaagtg ctgtttagta gttgaaactt
      aaactattta
10321 atgtcattta ataaagtgac caaatgtgt tgtgctcttt attgtatttt
      cacagctttg
```

```
-continued
10381 aaaatctgtg cacatactgt ttcatagaaa atgtatagct tttgttgtcc
      tatataatgg
10441 tggttctttt gcacatttag ttatttaata ttgagaggtc acgaagtttg
      gttattgaat
10501 ctgttatata ctaaattctg taaagggaga tctctcatct caaaaagaat
      ttacatacca
10561 ggaagtccat gtgtgtttgt gttagttttg gatgtctttg tgtaatccag
      ccccatttcc
10621 tgtttcccaa cagctgtaac actcatttta agtcaagcag ggctaccaac
      ccacacttga
10681 tagaaaagct gcttaccatt cagaagcttc cttattacct ggcctccaaa
      tgagctgaat
10741 attttgtagc cttcccttag ctatgttcat tttccctcca ttatcataaa
      atcagatcga
10801 tatttatgtg ccccaaacaa aactttaaga gcagttacat tctgtcccag
      tagcccttgt
10861 ttcctttgag agtagcatgt tgtgaggcta tagagactta ttctaccagt
      aaaacaggtc
10921 aatcctttta catgtttatt atactaaaaa ttatgttcag ggtatttact
      actttatttc
10981 accagactca gtctcaagtg acttggctat ctccaaatca gatctaccct
      tagagaataa
11041 acatttttct accgttattt ttttttcaagt ctataatctg agccagtccc
      aaaggagtga
11101 tcaagtttca gaaatgcttt catcttcaca acattttata tatactatta
      tatggggtga
11161 ataaagtttt aaatccgaaa tataaaaaaa aaaaaaaaa aa
```

Homo sapiens alpha thalassemia/mental retardation syndrome X-linked (ATRX) isoform 2
(SEQ ID NO: 7)

```
  1 mtaepmsesk lntlvqklhd flahsseese etsspprlam nqntdkisgs
    gsnsdmmens
 61 keegtsssek skssgssrsk rkpsivtkyv esddekpldd etvnedasne
    nsenditmqs
121 lpkedglhgi vsctacgqqv nhfqkdsiyr hpslqvlick ncfkyymsdd
    isrdsdgmde
181 qcrwcaeggn liccdfchna fckkcilrnl grkelstimd ennqwycyic
    hpeplldlvt
241 acnsvfenle qllqqnkkki kvdseksnkv yehtsrfspk ktssncngee
    kklddscsgs
301 vtysysaliv pkemikkakk liettanmns syvkflkqat dnseissatk
    lrqlkafksv
```

```
 361 ladikkahla leedlnsefr amdavnkekn tkehkvidak fetkarkgek
     pcalekkdis
 421 kseaklsrkg vdsehmhqnv pteeqrtnks tggehkksdr keepqyepan
     tsedldmdiv
 481 svpssvpedi fenletamev qssvdhqgdg ssgteqeves ssvklnissk
     dnrggikskt
 541 takvtkelyv kltpvslsns pikgadcqev pqdkdgyksc glnpklekcg
     lgqensdneh
 601 lvenevslll eesdlrrspr vkttplrrpt etnpvtsnsd eecnetvkek
     qklsvpvrkk
 661 dkrnssdsai dnpkpnklpk skqsetvdqn sdsdemlail kevsrmshss
     ssdtdineih
 721 tnhktlydlk tqagkddkgk rkrksstsgs dfdtkkgksa kssiiskkkr
     qtqsessnyd
 781 selekeiksm skigaarttk kripntkdfd ssedekhskk gmdnqghknl
     ktsqegssdd
 841 aerkqeretf ssaegtvdkd ttimelrdrl pkkqqasast dgvdklsgke
     qsftslevrk
 901 vaetkekskh lktktckkvq dglsdiaekf lkkdqsdets eddkkqskkg
     teekkkpsdf
 961 kkkvikmeqq yesssdgtek lpereeichf pkgikqikng ttdgekkskk
     irdktskkkd
1021 elsdyaekst gkgdscdsse dkkskngayg rekkrckllg kssrkrqdcs
     ssdtekysmk
1081 edgcnssdkr lkrielrerr nlsskrntke iqsgsssssda eessednkkk
     kqrtsskkka
1141 vivkekkrns lrtstkrkqa ditsssssdi edddqnsige gssdeqkikp
     vtenlvlssh
1201 tgfcqssgde alsksvpvtv dddddndpe nriakkmlle eikanlssde
     dgssddepee
1261 gkkrtgkqne enpgdeeakn qvnsesdsds eeskkpryrh rllrhkltvs
     dgesgeekkt
1321 kpkehkevkg rnrrkvssed sedsdfqesg vseevsesed eqrprtrsak
     kaeleenqrs
1381 ykqkkkrrri kvqedsssen ksnseeeeee keeeeeeeee eeeeeedend
     dskspgkgrk
1441 kirkilkddk lrtetqnalk eeeerrkria erereereklr evieiedasp
     tkcpittklv
1501 ldedeetkep lvqvhrnmvi klkphqvdgv qfmwdccces vkktkkspgs
     gcilahcmgl
```

```
1561  gktlqvvsfl htvllcdkld fstalvvcpl ntalnwmnef ekwqeglkdd
      eklevselat 1621  vkrpqersym lqrwqedggv miigyemyrn laqgrnvksr klkeifnkal
      vdpgpdfvvc 1681  deghilknea sayskamnsi rsrrriiltg tplqnnliey hcmvnfiken
      llgsikefrn 1741  rfinpiqngq cadstmvdvr vmkkrahily emlagcvqrk dytaltkflp
      pkheyvlavr 1801  mtsiqcklyq yyldhltgvg nnseggrgka gaklfqdfqm lsriwthpwc
      lqldyisken 1861  kgyfdedsmd efiasdsdet smslssddyt kkkkkgkkgk kdssssgsgs
      dndvevikvw 1921  nsrsrgggeg nvdetgnnps vslkleeska tsssnpsspa pdwykdfvtd
      adaevlehsg 1981  kmvllfeilr maeeigdkvl vfsqslisld liedflelas rektedkdkp
      liykgegkwl 2041  rnidyyrldg sttaqsrkkw aeefndetnv rgrlfiistk agslginlva
      anrviifdas 2101  wnpsydiqsi frvyrfgqtk pvyvyrflaq gtmedkiydr qvtkqslsfr
      vvdqqqverh 2161  ftmneltely tfepdllddp nsekkkkrdt pmlpkdtila ellqihkehi
      vgyhehdsll 2221  dhkeeeelte eerkaawaey eaekkgltmr fniptgtnlp pvsfnsqtpy
      ipfnlgalsa 2281  msnqqledli nqgrekvvea tnsvtavriq plediisavw kenmnlseaq
      vqalalsrqa 2341  sqeldvkrre aiyndvltkq qmliscvqri lmnrrlqqqy nqqqqqmty
      qqatlghlmm 2401  pkppnlimnp snyqqidmrg myqpvaggmq ppplqrappp mrsknpgpsq gksm
```
Homo sapiens alpha thalassemia/mental retardation syndrome X-linked (ATRX), transcript variant 2, mRNA (SEQ ID NO: 8)
```
   1  aattctcctg cctgagcctc ggcccaacaa aatggcggcg gcagcggtgt
      cgctttgttt 61  ccgcggctcc tgcggcggtg gcagtggtag cggcctttga gctgtgggga
      ggttccagca 121  gcagctacag tgacgactaa gactccagtg catttctatc gtaaccgggc
      gcggggagc 181  gcagatcggc gcccagcaat cacagaagcc gacaaggcgt tcaagcgaaa
      acatgaccgc 241  tgagcccatg agtgaaagca gttgaataca attggtgcag aagcttcatg
      acttccttgc
```

```
 301 acactcatca gaagaatctg aagaaacaag ttctcctcca cgacttgcaa
     tgaatcaaaa 361 cacagataaa atcagtggtt ctggaagtaa ctctgatatg atggaaaaca
     gcaaggaaga 421 gggaactagc tcttcagaaa aatccaagtc ttcaggatcg tcacgatcaa
     agaggaaacc 481 ttcaattgta acaaagtatg tagaatcaga tgatgaaaaa cctttggatg
     atgaaactgt 541 aaatgaagat gcgtctaatg aaaattcaga aaatgatatt actatgcaga
     gcttgccaaa 601 agaagatggg cttcatggga ttgtgagctg cactgcttgt ggacaacagg
     tcaatcattt 661 tcaaaaagat tccatttata gacacccttc attgcaagtt cttatttgta
     agaattgctt 721 taagtattac atgagtgatg atattagccg tgactcagat ggaatggatg
     aacaatgtag 781 gtggtgtgcg gaaggtggaa acttgatttg ttgtgacttt tgccataatg
     ctttctgcaa 841 gaaatgcatt ctacgcaacc ttggtcgaaa ggagttgtcc acaataatgg
     atgaaaacaa 901 ccaatggtat tgctacattt gtcacccaga gcctttgttg gacttggtca
     ctgcatgtaa 961 cagcgtattt gagaatttag aacagttgtt gcagcaaaat aagaagaaga
     taaaagttga 1021 cagtgaaaag agtaataaag tatatgaaca tacatccaga ttttctccaa
     agaagactag 1081 ttcaaattgt aatggagaag aaaagaaatt agatgattcc tgttctggct
     ctgtaaccta 1141 ctcttattcc gcactaattg tgcccaaaga gatgattaag aaggcaaaaa
     aactgattga 1201 gaccacagcc aacatgaact ccagttatgt taaattttta aagcaggcaa
     cagataattc 1261 agaaatcagt tctgctacaa aattacgtca gcttaaggct tttaagtctg
     tgttggctga 1321 tattaagaag gctcatcttg cattggaaga agacttaaat tccgagtttc
     gagcgatgga 1381 tgctgtaaac aaagagaaaa ataccaaaga gcataaagtc atagatgcta
     agtttgaaac 1441 aaaagcacga aaaggagaaa aaccttgtgc tttggaaaag aaggatattt
     caaagtcaga
```

-continued

```
1501  agctaaactt tcaagaaaac aggtagatag tgagcacatg catcagaatg
      ttccaacaga
1561  ggaacaaaga acaaataaaa gtaccggtgg tgaacataag aaatctgata
      gaaaagaaga
1621  acctcaatat gaacctgcca acacttctga agatttagac atggatattg
      tgtctgttcc
1681  ttcctcagtt ccagaagaca ttttttgagaa tcttgagact gctatggaag
      ttcagagttc
1741  agttgatcat caaggggatg gcagcagtgg aactgaacaa gaagtggaga
      gttcatctgt
1801  aaaattaaat atttcttcaa aagacaacag aggaggtatt aaatcaaaaa
      ctacagctaa
1861  agtaacaaaa gaattatatg ttaaactcac tcctgtttcc ctttctaatt
      ccccaattaa
1921  aggtgctgat tgtcaggaag ttccacaaga taaagatggc tataaaagtt
      gtggtctgaa
1981  ccccaagtta gagaaatgtg gacttggaca ggaaaacagt gataatgagc
      atttggttga
2041  aaatgaagtt tcattacttt tagaggaatc tgatcttcga agatccccac
      gtgtaaagac
2101  tacacccttg aggcgaccga cagaaactaa ccctgtaaca tctaattcag
      atgaagaatg
2161  taatgaaaca gttaaggaga aacaaaaact atcagttcca gtgagaaaaa
      aggataagcg
2221  taattcttct gacagtgcta tagataatcc taagcctaat aaaattgccaa
      aatctaagca
2281  atcagagact gtggatcaaa attcagattc tgatgaaatg ctagcaatcc
      tcaaagaggt
2341  gagcaggatg agtcacagtt cttcttcaga tactgatatt aatgaaattc
      atacaaacca
2401  taagactttg tatgatttaa agactcaggc ggggaaagat gataaaggaa
      aaaggaaacg
2461  aaaaagttct acatctggct cagattttga tactaaaaag ggcaaatcag
      ctaagagctc
2521  tataatttct aaaaagaaac gacaaaccca gtctgagtct tctaattatg
      actcagaatt
2581  agaaaaagag ataaagagca tgagtaaaat tggtgctgcc agaaccacca
      aaaaaagaat
2641  tccaaataca aaagattttg actcttctga agatgagaaa cacagcaaaa
      aaggaatgga
```

-continued

```
2701 taatcaaggg cacaaaaatt tgaagacctc acaagaagga tcatctgatg
     atgctgaaag 2761 aaaacaagag agagagactt tctcttcagc agaaggcaca gttgataaag
     acacgaccat 2821 catggaatta agagatcgac ttcctaagaa gcagcaagca agtgcttcca
     ctgatggtgt 2881 cgataagctt tctgggaaag agcagagttt tacttctttg gaagttagaa
     aagttgctga 2941 aactaaagaa aagagcaagc atctcaaaac caaaacatgt aaaaaagtac
     aggatggctt 3001 atctgatatt gcagagaaat tcctaaagaa agaccagagc gatgaaactt
     ctgaagatga 3061 taaaaagcag agcaaaaagg gaactgaaga aaaaaagaaa ccttcagact
     ttaagaaaaa 3121 agtaattaaa atggaacaac agtatgaatc ttcatctgat ggcactgaaa
     agttacctga 3181 gcgagaagaa atttgtcatt ttcctaaggg cataaaacaa attaagaatg
     gaacaactga 3241 tggagaaaag aaaagtaaaa aaataagaga taaaacttct aaaaagaagg
     atgaattatc 3301 tgattatgct gagaagtcaa cagggaaagg agatagttgt gactcttcag
     aggataaaaa 3361 gagtaagaat ggagcatatg gtagagagaa gaaaaggtgc aagttgcttg
     gaaagagttc 3421 aaggaagaga caagattgtt catcatctga tactgagaaa tattccatga
     aagaagatgg 3481 ttgtaactct tctgataaga gactgaaaag aatagaattg agggaaagaa
     gaaatttaag 3541 ttcaaagaga aatactaagg aaatacaaag tggctcatca tcatctgatg
     ctgaggaaag 3601 ttctgaagat aataaaaaga gaagcaaag aacttcatct aaaaagaagg
     cagtcattgt 3661 caaggagaaa aagagaaact ccctaagaac aagcactaaa aggaagcaag
     ctgacattac 3721 atcctcatct tcttctgata tagaagatga tgatcagaat tctataggtg
     agggaagcag 3781 cgatgaacag aaaattaagc ctgtgactga aaatttagtg ctgtcttcac
     atactggatt 3841 ttgccaatct tcaggagatg aagccttatc taaatcagtg cctgtcacag
     tggatgatga
```

```
3901  tgatgacgac aatgatcctg agaatagaat tgccaagaag atgcttttag
      aagaaattaa
3961  agccaatctt tcctctgatg aggatggatc ttcagatgat gagccagaag
      aagggaaaaa
4021  aagaactgga aaacaaaatg aagaaaaccc aggagatgag gaagcaaaaa
      atcaagtcaa
4081  ttctgaatca gattcagatt ctgaagaatc taagaagcca agatacagac
      ataggctttt
4141  gcggcacaaa ttgactgtga gtgacggaga atctggagaa gaaaaaaaga
      caaagcctaa
4201  agagcataaa gaagtcaaag gcagaaacag aagaaaggtg agcagtgaag
      attcagaaga
4261  ttctgatttt caggaatcag gagttagtga agaagttagt gaatccgaag
      atgaacagcg
4321  gcccagaaca aggtctgcaa agaaagcaga gttggaagaa aatcagcgga
      gctataaaca
4381  gaaaagaaa aggcgacgta ttaaggttca agaagattca tccagtgaaa
      acaagagtaa
4441  ttctgaggaa gaagaggagg aaaaagaaga ggaggaggaa gaggaggagg
      aggaggaaga
4501  ggaggaggaa gatgaaaatg atgattccaa gtctcctgga aaaggcagaa
      agaaaattcg
4561  gaagattctt aaagatgata aactgagaac agaaacacaa aatgctctta
      aggaagagga
4621  agagagacga aaacgtattg ctgagaggga gcgtgagcga gaaaaattga
      gagaggtgat
4681  agaaattgaa gatgcttcac ccaccaagtg tccaataaca accaagttgg
      ttttagatga
4741  agatgaagaa accaaagaac ctttagtgca ggttcataga aatatggtta
      tcaaattgaa
4801  accccatcaa gtagatggtg ttcagtttat gtgggattgc tgctgtgagt
      ctgtgaaaaa
4861  aacaaagaaa tctccaggtt caggatgcat tcttgcccac tgtatgggcc
      ttggtaagac
4921  tttacaggtg gtaagttttc ttcatacagt tcttttgtgt gacaaactgg
      atttcagcac
4981  ggcgttagtg gtttgtcctc ttaatactgc tttgaattgg atgaatgaat
      ttgagaagtg
5041  gcaagaggga ttaaaagatg atgagaagct tgaggtttct gaattagcaa
      ctgtgaaacg
```

```
5101  tcctcaggag agaagctaca tgctgcagag gtggcaagaa gatggtggtg
      ttatgatcat 5161  aggctatgag atgtatagaa atcttgctca aggaaggaat gtgaagagtc
      ggaaacttaa 5221  agaaatattt aacaaagctt tggttgatcc aggccctgat tttgttgttt
      gtgatgaagg 5281  ccatattcta aaaaatgaag catctgctgt ttctaaagct atgaattcta
      tacgatcaag 5341  gaggaggatt attttaacag gaacaccact tcaaaataac ctaattgagt
      atcattgtat 5401  ggttaatttt atcaaggaaa atttacttgg atccattaag gagttcagga
      atagatttat 5461  aaatccaatt caaaatggtc agtgtgcaga ttctaccatg gtagatgtca
      gagtgatgaa 5521  aaaacgtgct cacattctct atgagatgtt agctggatgt gttcagagga
      aagattatac 5581  agcattaaca aaattcttgc ctccaaaaca cgaatatgtg ttagctgtga
      gaatgacttc 5641  tattcagtgc aagctctatc agtactactt agatcactta acaggtgtgg
      gcaataatag 5701  tgaaggtgga agaggaaagg caggtgcaaa gcttttccaa gattttcaga
      tgttaagtag 5761  aatatggact catccttggt gtttgcagct agactacatt agcaaagaaa
      ataagggtta 5821  ttttgatgaa gacagtatgg atgaatttat agcctcagat tctgatgaaa
      cctccatgag 5881  tttaagctcc gatgattata caaaaaagaa gaaaaaaggg aaaaagggga
      aaaagatag 5941  tagctcaagt ggaagtggca gtgacaatga tgttgaagtg attaaggtct
      ggaattcaag 6001  atctcgggga ggtggtgaag gaaatgtgga tgaaacagga aacaatcctt
      ctgtttcttt 6061  aaaactggaa gaaagtaaag ctacttcttc ttctaatcca agcagcccag
      ctccagactg 6121  gtacaaagat tttgttacag atgctgatgc tgaggtttta gagcattctg
      ggaaaatggt 6181  acttctcttt gaaattcttc gaatggcaga ggaaattggg gataaagtcc
      ttgttttcag 6241  ccagtccctc atatctctgg acttgattga agattttctt gaattagcta
      gtagggagaa
```

-continued

```
6301  gacagaagat aaagataaac cccttattta taaaggtgag gggaagtggc
      ttcgaaacat
6361  tgactattac cgtttagatg gttccactac tgcacagtca aggaagaagt
      gggctgaaga
6421  atttaatgat gaaactaatg tgagaggacg attatttatc atttctacta
      aagcaggatc
6481  tctaggaatt aatctggtag ctgctaatcg agtaattata ttcgacgctt
      cttggaatcc
6541  atcttatgac atccagagta tattcagagt ttatcgcttt ggacaaacta
      agcctgttta
6601  tgtatatagg ttcttagctc agggaaccat ggaagataag atttatgatc
      ggcaagtaac
6661  taagcagtca ctgtcttttc gagttgttga tcagcagcag gtggagcgtc
      attttactat
6721  gaatgagctt actgaacttt atacttttga gccagactta ttagatgacc
      ctaattcaga
6781  aaagaagaag aagagggata ctcccatgct gccaaaggat accatacttg
      cagagctcct
6841  tcagatacat aaagaacaca ttgtaggata ccatgaacat gattctcttt
      tggaccacaa
6901  agaagaagaa gagttgactg aagaagaaag aaaagcagct tgggctgagt
      atgaagcaga
6961  gaagaaggga ctgaccatgc gtttcaacat accaactggg accaatttac
      ccctgtcag
7021  tttcaactct caaactcctt atattccttt caatttggga gccctgtcag
      caatgagtaa
7081  tcaacagctg gaggacctca ttaatcaagg aagagaaaaa gttgtagaag
      caacaaacag
7141  tgtgacagca gtgaggattc aacctcttga ggatataatt tcagctgtat
      ggaaggagaa
7201  catgaatctc tcagaggccc aagtacaggc gttagcatta agtagacaag
      ccagccagga
7261  gcttgatgtt aaacgaagag aagcaatcta caatgatgta ttgacaaaac
      aacagatgtt
7321  aatcagctgt gttcagcgaa tacttatgaa cagaaggctc cagcagcagt
      acaatcagca
7381  gcaacagcaa caaatgactt atcaacaagc aacactgggt cacctcatga
      tgccaaagcc
7441  cccaaatttg atcatgaatc cttctaacta ccagcagatt gatatgagag
      gaatgtatca
```

-continued

```
7501  gccagtggct ggtggtatgc agccaccacc attacagcgt gcaccacccc
      caatgagaag
7561  caaaaatcca ggaccttccc aagggaaatc aatgtgattt tgcactaaaa
      gcttaatgga
7621  ttgttaaaat catagaaaga tcttttattt ttttaggaat caatgactta
      acagaactca
7681  actgtataaa tagtttggtc cccttaaatg ccaatcttcc atattagttt
      tacttttttt
7741  tttttaaat agggcatacc atttcttcct gacatttgtc agtgatgttg
      cctagaatct
7801  tcttacacac gctgagtaca gaagatattt caaattgttt tcagtgaaaa
      caagtccttc
7861  cataatagta acaactccac agatttcctc tctaaatttt tatgcctgct
      tttagcaacc
7921  ataaaattgt cataaaatta ataaatttag gaagaataa agatttatat
      attcattctt
7981  tacatataaa aacacacagc tgagttctta gagttgattc ctcaagttat
      gaaatacttt
8041  tgtacttaat ccatttcttg attaaagtga ttgaaatggt tttaatgttc
      ttttgactga
8101  agtctgaaac tgggctcctg ctttattgtc tctgtgactg aaagttagaa
      actgagggtt
8161  atctttgaca cagaattgtg tgcaatattc ttaaatacta ctgctctaaa
      agttggagaa
8221  gtcttgcagt tatcttagca ttgtataaac agccttaagt atagcctaag
      aagagaattc
8281  cttttctcc tttagtcctt ctgccatttt ttatttcag ttatatgtgc
      tgaaataatt
8341  actggtaaaa tttcagggtt gtggattatc ttccacacat gaattttctc
      tctcctggca
8401  cgaatataaa gcacatctct taactgcatg gtgccagtgc taatgcttca
      tcctgttgct
8461  ggcagtggga tgtggactta gaaaatcaag ttctagcatt ttagtaggtt
      aacactgaag
8521  ttgtggttgt taggttcaca ccctgtttta taaacaacat caaaatggca
      gaaccattgc
8581  tgactttagg ttcacatgag gaatgtactt ttaacaattc ccagtactat
      cagtattgtg
8641  aaataattcc tctgaaagat aagaatcact ggcttctatg cgcttctttt
      ctctcatcat
```

-continued

```
8701  catgttcttt taccccagtt tccttacatt tttttaaatt gtttcagagt
      ttgtttttt
8761  tttagtttag attgtgaggc aattattaaa tcaaaattaa ttcatccaat
      accccttac
8821  tagaagtttt actagaaaat gtattacatt ttattttttc ttaatccagt
      tctgcaaaaa
8881  tgacctataa atttattcat gtacaatttt ggttacttga attgttaaag
      aaaacattgt
8941  ttttgactat gggagtcaac tcaacatggc agaaccattt ttgagatgat
      gatacaacag
9001  gtagtgaaac agcttaagaa ttccaaaaaa aaaaaaaaaa aaaaaaaaa
      gaaaactggg
9061  tttgggcttt gctttaggta tcactggatt agaatgagtt taacattagc
      taaaactgct
9121  ttgagttgtt tggatgatta agagattgcc attttatct tggaagaact
      agtggtaaaa
9181  catccaagag cactaggatt gtgatacaga atttgtgagg tttggtggat
      ccacgcccct
9241  ctcccccact ttcccatgat gaaatatcac taataaatcc tgtatattta
      gatattatgc
9301  tagccatgta atcagattta tttaattggg tggggcaggt gtgtatttac
      tttagaaaaa
9361  atgaaaaaga caagatttat gagaaatatt tgaaggcagt acactctggc
      caactgttac
9421  cagttggtat ttctacaagt tcagaatatt ttaaacctga tttactagac
      ctgggaattt
9481  tcaacatggt ctaattattt actcaaagac atagatgtga aaattttagg
      caaccttcta
9541  aatcttttc accatggatg aaactataac ttaaagaata atacttagaa
      gggttaattg
9601  gaaatcagag tttgaaataa aacttggacc actttgtata cactcttctc
      acttgacatt
9661  ttagctatat aatatgtact tgagtataa catcaagctt taacaaatat
      ttaaagacaa
9721  aaaaatcacg tcagtaaaat actaaaaggc tcattttat atttgtttta
      gatgttttaa
9781  atagttgcaa tggattaaaa atgatgattt aaaatgttgc ttgtaataca
      gttttgcctg
9841  ctaaattctc cacattttgt aacctgtttt atttctttgg gtgtaaagcg
      tttttgctta
```

-continued

```
 9901 gtattgtgat attgtatatg ttttgtccca gttgtatagt aatgtttcag
      tccatcatcc
 9961 agctttggct gctgaaatca tacagctgtg aagacttgcc tttgtttctg
      ttagactgct
10021 tttcagttct gtattgagta tcttaagtac tgtagaaaag atgtcacttc
      ttcctttaag
10081 gctgttttgt aatatatata aggactggaa ttgtgttttt aaagaaaagc
      attcaagtat
10141 gacaatatac tatctgtgtt ttcaccattc aaagtgctgt ttagtagttg
      aaacttaaac
10201 tatttaatgt catttaataa agtgaccaaa atgtgttgtg ctctttattg
      tattttcaca
10261 gctttgaaaa tctgtgcaca tactgtttca tagaaaatgt atagcttttg
      ttgtcctata
10321 taatggtggt tcttttgcac atttagttat ttaatattga gaggtcacga
      agtttggtta
10381 ttgaatctgt tatatactaa attctgtaaa gggagatctc tcatctcaaa
      aagaatttac
10441 ataccaggaa gtccatgtgt gtttgtgtta gttttggatg tctttgtgta
      atccagcccc
10501 atttcctgtt tcccaacagc tgtaacactc attttaagtc aagcagggct
      accaacccac
10561 acttgataga aaagctgctt accattcaga agcttcctta ttacctggcc
      tccaaatgag
10621 ctgaatattt tgtagccttc ccttagctat gttcattttc cctccattat
      cataaaatca
10681 gatcgatatt tatgtgcccc aaacaaaact ttaagagcag ttacattctg
      tcccagtagc
10741 ccttgttttcc tttgagagta gcatgttgtg aggctataga gacttattct
      accagtaaaa
10801 caggtcaatc cttttacatg tttattatac taaaaattat gttcagggta
      tttactactt
10861 tatttcacca gactcagtct caagtgactt ggctatctcc aaatcagatc
      tacccttaga
10921 gaataaacat ttttctaccg ttatttttt tcaagtctat aatctgagcc
      agtcccaaag
10981 gagtgatcaa gtttcagaaa tgctttcatc ttcacaacat tttatatata
      ctattatatg
11041 gggtgaataa agttttaaat ccgaaatata aaaaaaaaa aaaaaaa
```

A subject in need thereof may have reduced expression, haploinsufficiency, and/or loss of function of ARID1A. For example, a subject may comprise a mutation selected from the group consisting of a nonsense mutation for the wild type residue cysteine (C) at amino acid position 884 of SEQ ID NO: 11 (C884*), a substitution of lysine (K) for the wild type residue glutamic acid (E) at amino acid position 966 (E966K), a nonsense mutation for the wild type residue glutamine (Q) at amino acid position 1411 of SEQ ID NO: 11 (Q1411*), a frame shift mutation at the wild type residue phenylalanine (F) at amino acid position 1720 of SEQ ID NO: 11 (F1720fs), a frame shift mutation after the wild type residue glycine (G) at amino acid position 1847 of SEQ ID NO: 11 (G1847fs), a frame shift mutation at the wild type residue cysteine (C) at amino acid position 1874 of SEQ ID NO: 11 (C1874fs), a substitution of glutamic acid (E) for the wild type residue aspartic acid (D) at amino acid position 1957 (D1957E), a nonsense mutation for the wild type residue glutamine (Q) at amino acid position 1430 of SEQ ID NO: 11 (Q1430*), a frame shift mutation at the wild type residue arginine (R) at amino acid position 1721 of SEQ ID NO: 11 (R1721fs), a substitution of glutamic acid (E) for the wild type residue glycine (G) at amino acid position 1255 (G1255E), a frame shift mutation at the wild type residue glycine (G) at amino acid position 284 of SEQ ID NO: 11 (G284fs), a nonsense mutation for the wild type residue arginine (R) at amino acid position 1722 of SEQ ID NO: 11 (R1722*), a frame shift mutation at the wild type residue methionine (M) at amino acid position 274 of SEQ ID NO: 11 (M274fs), a frame shift mutation at the wild type residue glycine (G) at amino acid position 1847 of SEQ ID NO: 11 (G1847fs), a frame shift mutation at the wild type residue P at amino acid position 559 of SEQ ID NO: 11 (P559fs), a nonsense mutation for the wild type residue arginine (R) at amino acid position 1276 of SEQ ID NO: 11 (R1276*), a frame shift mutation at the wild type residue glutamine (Q) at amino acid position 2176 of SEQ ID NO: 11 (Q2176fs), a frame shift mutation at the wild type residue histidine (H) at amino acid position 203 of SEQ ID NO: 11 (H203fs), a frame shift mutation at the wild type residue alanine (A) at amino acid position 591 of SEQ ID NO: 11 (A591fs), a nonsense mutation for the wild type residue glutamine (Q) at amino acid position 1322 of SEQ ID NO: 11 (Q1322*), a nonsense mutation for the wild type residue serine (S) at amino acid position 2264 of SEQ ID NO: 11 (S2264*), a nonsense mutation for the wild type residue glutamine (Q) at amino acid position 586 of SEQ ID NO: 11 (Q586*), a frame shift mutation at the wild type residue glutamine (Q) at amino acid position 548 of SEQ ID NO: 11 (Q548fs), and a frame shift mutation at the wild type residue asparagine (N) at amino acid position 756 of SEQ ID NO: 11 (N756fs). "*" used herein refers to a stop codon. "fs" used herein refers to a frame shift.

```
AT-rich interactive domain-containing protein 1A (ARID1A)
isoform a [Homo sapiens]
                                                    (SEQ ID NO: 9)
     1  maaqvapaaa sslgnppppp pselkkaeqq qreeaggeaa aaaaaergem
        kaaagqeseg 61  pavgppqplg kelqdgaesn ggggggags gggpgaepdl knsngnagpr
        palnnnltep 121  pgggggssd gvgapphsaa aalpppaygf gqpygrspsa vaaaaaavfh
        qqhggqqspg 181  laalqsgggg glepyagpqq nshdhgfpnh qynsyypnrs aypppapaya
        lssprggtpg 241  sgaaaaagsk pppsssasas sssssfaqqr fgamggggps aagggtpqpt
        atptlnqllt 301  spssargyqg ypggdysggp qdggagkgpa dmasqcwgaa aaaaaaaas
        ggaqqrshha 361  pmspgssggg gqplartpqp sspmdgmgkm rpqpyggtnp ysqqqgppsg
        pqqghgypgq 421  pygsqtpqry pmtmqgraqs amgglsytqq ippygqqgps gygqqgqtpy
        ynqqsphpqq 481  qqppysqqpp sqtphaqpsy qqqpqsqppq lqssqppysq qpsqpphqqs
        papypsqqst 541  tqqhpqsqpp ysqpqaqspy qqqqpqqpap stlsqqaayp qpqsqqsqqt
        aysqqrfppp 601  qelsqdsfgs qassapsmts skggqedmnl slqsrpsslp dlsgsiddlp
        mgtegalspg 661  vstsgisssq geqsnpaqsp fsphtsphlp girgpspspv gspasvaqsr
        sgplspaavp 721  gnqmpprpps gqsdsimhps mngssiaqdr gymqrnpqmp qysspqpgsa
        lsprqpsggq 781  ihtgmgsyqq nsmgsygpqg gqygpqggyp rqpnynalpn anypsagmag
        ginpmgaggq 841  mhgqpgippy gtlppgrmsh asmgnrpygp nmanmppqvg sgmcpppggm
        nrktqetava
```

-continued

```
 901  mhvaansiqn rppgypnmnq ggmmgtgppy gqginsmagm inpqgppysm
      ggtmannsag 961  maaspemmgl gdvkltpatk mnnkadgtpk teskskksss stttnekitk
      lyelggeper 1021  kmwvdrylaf teekamgmtn lpavgrkpld lyrlyvsvke iggltqvnkn
      kkwrelatnl 1081  nvgtsssaas slkkgyiqcl yafeckierg edpppdifaa adskksqpki
      qppspagsgs 1141  mqgpqtpgst sssmaeggdl kpptpastph sqipplpgms rsnsvgiqda
      fndgsdstfq 1201  krnsmtpnpg yqpsmntsdm mgrmsyepnk dpygsmrkap gsdpfmssgq
      gpnggmgdpy 1261  sraagpglgn vamgprqhyp yggpydrvrt epgigpegnm stgapqpnlm
      psnpdsgmys 1321  psryppqqqq qqqqrhdsyg nqfstqgtps gspfpsqqtt myqqqqnyk
      rpmdgtygpp 1381  akrhegemys vpystgqgqp qqqqlppaqp qpasqqqaaq pspqqdvynq
      ygnaypatat 1441  aaterrpagg pqnqfpfqfg rdrvsappgt naqqnmppqm mggpiqasae
      vaqqgtmwqg 1501  rndmtynyan rqstgsapqg payhgvnrtd emlhtdqran hegswpshgt
      rqppygpsap 1561  vppmtrppps nyqpppsmqn hipqvsspap lprpmenrts pskspflhsg
      mkmqkagppv 1621  pashiapapv qppmirrdit fppgsveatq pvlkgrrrlt mkdigtpeaw
      rvmmslksgl 1681  laestwaldt inillyddns imtfnlsqlp gllellveyf rrclieifgi
      lkeyevgdpg 1741  qrtlldpgrf skvsspapme ggeeeeellg pkleeeeeee vvendeeiaf
      sgkdkpasen 1801  seekliskfd klpvkivqkn dpfvvdcsdk lgrvqefdsg llhwrigggd
      ttehiqthfe 1861  sktellpsrp hapcppaprk hvttaegtpg ttdgegpppd gppekritat
      mddmlstrss 1921  tltedgakss eaikesskfp fgispaqshr nikiledeph skdetplctl
      ldwqdslakr 1981  cvcvsntirs lsfvpgndfe mskhpgllli lgkllillhhk hperkqaplt
      yekeeeqdqg 2041  vscnkvewww dclemlrent lvtlanisgq ldlspypesi clpvldgllh
      wavcpsaeaq 2101  dpfstlgpna vlspqrlvle tlsklsiqdn nvdlilatpp fsrleklyst
      mvrflsdrkn 2161  pvcremavvl lanlaggdsl aaraiavqkg signllgfle dslaatqfqq
      sgasllhmqn 2221  ppfeptsvdm mrraaralla lakvdenhse ftlyesrlld isysplmnsl
      vsqvicdvlf 2281  ligqs
```

*Homo sapiens* AT rich interactive domain 1A (SWI-like) (ARID1A), transcript variant 1, mRNA (SEQ ID NO: 10)

```
   1  cagaaagcgg agagtcacag cggggccagg ccctggggag cggagcctcc
      accgccccc 61  tcattcccag gcaagggctt gggggaatg agccgggaga gccgggtccc
      gagcctacag
```

```
 121 agccgggagc agctgagccg ccggcgcctc ggccgccgcc gccgcctcct
     cctcctccgc 181 cgccgccagc ccggagcctg agccggcggg gcggggggga gaggagcgag
     cgcagcgcag 241 cagcggagcc ccgcgaggcc cgcccgggcg ggtggggagg gcagcccggg
     ggactgggcc 301 ccggggcggg gtgggagggg gggagaagac gaagacaggg ccgggtctct
     ccgcggacga 361 gacagcgggg atcatggccg cgcaggtcgc ccccgccgcc gccagcagcc
     tgggcaaccc 421 gccgccgccg ccgcccctcg gagctgaagaa agccgagcag cagcagcggg
     aggaggcggg 481 gggcgaggcg cggcggcgg cagcggccga cgcgggaa atgaaggcag
     ccgccgggca 541 ggaaagcgag ggccccgccg tggggccgcc gcagccgctg ggaaaggagc
     tgcaggacgg 601 ggccgagagc aatggggtg gcggcggcgg cggagccggc agcggcggcg
     ggcccggcgc 661 ggagccggac ctgaagaact cgaacgggaa cgcgggccct aggcccgccc
     tgaacaataa 721 cctcacggag ccgcccggcg gcggcggtgg cggcagcagc gatggggtgg
     gggcgcctcc 781 tcactcagcc gcggccgcct tgccgccccc agcctacggc ttcgggcaac
     cctacggccg 841 gagcccgtct gccgtcgccg ccgccgcggc cgccgtcttc caccaacaac
     atggcggaca 901 acaaagcccc ggcctggcag cgctgcagag cggcggcggc ggggcctgg
     agccctacgc 961 ggggcccag cagaactctc acgaccacgg cttccccaac caccagtaca
     actcctacta 1021 ccccaaccgc agcgcctacc ccccgcccgc cccggcctac gcgctgagct
     ccccgagagg 1081 tggcactccg ggctccggcg cggcggcggc tgccggctcc aagccgcctc
     cctcctccag 1141 cgcctccgcc tcctcgtcgt cttcgtcctt cgctcagcag cgcttcgggg
     ccatggggg 1201 aggcggcccc tccgcggccg gcggggggaac tccccagccc accgccaccc
     ccaccctcaa 1261 ccaactgctc acgtcgccca gctcggcccg ggctaccag ggctaccccg
     ggggcgacta 1321 cagtggcggg ccccaggacg ggggcgccgg caagggcccg gcggacatgg
     cctcgcagtg 1381 ttgggggct gcggcggcgg cagctgcggc ggcggccgcc tcgggagggg
     cccaacaaag 1441 gagccaccac gcgcccatga gccccgggag cagcggcggc gggggcagc
     cgctcgcccg 1501 gacccctcag ccatccagtc caatggatca gatgggcaag atgagacctc
     agccatatgg 1561 cgggactaac ccatactcgc agcaacaggg acctccgtca ggaccgcagc
     aaggacatgg 1621 gtacccaggg cagccatacg ggtcccagac cccgcagcgg taccgatga
     ccatgcaggg 1681 ccgggcgcag agtgccatgg gcggcctctc ttatacacag cagattcctc
     cttatggaca
```

-continued

```
1741  acaaggcccc agcgggtatg gtcaacaggg ccagactcca tattacaacc
      agcaaagtcc 1801  tcaccctcag cagcagcagc caccctactc ccagcaacca ccgtcccaga
      cccctcatgc 1861  ccaaccttcg tatcagcagc agccacagtc tcaaccacca cagctccagt
      cctctcagcc 1921  tccatactcc cagcagccat cccagcctcc acatcagcag tccccggctc
      catacccctc 1981  ccagcagtcg acgacacagc agcaccccca gagccagccc ccctactcac
      agccacaggc 2041  tcagtctcct taccagcagc agcaacctca gcagccagca ccctcgacgc
      tctcccagca 2101  ggctgcgtat cctcagcccc agtctcagca gtcccagcaa actgcctatt
      cccagcagcg 2161  cttccctcca ccgcaggagc tatctcaaga ttcatttggg tctcaggcat
      cctcagcccc 2221  ctcaatgacc tccagtaagg gagggcaaga agatatgaac ctgagccttc
      agtcaagacc 2281  ctccagcttg cctgatctat ctggttcaat agatgacctc cccatgggga
      cagaaggagc 2341  tctgagtcct ggagtgagca catcagggat ttccagcagc caaggagagc
      agagtaatcc 2401  agctcagtct cctttctctc ctcatacctc ccctcacctg cctggcatcc
      gaggcccttc 2461  cccgtcccct gttggctctc ccgccagtgt tgctcagtct cgctcaggac
      cactctcgcc 2521  tgctgcagtg ccaggcaacc agatgccacc tcggccaccc agtggccagt
      cggacagcat 2581  catgcatcct tccatgaacc aatcaagcat tgcccaagat cgaggttata
      tgcagaggaa 2641  cccccagatg ccccagtaca gttcccccca gcccggctca gccttatctc
      cgcgtcagcc 2701  ttccggagga cagatacaca caggcatggg ctcctaccag cagaactcca
      tggggagcta 2761  tggtccccag ggggtcagt atggcccaca aggtggctac cccaggcagc
      caaactataa 2821  tgccttgccc aatgccaact accccagtgc aggcatggct ggaggcataa
      accccatggg 2881  tgccggaggt caaatgcatg gacagcctgg catcccacct tatggcacac
      tccctccagg 2941  gaggatgagt cacgcctcca tgggcaaccg gccttatggc cctaacatgg
      ccaatatgcc 3001  acctcaggtt gggtcaggga tgtgtccccc accaggggc atgaaccgga
      aaacccaaga 3061  aactgctgtc gccatgcatg ttgctgccaa ctctatccaa aacaggccgc
      caggctaccc 3121  caatatgaat caaggggca tgatgggaac tggacctcct tatggacaag
      ggattaatag 3181  tatggctggc atgatcaacc ctcagggacc cccatattcc atgggtggaa
      ccatggccaa 3241  caattctgca gggatggcag ccagcccaga gatgatgggc cttggggatg
      taaagttaac 3301  tccagccacc aaaatgaaca acaaggcaga tgggacaccc aagacagaat
      ccaaatccaa
```

```
3361  gaaatccagt tcttctacta caaccaatga gaagatcacc aagttgtatg
      agctgggtgg 3421  tgagcctgag aggaagatgt gggtggaccg ttatctggcc ttcactgagg
      agaaggccat 3481  gggcatgaca aatctgcctg ctgtgggtag gaaacctctg gacctctatc
      gcctctatgt 3541  gtctgtgaag gagattggtg gattgactca ggtcaacaag aacaaaaaat
      ggcgggaact 3601  tgcaaccaac ctcaatgtgg gcacatcaag cagtgctgcc agctccttga
      aaaagcagta 3661  tatccagtgt ctctatgcct ttgaatgcaa gattgaacgg ggagaagacc
      ctcccccaga 3721  catctttgca gctgctgatt ccaagaagtc ccagcccaag atccagcctc
      cctctcctgc 3781  gggatcagga tctatgcagg ggcccagac tccccagtca accagcagtt
      ccatggcaga 3841  aggaggagac ttaaagccac caactccagc atccacacca cacagtcaga
      tcccccatt 3901  gccaggcatg agcaggagca attcagttgg gatccaggat gcctttaatg
      atggaagtga 3961  ctccacattc cagaagcgga attccatgac tccaaaccct gggtatcagc
      ccagtatgaa 4021  tacctctgac atgatggggc gcatgtccta tgagccaaat aaggatcctt
      atggcagcat 4081  gaggaaagct ccagggagtg atcccttcat gtcctcaggg cagggcccca
      acggcgggat 4141  gggtgacccc tacagtcgtg ctgccggccc tgggctagga aatgtggcga
      tgggaccacg 4201  acagcactat ccctatggag gtccttatga cagagtgagg acggagcctg
      gaatagggcc 4261  tgagggaaac atgagcactg gggccccaca gccgaatctc atgccttcca
      acccagactc 4321  ggggatgtat tctcctagcc gctaccccc gcagcagcag cagcagcagc
      agcaacgaca 4381  tgattcctat ggcaatcagt tctccaccca aggcacccct tctggcagcc
      ccttcccag 4441  ccagcagact acaatgtatc aacagcaaca gcagaattac aagcggccaa
      tggatggcac 4501  atatggccct cctgccaagc ggcacgaagg ggagatgtac agcgtgccat
      acagcactgg 4561  gcaggggcag cctcagcagc agcagttgcc cccagcccag ccccagcctg
      ccagccagca 4621  acaagctgcc cagccttccc ctcagcaaga tgtatacaac cagtatggca
      atgcctatcc 4681  tgccactgcc acagctgcta ctgagcgccg accagcaggc ggcccccaga
      accaatttcc 4741  attccagttt ggccgagacc gtgtctctgc acccctggc accaatgccc
      agcaaaacat 4801  gccaccacaa atgatgggcg gccccataca ggcatcagct gaggttgctc
      agcaaggcac 4861  catgtggcag gggcgtaatg acatgaccta taattatgcc aacaggcaga
      gcacgggctc 4921  tgccccccag ggccccgcct atcatggcgt gaaccgaaca gatgaaatgc
      tgcacacaga
```

```
-continued
4981  tcagagggcc aaccacgaag gctcgtggcc ttcccatggc acacgccagc
      ccccatatgg 5041  tccctctgcc cctgtgcccc ccatgacaag gcccctcca tctaactacc
      agcccccacc 5101  aagcatgcag aatcacattc ctcaggtatc cagccctgct ccctgcccc
      ggccaatgga 5161  gaaccgcacc tctcctagca agtctccatt cctgcactct gggatgaaaa
      tgcagaaggc 5221  aggtccccca gtacctgcct cgcacatagc acctgcccct gtgcagcccc
      ccatgattcg 5281  gcgggatatc accttcccac ctggctctgt tgaagccaca cagcctgtgt
      tgaagcagag 5341  gaggcggctc acaatgaaag acattggaac cccggaggca tggcgggtaa
      tgatgtccct 5401  caagtctggt ctcctggcag agagcacatg ggcattagat accatcaaca
      tcctgctgta 5461  tgatgacaac agcatcatga ccttcaacct cagtcagctc ccagggttgc
      tagagctcct 5521  tgtagaatat ttccgacgat gcctgattga gatctttggc attttaaagg
      agtatgaggt 5581  gggtgaccca ggacagagaa cgctactgga tcctgggagg ttcagcaagg
      tgtctagtcc 5641  agctcccatg gagggtgggg aagaagaaga agaacttcta ggtcctaaac
      tagaagagga 5701  agaagaagag gaagtagttg aaaatgatga ggagatagcc ttttcaggca
      aggacaagcc 5761  agcttcagag aatagtgagg agaagctgat cagtaagttt gacaagcttc
      cagtaaagat 5821  cgtacagaag aatgatccat ttgtggtgga ctgctcagat aagcttgggc
      gtgtgcagga 5881  gtttgacagt ggcctgctgc actggcggat tggtgggggg gacaccactg
      agcatatcca 5941  gacccacttc gagagcaaga cagagctgct gccttcccgg cctcacgcac
      cctgcccacc 6001  agcccctcgg aagcatgtga caacagcaga gggtacacca gggacaacag
      accaggaggg 6061  gcccccacct gatggacctc cagaaaaacg gatcacagcc actatggatg
      acatgttgtc 6121  tactcggtct agcaccttga ccgaggatgg agctaagagt tcagaggcca
      tcaaggagag 6181  cagcaagttt ccatttggca ttagcccagc acagagccac cggaacatca
      agatcctaga 6241  ggacgaaccc cacagtaagg atgagacccc actgtgtacc cttctggact
      ggcaggattc 6301  tcttgccaag cgctgcgtct gtgtgtccaa taccattcga agcctgtcat
      ttgtgccagg 6361  caatgacttt gagatgtcca acacccagg gctgctgctc atcctgggca
      agctgatcct 6421  gctgcaccac aagcacccag aacggaagca ggcaccacta acttatgaaa
      aggaggagga 6481  acaggaccaa ggggtgagct gcaacaaagt ggagtggtgg tgggactgct
      tggagatgct 6541  ccgggaaaac accttggtta cactcgccaa catctcgggg cagttggacc
      tatctccata
```

```
6601  ccccgagagc atttgcctgc ctgtcctgga cggactccta cactgggcag
      tttgcccttc 6661  agctgaagcc caggacccct tttccaccct gggcccaat gccgtccttt
      ccccgcagag 6721  actggtcttg gaaaccctca gcaaactcag catccaggac aacaatgtgg
      acctgattct 6781  ggccacaccc cccttcagcc gcctggagaa gttgtatagc actatggtgc
      gcttcctcag 6841  tgaccgaaag aacccggtgt gccgggagat ggctgtggta ctgctggcca
      acctggctca 6901  gggggacagc ctggcagctc gtgccattgc agtgcagaag ggcagtatcg
      gcaacctcct 6961  gggcttccta gaggacagcc ttgccgccac acagttccag cagagccagg
      ccagcctcct 7021  ccacatgcag aacccaccct ttgagccaac tagtgtggac atgatgcggc
      gggctgcccg 7081  cgcgctgctt gccttggcca aggtggacga gaaccactca gagtttactc
      tgtacgaatc 7141  acggctgttg gacatctcgg tatcaccgtt gatgaactca ttggtttcac
      aagtcatttg 7201  tgatgtactg tttttgattg gccagtcatg acagccgtgg gacacctccc
      cccccgtgt 7261  gtgtgtgcgt gtgtggagaa cttagaaact gactgttgcc ctttatttat
      gcaaaaccac 7321  ctcagaatcc agtttaccct gtgctgtcca gcttctccct tgggaaaaag
      tctctcctgt 7381  ttctctctcc tccttccacc tcccctccct ccatcacctc acgcctttct
      gttccttgtc 7441  ctcaccttac tcccctcagg accctacccc accctctttg aaaagacaaa
      gctctgccta 7501  catagaagac ttttttttatt ttaaccaaag ttactgttgt ttacagtgag
      tttggggaaa 7561  aaaaataaaa taaaaatggc tttcccagtc cttgcatcaa cgggatgcca
      catttcataa 7621  ctgttttttaa tggtaaaaaa aaaaaaaaaa aatacaaaaa aaaattctga
      aggacaaaaa 7681  aggtgactgc tgaactgtgt gtggtttatt gttgtacatt cacaatcttg
      caggagccaa 7741  gaagttcgca gttgtgaaca gaccctgttc actggagagg cctgtgcagt
      agagtgtaga 7801  cccttttcatg tactgtactg tacacctgat actgtaaaca tactgtaata
      ataatgtctc 7861  acatggaaac agaaacgct gggtcagcag caagctgtag tttttaaaaa
      tgttttttagt 7921  taaacgttga ggagaaaaaa aaaaaaggct tttcccccaa agtatcatgt
      gtgaacctac 7981  aacaccctga cctctttctc tcctccttga ttgtatgaat aaccctgaga
      tcacctctta 8041  gaactggttt taacctttag ctgcagcggc tacgctgcca cgtgtgtata
      tatatgacgt 8101  tgtacattgc acatacccctt ggatccccac agtttggtcc tcctcccagc
      tacccctttta 8161  tagtatgacg agttaacaag ttggtgacct gcacaaagcg agacacagct
      atttaatctc
```

```
8221  ttgccagata  tcgcccctct  tggtgcgatg  ctgtacaggt  ctctgtaaaa
      agtccttgct 8281  gtctcagcag  ccaatcaact  tatagtttat  ttttttctgg  gttttgtttt
      tgttttgttt 8341  tctttctaat  cgaggtgtga  aaaagttcta  ggttcagttg  aagttctgat
      gaagaaacac 8401  aattgagatt  ttttcagtga  taaaatctgc  atatttgtat  ttcaacaatg
      tagctaaaac 8461  ttgatgtaaa  ttcctccttt  ttttccttt   ttggcttaat  gaatatcatt
      tattcagtat 8521  gaaatcttta  tactatatgt  tccacgtgtt  aagaataaat  gtacattaaa
      tcttggtaag 8581  acttt
```

AT-rich interactive domain-containing protein 1A (ARID1A)
isoform b (SEQ ID NO: 11)

```
   1  maaqvapaaa  sslgnppppp  pselkkaeqq  qreeaggeaa  aaaaaergem
      kaaagqeseg 61  pavgppqplg  kelqdgaesn  gggggggags  gggpgaepdl  knsngnagpr
      palnnnltep 121  pgggggssd   gvgapphsaa  aalpppaygf  gqpygrspsa  vaaaaaavfh
      qqhggqqspg 181  laalqsgggg  glepyagpqq  nshdhgfpnh  qynsyypnrs  ayppppapaya
      lssprggtpg 241  sgaaaaagsk  pppsssasas  sssssfaqqr  fgamggggps  aagggtpqpt
      atptlnqllt 301  spssargyqg  ypggdysggp  qdggagkgpa  dmasqcwgaa  aaaaaaaas
      ggaqqrshha 361  pmspgssggg  gqplartpqp  sspmdgmgkm  rpqpyggtnp  ysqqqgppsg
      pqqghgypgq 421  pygsqtpqry  pmtmqgraqs  amgglsytqq  ippygqqgps  gygqqgqtpy
      ynqqsphpqq 481  qqppysqqpp  sqtphaqpsy  qqqpqsqppq  lqssqppysq  qpsqpphqqs
      papypsqqst 541  tqqhpqsqpp  ysqpqaqspy  qqqqpqqpap  stlsqqaayp  qpqsqqsqqt
      aysqqrfppp 601  qelsqdsfgs  qassapsmts  skggqedmnl  slqsrpsslp  dlsgsiddlp
      mgtegalspg 661  vstsgisssq  geqsnpaqsp  fsphtsphlp  girgpspspv  gspasvaqsr
      sgplspaavp 721  gnqmpprpps  gqsdsimhps  mngssiaqdr  gymqrnpqmp  qysspqpgsa
      lsprqpsggq 781  ihtgmgsyqq  nsmgsygpqg  gqygpqggyp  rqpnynalpn  anypsagmag
      ginpmgaggq 841  mhgqpgippy  gtlppgrmsh  asmgnrpygp  nmanmppqvg  sgmcpppggm
      nrktqetava 901  mhvaansiqn  rppgypnmnq  ggmmgtgppy  gqginsmagm  inpqgppysm
      ggtmannsag 961  maaspemmgl  gdvkltpatk  mnnkadgtpk  teskskksss  stttnekitk
      lyelggeper 1021  kmwvdrylaf  teekamgmtn  lpavgrkpld  lyrlyvsvke  iggltqvnkn
      kkwrelatnl 1081  nvgtsssaas  slkkgyiqcl  yafeckierg  edpppdifaa  adskksqpki
      qppspagsgs
```

-continued

```
1141  mqgpqtpgst  sssmaeggdl  kpptpastph  sqipplpgms  rsnsvgiqda
      fndgsdstfq 1201  krnsmtpnpg  yqpsmntsdm  mgrmsyepnk  dpygsmrkap  gsdpfmssgq
      gpnggmgdpy 1261  sraagpglgn  vamgprqhyp  yggpydrvrt  epgigpegnm  stgapqpnlm
      psnpdsgmys 1321  psryppqqqq  qqqqrhdsyg  nqfstqgtps  gspfpsqqtt  myqqqqvss
      paplprpmen 1381  rtspskspfl  hsgmkmqkag  ppvpashiap  apvqppmirr  ditfppgsve
      atqpvlkgrr 1441  rltmkdigtp  eawrvmmslk  sgllaestwa  ldtinillyd  dnsimtfnls
      qlpgllellv 1501  eyfrrcliei  fgilkeyevg  dpgqrtlldp  grfskvsspa  pmeggeeeee
      llgpkleeee 1561  eeevvendee  iafsgkdkpa  senseeklis  kfdklpvkiv  qkndpfvvdc
      sdklgrvqef 1621  dsgllhwrig  ggdttehiqt  hfesktellp  srphapcppa  prkhvttaeg
      tpgttdgegp 1681  ppdgppekri  tatmddmlst  rsstltedga  ksseaikess  kfpfgispaq
      shrnikiled 1741  ephskdetpl  ctlldwqdsl  akrcvcvsnt  irslsfvpgn  dfemskhpgl
      llilgklill 1801  hhkhperkqa  pltyekeeeq  dqgvscnkve  wwwdclemlr  entlvtlani
      sgqldlspyp 1861  esiclpvldg  llhwavcpsa  eaqdpfstlg  pnavlspqrl  vletlsklsi
      qdnnvdlila 1921  tppfsrlekl  ystmvrflsd  rknpvcrema  vvllanlaqg  dslaaraiav
      qkgsignllg 1981  fledslaatq  fqqsgasllh  mqnppfepts  vdmmrraara  llalakvden
      hseftlyesr 2041  lldisysplm  nslvsqvicd  vlfligqs
```

*Homo sapiens* AT rich interactive domain 1A (SWI-like)
(ARID1A), transcript variant 2, mRNA (SEQ ID NO: 12)

```
  1  cagaaagcgg  agagtcacag  cggggccagg  ccctggggag  cggagcctcc
     accgccccc 61  tcattcccag  gcaagggctt  gggggggaatg  agccgggaga  gccgggtccc
     gagcctacag 121  agccgggagc  agctgagccg  ccggcgcctc  ggccgccgcc  gccgcctcct
     cctcctccgc 181  cgccgccagc  ccggagcctg  agccggcggg  gcgggggggga  gaggagcgag
     cgcagcgcag 241  cagcggagcc  ccgcgaggcc  cgcccgggcg  ggtggggagg  gcagcccggg
     ggactgggcc 301  ccggggcggg  gtgggagggg  gggagaagac  gaagacaggg  ccgggtctct
     ccgcggacga 361  gacagcgggg  atcatggccg  cgcaggtcgc  ccccgccgcc  gccagcagcc
     tgggcaaccc 421  gccgccgccg  ccgcccctcgg  agctgaagaa  agccgagcag  cagcagcggg
     aggaggcggg 481  gggcgaggcg  gcggcggcgg  cagcggccga  gcgcggggaa  atgaaggcag
     ccgccgggca 541  ggaaagcgag  ggccccgccg  tggggccgcc  gcagccgctg  ggaaaggagc
     tgcaggacgg
```

-continued

```
 601 ggccgagagc aatgggggtg gcggcggcgg cggagccggc agcggcggcg
     ggcccggcgc 661 ggagccggac ctgaagaact cgaacgggaa cgcgggccct aggcccgccc
     tgaacaataa 721 cctcacggag ccgcccggcg gcggcggtgg cggcagcagc gatggggtgg
     gggcgcctcc 781 tcactcagcc gcggccgcct tgccgccccc agcctacggc ttcgggcaac
     cctacggccg 841 gagcccgtct gccgtcgccg ccgccgcggc cgccgtcttc caccaacaac
     atggcggaca 901 acaaagccct ggcctggcag cgctgcagag cggcggcggc ggggcctgg
     agccctacgc 961 ggggcccag cagaactctc acgaccacgg cttccccaac caccagtaca
     actcctacta 1021 ccccaaccgc agcgcctacc ccccgcccgc cccggcctac gcgctgagct
     ccccgagagg 1081 tggcactccg ggctccggcg cggcggcggc tgccggctcc aagccgcctc
     cctcctccag 1141 cgcctccgcc tcctcgtcgt cttcgtcctt cgctcagcag cgcttcgggg
     ccatgggggg 1201 aggcggcccc tccgcggccg gcgggggaac tccccagccc accgccaccc
     ccaccctcaa 1261 ccaactgctc acgtcgccca gctcggcccg gggctaccag ggctaccccg
     ggggcgacta 1321 cagtggcggg ccccaggacg ggggcgccgg caagggcccg gcggacatgg
     cctcgcagtg 1381 ttgggggct gcggcggcgg cagctgcggc ggcggccgcc tcgggagggg
     cccaacaaag 1441 gagccaccac gcgcccatga gccccgggag cagcggcggc gggggcagc
     cgctcgcccg 1501 gaccctcag ccatccagtc caatggatca gatgggcaag atgagacctc
     agccatatgg 1561 cgggactaac ccatactcgc agcaacaggg acctccgtca ggaccgcagc
     aaggacatgg 1621 gtacccaggg cagccatacg ggtcccagac cccgcagcgg tacccgatga
     ccatgcaggg 1681 ccgggcgcag agtgccatgg gcggcctctc ttatacacag cagattcctc
     cttatggaca 1741 acaaggcccc agcgggtatg gtcaacaggg ccagactcca tattcaacc
     agcaaagtcc 1801 tcaccctcag cagcagcagc caccctactc ccagcaacca ccgtcccaga
     cccctcatgc 1861 ccaaccttcg tatcagcagc agccacagtc tcaaccacca cagctccagt
     cctctcagcc 1921 tccatactcc cagcagccat cccagcctcc acatcagcag tccccggctc
     catcccctc 1981 ccagcagtcg acgacacagc agcacccca gagccagccc cctactcac
     agccacaggc 2041 tcagtctcct taccagcagc agcaacctca gcagccagca ccctcgacgc
     tctcccagca 2101 ggctgcgtat cctcagcccc agtctcagca gtcccagcaa actgcctatt
     cccagcagcg 2161 cttccctcca ccgcaggagc tatctcaaga ttcatttggg tctcaggcat
     cctcagcccc
```

```
2221  ctcaatgacc tccagtaagg gagggcaaga agatatgaac ctgagccttc
      agtcaagacc 2281  ctccagcttg cctgatctat ctggttcaat agatgacctc cccatgggga
      cagaaggagc 2341  tctgagtcct ggagtgagca catcagggat ttccagcagc caaggagagc
      agagtaatcc 2401  agctcagtct cctttctctc ctcatacctc ccctcacctg cctggcatcc
      gaggcccttc 2461  cccgtcccct gttggctctc ccgccagtgt tgctcagtct cgctcaggac
      cactctcgcc 2521  tgctgcagtg ccaggcaacc agatgccacc tcggccaccc agtggccagt
      cggacagcat 2581  catgcatcct tccatgaacc aatcaagcat tgcccaagat cgaggttata
      tgcagaggaa 2641  ccccagatg ccccagtaca gttcccccca gcccggctca gccttatctc
      cgcgtcagcc 2701  ttccggagga cagatacaca caggcatggg ctcctaccag cagaactcca
      tggggagcta 2761  tggtcccag ggggtcagt atggcccaca aggtggctac cccaggcagc
      caaactataa 2821  tgccttgccc aatgccaact accccagtgc aggcatggct ggaggcataa
      accccatggg 2881  tgccggaggt caaatgcatg gacagcctgg catcccacct tatggcacac
      tccctccagg 2941  gaggatgagt cacgcctcca tgggcaaccg gccttatggc cctaacatgg
      ccaatatgcc 3001  acctcaggtt gggtcaggga tgtgtccccc accagggggc atgaaccgga
      aaacccaaga 3061  aactgctgtc gccatgcatg ttgctgccaa ctctatccaa aacaggccgc
      caggctaccc 3121  caatatgaat caaggggca tgatgggaac tggacctcct tatggacaag
      ggattaatag 3181  tatggctggc atgatcaacc ctcagggacc cccatattcc atgggtggaa
      ccatggccaa 3241  caattctgca gggatggcag ccagcccaga gatgatgggc cttggggatg
      taaagttaac 3301  tccagccacc aaaatgaaca acaaggcaga tgggacaccc aagacagaat
      ccaaatccaa 3361  gaaatccagt tcttctacta caaccaatga agagatcacc aagttgtatg
      agctgggtgg 3421  tgagcctgag aggaagatgt gggtggaccg ttatctggcc ttcactgagg
      agaaggccat 3481  gggcatgaca aatctgcctg ctgtgggtag gaaacctctg gacctctatc
      gcctctatgt 3541  gtctgtgaag gagattggtg gattgactca ggtcaacaag aacaaaaaat
      ggcgggaact 3601  tgcaaccaac ctcaatgtgg gcacatcaag cagtgctgcc agctccttga
      aaaagcagta 3661  tatccagtgt ctctatgcct ttgaatgcaa gattgaacgg ggagaagacc
      ctcccccaga 3721  catctttgca gctgctgatt ccaagaagtc ccagcccaag atccagcctc
      cctctcctgc 3781  gggatcagga tctatgcagg gccccagac tccccagtca accagcagtt
      ccatggcaga
```

```
3841  aggaggagac ttaaagccac caactccagc atccacacca cacagtcaga
      tcccccatt 3901  gccaggcatg agcaggagca attcagttgg gatccaggat gcctttaatg
      atggaagtga 3961  ctccacattc cagaagcgga attccatgac tccaaaccct gggtatcagc
      ccagtatgaa 4021  tacctctgac atgatggggc gcatgtccta tgagccaaat aaggatcctt
      atggcagcat 4081  gaggaaagct ccagggagtg atcccttcat gtcctcaggg cagggcccca
      acggcgggat 4141  gggtgacccc tacagtcgtg ctgccggccc tgggctagga aatgtggcga
      tgggaccacg 4201  acagcactat ccctatggag gtccttatga cagagtgagg acggagcctg
      gaatagggcc 4261  tgagggaaac atgagcactg gggccccaca gccgaatctc atgccttcca
      acccagactc 4321  ggggatgtat tctcctagcc gctacccccc gcagcagcag cagcagcagc
      agcaacgaca 4381  tgattcctat ggcaatcagt tctccaccca aggcaccct tctggcagcc
      ccttccccag 4441  ccagcagact acaatgtatc aacagcaaca gcaggtatcc agccctgctc
      ccctgccccg 4501  gccaatggag aaccgcacct ctcctagcaa gtctccattc ctgcactctg
      ggatgaaaat 4561  gcagaaggca ggtcccccag tacctgcctc gcacatagca cctgcccctg
      tgcagccccc 4621  catgattcgg cgggatatca ccttcccacc tggctctgtt gaagccacac
      agcctgtgtt 4681  gaagcagagg aggcggctca caatgaaaga cattggaacc ccggaggcat
      ggcgggtaat 4741  gatgtccctc aagtctggtc tcctggcaga gagcacatgg gcattagata
      ccatcaacat 4801  cctgctgtat gatgacaaca gcatcatgac cttcaacctc agtcagctcc
      cagggttgct 4861  agagctcctt gtagaatatt tccgacgatg cctgattgag atctttggca
      ttttaaagga 4921  gtatgaggtg ggtgacccag gacagagaac gctactggat cctgggaggt
      tcagcaaggt 4981  gtctagtcca gctcccatgg agggtgggga agaagaagaa gaacttctag
      gtcctaaact 5041  agaagaggaa gaagaagagg aagtagttga aaatgatgag gagatagcct
      tttcaggcaa 5101  ggacaagcca gcttcagaga atagtgagga gaagctgatc agtaagtttg
      acaagcttcc 5161  agtaaagatc gtacagaaga atgatccatt tgtggtggac tgctcagata
      agcttgggcg 5221  tgtgcaggag tttgacagtg gcctgctgca ctggcggatt ggtggggggg
      acaccactga 5281  gcatatccag acccacttcg agagcaagac agagctgctg ccttcccggc
      ctcacgcacc 5341  ctgcccacca gcccctcgga agcatgtgac aacagcagag ggtacaccag
      ggacaacaga 5401  ccaggagggg cccccacctg atggacctcc agaaaaacgg atcacagcca
      ctatggatga
```

-continued

```
5461  catgttgtct actcggtcta gcaccttgac cgaggatgga gctaagagtt
      cagaggccat 5521  caaggagagc agcaagtttc catttggcat tagcccagca cagagccacc
      ggaacatcaa 5581  gatcctagag gacgaacccc acagtaagga tgagacccca ctgtgtaccc
      ttctggactg 5641  gcaggattct cttgccaagc gctgcgtctg tgtgtccaat accattcgaa
      gcctgtcatt 5701  tgtgccaggc aatgactttg agatgtccaa cacccaggg ctgctgctca
      tcctgggcaa 5761  gctgatcctg ctgcaccaca agcacccaga acggaagcag gcaccactaa
      cttatgaaaa 5821  ggaggaggaa caggaccaag gggtgagctg caacaaagtg gagtggtggt
      gggactgctt 5881  ggagatgctc cgggaaaaca ccttggttac actcgccaac atctcggggc
      agttggacct 5941  atctccatac cccgagagca tttgcctgcc tgtcctggac ggactcctac
      actgggcagt 6001  ttgcccttca gctgaagccc aggacccctt ttccacccctg ggccccaatg
      ccgtcctttc 6061  cccgcagaga ctggtcttgg aaaccctcag caaactcagc atccaggaca
      acaatgtgga 6121  cctgattctg gccacacccc ccttcagccg cctggagaag ttgtatagca
      ctatggtgcg 6181  cttcctcagt gaccgaaaga acccggtgtg ccgggagatg gctgtggtac
      tgctggccaa 6241  cctggctcag ggggacagcc tggcagctcg tgccattgca gtgcagaagg
      gcagtatcgg 6301  caacctcctg ggcttcctag aggacagcct tgccgccaca cagttccagc
      agagccaggc 6361  cagcctcctc cacatgcaga acccaccctt tgagccaact agtgtggaca
      tgatgcggcg 6421  ggctgcccgc gcgctgcttg ccttggccaa ggtggacgag aaccactcag
      agtttactct 6481  gtacgaatca cggctgttgg acatctcggt atcaccgttg atgaactcat
      tggtttcaca 6541  agtcatttgt gatgtactgt ttttgattgg ccagtcatga cagccgtggg
      acacctcccc 6601  cccccgtgtg tgtgtgcgtg tgtggagaac ttagaaactg actgttgccc
      tttatttatg 6661  caaaaccacc tcagaatcca gtttaccctg tgctgtccag cttctccctt
      gggaaaagt 6721  ctctcctgtt tctctctcct ccttccacct cccctccctc catcacctca
      cgcctttctg 6781  ttccttgtcc tcaccttact cccctcagga ccctacccca ccctctttga
      aaagacaaag 6841  ctctgcctac atagaagact ttttttattt taaccaaagt tactgttgtt
      tacagtgagt 6901  ttggggaaaa aaataaaat aaaaatggct ttcccagtcc ttgcatcaac
      gggatgccac 6961  atttcataac tgttttaat ggtaaaaaaa aaaaaaaaa atacaaaaaa
      aaattctgaa 7021  ggacaaaaaa ggtgactgct gaactgtgtg tggtttattg ttgtacattc
      acaatcttgc
```

```
-continued
7081  aggagccaag  aagttcgcag  ttgtgaacag  accctgttca  ctggagaggc
      ctgtgcagta 7141  gagtgtagac  cctttcatgt  actgtactgt  acacctgata  ctgtaaacat
      actgtaataa 7201  taatgtctca  catggaaaca  gaaaacgctg  ggtcagcagc  aagctgtagt
      ttttaaaaat 7261  gtttttagtt  aaacgttgag  gagaaaaaaa  aaaaaggctt  ttcccccaaa
      gtatcatgtg 7321  tgaacctaca  acaccctgac  ctctttctct  cctccttgat  tgtatgaata
      accctgagat 7381  cacctcttag  aactggtttt  aaccttagc   tgcagcggct  acgctgccac
      gtgtgtatat 7441  atatgacgtt  gtacattgca  catacccttg  gatcccaca   gtttggtcct
      cctcccagct 7501  accccttat   agtatgacga  gttaacaagt  tggtgacctg  cacaaagcga
      gacacagcta 7561  tttaatctct  tgccagatat  cgcccctctt  ggtgcgatgc  tgtacaggtc
      tctgtaaaaa 7621  gtccttgctg  tctcagcagc  caatcaactt  atagtttatt  tttttctggg
      tttttgtttt 7681  gttttgtttt  ctttctaatc  gaggtgtgaa  aaagttctag  gttcagttga
      agttctgatg 7741  aagaaacaca  attgagattt  tttcagtgat  aaaatctgca  tatttgtatt
      tcaacaatgt 7801  agctaaaact  tgatgtaaat  tcctccttt   tttccttttt  tggcttaatg
      aatatcattt 7861  attcagtatg  aaatctttat  actatatgtt  ccacgtgtta  agaataaatg
      tacattaaat 7921  cttggtaaga  cttt
```

The present invention also provides methods of inducing neuronal differentiation by contacting a cell with a compound (i.e., an EZH2 inhibitor) of the invention. Preferably, the compound is in an amount sufficient to increase expression of at least one gene selected from the group consisting of CD133 (also called PROM1), DOCK4, PTPRK, PROM2, LHX1, LHX6, LHX9, PAX6, PAX7, VEFGA, FZD3B, FYN, HIF1A, HTRA2, EVX1, CCDC64, and GFAP.

The term "inducing neuronal differentiation" used herein refers to causing a cell to develop into a cell of the neuronal lineage as a result of a direct or intentional effect on the cell.

The present invention also provides methods of inducing cell cycle inhibition by contacting a cell with a compound of the invention. Preferably, the compound is in an amount sufficient to increase expression of at least one gene selected from the group consisting of CKDN1A, CDKN2A, MEN1, CHEK1, IRF6, ALOX15B, CYP27B1, DBC1, NME6, GMNN, HEXIM1, LATS1, MYC, HRAS, TGFB1, IFNG, WNT1, TP53, THBS1, INHBA, IL8, IRF1, TPR, BMP2, BMP4, ETS1, HPGD, BMP7, GATA3, NR2F2, APC, PTPN3, CALR, IL12A, IL12B, PML, CDKN2B, CDKN2C, CDKN1B, SOX2, TAF6, DNA2, PLK1, TERF1, GAS1, CDKN2D, MLF1, PTEN, TGFB2, SMAD3, FOXO4, CDK6, TFAP4, MAP2K1, NOTCH2, FOXC1, DLG1, MAD2L1, ATM, NAE1, DGKZ, FHL1, SCRIB, BTG3, PTPRK, RPS6KA2, STK11, CDKN3, TBRG1, CDC73, THAP5, CRLF3, DCUN1D3, MYOCD, PAF1, LILRB1, UHMK1, PNPT1, USP47, HEXIM2, CDK5RAP1, NKX3-1, TIPIN, PCBP4, USP44, RBM38, CDT1, RGCC, RNF167, CLSPN, CHMP1A, WDR6, TCF7L2, LATS2, RASSF1, MLTK, MAD2L2, FBXO5, ING4, and TRIM35.

The term "inducing cell cycle inhibition" used herein refers to causing an accumulation or an arrest at any phase during cell division and/or duplication.

The present invention also provides methods of inducing tumor suppression by contacting a cell with a compound of the invention. Preferably, the compound is in an amount sufficient to increase expression of BIN1 or any tumor suppressors.

The term "inducing tumor suppression" may include, but is not limited to, a reduction in size of a tumor, a reduction in tumor volume, a decrease in number of tumors, a decrease in number of metastatic lesions in other tissues or organs distant from the primary tumor site, an increase in average survival time of a population of treated subjects in comparison to a population receiving carrier alone, an increase in average survival time of a population of treated subjects in comparison to a population of untreated subjects, an increase in average survival time of a population of treated subjects in comparison to a population receiving monotherapy with a drug that is not a compound of the present invention, a decrease in the mortality rate of a population of treated subjects in comparison to a population receiving carrier alone, a decrease in tumor growth rate, or a decrease in tumor regrowth rate.

The present invention also provides methods of inhibiting hedgehog signaling by contacting a cell with a compound of the invention. Preferably, the compound is in an amount sufficient to reduce expression of at least one gene selected from the group consisting of GLI1, PTCH1, SUFU, KIF7, GLI2, BMP4, MAP3K10, SHH, TCTN3, DYRK2, PTCHD1, and SMO.

The phrase "inhibiting hedgehog signaling" means the hedgehog signaling strength (intensity) with a compound treatment is reduced by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to the hedgehog signaling strength (intensity) without any compound treatment.

The present invention also provides methods of inducing a gene expression by contacting a cell with a compound of the invention. Preferably, the compound is in an amount sufficient to induce neuronal differentiation, cell cycle inhibition and/or tumor suppression. Such gene is selected from the group consisting of CD133 (also called PROM1), DOCK4, PTPRK, PROM2, LHX1, LHX6, LHX9, PAX6, PAX7, VEFGA, FZD3B, FYN, HIF1A, HTRA2, EVX1, CCDC64, GFAP, CKDN1A, CDKN2A, MEN1, CHEK1, IRF6, ALOX1SB, CYP27B1, DBC1, NME6, GMNN, HEXIM1, LATS1, MYC, HRAS, TGFB1, IFNG, WNT1, TP53, THBS1, INHBA, IL8, IRF1, TPR, BMP2, BMP4, ETS1, HPGD, BMP7, GATA3, NR2F2, APC, PTPN3, CALR, IL12A, IL12B, PML, CDKN2B, CDKN2C, CDKN1B, SOX2, TAF6, DNA2, PLK1, TERF1, GAS1, CDKN2D, MLF1, PTEN, TGFB2, SMAD3, FOXO4, CDK6, TFAP4, MAP2K1, NOTCH2, FOXC1, DLG1, MAD2L1, ATM, NAE1, DGKZ, FHL1, SCRIB, BTG3, PTPRK, RPS6KA2, STK11, CDKN3, TBRG1, CDC73, THAP5, CRLF3, DCUN1D3, MYOCD, PAF1, LILRB1, UHMK1, PNPT1, USP47, HEXIM2, CDK5RAP1, NKX3-1, TIPIN, PCBP4, USP44, RBM38, CDT1, RGCC, RNF167, CLSPN, CHMP1A, WDR6, TCF7L2, LATS2, RASSF1, MLTK, MAD2L2, FBXO5, ING4, TRIM35, BIN1 and any tumor suppressors.

The phrase "inducing a gene expression" means the expression level of a particular gene of interest is increased by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to the expression level of this gene without any compound treatment.

The present invention also provides methods of inhibiting a gene expression comprising contacting a cell with a compound of the invention. Preferably, the compound is in an amount sufficient to inhibit hedgehog signaling. Such gene is GLI1, PTCH1, SUFU, KIF7, GLI2, BMP4, MAP3K10, SHH, TCTN3, DYRK2, PTCHD1, or SMO.

The phrase "inhibiting a gene expression" means the expression level of a particular gene of interest is reduced by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to the expression level of this gene without any compound treatment.

Neuronal differentiation, cell cycle inhibition, tumor suppression and hedgehog signaling inhibition can be determined by any methods known in the art.

As used herein, a cell refers to any cell that can be obtained and used by a method described herein. For example, a cell may be obtained from a cell culture. Alternatively, a cell may be isolated from a subject. A cell may also refer to a cell of a subject.

A cell may comprise loss of function of SNF5, ARID1A, ATRX, and/or a component of the SWI/SNF complex. Preferably, a cell may comprise a deletion of SNF5.

A cell may be a cancer cell, where the cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epithelioid sarcoma, renal medullo carcinoma, diffuse large B-cell lymphoma, follicular lymphoma and not otherwise specified (NOS) sarcoma. More preferably a cell is a cancer cell of medulloblastoma, malignant rhabdoid tumor, or atypical teratoid rhabdoid tumor.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, polymorph, solvate, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate one or more symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, polymorph, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, polymorph, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating cancer can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating cancer can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating cancer can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating cancer can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleomorphism.

Treating cancer can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

As used herein, the term "selectively" means tending to occur at a higher frequency in one population than in another population. The compared populations can be cell populations. Preferably, a compound of the present invention, or a pharmaceutically acceptable salt, polymorph or solvate thereof, acts selectively on a cancer or precancerous cell but not on a normal cell. Preferably, a compound of the present invention, or a pharmaceutically acceptable salt, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, polymorph or solvate thereof, to a cell or a subject in need thereof can result in modulation (i.e., stimulation or inhibition) of an activity of a protein methyltransferase of interest.

Detection of methylation of H3-K27, formation of trimethylated H3-K27, conversion of monomethylated H3-K27 to dimethylated H3-K27, or conversion of dimethylated H3-K27 to trimethylated H3-K27 can be accomplished using any suitable method. Exemplary methods can be found in US20120071418, the contents of which are incorporated herein by reference.

Administering a compound of the present invention, or a pharmaceutically acceptable salt, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltransferase.

Preferably, an effective amount of a compound of the present invention, or a pharmaceutically acceptable salt, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, polymorph or solvate thereof, can induce or activate cell death selectively in cancer cells. Administering to a subject in need thereof a compound of the present invention, or a pharmaceutically acceptable salt, polymorph or solvate thereof, can induce or activate cell death selectively in cancer cells. Contacting a cell with a compound of the present invention, or a pharmaceutically acceptable salt, polymorph or solvate thereof, can induce cell death selectively in one or more cells affected by a cell proliferative disorder. Preferably, administering to a subject in need thereof a compound of the present invention, or a pharmaceutically acceptable salt, polymorph or solvate thereof, induces cell death selectively in one or more cells affected by a cell proliferative disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, 18$^{th}$ edition (1990). These texts can, of course, also be referred to in making or using an aspect of the invention.

A compound (i.e., an EZH2 inhibitor) that can be used in any methods described herein may have the following Formula I.

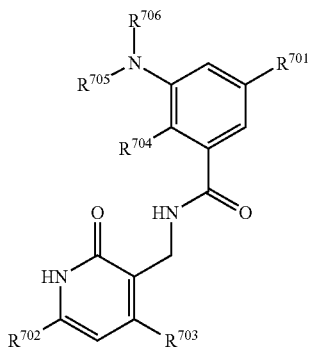

(I)

or a pharmaceutically acceptable salt thereof, wherein $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}$ alkyl$)_2$ wherein one of the $C_{1-4}$ alkyl is unsubstituted and the other is substituted with methoxy.

For example, $R^{706}$ is

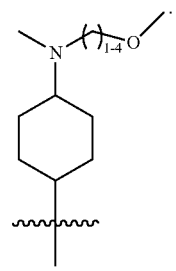

For example, the compound is of Formula II.

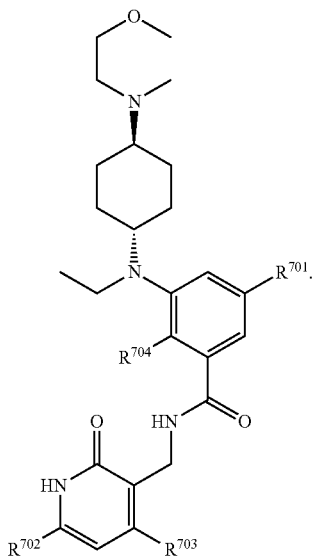

(II)

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

A compound (i.e., an EZH2 inhibitor) that can be used in any methods described herein may have the following Formula III:

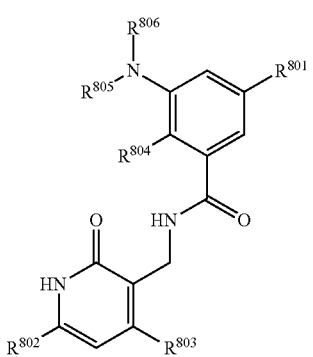

(III)

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein Q2 is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$ and $Q_2$ independently is a bond or methyl linker, and each of $T_x$ and $T_2$ independently is tetrahydropyranyl, piperidinyl substituted by 1, 2, or 3 $C_{1-4}$ alkyl groups, or cyclohexyl substituted by $N(C_{1-4}$ alkyl$)_2$ wherein one or both of the $C_{1-4}$ alkyl is optionally substituted with $C_{1-6}$ alkoxy;

For example, $R^{806}$ is cyclohexyl substituted by $N(C_{1-4}$ alkyl$)_2$ or $R^{806}$ is tetrahydropyranyl.

For example, $R^{806}$ is

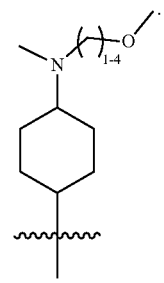

For example, $R^{801}$ is phenyl or 5- or 6-membered heteroaryl substituted with O—$C_{1-6}$ alkyl-$R_x$, or $R^{801}$ is phenyl substituted with $CH_2$-tetrahydropyranyl.

For example, a compound of the present invention is of Formula IVa or IVb:

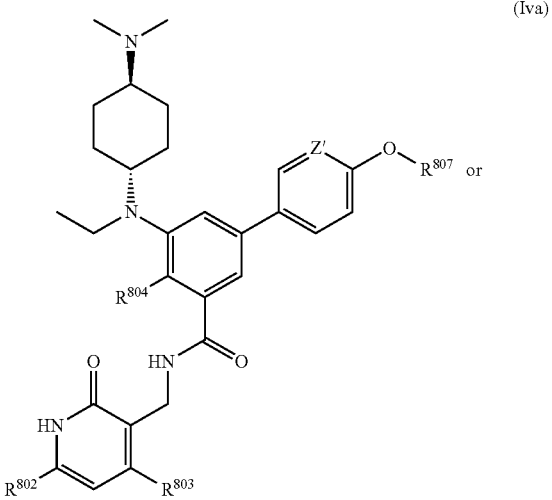

(Iva)

-continued

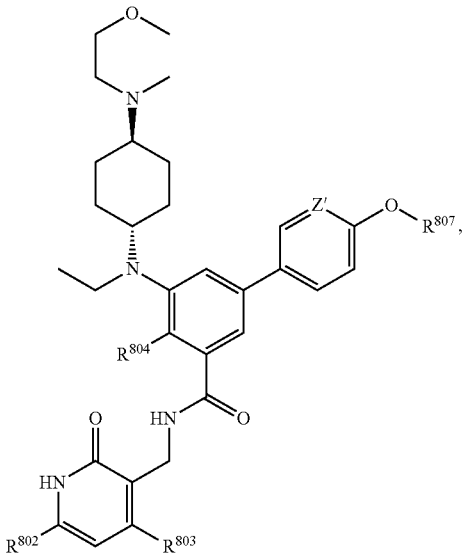

(IVb)

wherein Z' is CH or N, and $R^{807}$ is $C_{2-3}$ alkyl-$R_x$.

For example, $R^{807}$ is —$CH_2CH_2OH$, —$CH_2CH_2OCH_3$, or —$CH_2CH_2OCH_2CH_2OCH_3$.

For example, $R^{802}$ is methyl or isopropyl and $R^{803}$ is methyl or methoxyl.

For example, $R^{804}$ is methyl.

A compound of the present invention may have the following Formula (V):

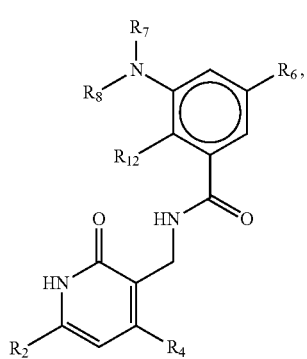

(V)

or a pharmaceutically acceptable salt or ester thereof.

In this formula:

$R_2$, $R_4$ and $R_{12}$ are each independently $C_{1-6}$ alkyl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, and the 4 to 11-membered heterocycloalkyl ring formed by $R_7$ and $R_8$ is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$$R_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo.

For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —OR$_a$, —NR$_a$R$_b$, —(NR$_a$R$_b$R$_c$)$^+$A$^-$, —C(O)NR$_a$R$_b$, —NR$_b$C(O)R$_a$, —S(O)$_2$R$_a$, or R$_{S2}$, in which each of R$_a$ and R$_b$, independently is H or R$_{S3}$, each of R$_{S2}$ and R$_{S3}$, independently, is $C_1$-$C_6$ alkyl, or R$_a$ and R$_b$, together with the N atom to which they are attached, form a 4 to 7-membered heterocycloalkyl ring having 0 or 1 additional heteroatom, and each of R$_{S2}$, R$_{S3}$, and the 4 to 7-membered heterocycloalkyl ring formed by R$_a$ and R$_b$, is optionally, independently substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, OR$_d$, —S(O)$_2$R$_d$, and —NR$_d$R$_e$, each of R$_d$ and R$_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

For example, the compound of the present invention is of Formula (VI):

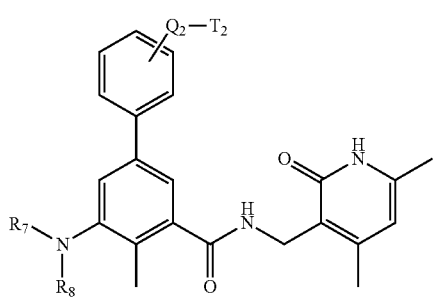

(VI)

or a pharmaceutically acceptable salt thereof, wherein $Q_2$ is a bond or methyl linker, $T_2$ is H, halo, —OR$_a$, —NR$_a$R$_b$, —(NR$_a$R$_b$R$_c$)$^+$A$^-$, or —S(O)$_2$NR$_a$R$_b$, $R_7$ is piperidinyl, tetrahydropyran, cyclopentyl, or cyclohexyl, each optionally substituted with one -$Q_5$-$T_5$ and $R_8$ is ethyl.

A compound of the present invention may have the following Formula (VIa):

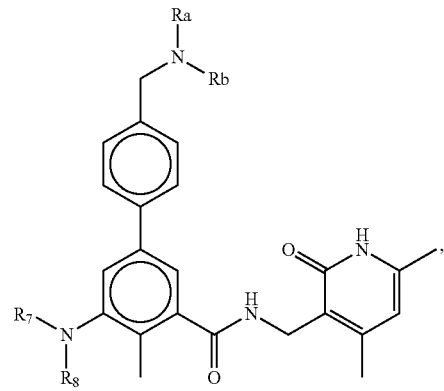

(VIa)

wherein
each of R$_a$ and R$_b$, independently is H or R$_{S3}$, R$_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or R$_a$ and R$_b$, together with the N atom to which they are attached, form a 4 to 12-membered heterocycloalkyl ring having 0 or 1 additional heteroatom, and each of R$_{S3}$ and the 4 to 12-membered heterocycloalkyl ring formed by R$_a$ and R$_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, OR$_d$, COOR$_d$, —S(O)$_2$R$_d$, —NR$_d$R$_e$, and —C(O)NR$_d$R$_e$, each of R$_d$ and R$_e$ independently being H or $C_1$-$C_6$ alkyl, or -$Q_3$-$T_3$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, NR$_f$R$_g$, —OR$_f$, —C(O)R$_f$, —C(O)OR$_f$, —C(O)NR$_f$R$_g$, —C(O)NR$_f$OR$_g$, —NR$_f$C(O)R$_g$, —S(O)$_2$R$_f$, or R$_{S4}$, in which each of R$_f$ and R$_g$, independently is H or R$_{S5}$, each of R$_{S4}$ and R$_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of R$_{S4}$ and R$_{S5}$ is optionally substituted with one or more -$Q_5$-$T_5$, wherein $Q_5$ is a bond, C(O), C(O)NR$_k$, NR$_k$C(O), S(O)$_2$, or $C_1$-$C_3$ alkyl linker, R$_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or S(O)$_q$R$_q$ in which q is 0, 1, or 2 and R$_q$ is $C_1$-$C_6$ alkyl, $C_2$-$C_6$ alkenyl, $C_2$-$C_6$ alkynyl, $C_3$-$C_8$cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_5$ is H, halo, hydroxyl, or cyano; or -$Q_5$-$T_5$ is oxo; provided that $R_7$ is not H; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring which has 0 to 2 additional heteroatoms and is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo.

For example, $R_a$ and $R_b$, together with the N atom to which they are attached, form a 4 to 7-membered heterocycloalkyl ring having 0 or 1 additional heteroatoms to the N atom and the ring is optionally substituted with one or more -$Q_3$-$T_3$, wherein the heterocycloalkyl is azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, or morpholinyl.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

In some embodiments, a compound that can be used in any methods presented here is:

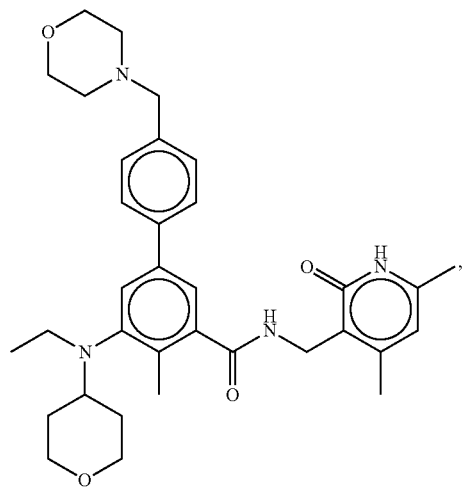

(Compound A)

stereoisomers thereof or pharmaceutically acceptable salt or solvate thereof.

In some embodiments, a compound that can be used in any methods presented here is:

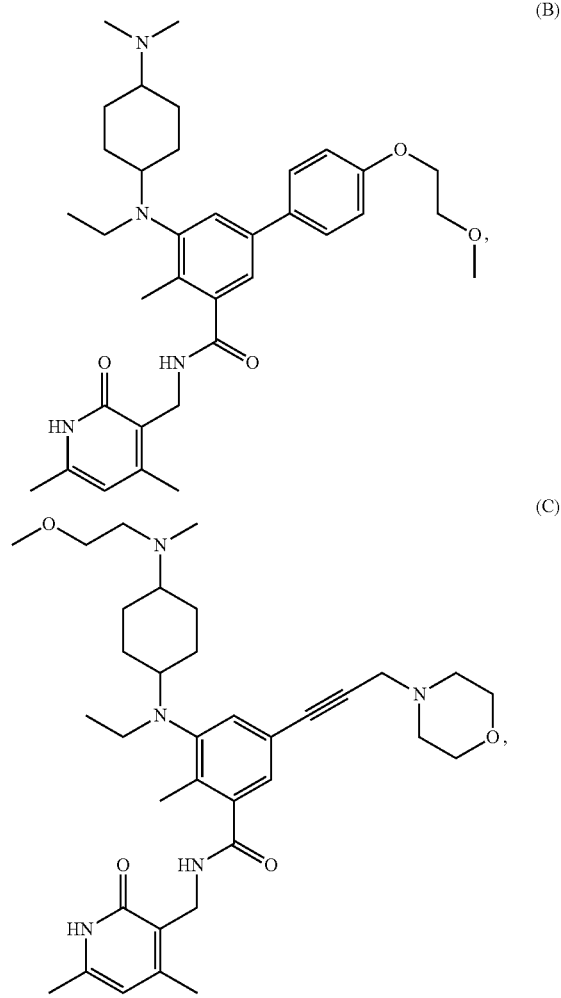

121
-continued

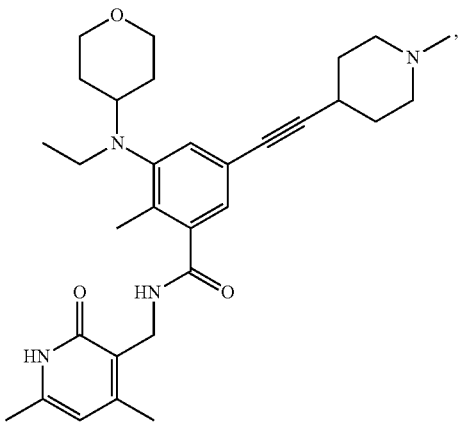
(D)

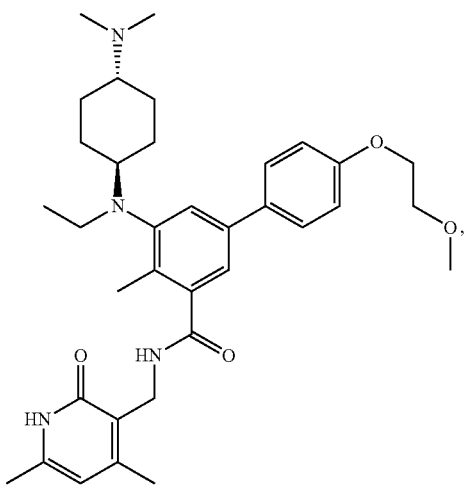
(E)

stereoisomers thereof or pharmaceutically acceptable salts and solvates thereof.

In some embodiments, a compound that can be used in any methods presented here is:

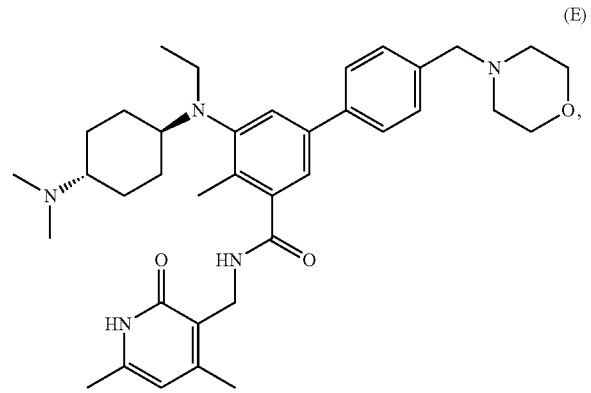

122
-continued

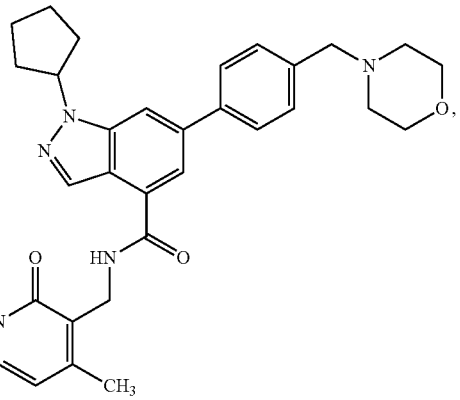
(F)

stereoisomers thereof or pharmaceutically acceptable salts and solvates thereof.

In some embodiments, the compounds suitable for use in the method of this invention include compounds of Formula (VII):

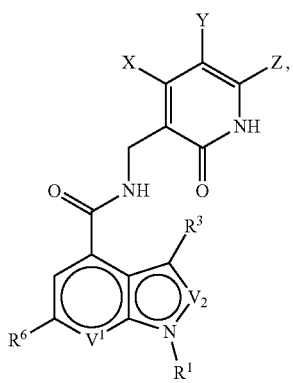
(VII)

wherein,

V1 is N or $CR^7$,

V2 is N or $CR^2$, provided when V1 is N, V2 is N,

X and Z are selected independently from the group consisting of hydrogen, ($C_1$-$C_8$)alkyl, ($C_2$-$C_8$)alkenyl, ($C_2$-$C_8$)alkynyl, unsubstituted or substituted ($C_3$-$C_8$)cycloalkyl, unsubstituted or substituted ($C_3$-$C_8$)cycloalkyl-($C_1$-$C_8$)alkyl or —($C_2$-$C_8$)alkenyl, unsubstituted or substituted ($C_5$-$C_8$)cycloalkenyl, unsubstituted or substituted ($C_5$-$C_8$)cycloalkenyl-($C_1$-$C_8$)alkyl or —($C_2$-$C_8$)alkenyl, ($C_6$-$C_{10}$)bicycloalkyl, unsubstituted or substituted heterocycloalkyl, unsubstituted or substituted heterocycloalkyl-($C_1$-$C_8$)alkyl or —($C_2$-$C_8$)alkenyl, unsubstituted or substituted aryl, unsubstituted or substituted aryl-($C_1$-$C_8$)alkyl or —($C_2$-$C_8$)alkenyl, unsubstituted or substituted heteroaryl, unsubstituted or substituted heteroaryl-($C_1$-$C_8$)alkyl or —($C_2$-$C_8$)alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aNSO_2NR^aR^b$, —$NR^aNR^aR^b$, —$NR^aNR^aC(O)R^b$, —$NR^aNR^aC(O)NR^aR^b$, —$NR^aNR^aC(O)OR_a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C^{10})$bicycloalkyl, unsubstituted or substituted heterocycloalkyl or —$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, —$CONR^aNR^aR^b$;

$R^2$ is hydrogen, $(C_1-C_8)$alkyl, trifluoromethyl, alkoxy, or halo, in which said $(C_1-C_8)$alkyl is optionally substituted with one to two groups selected from amino and $(C_1-C_3)$alkylamino;

$R^7$ is hydrogen, $(C_1-C_3)$alkyl, or alkoxy;

$R^3$ is hydrogen, $(C_1-C_8)$alkyl, cyano, trifluoromethyl, —$NR^aR^b$, or halo;

$R^6$ is selected from the group consisting of hydrogen, halo, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R_a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, —$(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, $OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO2R^b$, —$NR^aSO_2NR^aR^b$, —$OR^a$, —$OC(O)R^a$, and —$OC(O)NR^aR^b$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —$CO_2H$, —$CO_2(C_1-C_4)$alkyl, —$CONH_2$, —$CONH(C_1-C_4)$alkyl, —$CON((C_1-C_4)$alkyl$)((C_1-C_4)$alkyl$)$, —$SO_2(C_1-C_4)$alkyl, —$SO_2NH_2$, —$SO_2NH(C_1-C_4)$alkyl, and $SO_2N((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

each $R^c$ is independently $(C_1-C_4)$alkylamino, —$NR^aSO2R^b$, —$SOR^a$, —$SO_2R^a$, —$NR^aC(O)OR^a$, —$NR^aR^b$, or —$CO_2R^a$;

or a salt thereof.

Subgroups of the compounds encompassed by the general structure of Formula (I) are represented as follows:

Subgroup A of Formula (VII)

X and Z are selected from the group consisting of $(C_1-C_8)$alkyl, $(C_3-C_8)$cycloalkyl, heterocycloalkyl, aryl, heteroaryl, —$NR^aR^b$, and —$OR^a$;

Y is H or F;

$R^1$ is selected from the group consisting of $(C_1-C_8)$alkyl, $(C_3-C_8)$cycloalkyl, heterocycloalkyl, aryl, and heteroaryl;

$R^2$ is hydrogen, $(C_1-C_8)$alkyl, trifluoromethyl, alkoxy, or halo, in which said $(C_1-C_8)$alkyl is optionally substituted with one to two groups selected from amino and $(C_1-C_3)$alkylamino;

$R^7$ is hydrogen, $(C_1-C_3)$alkyl, or alkoxy;

$R^3$ is selected from the group consisting of hydrogen, $(C_1-C_8)$alkyl, cyano, trifluoromethyl, —$NR^aR^b$, and halo;

$R^6$ is selected from the group consisting of hydrogen, halo, cyano, trifluoromethyl, amino, $(C_1-C_8)$alkyl, $(C_3-C_8)$cycloalkyl, aryl, heteroaryl, acylamino; $(C_2-C_8)$alkynyl, arylalkynyl, heteroarylalkynyl; —$SO_2R^a$; —$SO_2NR^aR^b$ and —$NR^aSO_2R^b$;

wherein any $(C_1-C_8)$alkyl, $(C_3-C_8)$cycloalkyl, $(C_2-C_8)$alkynyl, arylalkynyl, heteroarylalkynyl group is optionally substituted by 1, 2 or 3 groups independently selected from —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, —$(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, and heteroaryl (C$_1$-C$_4$)alkyl;

R$^a$ and R$^b$ are each independently hydrogen, (C$_1$-C$_8$)alkyl, (C$_2$-C$_8$)alkenyl, (C$_2$-C$_8$)alkynyl, (C$_3$-C$_8$)cycloalkyl, (C$_5$-C$_8$)cycloalkenyl, (C$_6$-C$_{10}$)bicycloalkyl, heterocycloalkyl, aryl, or heteroaryl, wherein said (C$_1$-C$_8$)alkyl, (C$_2$-C$_8$)alkenyl, (C$_2$-C$_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C$_1$-C$_4$)alkoxy, amino, (C$_1$-C$_4$)alkylamino, ((C$_1$-C$_4$)alkyl)((C$_1$-C$_4$)alkyl)amino, —CO$_2$H, —CO$_2$(C$_1$-C$_4$)alkyl, —CONH$_2$, —CONH(C$_1$-C$_4$)alkyl, —CON((C$_1$-C$_4$)alkyl)((C$_1$-C$_4$)alkyl), —SO$_2$(C$_1$-C$_4$)alkyl, —SO$_2$NH$_2$, —SO$_2$NH(C$_1$-C$_4$)alkyl, and —SO$_2$N((C$_1$-C$_4$)alkyl)((C$_1$-C$_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C$_1$-C$_4$)alkyl, (C$_1$-C$_4$)haloalkyl, amino, (C$_1$-C$_4$)alkylamino, ((C$_1$-C$_4$)alkyl)((C$_1$-C$_4$)alkyl)amino, hydroxyl, oxo, (C$_1$-C$_4$)alkoxy, and (C$_1$-C$_4$)alkoxy(C$_1$-C$_4$)alkyl, wherein said ring is optionally fused to a (C$_3$-C$_8$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

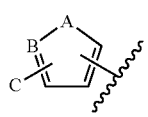

(1)

wherein in (1),
A is O, NH, or S; B is CH or N, and C is hydrogen or C$_1$-C$_8$ alkyl; or

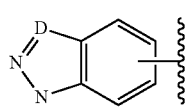

(2)

wherein in (2),
D is N or C optionally substituted by hydrogen or C$_1$-C$_8$ alkyl; or

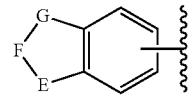

(3)

wherein in (3),
E is NH or CH$_2$; F is O or CO; and G is NH or CH$_2$; or

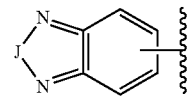

(4)

wherein in (4),
J is O, S or CO; or

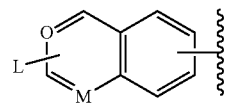

(5)

wherein in (5),
Q is CH or N;
M is CH or N; and
L/(5) is hydrogen, halo, amino, cyano, (C$_1$-C$_8$)alkyl, (C$_3$-C$_8$)cycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R', —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$,
wherein any (C$_1$-C$_8$)alkyl or (C$_3$-C$_8$)cycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$) haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; wherein R$^a$ and R$^b$ are defined as above; or

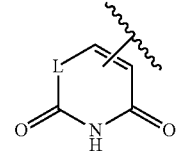

(6)

wherein in (6),
L/(6) is NH or CH$_2$; or

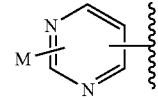

(7)

wherein in 7,
M/(7) is hydrogen, halo, amino, cyano, $(C_1-C_8)$alkyl, $(C_3-C_8)$cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNRC(O)R^b$, —$NR^aNR^aC(O)NR^aR^b$, or —$OR^a$,
wherein any $(C_1-C_5)$alkyl, $(C_3-C_5)$cycloalkyl, or heterocycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$ haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above; or

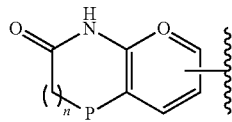
(8)

wherein in (8),
P is $CH_2$, NH, O, or S; Q/(8) is CH or N; and n is 0-2; or

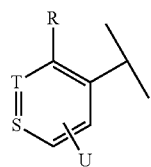
(9)

wherein in (9),
S/(9) and T/(9) is C, or S/(9) is C and T/(9) is N, or S/(9) is N and T/(9) is C;
R is hydrogen, amino, methyl, trifluoromethyl, or halo;
U is hydrogen, halo, amino, cyano, nitro, trifluoromethyl, $(C_1-C_8)$alkyl, $(C_3-C_5)$cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, or 4-(1H-pyrazol-4-yl),
wherein any $(C_1-C_8)$alkyl or $(C_3-C_5)$cycloalkyl group is optionally substituted by 1, 2 or 3 groups independently selected from $(C_1-C_6)$alkyl, $(C_3-C_8)$cycloalkyl, $(C_5-C_8)$ cycloalkenyl, $(C_1-C_6)$ haloalkyl, cyano, —$COR^a$, —$CO_2R^a$, —$CONR^aR^b$, —$SR^a$, $SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above.
Subgroup B of Formula (VII)
X and Z are selected independently from the group consisting of $(C_1-C_5)$alkyl, $(C_3-C_8)$cycloalkyl, heterocycloalkyl, aryl, heteroaryl, —$NR^aR^b$, and —$OR^a$;
Y is H;
$R^1$ is $(C_1-C_8)$alkyl, $(C_3-C_8)$cycloalkyl, or heterocycloalkyl;
$R^2$ is hydrogen, $(C_1-C_3)$alkyl, or halo, in which said $(C_1-C_3)$alkyl is optionally substituted with one to two groups selected from amino and $(C_1-C_3)$alkylamino;
$R^7$ is hydrogen, $(C_1-C_3)$alkyl, or alkoxy;
$R^3$ is hydrogen, $(C_1-C_8)$alkyl or halo;
$R^6$ is hydrogen, halo, cyano, trifluoromethyl, amino, $(C_1-C_8)$alkyl, $(C_3-C_8)$cycloalkyl, aryl, heteroaryl, acylamino; $(C_2-C_8)$alkynyl, arylalkynyl, heteroarylalkynyl, —$SO_2R^a$, —$SO_2NR^aR^b$, or —$NR^aSO_2R^b$;
wherein any $(C_1-C_8)$alkyl, $(C_3-C_8)$cycloalkyl, $(C_2-C_8)$ alkynyl, arylalkynyl, or heteroarylalkynyl group is optionally substituted by 1, 2 or 3 groups independently selected from halo, $(C_1-C_6)$alkyl, $(C_3-C_5)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;
$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$ alkoxy, amino, $(C_1-C_4)$alkylamino, $((C_1-C_4)$alkyl$)((C_1-C_4)$alkyl$)$amino, —$CO_2H$, —$CO_2(C_1-C_4)$alkyl, —$CONH_2$, —$CONH(C_1-C_4)$alkyl, —$CON((C_1-C_4)$alkyl$)((C_1-C_4)$alkyl$)$, —$SO_2(C_1-C_4)$alkyl, —$SO_2NH_2$, —$SO_2NH(C_1-C_4)$alkyl, and —$SO_2N((C_1-C_4)$alkyl$)((C_1-C_4)$alkyl$)$;
or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$ alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;
or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or a compound of another aryl or heteroaryl group as follows:

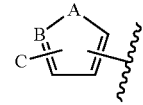
(1)

wherein in (1),
 A is O, NH, or S; B is CH or N, and C is hydrogen or $C_1$-$C_8$ alkyl; or

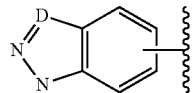
(2)

wherein in (2),
 D is N or C optionally substituted by hydrogen or $C_1$-$C_8$ alkyl; or

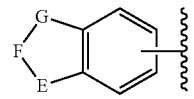
(3)

wherein in (3),
 E is NH or $CH_2$; F is O or CO; and G is NH or $CH_2$; or

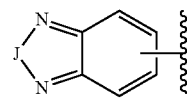
(4)

wherein in (4),
 J is O, S or CO; or

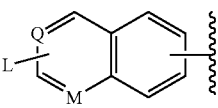
(5)

wherein in (5),
 Q is CH or N;
 M is CH or N; and
 L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$,
 wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, $NR^aSO_2R^b$, —$NR^aSO_2NR^aR^b$, —$OR^a$, —$OC(O)R^a$, and —$OC(O)NR^aR^b$, wherein $R^a$ and $R^b$ are defined as above; or

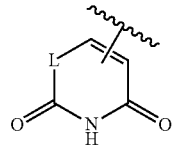
(6)

wherein in (6),
 L/(6) is NH or $CH_2$; or

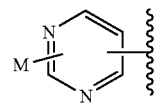
(7)

wherein in (7),
 M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$,
 wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, $NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

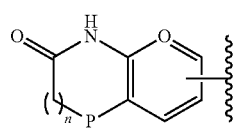
(8)

wherein in (8),
 P is $CH_2$, NH, O, or S; Q/(8) is CH or N; and n is 0-2; or

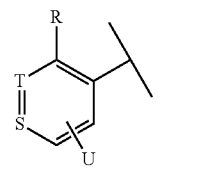
(9)

wherein in (9),
 S/(9) and T/(9) is C, or S/(9) is C and T/(9) is N, or S/(9) is N and T/(9) is C;
 R is hydrogen, amino, methyl, trifluoromethyl, halo;
 U is hydrogen, halo, amino, cyano, nitro, trifluoromethyl, ($C_1$-$C_8$)alkyl, ($C_3$-$C_5$)cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —NR$^a$SO$_2$NR$^a$R$^b$,  —NR$^a$NR$^a$R$^b$,  —NR$^a$NR$^a$C(O)R$^b$, —OR$^a$, or 4-(1H-pyrazol-4-yl), wherein any (C$_1$-C$_8$)alkyl, or (C$_3$-C$_8$)cycloalkyl group is optionally substituted by 1, 2 or 3 groups independently selected from (C$_1$-C$_6$)alkyl, (C$_3$-C$_8$)cycloalkyl, (C$_5$-C$_8$) cycloalkenyl, (C$_1$-C$_6$) haloalkyl, cyano, —COR$^a$, —CO$_2$R$^a$, —CONR$^a$R$^b$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$, wherein R$^a$ and R$^b$ are defined as above.

In some embodiments, the EZH2 inhibitor is:

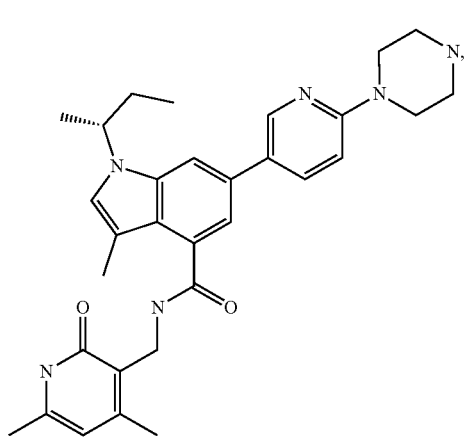

(G)

stereoisomers thereof or pharmaceutically acceptable salt or solvate thereof.

In some embodiments, the EZH2 inhibitor is

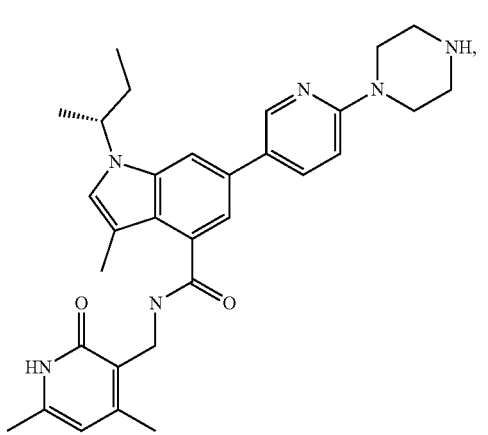

(H)

stereoisomers thereof or pharmaceutically acceptable salt or solvate thereof.

The compounds described herein can be synthesized according to any method known in the art. For example, the compounds having the Formula (VII) can be synthesized according to the method described in WO 2011/140325; WO 2011/140324; and WO 2012/005805, each of which is incorporated by reference in its entirety.

As used herein, "alkyl", "C$_1$, C$_2$, C$_3$, C$_4$, C$_5$ or C$_6$ alkyl" or "C$_1$-C$_6$ alkyl" is intended to include C$_1$, C$_2$, C$_3$, C$_4$, C$_5$ or C$_6$ straight chain (linear) saturated aliphatic hydrocarbon groups and C$_3$, C$_4$, C$_5$ or C$_6$ branched saturated aliphatic hydrocarbon groups. For example, C$_1$-C$_6$ alkyl is intended to include C$_1$, C$_2$, C$_3$, C$_4$, C$_5$ and C$_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., C$_1$-C$_6$ for straight chain, C$_3$-C$_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., C$_3$-C$_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include C$_1$, C$_2$, C$_3$, C$_4$, C$_5$ or C$_6$ straight chain (linear) saturated divalent aliphatic hydrocarbon groups and C$_3$, C$_4$, C$_5$ or C$_6$ branched saturated aliphatic hydrocarbon groups. For example, C$_1$-C$_6$ alkyl linker is intended to include C$_1$, C$_2$, C$_3$, C$_4$, C$_5$ and C$_6$ alkyl linker groups. Examples of alkyl linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH₃CH₂CH₂CH₂—) or n-hexyl (—CH₂CH₂CH₂CH₂CH₂CH₂—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew.*

Chem. 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

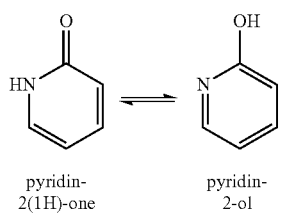 [SMILES: O=c1cccc[nH]1 ; Oc1ccccn1]

pyridin-2(1H)-one    pyridin-2-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any of Formulae disclosed herein include the compounds themselves, as well as their salts or their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any Formula disclosed herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, polymorph or solvate thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5th edition, John Wiley & Sons: New York, 2001; Greene, T. W., Wuts, P. G. M., *Protective Groups in Organic Synthesis*, 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with any Formula disclosed herein may be prepared according to the procedures illustrated in Schemes 1-10 below, from commercially available starting materials or starting materials which can be prepared using literature procedures. The Z and R groups (such as $R_2$, $R_3$, $R_4$, $R_6$, $R_7$, $R_8$, and $R_{12}$) in Schemes 1-10 are as defined in any of Formulae disclosed herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3rd edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
Ac acetyl
AcOH acetic acid
aq. aqueous
BID or b.i.d. bis in die (twice a day)
BOC tert-butoxy carbonyl
Cbz benzyloxy carbonyl
$CDCl_3$ deuterated chloroform
$CH_2Cl_2$ dichloromethane
DCM dichloromethane
DMB 2,4 dimethoxy benzyl
DMF N,N-Dimethylformamide
DMSO Dimethyl sulfoxide
EA or EtOAc Ethyl acetate EDC or EDCI N-(3-Dimethylaminopropyl)-N'-ethylcarbodiimide
ESI− Electrospray negative mode
ESI+ Electrospray positive mode
EtOH ethanol
h hours
H$_2$O water
HOBt 1-Hydroxybenzotriazole
HCl hydrogen chloride or hydrochloric acid
HPLC High performance liquid chromatography
K$_2$CO$_3$ potassium carbonate
LC/MS or LC-MS Liquid chromatography mass spectrum
M Molar
MeCN Acetonitrile
min minutes
Na$_2$CO$_3$ sodium carbonate
Na$_2$SO$_4$ sodium sulfate
NaHCO$_3$ sodium bicarbonate
NaHMDs Sodium hexamethyldisilazide
NaOH sodium hydroxide
NaHCO$_3$ sodium bicarbonate
Na$_2$SO$_4$ sodium sulfate
NMR Nuclear Magnetic Resonance
Pd(OH)$_2$ Palladium dihydroxide
PMB para methoxybenzyl
p.o. per os (oral administration)
ppm parts per million
prep HPLC preparative High Performance Liquid Chromatography
PYBOP (Benzotriazol-1-yloxy)tripyrrolidinophosphonium hexafluorophosphate
Rt or RT Room temperature
TBME tert-Butyl methyl ether
TFA trifluoroacetic acid
THE tetrahydrofuran
THP tetrahydropyran The present invention also provides pharmaceutical compositions comprising a compound of any Formula disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

An EZH2 inhibitor of the present invention may, if desired, be presented in a kit (e.g., a pack or dispenser device) which may contain one or more unit dosage forms containing the EZH2 inhibitor. The pack may for example comprise metal or plastic foil, such as a blister pack. The pack or dispenser device may be accompanied by instructions for administration. Compositions comprising an EZH2 inhibitor of the invention formulated in a compatible pharmaceutical carrier may also be prepared, placed in an appropriate container, and labeled for treatment of an indicated condition. Instructions for use may also be provided.

Also provided herein are kits comprising a plurality of methylation detection reagents that detect the methylated H3-K27. For example, the kit includes mono-methylated H3-K27, di-methylated H3-K27 and tri-methylated H3-K27 detection reagents. The detection reagent is for example antibodies or fragments thereof, polypeptide or aptamers.

A kit may also include reagents for detecting loss of function of at least one component of the SWI/SNF complex, e.g., nucleic acids that specifically identify a mutant component nucleic acid sequence by having homologous nucleic acid sequences, such as oligonucleotide sequences, complementary to a portion of the mutant component nucleic acid sequence or antibodies to proteins encoded by the wild type and/or mutant component nucleic acids packaged together in the form of a kit. The oligonucleotides can be fragments of the component gene. For example the oligonucleotides can be 200, 150, 100, 50, 25, 10 or less nucleotides in length. The kit may contain in separate containers an aptamer or an antibody, control formulations (positive and/or negative), and/or a detectable label such as fluorescein, green fluorescent protein, rhodamine, cyanine dyes, Alexa dyes, luciferase, radiolabels, among others. In addition, reagents for detecting the biological activity of the SWI/SNF complex (such as its chromatin remodeling activity) may be included in the kit.

Instructions (e.g., written, tape, VCR, CD-ROM, etc.) for carrying out the assay may be included in the kit. The assay may for example be in the form of a Western Blot analysis, Immunohistochemistry (IHC), immunofluorescence (IF), sequencing and Mass spectrometry (MS) as known in the art.

Example 1: Durable Tumor Regression in Genetically Altered Lymphomas and Malignant Rhabdoid Tumors by Inhibition of EZH2

Compound A is a potent and selective inhibitor of EZH2: Cell free biochemical assays that included radiolabeled SAM and either chicken erythrocyte oligonucleosomes or peptides corresponding to H3K27 as substrates showed that Compound A selectively inhibited the activity of human PRC2 containing wild-type EZH2 with an inhibition constant (Ki) value of 2.5±0.5 nmol/L and $IC_{50}$ values of 11±5 nM (nucleosome assay) or 16±12 nM (peptide assay). The $IC_{50}$ values were similar for human and rat EZH2 enzymes as well as for EZH2 proteins bearing all known lymphoma change-of-function mutations. The $IC_{50}$ value of Compound A increased with increasing concentration of SAM, but was minimally affected by increasing the amount of oligonucleosome which is consistent with a SAM-competitive and nucleosome-noncompetitive modality of inhibition. In order to demonstrate HMT selectivity, inhibition by Compound A against a panel of HMTs other than EZH2 encompassing both lysine and arginine HMTs was assessed. Compound A displayed a 35-fold selectivity versus EZH1 and greater than 4500-fold selectivity relative to the 14 other HMTs tested.

Compound A specifically inhibits cellular H3K27 methylation in cells: When WSU-DLCL2 EZH2 Y641F mutant lymphoma cells were incubated with Compound A for 4 days, a concentration-dependent reduction in global H3K27Me3 levels was observed with an average $IC_{50}$ value of 0.26 μM (H3K27Me3 levels determined by ELISA). When studying the kinetics of methylation inhibition, the half-life of H3K27Me3 was approximately 1 day as 90% inhibition was only achieved after 3 to 4 days of incubation. When OCI-LY19 EZH2 wild-type lymphoma cells were incubated with 2.7 μM Compound A for 4 days, the only methyl marks affected were the H3K27Me1, H3K27Me2 and H3K27Me3, the three known products of PRC2 catalysis. Incubation with Compound A also resulted in an increase in H3K27 acetylation. The ability of Compound A to reduce global H3K27 trimethylation levels was further tested in several other human lymphoma cell lines including lines expressing either wild-type or mutant EZH2. Compound A reduced H3K27Me3 with similar potency in all cell lines independent of the EZH2 status (Table 1).

Compound A leads to selective killing of lymphoma cell lines bearing EZH2 point mutations: Incubation of WSU-DLCL2 EZH2 Y641F mutant cells with Compound A lead to anti-proliferative effects with an average $IC_{50}$ value of 0.28±0.14 μM in a 6 day proliferation assay. The kinetics of the effect of Compound A on viable cell number was further tested over an extended period of 11 days. The antiproliferative effect of Compound A was apparent after WSU-DLCL2 cells had been exposed to compound for longer than 4 days, consistent with the kinetics of Compound A-mediated cellular H3K27 methylation inhibition. The $IC_{50}$ value for Compound A inhibition of proliferation of WSU-DLCL2 cells in the 11-day assay (0.0086 μM, Table 1) was lower when compared with results obtained with a 6-day proliferation assay, suggesting increased sensitivity with longer incubation periods. In contrast to the WSU-DLCL2 cells, the growth of OCI-LY19 human lymphoma cells (EZH2 wild type for residue Y641) over 11 days was not significantly affected, despite comparable $IC_{50}$ values for H3K27Me3 inhibition for both cell lines (Table 1). In order to identify a concentration at which cells stop proliferating considering the entire incubation period of 11 days, the lowest cytotoxic concentration (LCC) for a particular cell line was calculated. The LCC value for WSU-DLCL2 EZH2 Y641F mutant human lymphoma cells was significantly lower when compared with OCI-LY19 cells that are wild type for EZH2 (Table 1). This context specific cell killing was further supported by results from 11-day proliferation assays with an extended lymphoma cell line panel. All cell lines harboring an EZH2 mutation, with the exception of the RL cell line (EZH2 Y641N), were more sensitive to the antiproliferative effects of Compound A when compared with cell lines with wild-type EZH2 (Table 1). The Pfeiffer cell line (EZH2 A677G) showed a 20 to 300 fold increase in sensitivity to Compound A, as measured by $IC_{50}$ value and LCC, respectively, over the Y641 mutant cell lines. Next the minimum time of compound exposure necessary for sustained cell killing was investigated by washout experiments. The LCC values on day 11 or 14 for WSU-DLCL2 cells that were either incubated with Compound A for 7 days (followed by 7 days of compound washout) or continuously for 14 days were similar (Table 2). Drug exposure for only 4 days, however, was not sufficient to induce LCC values similar to continuous incubation.

Compound A induces $G_1$ arrest and apoptosis in EZH2 mutant lymphoma cells: Next, the effects of incubation with Compound A (1 µM) for 7 days on cell cycle progression and apoptosis in WSU-DLCL2 cells were assessed. An increase in the percentage of cells in $G_1$ phase, and a decrease in the percentage of cells in S phase and G2/M phase was apparent after 2 days of Compound A incubation. The maximum effect was achieved after 4 days. There was no apparent increase in the sub-$G_1$ fraction suggesting that apoptosis was not induced by Compound A incubation for 7 days. This is in agreement with the growth curves of WSU-DLCL2 cells in the presence of Compound A indicating that cytotoxic effects were observed only after 7 days of incubation. Following incubation of WSU-DLCL2 cells with Compound A for up to 14 days, the fraction of apoptotic cells determined by TUNEL assay was significantly increased on day 14 compared to vehicle, indicating that Compound A-mediated cell death occurred through the induction of apoptosis.

Oral administration of Compound A leads to EZH2 target inhibition in EZH2 mutant xenograft models in mice: The effect of oral dosing of Compound A on systemic compound exposure and in vivo target inhibition in mice bearing EZH2 mutant lymphoma xenografts was investigated. First, SCID mice implanted subcutaneously with WSU-DLCL2 xenografts were orally dosed with Compound A for 4 or 7 days. Measuring Compound A plasma levels either 5 minutes before or 3 hours after the last dose revealed a clear dose dependent increase in exposure. Only animals dosed at 160 mg/kg TID or 213 mg/kg BID maintained mean compound levels in plasma above the LCC for WSU-DLCL2 cells throughout a dosing cycle (1652 ng/mL, with mouse plasma protein binding considered). Compound determination in homogenates from tumors collected 3 hours after the last dose revealed that only for the highest dose groups compound levels in the 2 compartments were similar. When H3K27Me3 levels in tumors were analyzed, dose dependent EZH2 target inhibition was observed. H3K27Me3 inhibition was less in tumors from mice dosed at 213 mg/kg QD, suggesting that maintaining a plasma concentration above LCC throughout a dosing cycle is required for optimal target inhibition. Dosing for 4 days at 160 mg/kg TID resulted in slightly lower target inhibition than dosing for 7 days at the same dose and schedule, indicating that prolonged dosing increased the degree of target inhibition in WSU-DLCL2 tumors. A similar 7-day study in nude mice implanted subcutaneously with KARAPS-422 xenografts assessing both BID and QD schedules was performed. Compound A induced a dose-dependent reduction of tumor H3K27Me3 levels at both regimens.

Compound A induces significant antitumor effects in several EZH2 mutant lymphoma xenografts: When WSU-DLCL2 EZH2 Y641F mutant xenograft tumor bearing SCID mice were treated with Compound A for 28 days, dose-dependent tumor growth inhibition, 58% at the highest dose of 150 mg/kg TID, was observed. Only animals administered the highest dose maintained mean Compound A plasma levels above LCC for WSU-DLCL2 cells throughout the dosing cycle. Dosing of Compound A for 28 days led to a relative compound accumulation in tumor tissue compared with plasma, in contrast to what was observed with 7-day dosing. ELISA analysis of histones from tumors collected on day 28 indicated dose-dependent target inhibition. H3K27Me3 levels in WSU-DLCL2 xenografts were lower in mice dosed for 28 days compared with 7 days indicating that prolonged administration of Compound A increased the degree of target inhibition. In KARPAS-422 EZH2 Y461N mutant xenografts, 28-day dosing of Compound A on a BID schedule had much more dramatic effects. Tumor growth inhibition was observed at doses as low as 80.5 mg/kg BID, but higher doses eradicated the xenografts, and no re-growth was observed for up to 90 days after cessation of dosing. When intermittent dosing schedules were investigated in KARPAS-422 xenograft bearing mice, Compound A again showed significant dose-dependent antitumor effects with two cycles of 7-day on/7-day off and 21 day on/7 day off schedules. For all dosing schedules, tumor growth inhibition and complete regressions were observed at 90 and 361 mg/kg BID, respectively. The Pfeiffer EZH2 A677G mutant xenograft model was the most sensitive tumor model, as suggested by the potent anti-proliferative effects of Compound A on this cell line in vitro. All Compound A dose groups (QD schedule) except the lowest one (30 mg/kg QD) showed complete tumor regressions in all animals. Again, tumor re-growth was not observed until the end of the study (36 days after stopping Compound A administration). Although tumor re-growth was observed at 30 mg/kg QD, this very low dose induced tumor stasis during the administration period. Due to tolerability issues dosing was stopped on day 12 for mice administered 1140 mg/kg QD; still, durable complete regressions were observed in this group that were only exposed to Compound A for 12 days.

Compound A selectively kills SMARCB1 mutant MRT cells in vitro and in vivo: Whether EZH2 inhibition had any effects on the growth and survival of SMARCB1-deleted MRT cells was tested. Incubating SMARCB1-deleted MRT cell lines G401 and A204 with Compound A in a 14-day proliferation assay in vitro induced strong anti-proliferative effects with $IC_{50}$ values in the nM range while the control cell lines RD and SJCRH30 which expressed SMARCB1 were minimally affected (Table 3). Dosing of SCID mice bearing subcutaneous G401 xenografts with Compound A at 266 or 532 mg/kg BID for 28 days eliminated those extremely fast growing tumors. Similar to the KARPAS-422 and Pfeiffer EZH2 mutant NHL xenograft models re-growth was not observed at study end, 32 days after dosing stop. Compound A dosed at 133 mg/kg induced stasis during the administration period, and produced a significant tumor growth delay compared to vehicle after dosing stop. Tumors that were harvested from subsets of mice from each group on day 21 showed strong EZH2 target inhibition at all doses.

Compound A inhibits H3K27 methylation in nontumor tissues in a dose dependent manner: The data described above demonstrate that Compound A represents a new treatment modality for SWI/SNF driven cancers and MRTs. Measuring pharmacodynamic biomarker modulation post-dose is often performed in early clinical trials to assess the degree of target inhibition that is predicted to produce a response based on data from preclinical models. Since the collection of post-dose tumor biopsies is often not possible, easier accessible surrogate tissues such as peripheral blood mononuclear cells (PBMCs), skin or bone marrow are often collected instead. To test EZH2 target inhibition in surrogate tissues male and female Sprague Dawley rats were orally administered 100, 300, or 1000 mg/kg Compound A for 28 days, and PBMCs, bone marrow and skin samples were collected at study end. Plasma levels of Compound A increased dose-dependently in both male and female rats, and the plasma levels were generally higher in females compared with those in males. Due to tolerability issues, females in the 1000 mg/kg group had to be euthanized on day 23. Dose-dependent target inhibition was observed in PBMCs and bone marrow from rats dosed with Compound A, as measured by ELISA. The degree of target inhibition was less pronounced for PBMCs from females that were dosed for 22 days compared with males that were dosed for 28 days (same dose of 1000 mg/kg). A dose dependent reduction in H3K27Me3 positive cells was observed in the epidermis of skin of Compound A-dosed rats, as assessed by an IHC assay. The maximum effect was observed at the highest dose, and was already evident after 22 days of Compound A administration.

Compound A displayed similar properties as other EZH2 inhibitors in vitro, such as very high specificity for EZH2 in biochemical assays when compared with other HMTs and specific inhibition of cellular H3K27 methylation leading to context specific killing of EZH2 mutated NHL cell lines. However, this compound achieved an approximately 10-fold increase in potency, reflected by decreased $K_i$ and $IC_{50}$ values determined in biochemical and cell-functional assays. In addition, Compound A showed excellent oral bioavailability when administered to rodents which lead to dose dependent EZH2 target inhibition in xenograft tumor and nontumor tissues. Importantly, dosing of Compound A induced significant antitumor effects in mice bearing EZH2 mutant lymphoma xenografts. The responses ranged from tumor eradication (no regrowth after dosing cessation) to dose-dependent tumor growth inhibition. The delayed onset of antitumor activity (after 4 to 7 days) was consistent with the kinetics of methylation inhibition and antiproliferative activity induced by incubation of cells with Compound A in vitro. Keeping Compound A plasma levels above LCC throughout a dosing cycle was necessary for the WSU-DLCL2 xenograft model to induce maximal target inhibition and antitumor response. The other two lymphoma xenograft models (KARPAS-422 and Pfeiffer), however, were extremely sensitive to Compound A administration, and keeping plasma levels above LCC was not necessary. Pfeiffer EZH2 A677G mutant xenograft tumors disappeared permanently with very low doses or short dosing periods, suggesting that patients with this type of genetically defined NHL would have a significant treatment effect with Compound A.

MRTs are extremely aggressive pediatric cancers of the brain, kidney, and soft tissues that are highly malignant, locally invasive, frequently metastatic, and particularly lethal, but they are typically diploid and lack genomic aberrations. They are, however, characterized by an almost complete penetrance of loss of expression of the SMARCB1, a core component of the SWI/SNF chromatin remodeling complex. The biallelic inactivation of SMARCB1, for instance induced by mutations, is in essence the sole genetic event in MRTs which suggests a driver role for this genetic aberration. Through genetic studies it has been suggested that PRC2 and SWI/SNF antagonistically regulate gene expression around the RB, Cyclin D1 and MYC pathways. Here, it has been demonstrated pharmacological EZH2 inhibition induced antiproliferative effects in SMARCB1 deleted MRT cell lines and permanently eradicated MRT xenografts in mice. This confirms the dependency of such cancers, in which EZH2 itself is not genetically altered, on PRC2 activity.

Compound A represents a new treatment modality for genetically defined subsets of NHL and for MRTs. The ability to measure dose-dependent changes in H3K27Me3 levels in skin, PBMCs and bone marrow portends the use of signal from these surrogate tissues as a non-invasive pharmacodynamics biomarker in human clinical trials.

TABLE 1

$IC_{50}$ Values for Methylation and Proliferation as well as LCC Values for Compound A in Human Lymphoma Cell Lines

| Cell Line | EZH2 Status | Methylation $IC_{50}$ (nmol/L)[a] | Proliferation $IC_{50}$ (μmol/L)[b] | LCC (μmol/L)[b] |
|---|---|---|---|---|
| DOHH-2 | Wild Type | ND | 1.7 | >10 |
| Farage | Wild Type | ND | 0.099 | >10 |
| OCI-LY19 | Wild Type | 8 | 6.2 | 10-25 |
| Toledo | Wild Type | ND | 7.6 | >10 |
| Karpas-422 | Y641N | 90 | 0.0018 | 0.12 |
| Pfeiffer | A677G | 2 | 0.00049 | 0.0005 |
| RL | Y641N | 22 | 5.8 | >25 |
| SU-DHL-10 | Y641F | ND | 0.0058 | 0.14 |
| SU-DHL-6 | Y641N | 20 | 0.0047 | 0.21 |
| WSU-DLCL2 | Y641F | 9 | 0.0086 | 0.17 |

[a]Derived after incubation for 4 days by immunoblot. Values represent the result from one experiment.

[b]Derived after incubation for 11 days. Compound incubations for each experiment were performed in triplicate, and values represent one experiment for all cell lines except OCI-LY19, Pfeiffer, and WSU-DLCL2. For the remaining three cell lines, values represent the mean from the following number of experiments: OCI-LY19 n = 9; Pfeiffer n = 2 and WSU-DLCL2 n = 15.

TABLE 2

LCC Values for Compound A for WSU-DLCL2 Human Lymphoma Cells Dosed Either Continuously or After Compound Washout

| WSU-DLCL2 Washout | Day 11 LCC (μM) | Day 14 LCC (μM) |
|---|---|---|
| No Washout | 0.17 | 0.11 |
| 4-day Compound A; 11-day Washout | 0.36 | 0.42 |
| 7-day Compound A; 7-day Washout | 0.19 | 0.075 |

Values represent the mean of duplicate experiments with three replicates per incubation concentration within the experiments.

TABLE 3

IC$_{50}$ Values for Compound A for SMARCB1 Negative MRT Cell Lines and SMARCB1 Positive Control Cell Lines

| Cell Line | SMARCB1 Status | Proliferation IC$_{50}$ (μM), day 7 | Proliferation IC$_{50}$ (μM), day 14 |
|---|---|---|---|
| RD | Wild Type | 9.2 | 5.2 |
| SJCRH30 | Wild Type | 6.1 | 8.8 |
| G401 | Mutant | 0.087 | 0.042 |
| A204 | Mutant | 3.2 | 0.14 |

Values represent the mean of duplicate experiments with three replicates per incubation concentration within the experiments.

Example 2: Durable Tumor Regression in Genetically Altered Malignant Rhabdoid Tumors by Inhibition of EZH2

Compound A is a potent and selective inhibitor of EZH2: Compound A was developed through iterative medicinal chemistry (FIG. 10A). Compound A inhibited the activity of human PRC2 containing wild-type EZH2 with an inhibition constant (Ki) value of 2.5±0.5 nM, and similar potency was observed for EZH2 proteins bearing all known lymphoma change-of-function mutations (Table 5). The compound was found to be SAM-competitive and nucleosome-noncompetitive by steady state kinetic studies (FIG. 11). Inhibition by Compound A against a panel of HMTs other than EZH2 encompassing both lysine and arginine HMTs was also assessed. Compound A displayed a 35-fold selectivity versus EZH1 and >4500-fold selectivity relative to 14 other HMTs tested (Table 5).

TABLE 4

Histone Methyltransferase Inhibition by Compound A

| Enzyme Assay | IC$_{50}$ (nM) | % Inhibition at 1 μM Compound A[a] |
|---|---|---|
| CARM1 | >50,000[b] | 5 ± 3 |
| DOT1L | >50,000[c] | 2 ± 8 |
| EHMT1 | >50,000[c] | 6 ± 6 |
| EHMT2 | >50,000[c] | 7 ± 3 |
| EZH1[d,e] | 392 ± 72[f] | 98 ± 1 |
| EZH2 Peptide Assay[d,e] | 11 ± 5[f] | ND |
| EZH2 Nucleosome Assay[d] | 16 ± 12[f] | 100 ± 1 |
| A677G EZH2[d,e] | 2[b] | ND |
| A687V EZH2[d,e] | 2[b] | ND |
| Y641F EZH2[d,e] | 14 ± 5[f] | ND |
| Y641C EZH2[d,e] | 16[c] | ND |
| Y641H EZH2[d,e] | 6[c] | ND |
| Y641N EZH2[d,e] | 38[b] | ND |
| Y641S EZH2[d,e] | 6[c] | ND |
| rat EZH2[d,e] | 4[c] | ND |
| PRMT1 | >50,000[c] | 5 ± 4 |
| PRMT3 | ND | 2 ± 2 |
| PRMT5/MEP50 | >50,000[c] | 2 ± 6 |
| PRMT6 | ND | 3 ± 3 |
| PRMT8 | >50,000[c] | 7 ± 3 |
| SETD7 | ND | 4 ± 3 |
| SMYD2 | >50,000[c] | 1 ± 2 |
| SMYD3 | ND | 0 ± 5 |
| WHSC1 | >100,000[c] | 8 ± 3 |
| WHSC1L1 | >100,000[c] | 9 ± 8 |

[a]Values represent the mean and standard deviation of duplicate experiments determined at 10 μmol/L Compound A.
[b]Values represent the mean of duplicate experiments with two replicates per experiment.
[c]Values represent one experiment with two replicates per experiment.
[d]All EZH1 and EZH2 proteins were assayed in the context of 4 PRC2 components (EZH1/2, SUZ12, RBAP48, EED).
[e]Assayed with H3K27 peptides as substrates.

Compound A specifically inhibits cellular H3K27 methylation leading to selective apoptotic killing of SMARCB1 mutant MRT cells. A panel of SMARCB1 deficient MRT cells and SMARCB1 wild-type control cells (confirmed by immunoblot, FIG. 12A) were treated with Compound A for 4 days, resulting in concentration-dependent reductions in global H3K27Me3 levels (FIG. 10B and table 6). Treatment of either wild-type or mutant cells resulted in diminution only of methyl marks on H3K27, with no other histone methyl marks being affected (FIG. 12B). In vitro treatment of SMARCB1-deleted MRT cell lines with Compound A induced strong anti-proliferative effects with IC$_{50}$ values in the nM range; while the control (wild-type) cell lines were minimally affected (FIG. 10C and table 6). Antiproliferative effects were apparent in SMARCB1-deleted MRT cells after 7 days of compound exposure, but required 14 days of exposure for maximal activity. The effects of incubation with Compound A (1 μM) for 14 days on cell cycle progression and apoptosis in G401 and RD cells were also assessed. Compound A incubation of RD SMARCB1 wild-type cells showed no changes in cell cycle or apoptosis compared to the DMSO control (FIG. 13A). In contrast, G401 SMARCB1-deleted cells showed an increase in the percentage of cells in G$_1$ phase, and a concomitant decrease in S phase and G2/M phase after 7 days (FIG. 13B). There was no apparent increase in the sub-G$_1$ fraction through day 7, suggesting that apoptosis was not yet induced by that time. This coincides with the growth curves of G401 cells in the presence of Compound A that display cytotoxicity only after 7 days of incubation (FIG. 10C). Following Compound A treatment of G401 cells for up to 14 days, the fraction of cells in sub-G$_1$ as well as apoptotic cells determined by TUNEL assay increased in a time dependent manner through days 11 and 14, indicating that Compound A-mediated cell death occurred through the induction of apoptosis (FIG. 13B).

TABLE 6

| Cell Line | SMARCB1 Status | Methylation IC$_{50}$ (nM)[a] | Proliferation IC$_{50}$ on Day 14 (nM)[b] |
|---|---|---|---|
| G401 | mutant | 2.7 | 135 |
| A204 | mutant | 1.4 | 590 |
| G402 | mutant | 1.7 | 144 |
| KYM-1 | mutant | 4.3 | 32 |
| RD | wild-type | 5.6 | 6100, >10000[c] |
| 293 | wild-type | 2.4 | >10000 |
| SJCRH30 | wild-type | 4.9 | 5100, >10000[c] |

[a]Derived after incubation for 4 days, extraction of histones, immunoblot and densitometry. Values represent the mean from two experiments.
[b]Compound incubations for each experiment were performed in triplicate, and values represent the mean of 2 experiments for all cell lines.
[c]Mean calculation of duplicate experiment not possible.

Compound A induces genes of neuronal differentiation and cell cycle inhibition while suppressing expression of hedgehog pathway genes, MYC and EZH2: It has been suggested that SMARCB1 loss drives cancer formation through simultaneous epigenetic perturbation of key cancer pathways. The present data confirmed the previously described reduced expression of genes important for neuronal differentiation (CD133, DOCK4, PTPRK), cell cycle inhibition (CDKN2A) and tumor suppression (BIN1), as well as increased expression of the hedgehog pathway gene GLI1 in SMARCB1-deleted G401 cells compared to control cells (FIG. 14A). Compound A treatment of G401 cells for up to 7 days strongly induced expression of CD133, DOCK4 and PTPRK and up-regulated cell cycle inhibitors CDKN1A and CDKN2A and tumor suppressor BIN1, all in a time-dependent manner (FIG. 14B). Simultaneously, the expression of hedgehog pathway genes, MYC and EZH2 were reduced. Notably, G402 SMARCB1-deleted cells exposed to Compound A for 14 days assumed a neuron-like morphology (FIG. 14C). In contrast, Compound A incubation of RD control cells had minimal effect on expression of the above-mentioned genes.

Figure 16C:
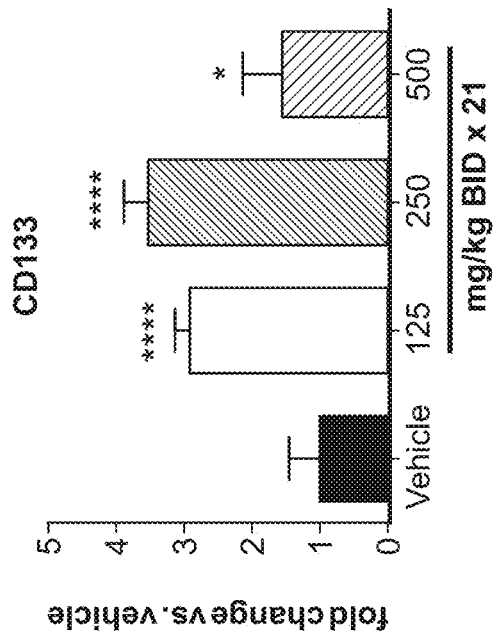
Figure 16E:
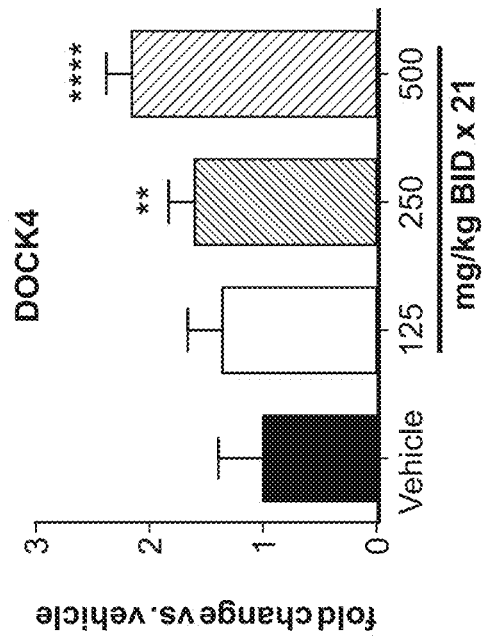

Compound A eradicates SMARCB1 mutant MRT xenografts: Oral dosing of Compound A led to systemic compound exposure, in vivo target inhibition and antitumor activity in mice bearing SMARCB1-deleted MRT xenografts. A study in SCID mice bearing subcutaneous G401 xenografts was performed where animals were dosed for 21 days with Compound A. Half of the mice per group were euthanized on day 21 to collect blood and tissues, while the remaining animals were treated for an additional 7 days and then left without dosing for another 32 days. Compound A was well tolerated at all doses with minimal effect on body weight (FIG. 15A). Dosing at 250 or 500 mg/kg twice daily (BID) for 21 to 28 days practically eliminated the fast-growing G401 tumors (FIGS. 15B, 14C and 16A). Regrowth was not observed for 32 days after dose cessation. Compound A dosed at 125 mg/kg induced tumor stasis during the administration period, and produced a significant tumor growth delay compared to vehicle after the dosing period. Measuring Compound A plasma levels either 5 min before or 3 h after dosing on day 21 revealed a clear dose-dependent increase in systemic exposure (FIG. 15D). Tumors that were harvested from subsets of mice from each group on day 21 showed strong inhibition of H3K27me3, correlating with the antitumor activity (maximum effect achieved at 250 mg/kg, FIG. 16B). In addition, dose-dependent changes in the expression of CD133, PTPRK, DOCK4 and GLI1 were detected in the G401 xenograft tumors (FIG. 16C).

The present data demonstrate that pharmacological inhibition of EZH2 induced antiproliferative effects specifically in SMARCB1-deleted MRT cell lines and permanently eradicated MRT xenografts in mice. This confirms the dependency of such cancers on PRC2 activity, despite the fact that EZH2 itself is not genetically altered in this context. Data presented herein show that in the context of SMARCB1-deleted MRT, inhibition of EZH2 functions as a SMARCB1 surrogate and de-represses neuronal differentiation genes, cell cycle inhibitors and tumor suppressors while reducing GLI1, PTCH1, MYC and EZH2. The sum of the effects of Compound A mediated EZH2 inhibition on several cancer pathways is the cause for the dramatic and permanent anti-tumor activity seen in MRT models. Thus, Compound A represents a new treatment modality for these lethal childhood tumors.

Furthermore, since several members of the SWI/SNF complex are genetically altered in other cancer types besides MRT, it is conceivable that EZH2 also plays a role in tumor maintenance and survival in a spectrum of cancer types. Combined with recent reports demonstrating the effectiveness of EZH2 inhibitors in selective killing of EZH2 mutant bearing non-Hodgkin lymphomas, the present data demonstrate that small molecule-based inhibition of EZH2 is an effective mechanism of therapeutic intervention in a variety of hematologic and solid tumors for which genetic alterations—either target-directed or indirect—confer a proliferative dependency on EZH2 enzymatic activity.

Example 3: Material and Methods

Cell Culture: Cell lines 293T, RD, SJCRH30, A204, G401, G402, and KYM-1. 293T (CRL-11268), RD (CRL-136), SJCRH30 (CRL-2061), A204 (HTB-82), G401 (CRL-1441), and G402 (CRL-1440) were obtained from ATCC. KYM-1 (JCRB0627) was obtained from JCRB. 293T and RD cells were cultured in DMEM+10% FBS. SJCRH30 cells were cultured in RPMI+10% FBS. A204, G401, and G402 cells were cultured in McCoys 5a+10% FBS. KYM-1 cells were cultured in DMEM/Ham's F12+10% FBS.

Western blots analysis: Histones were acid extracted as previously described (Daigle et al., Blood. 2013 Aug. 8; 122(6):1017-25). Western blots for acid extracted histones were performed as previously described (Knutson et al., Proc Natl Acad Sci USA. 2013 May 7; 110(19):7922-7). Whole cell lysates (WCL) were prepared using a modified RIPA buffer (10×RIPA Lysis Buffer (Millipore #20-188), 0.1% SDS (Invitrogen AM9823), protease mini-tablet (Roche #1836153)). Cells were pelleted, washed with ice cold PBS, resuspended in ice cold RIPA buffer, and incubated on ice for 5 minutes. Lysates were sonicated 3× for 10 sec at 50% power, then incubated on ice for 10 minutes. Lysates were then centrifuged at max speed for 15 minutes at 4 degrees in a table top centrifuge. Clarified lysates were aliquoted to a fresh tube, and protein concentrations for WCL were determined by BCA assay (Pierce). Ten micrograms of each lysate was fractionated on 10-20% Tris-Glycine gel (Biorad), transferred using iBlot (7 minutes on program 3, using Nitrocellulose transfer stacks), and probed with the following antibodies in Odyssey blocking buffer: SNF5 (CST #8745), EZH2 (CST #5246), and Beta-actin (CST #3700).

In vitro cell assays: For the adherent cell line proliferation assays (all cell lines except KYM-1, which was analyzed as previously described for suspension cell lines (Daigle et al., Blood. 2013 Aug. 8; 122(6):1017-25), plating densities for each cell line were determined based on growth curves (measured by ATP viability) and density over a 7 day timecourse. On the day before compound treatment, cells were plated in either 96-well plates in triplicate (for the day 0-7 timecourse) or 6-well plates (for replating on day 7 for the remainder of the timecourse). On Day 0, cells were either untreated, DMSO-treated, or treated with Compound A starting at 10 uM and decreasing in either 3- or 4-fold dilutions. Plates were read on Day 0, Day 4, and Day 7 using CellTiter-Glo® (Promega), with compound/media being replenished on Day 4. On Day 7, the 6-well plates were trypsinized, centrifuged, and resuspended in fresh media for counting by Vi-Cell. Cells from each treatment were replated at the original density in 96-well plates in triplicate. Cells were allowed to adhere to the plate overnight, and cells were treated as on Day 0. On Day 7, 11 and 14, plates were read using CellTiter-Glo®, with compound/media being replenished on Day 11. Averages of triplicates were used to plot proliferation over the timecourse, and calculate $IC_{50}$ values. For cell cycle and apoptosis, G401 and RD cells were plated in 15 cm dishes in duplicate at a density of $1 \times 10^6$ cells per plate. Cells were incubated with Compound A at 1 uM, in a total of 25 mL, over a course of 14 days, with cells being split back to original plating density on day 4, 7, and 11. Cell cycle analysis and TUNEL assay were performed using a Guava® flow cytometer, following the manufacturer's protocol.

Gene Expression Analysis: G401 and RD cells were plated in T-75 flasks at 175,000 cells/flask and 117,000 cells/flask respectively and allowed to adhere overnight. On Day 0, cells were treated in duplicates with DMSO or 1 uM Compound A. Cells were harvested and pelleted on Day 2, 4, and 7 with media and compound being replenished on Day 4. Tumor tissue from the G401 xenograft animals dosed for 21 days (vehicle, 125 mg/kg, and 250 mg/kg (6 animals each) and 500 mg/kg (4 animals) Compound A dose groups) were used for gene expression analysis. Total mRNA was extracted from cell pellets and tumor tissue using the RNeasy Mini Kit (Qiagen #74106) and reverse transcribed by the High Capacity cDNA Reverse Transcription Kit (Applied Biosystems (AB) #4368813). RT-PCR was performed by ViiA™ 7 Real-Time PCR Systems (AB) using TaqMan Fast Advanced Master Mix (AB #4444964) and TaqMan primer/probe sets in table below. Gene expression was normalized to 18S (AB #Hs99999901_s1) and fold change was calculated using the ΔΔCt method. For the in vivo samples, the average Ct value+/−SD was determined for each dose group and fold change compared to vehicle dose group was calculated using the ΔΔCt method.

| Gene | AB# |
|---|---|
| MYC | Hs00153408_m1 |
| EZH2 | Hs00172783_m1 |
| PTCH1 | Hs00181117_m1 |
| PROM1 (CD133) | Hs01009250_m1 |
| GLI1 | Hs01110766_m1 |
| DOCK4 | Hs00206807_m1 |
| PTPRK | Hs00267788_m1 |
| BIN1 | Hs00184913_m1 |

ELISA: Histones were isolated from tumors as previously described (Daigle et al) and were prepared in equivalent concentrations (0.5 ng/ul for H3 and 4 ng/ul for H3K27Me3) in coating buffer (PBS with 0.05% BSA). Sample or standard (100 μL) was added in duplicate to two 96-well ELISA plates (Thermo Labsystems, Immulon 4HBX #3885). Histones isolated from G401 cells that were treated with DMSO or 10 μmol/L Compound A for 4 days were added to control wells at the same histone concentration as the tumor histone samples. The plates were sealed and incubated overnight at 4° C. The following day, plates were washed 3 times with 300 μL/well PBST (PBS with 0.05% Tween 20; 10×PBST, KPL #51-14-02) on a Bio Tek plate washer. Plates were blocked with 300 μL/well of diluent (PBS+2% BSA+0.05% Tween 20), incubated at room temperature for 2 hours, and washed 3 times with PBST. All antibodies were diluted in diluent. 100 uL/well of anti-H3K27Me3 (CST #9733, 50% glycerol stock 1:1000) or anti-total H3 (Abcam #ab1791, 50% glycerol stock 1:10,000) was added to each plate. Plates were incubated for 90 minutes at room temperature and washed 3 times with PBST. 100 μL/well of anti-Rb-IgG-HRP (Cell Signaling Technology, 7074) was added 1:2000 to the H3K27Me3 plate and 1:6000 to the H3 plate and incubated for 90 minutes at room temperature. Plates were washed 4 times with PBST. For detection, 100 μL/well of TMB substrate (BioFx Laboratories, #TMBS) was added and plates incubated in the dark at room temperature for 5 minutes. Reaction was stopped with 100 μL/well 1N $H_2SO_4$. Absorbance at 450 nm was read on SpectraMax M5 Microplate reader.

Xenograft study: All the procedures related to animal handling, care and the treatment in this study were performed according to the guidelines approved by the Institutional Animal Care and Use Committee (IACUC) of Shanghai Chemparner following the guidance of the Association for Assessment and Accreditation of Laboratory Animal Care (AAALAC). For the in vivo study, mice were inoculated subcutaneously at the right flank with G-401 tumor cells ($5 \times 10^6$/mouse) in 0.2 ml mixture of base media and Matrigel (McCoy's 5A:Matrigel=1:1) for tumor development. The treatments were started when the tumor size reached approximately 157 mm3 for the tumor efficacy study (n=16 mice per group). Compound A or vehicle (0.5% NaCMC+0.1% Tween-80 in water) was administered orally BID at a dose volume of 10 μL/g for either 21 or 28 days. Animal body weights were measured every day during the first week, then twice weekly for the remainder of the study. Tumor size was measured twice weekly in two dimensions using a caliper, and the volume was expressed in $mm^3$. For PK/PD analysis, 8 mice with the largest tumor burden were euthanized for tumor and blood collection after 21 days of dosing. The remaining mice continued dosing for one more week, and from day 29, treatment was stopped and the mice were enrolled in a tumor growth delay study. Mice were observed as individuals until they reached the tumor weight endpoint (2000 $mm^3$) or until day 60 (whichever came first).

Pharmacokinetic analyses: Dexamethasone was used as internal standard. An aliquot of 30 μL plasma sample was added with 30 μL IS (Dexamethasone, 1000 ng/mL) and 150 μL ACN. The mixture was vortexed for 5 min and centrifuged at 14000 rpm for 5 min. An aliquot of 2 μL supernatant was injected for LC-MS/MS analysis (Q-trap 3200). For 10-fold diluted plasma samples an aliquot of 3 μL plasma sample was added with 27 μL blank plasma, the dilution factor was 10, then added with 30 μL IS (Dexamethasone, 1000 ng/mL) and 150 μL ACN. The mixture was vortexed for 5 min and centrifuged at 14000 rpm for 5 min. An aliquot of 2 μL supernatant was injected for LC-MS/MS analysis. Tumor samples were homogenized on Beadbeater® for 30 seconds with 3×PBS (w/v) to obtain a tumor homogenate. An aliquot of 30 μL tumor homogenate sample was added with 30 μL IS (Dexamethasone, 1000 ng/mL) and 150 μL ACN. The mixture was vortexed for 5 min and centrifuged at 14000 rpm for 5 min. An aliquot of 2 μL supernatant was injected for LC-MS/MS analysis.

Example 4: General Experimental Procedures

NMR $^1$H-NMR spectra were taken using $CDCl_3$ unless otherwise stated and were recorded at 400 or 500 MHz using a Varian or Oxford instruments magnet (500 MHz) instruments. Multiplicities indicated are s=singlet, d=doublet, t=triplet, q=quartet, quint=quintet, sxt=sextet, m=multiplet, dd=doublet of doublets, dt=doublet of triplets; br indicates a broad signal.

LCMS and HPLC

Shimadzu LC-Q, Shimadzu LCMS-2010EV or Waters Acquity Ultra Performance LC. HPLC: Products were analyzed by Shimadzu SPD-20A with 150×4.5 mm YMC ODS-M80 column or 150×4.6 mm YMC-Pack Pro C18 column at 1.0 ml/min.

Mobile phase was MeCN:H2O=3:2 (containing 0.3% SDS and 0.05% $H_3PO_4$), 0.05% TFA in water, 0.05% TFA in acetonitrile (gradient Initial 20%, then 0.05% TFA/MeCN to conc. to 95% in 3 min. holds for 0.5 min. at 3.51 to 4.50 min then 0.05% TFA/MeCN conc. 20%).

Alternatively the LCMS, 2 different methods were used; the one we use the most is the high pH (METCR1600) and the other one for more standard compounds (METCR1416).

0.1% Formic acid in water—Mobile phase "A" 0.1% Formic acid in acetonitrile—Mobile phase "B" utilizing Waters Atlantis dC18, 2.1 mm×100 mm, 3 μm column, with a flow rate=0.6 ml/min Column temperature=40° C.; Time (mins) % B 0.00 min 5% B. 5.0 mins 100% B, 5.4 mins 100% B and 0.42 mins 5% B 3.5 minute method refers to Atlantis dC18, 2.1 mm×50 mm, 3 μm column, flow rate of 1 ml/min at 40 C. Mobile phase A Formic acid (aq.) 0.1% mobile phase B formic acid (MeCN) 0.1%, injection 3 μL, gradient 0 mins (5% organic), 2.5 min (100% organic), 2.7 mins (100% organic), 2.71 min (5% organic), 3.5 min (5% organic)

7.0 minute method refers to Atlantis dC18, 2.1 mm×100 mm, 3 μm column, flow rate of 0.6 ml/min at 40 C. Mobile phase A Formic acid (aq.) 0.1% mobile phase B formic acid (MeCN) 0.1%, injection 3 μL, gradient 0 mins (5% organic), 5 min (100% organic), 5.4 mins (100% organic), 5.42 min (5% organic), 7 min (5% organic)

Both the 3. 5 and 7 minute methods were performed on a MS18 Shimadzu LCMS-2010EV or a MS19 Shimadzu LCMS-2010EV system utilizing LC-20AB pumps and SPD-M20A PDA detectors.

Products were purified by HPLC/MS using Waters AutoPurification System with 3100 Mass Detector.

HPLC analyses may also be performed on a Shimdazu LC-2010CHT using an YMC ODS-A, C18, (150×4.6×5 μm) column at ambient temperature with a flow Rate of 1.4 ml/min. An injection volume of 10 μl is utilized and detection occurs via UV/PDA. Mobile Phase A is 0.05% TFA in water and Mobile Phase B is 0.05% TFA in acetonitrile with a gradient program of Initial 5% B to 95% B in 8 min, hold for 1.5 min, at 9.51 to 12 min B. conc. 0.5%. The diluent is the mobile phase Other Automated flash column chromatography was performed on a Biotage Isolera version 4. 10 g SNAP cartridge running at 12 ml/min or a 25 g SNAP cartridge running at 25 ml/min and detecting at 254 nm and 280 nm.

Select Nitrile reductions may be performed on a ThalesNano H-Cube® according to the conditions described in the experimental procedure.

Other related general procedures can also be found in PCT publication No. WO12/118812, PCT application No. PCT/US2012/033648 and PCT application No. PCT/US2012/033662, each of which is incorporated herein by reference in its entirety.

Example 5: Synthesis of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide

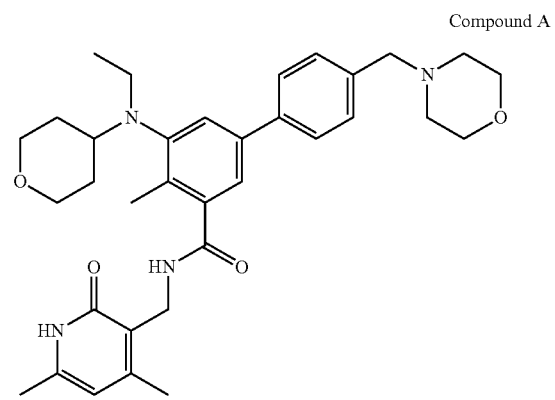 [SMILES: CCN(c1cc(-c2ccc(CN3CCOCC3)cc2)cc(C(=O)NCc2c(C)cc(C)[nH]c2=O)c1C)C1CCOCC1]

Compound A

Step 1: Synthesis of 5-bromo-2-methyl-3-nitrobenzoic acid

To stirred solution of 2-methyl-3-nitrobenzoic acid (100 g, 552 mmol) in conc. $H_2SO_4$ (400 mL), 1,3-dibromo-5,5-dimethyl-2,4-imidazolidinedione (88 g, 308 mmol) was added in a portion wise manner at room temperature and the reaction mixture was then stirred at room temperature for 5 h. The reaction mixture was poured onto ice cold water, the precipitated solid was filtered off, washed with water and dried under vacuum to afford the desired compound as a solid (140 g, 98%). The isolated compound was taken directly into the next step. $^1$H NMR (DMSO-$d_6$, 400 MHz) δ 8.31 (s, 1H), 8.17 (s, 1H), 2.43 (s, 3H).

Step 2: Synthesis of methyl 5-bromo-2-methyl-3-nitrobenzoate

To a stirred solution of 5-bromo-2-methyl-3-nitrobenzoic acid (285 g, 1105 mmol) in DMF (2.8 L) at room temperature was added sodium carbonate (468 g, 4415 mmol) followed by addition of methyl iodide (626.6 g, 4415 mmol).

The resulting reaction mixture was heated at 60° C. for 8 h. After completion (monitored by TLC), the reaction mixture was filtered (to remove sodium carbonate) and washed with ethyl acetate (1 L×3). The combined filtrate was washed with water (3 L×5) and the aqueous phase was back extracted with ethyl acetate (1 L×3). The combined organic layers were dried over anhydrous sodium sulfate, filtered and concentrated under reduced pressure to afford the title compound as a solid (290 g, 97% yield). The isolated compound was taken directly into the next step. $^1$H NMR (CDCl$_3$, 400 MHz) δ 8.17 (s, 1H), 7.91 (s, 1H), 3.96 (s, 3H), 2.59 (s, 3H).

Step 3: Synthesis of methyl 3-amino-5-bromo-2-methylbenzoate

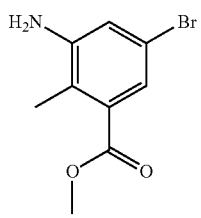

To a stirred solution of methyl 5-bromo-2-methyl-3-nitrobenzoate (290 g, 1058 mmol) in ethanol (1.5 L) was added aqueous ammonium chloride (283 g, 5290 mmol dissolved in 1.5 L water). The resulting mixture was stirred at 80° C. to which iron powder (472 g, 8451 mmol) was added in a portion wise manner. The resulting reaction mixture was heated at 80° C. for 12 h. Upon completion as determined by TLC, the reaction mixture was hot filtered over Celite® and the celite bed was washed with methanol (5 L) followed by washing with 30% MeOH in DCM (5 L). The combined filtrate was concentrated in-vacuo, the residue obtained was diluted with aqueous sodium bicarbonate solution (2 L) and extracted with ethyl acetate (5 L×3). The combined organic layers were dried over anhydrous sodium sulfate, filtered and concentrated under reduced pressure to afford the title compound as a solid (220 g, 85%). The compound was taken directly into the next step. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

Step 4: Synthesis of methyl 5-bromo-2-methyl-3-((tetrahydro-2H-pyran-4-yl) amino) benzoate

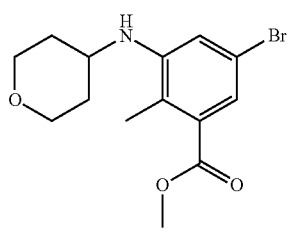 [SMILES: COC(=O)c1cc(Br)cc(NC2CCOCC2)c1C]

To a stirred solution of methyl 3-amino-5-bromo-2-methylbenzoate (15 g, 61.5 mmol) and dihydro-2H-pyran-4(3)-one (9.2 g, 92 mmol) in dichloroethane (300 mL) was added acetic acid (22 g, 369 mmol) and the reaction mixture stirred at room temperature for 15 minutes, then the reaction mixture was cooled to 0° C. and sodium triacetoxyborohydride (39 g, 184 mmol) was added. The reaction mixture was stirred overnight at room temperature. Upon completion of the reaction as determined by TLC, aqueous sodium bicarbonate solution was added to the reaction mixture until a pH of 7-8 was obtained. The organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a solid (14 g, 69%). $^1$H NMR (DMSO-d$_6$, 400 MHz) δ 7.01 (s, 1H), 6.98 (s, 1H), 5.00 (d, 1H, J=7.6 Hz), 3.84-3.87 (m, 2H), 3.79 (s, 3H), 3.54-3.56 (m, 1H), 3.43 (t, 2H, J=12 Hz), 2.14 (s, 3H), 1.81-1.84 (m, 2H), 1.47-1.55 (m, 2H).

Step 5: Synthesis of methyl 5-bromo-3-(ethyl (tetrahydro-2H-pyran-4-yl) amino)-2-methylbenzoate

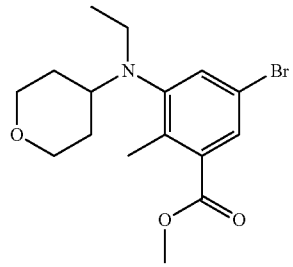 [SMILES: CCN(c1cc(Br)cc(C(=O)OC)c1C)C1CCOCC1]

To a stirred solution of methyl 5-bromo-2-methyl-3-((tetrahydro-2H-pyran-4-yl) amino) benzoate (14 g, 42.7 mmol) in dichloroethane (150 mL) was added acetaldehyde (3.75 g, 85.2 mmol) and acetic acid (15.3 g, 256 mmol). The resulting reaction mixture was stirred at room temperature for 15 minutes. The mixture was cooled to 0° C. and sodium triacetoxyborohydride (27 g, 128 mmol) was added. The reaction mixture was stirred at room temperature for 3 hours. Upon completion of the reaction as determined by TLC, aqueous sodium bicarbonate solution was added to the reaction mixture until a pH 7-8 was obtained, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a viscous liquid (14 g, 93%). $^1$H NMR (DMSO-d$_6$, 400 MHz) δ 7.62 (s, 1H), 7.52 (s, 1H), 3.80 (bs, 5H), 3.31 (t, 2H), 2.97-3.05 (m, 2H), 2.87-2.96 (m, 1H), 2.38 (s, 3H), 1.52-1.61 (m, 2H), 1.37-1.50 (m, 2H), 0.87 (t, 3H, J=6.8 Hz).

Step 6: Synthesis of 5-bromo-N-((4, 6-dimethyl-2-oxo-1, 2-dihydropyridin-3-yl) methyl)-3-(ethyl (tetrahydro-2H-pyran-4-yl) amino)-2-methylbenzamide

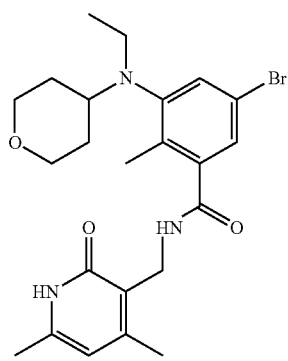 [SMILES: CCN(c1cc(Br)cc(C(=O)NCc2c(C)cc(C)[nH]c2=O)c1C)C1CCOCC1]

To a stirred solution of 5-bromo-3-(ethyl (tetrahydro-2H-pyran-4-yl) amino)-2-methylbenzoate (14 g, 39.4 mmol) in ethanol (100 mL) was added aqueous NaOH (2.36 g, 59.2 mmol in 25 mL water) and the resulting mixture was stirred at 60° C. for 1 h. Upon completion of the reaction as determined by TLC, the solvent was removed under reduced pressure and the residue obtained was acidified with 1N HCl until a pH 7 was obtained and then aqueous citric acid solution was added until a pH 5-6 was obtained. The aqueous layer was extracted with 10% MeOH in DCM (200 mL×3), the combined organic layers were dried over anhydrous sodium sulfate, filtered and concentrated under reduced pressure to give the respective acid (14 g, 100%).

The above acid (14 g, 40.9 mmol) was then dissolved in DMSO (70 mL) and 3-(amino methyl)-4, 6-dimethylpyridin-2(1H)-one (12.4 g, 81.9 mmol) was added to it. The reaction mixture was stirred at room temperature for 15 minutes, then PYBOP (31.9 g, 61.4 mmol) was added and stirring was continued for overnight at room temperature. Upon completion of the reaction as determined by TLC, the reaction mixture was poured onto ice-cold water (700 mL), stirred for 30 minutes and the precipitated solid was collected by filtration, washed with water (500 mL) and air dried. The solid obtained was stirred with acetonitrile (75 mL×2), filtered and air dried. The solid obtained was again stirred with 5% MeOH in DCM (100 mL), filtered and dried completely under vacuum to afford the title compound as a solid (14 g, 74%). $^1$H NMR (DMSO-$d_6$, 400 MHz) δ 11.47 (s, 1H), 8.23 (t, 1H), 7.30 (s, 1H), 7.08 (s, 1H), 5.85 (s, 1H), 4.23 (d, 2H, J=4.4 Hz), 3.81 (d, 2H, J=10.4 Hz), 3.20-3.26 (m, 2H), 3.00-3.07 (m, 1H), 2.91-2.96 (m, 2H), 2.18 (s, 3H), 2.14 (s, 3H), 2.10 (s, 3H), 1.58-1.60 (m, 2H), 1.45-1.50 (m, 2H), 0.78 (t, 3H, J=6.8 Hz).

Step 7: Synthesis of N-((4, 6-dimethyl-2-oxo-1, 2-dihydropyridin-3-yl) methyl)-5-(ethyl (tetrahydro-2H-pyran-4-yl) amino)-4-methyl-4'-(morpholinomethyl)-[1, 1'-biphenyl]-3-carboxamide

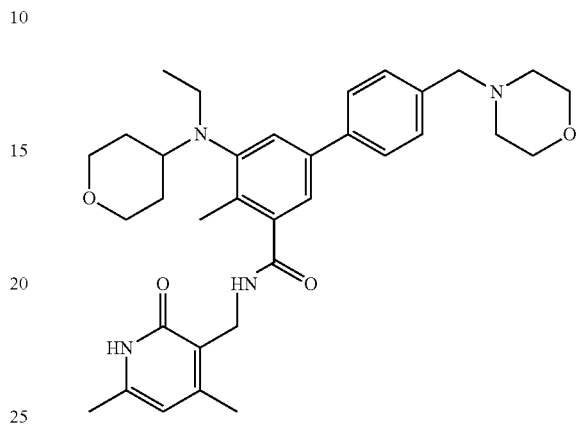

To a stirred solution of 5-bromo-N-((4, 6-dimethyl-2-oxo-1, 2-dihydropyridin-3-yl) methyl)-3-(ethyl (tetrahydro-2H-pyran-4-yl) amino)-2-methylbenzamide (14 g, 29.5 mmol) in dioxane/water mixture (70 mL/14 mL) was added 4-(4-(4, 4, 5, 5-tetramethyl-1, 3, 2-dioxaborolan-2-yl) benzyl) morpholine (13.4 g, 44.2 mmol) followed by addition of $Na_2CO_3$ (11.2 g, 106.1 mmol). The solution was purged with argon for 15 minutes and then Pd (PPh$_3$)$_4$ (3.40 g, 2.94 mmol) was added and the solution was again purged with argon for a further 10 min. The reaction mixture was heated at 100° C. for 4 h. After completion (monitored by TLC), the reaction mixture was diluted with water and extracted with 10% MeOH/DCM. The combined organic layers were dried over anhydrous sodium sulphate, filtered and concentrated under reduced pressure. The crude compound was purified by column chromatography (100-200 mesh silica gel) eluting with methanol: DCM to the title compound as a solid (12 g, 71%). Analytical Data: LCMS: 573.35 (M+1)$^+$; HPLC: 99.5% (@ 254 nm) (R$_t$: 3.999; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.19 (t, 1H), 7.57 (d, 2H, J=7.2 Hz), 7.36-7.39 (m, 3H), 7.21 (s, 1H), 5.85 (s, 1H), 4.28 (d, 2H, J=2.8 Hz), 3.82 (d, 2H, J=9.6 Hz), 3.57 (bs, 4H), 3.48 (s, 2H), 3.24 (t, 2H, J=10.8 Hz), 3.07-3.09 (m, 2H), 3.01 (m, 1H), 2.36 (m, 4H), 2.24 (s, 3H), 2.20 (s, 3H), 2.10 (s, 3H), 1.64-1.67 (m, 2H), 1.51-1.53 (m, 2H), 0.83 (t, 3H, J=6.4 Hz).

Step 8: Synthesis of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide trihydrochloride

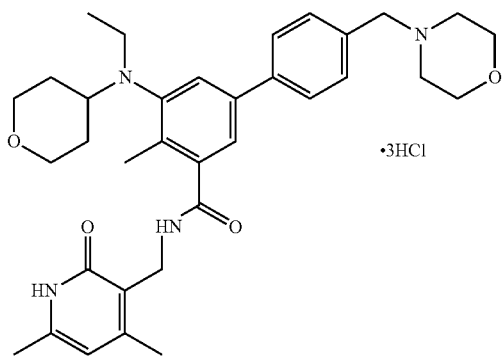 [SMILES: CCN(c1cc(-c2ccc(CN3CCOCC3)cc2)cc(C(=O)NCc2c(C)cc(C)[nH]c2=O)c1C)C1CCOCC1]

N-((4, 6-dimethyl-2-oxo-1, 2-dihydropyridin-3-yl) methyl)-5-(ethyl (tetrahydro-2H-pyran-4-yl) amino)-4-methyl-4'-(morpholinomethyl)-[1, 1'-biphenyl]-3-carboxamide (12 g, 21.0 mmol) was dissolved in methanolic HCl (200 mL) and stirred at room temperature for 3 h. After three hours of stirring, the reaction mixture was concentrated under reduced pressure. The solid obtained was stirred with ether (100 mL×2) to afford the desired salt as a solid (11 g, 77%). Analytical Data of the tri-HCl salt: LCMS: 573.40 (M+1)$^+$; HPLC: 99.1% (@ 254 nm) (R$_t$: 3.961; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (D$_2$O 400 MHz) δ 7.92 (bs, 1H) 7.80 (s, 1H), 7.77 (d, 2H, J=8 Hz), 7.63 (s, 1H), 7.61 (s, 1H), 6.30 (s, 1H), 4.48 (s, 2H), 4.42 (s, 2H), 4.09-4.11 (m, 4H), 3.95-3.97 (m, 2H), 3.77 (t, 3H, J=10.4 Hz), 3.44-3.47 (m, 3H), 3.24-3.32 (m, 3H), 2.42 (s, 3H), 2.35 (s, 3H), 2.26 (s, 3H), 2.01 (m, 2H), 1.76 (m, 2H), 1.04 (t, 3H, J=6.8 Hz).

Example 6: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(morpholinomethyl)-[1,1'-biphenyl]-3-carboxamide Compound E

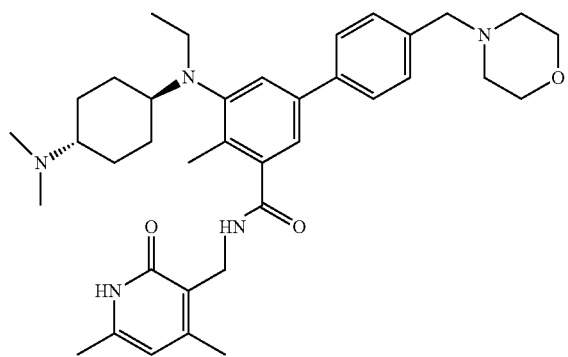

Step 1: 5-bromo-2-methyl-3-nitrobenzoic acid

To stirred solution of 2-methyl-3-nitrobenzoic acid (100 g, 552.48 mmol) in conc. H$_2$SO$_4$ (400 mL), 1,3-dibromo-5, 5-dimethyl-2,4-imidazolidinedione (87.98 g, 307.70 mmol) was added in a portion-wise manner at room temperature. The reaction mixture was then stirred at room temperature for 5 h. The reaction mixture was poured into ice cold water, the precipitated solid collected by filtration, washed with water and dried under vacuum to afford desired 5-bromo-2-methyl-3-nitrobenzoic acid as off-white solid (140 g, 97.90% yield). $^1$H NMR (DMSO-d$_6$, 400 MHz) δ 8.31 (s, 1H), 8.17 (s, 1H), 2.43 (s, 3H).

Step 2: methyl 5-bromo-2-methyl-3-nitrobenzoate

To a stirred solution of 5-bromo-2-methyl-3-nitrobenzoic acid (285 g, 1104.65 mmol) in DMF (2.8 L) was added sodium carbonate (468 g, 4415.09 mmol) followed by addition of methyl iodide (626.63 g, 4415 mmol) at room temperature. The resulting reaction mixture was stirred at 60° C. for 8 h. The reaction mixture was then filtered to remove suspended solids which were washed well with ethyl acetate (3×1 L). The combined filtrates were washed well with water (5×3 L) and the aqueous phase back extracted with ethyl acetate (3×1 L). The combined organic extracts dried over anhydrous sodium sulfate, filtered and concentrated under reduced pressure to afford methyl 5-bromo-2-methyl-3-nitrobenzoate as an off-white solid (290 g, 97% yield). $^1$H NMR (CDCl$_3$, 400 MHz) δ 8.17 (s, 1H), 7.91 (s, 1H), 3.96 (s, 3H), 2.59 (s, 3H).

Step 3: methyl 3-amino-5-bromo-2-methylbenzoate

To a stirred solution of methyl 5-bromo-2-methyl-3-nitrobenzoate (290 g, 1058.39 mmol) in ethanol (1.5 L) was added aqueous ammonium chloride (283 g, 5290 mmol dissolved in 1.5 L water). The resulting mixture was stirred and heated at 80° C. followed by addition of iron powder (472 g, 8451 mmol) in portions at 80° C. The resulting reaction mixture was heated at 80° C. for 12 h. The reaction mixture was then hot filtered through Celite® and the Celite® bed washed well methanol (5 L) and then with 30% MeOH in DCM (5 L). The combined filtrates were concentrated in vacuo and the residue obtained was diluted with aqueous bicarbonate (2 L) and extracted with ethyl acetate (3×5 L). The combined organic layers were dried over anhydrous sodium sulfate, filtered and concentrated under reduced pressure to afford methyl 3-amino-5-bromo-2-methylbenzoate as a brown solid (220 g, 89.41% yield).

A portion of the product (5 g) was dissolved in hot ethanol (20 mL), insoluble residue filtered off and mother liquor concentrated to obtain methyl 3-amino-5-bromo-2-methylbenzoate (3.5 g, 70% yield) with HPLC purity 93.81% as light brown solid. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

Step 4: methyl 5-bromo-3-(((1r,4r)-4-((tert-butoxycarbonyl)amino)cyclohexyl)amino)-2-methylbenzoate To a stirred solution of methyl 3-amino-5-bromo-2-methylbenzoate (5 g, 20.5 mmol) and tert-butyl (4-oxocyclohexyl)carbamate (5.69 g, 26.7 mmol) in dichloroethane (50 mL), acetic acid (7.4 g, 123 mmol) was added and the reaction was stirred at room temperature for 10 minutes. Sodium triacetoxyborohydride (13.1 g, 61.7 mmol) was then added at 0° C. and reaction was stirred at room temperature for 16 hours. The reaction was quenched with aqueous sodium bicarbonate, the organic phase separated and the aqueous phase extracted with dichloromethane. The combined organic layers were dried over anhydrous sodium sulfate and concentrated in vacuo. The crude product was purified by silica gel column chromatography (100-200 mesh size) eluting with 10% ethyl acetate in hexane to afford 3.5 g of the more polar (trans) isomer, methyl 5-bromo-3-(((1r,4r)-4-((tert-butoxycarbonyl)amino)cyclohexyl) amino)-2-methylbenzoate, as solid (38.46%). $^1$H NMR (CDCl$_3$, 400 MHz) δ 7.21 (s, 1H), 6.80 (s, 1H), 4.41 (bs, 1H), 3.85 (s, 3H), 3.60 (m, 1H), 3.45 (m, 1H), 3.20 (m, 1H), 2.22 (s, 3H), 2.15 (bs, 2H), 2.05 (bs, 2H), 1.45 (s, 9H), 1.30 (m, 4H).

Step 5: methyl 5-bromo-3-(((1r,4r)-4-((tert-butoxycarbonyl)amino)cyclohexyl)-(ethyl)amino)-2-methylbenzoate To a stirred solution of methyl 5-bromo-3-(((1r,4r)-4-((tert-butoxycarbonyl)amino)-cyclohexyl)(ethyl)amino)-2-methylbenzoate (55 g, 0.124 mol) and acetaldehyde (11 g, 0.25 mol) in dichloroethane (550 mL), acetic acid (44.64 g, 0.744 mol) was added and the reaction mixture stirred at room temperature for 10 minutes. Sodium triacetoxyborohydride (79 g, 0.372 mol) was then added at 0° C. and the reaction mixture was stirred at room temperature for 16 hours. The reaction was quenched with aqueous sodium bicarbonate, the organic phase separated and the aqueous phase extracted with dichloromethane. The combined extracts were dried over anhydrous sodium sulfate and concentrated in-vacuo. The crude compound was purified by silica gel column chromatography (100-200 mesh size) eluting with 10% ethyl acetate in hexane to afford 44 g of methyl 5-bromo-3-(((1r,4r)-4-((tert-butoxycarbonyl)amino) cyclohexyl)-(ethyl)amino)-2-methylbenzoate (75.2%) as solid. $^1$H NMR (DMSO-d6, 400 MHz) δ 7.55 (s, 1H), 7.45 (s, 1H), 6.65 (d, 1H), 3.80 (s, 3H), 3.15 (bs, 1H), 3.05 (q, 2H), 2.60 (m, 1H), 2.30 (s, 3H), 1.75 (m, 4H), 1.40 (m, 2H), 1.35 (s, 9H), 1.10 (m, 2H), 0.80 (t, 3H).

Step 6: tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)carbamate Aqueous NaOH (3.5 g, 0.08 mol in 10 mL H$_2$O) was added to a solution of methyl 5-bromo-3-(((1r,4r)-4-((tert-butoxycarbonyl)amino)cyclohexyl)-(ethyl)amino)-2-methylbenzoate (25 g, 0.053 mol) in EtOH (100 mL) and stirred at 60° C. for 1 h. The ethanol was then removed under reduced pressure and acidified to pH 8 with dilute HCl and to pH 6 with citric acid. The mixture was extracted with 10% methanol in DCM (3×200 mL). The combined organic layers were dried and concentrated giving the respective acid (24.2 g, 99.0%). $^1$H NMR (DMSO-d6, 400 MHz) δ 13.13 (s, 1H), 7.54 (s, 1H), 7.43 (s, 1H), 6.68 (d, 1H), 3.14 (bs, 1H), 3.03 (q, 2H), 2.56 (m, 1H), 2.33 (s, 3H), 1.80-1.65 (m, 4H), 1.40 (m, 2H), 1.35 (s, 9H), 1.10 (m, 2H), 0.77 (t, 3H).

The acid (24 g, 0.053 mol) was dissolved in DMSO (100 mL) and 3-(aminomethyl)-4,6-dimethylpyridin-2(1H)-one (16 g, 0.106 mol) and triethylamine (5.3 g, 0.053 mol) was added. The reaction mixture was stirred at room temperature for 15 min before PyBop (41 g, 0.079 mmol) was added and stirring was then continued for overnight at room temperature. The reaction mixture was poured into ice water (1 L). The resulting precipitate was collected by filtration, washed well with water (2×1 L) and dried. The product obtained was further purified by washings with acetonitrile (3×200 mL) and DCM (100 mL) to afford tert-butyl ((1r,4r)-4-((5-bromo-3-(((4,6-dimethyl-2-oxo-1,2-dihydropyridin-3-yl) methyl)carbamoyl)-2-methylphenyl)(ethyl)amino)cyclohexyl)-carbamate (24 g, 77%). $^1$H NMR (DMSO-d6, 400 MHz) δ 11.47 (s, 1H), 8.24 (t, 1H), 7.25 (s, 1H), 7.04 (s, 1H), 6.67 (d, 1H), 5.85 (s, 1H), 4.24 (d, 2H), 3.13 (bs, 1H), 3.01 (q, 2H), 2.53 (m, 1H), 2.18 (s, 3H), 2.10 (s, 6H), 1.80-1.65 (m, 4H), 1.40 (m, 2H), 1.35 (s, 9H), 1.10 (m, 2H), 0.77 (t, 3H).

Step 7: tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)cyclohexyl)carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)-carbamate (24 g, 0.041 mol) and 4-(4-(4,4,5,5-tetramethyl-1,3,2-dioxaborolan-2-yl)benzyl)morpholine (18 g, 0.061 mol) in dioxane/water mixture (160 mL+40 mL), Na$_2$CO$_3$ (15 g, 0.15 mol) was added and solution purged with argon for 15 min. Pd(PPh$_3$)$_4$ (4.7 g, 0.041 mol) was then added and the reaction mixture again purged with argon for 10 min. The reaction mixture was heated at 100° C. for 4 h. The reaction mixture was then diluted with 10% MeOH/DCM (500 mL) and filtered. The filtrate was concentrated, diluted with water (500 mL) and extracted with 10% MeOH in DCM (3×500 mL). The combined organic layers were dried over Na$_2$SO$_4$ and solvent removed under reduced pressure. The crude product was purified by silica gel column chromatography (100-200 mesh) eluting with 7% MeOH in DCM to afford tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)cyclohexyl) carbamate (20 g, 71.43%). H NMR (DMSO-d6, 400 MHz) δ 11.46 (s, 1H), 8.20 (t, 1H), 7.56 (d, 2H), 7.36 (m, 3H), 7.17 (s, 1H), 6.66 (d, 1H), 5.85 (s, 1H), 4.28 (d, 2H), 3.57 (bs, 4H), 3.48 (s, 2H), 3.20-3.05 (m, 3H), 2.62 (m, 1H), 2.36 (bs, 4H), 2.20 (s, 6H), 2.10 (s, 3H), 1.75 (m, 4H), 1.42 (m, 2H), 1.35 (s, 9H), 1.10 (m, 2H), 0.82 (t, 3H).

Step 8: 5-(((1r,4r)-4-aminocyclohexyl)(ethyl) amino)-N-((4,6-dimethyl-2-oxo-1,2-dihydropyridin-3-yl)methyl)-4-methyl-4'-(morpholinomethyl)-[1,1'-biphenyl]-3-carboxamide To a stirred solution of tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl) (ethyl)amino)cyclohexyl)carbamate (20 g, 0.03 mol) in DCM (200 mL) at 0° C., TFA (75 mL) was added and reaction was stirred for 2 h at room temperature. The reaction mixture was then concentrated to dryness and the residue basified with aqueous saturated bicarbonate solution (300 mL) to pH 8. The mixture was extracted with 20% methanol in DCM (4×200 m). The combined extracts were dried over Na$_2$SO$_4$ and the solvent removed under reduced pressure to afford 5-(((1r,4r)-4-aminocyclohexyl)(ethyl) amino)-N-((4,6-dimethyl-2-oxo-1,2-dihydropyridin-3-yl) methyl)-4-methyl-4'-(morpholinomethyl)-[1,1'-biphenyl]-3-carboxamide (15.5 g, 91%) which was used as is in the next reaction. $^1$H NMR (DMSO-d6, 400 MHz) δ 8.18 (bs, 1H), 7.57 (d, 2H), 7.38 (m, 3H), 7.20 (s, 1H), 5.85 (s, 1H), 4.29 (d, 2H), 3.57 (bs, 4H), 3.48 (s, 2H), 3.31 (bs, 2H), 3.10 (m, 2H), 2.91 (m, 1H), 2.67 (m, 1H), 2.36 (bs, 4H), 2.21 (s, 3H), 2.20 (s, 3H), 2.10 (s, 3H), 1.90 (m, 2H), 1.83 (m, 2H), 1.45 (m, 2H), 1.23 (m, 2H), 0.83 (t, 3H).

Step 9: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(morpholinomethyl)-[1,1'-biphenyl]-3-carboxamide To a stirred solution of 5-(((1r,4r)-4-aminocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide (14 g, 0.023 mol) in dichloromethane (150 mL) was added aqueous 35% formaldehyde solution (2.4 g, 0.080 mol) at 0° C. After stirring for 20 min, Na(OAc)$_3$BH (12.2 g, 0.057 mol) was added and stirring continued for 2 h at 0° C. Water (100 mL) was then added to the reaction mixture and the mixture extracted with 20% methanol in DCM (3×200 mL). The combined extracts were dried over Na$_2$SO$_4$ and the solvent removed under reduced pressure. The crude product was purified by basic alumina column chromatography eluting with 6-7% MeOH in DCM to afford the title compound (10 g, 63.6%). LCMS: 614.65 (M+1)$^+$; HPLC: 98.88% (@ 210-370 nm) (R$_t$; 3.724; Method: Column: YMC ODS-A 150 mm×4.6 mm×5; Mobile Phase: A; 0.05% TFA in water/B; 0.05% TFA in acetonitrile; Inj. Vol: 10 L, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.17 (t, 1H), 7.56 (d, 2H, J=8 Hz), 7.36 (m, 3H), 7.17 (s, 1H), 5.85 (s, 1H), 4.29 (d, 2H, J=4.4 Hz), 3.57 (bs, 4H), 3.48 (s, 2H), 3.09 (q, 2H), 2.66 (m, 1H), 2.36 (bs, 4H), 2.21 (s, 3H), 2.20 (s, 3H), 2.11 (s, 9H), 1.79 (m, 4H), 1.36 (m, 2H), 1.11 (m, 2H), 0.82 (t, 3H, J=6.4&6.8 Hz).

Example 7: Bioassay Protocol and General Methods

Protocol for Wild-Type and Mutant PRC2 Enzyme Assays

General Materials. S-adenosylmethionine (SAM), S-adenosylhomocysteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21-44 containing either an unmodified lysine 27 (H3K27me0) or dimethylated lysine 27 (H3K27me2) were synthesized with a C-terminal G (K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

H3K27me0:
(SEQ ID NO: 13)
ATKAARKSAPATGGVKKPHRYRPGGK(biotin)-amide

H3K27me2:
(SEQ ID NO: 14)
ATKAARK(me2)SAPATGGVKKPHRYRPGGK(biotin)-amide

Chicken erythrocyte oligonucleosomes were purified from chicken blood according to established procedures.

Recombinant PRC2 Complexes. Human PRC2 complexes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 7, below. The assays were stopped by the addition of non-radioactive SAM (10 μL) to a final concentration of 600 μM, which dilutes the $^3$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 7

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 L) was added to columns 11, 12, 23, 24, rows A-H for the maximum signal control, and SAH, a known product and inhibitor of PRC2 (1 µL) was added to columns 11, 12, 23, 24, rows I-P for the minimum signal control. A cocktail (40 µL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). The final concentrations were as follows: wild-type PRC2 enzyme was 4 nM, non-radioactive SAM was 430 nM, $^3$H-SAM was 120 nM, chicken erythrocyte olignonucleosome was 120 nM, SAH in the minimum signal control wells was 1 mM and the DMSO concentration was 1%. The assay was stopped by the addition of non-radioactive SAM (10 µL) to a final concentration of 600 µM, which dilutes the $^3$H-SAM to a level where its incorporation into the chicken erythrocyte olignonucleosome substrate is no longer detectable. 50 µL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek EL×405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation $$\% \ inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-parameter $IC_{50}$ fit $$Y = Bottom + \frac{(Top - Bottom)}{1 + \left( \frac{X}{IC_{50}} \right)^{Hill \ Coefficient}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Table 8 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, NY, USA. Extraction Buffer and Neutralization Buffer (5×) were purchased from Active Motif, Carlsbad, CA, USA. Rabbit anti-Histone H3 antibody was purchased from Abcam, Cambridge, MA, USA. Rabbit anti-H3K27me3 and HRP-conjugated anti-rabbit-IgG were purchased from Cell Signaling Technology, Danvers, MA, USA. TMB "Super Sensitive" substrate was sourced from BioFX Laboratories, Owings Mills, MD, USA. IgG-free Bovine Serum Albumin was purchased from Jackson ImmunoResearch, West Grove, PA, USA. PBS with Tween (10× PBST) was purchased from KPL, Gaithersburg, MD, USA. Sulfuric Acid was purchased from Ricca Chemical, Arlington, TX, USA. Immulon ELISA plates were purchased from Thermo, Rochester, NY, USA. V-bottom cell culture plates were purchased from Corning Inc., Corning, NY, USA. V-bottom polypropylene plates were purchased from Greiner Bio-One, Monroe, NC, USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 µL per well. Compound (1 µL) from 96 well source plates was added directly to V-bottom cell plate. Plates were incubated on a titer-plate shaker at 37° C., 5% CO2 for 96 hours. After four days of incubation, plates were spun at 241×g for five minutes and medium was aspirated gently from each well of cell plate without disturbing cell pellet. Pellet was resuspended in 200 µL DPBS and plates were spun again at 241×g for five minutes. The supernatant was aspirated and cold (4° C.) Extraction buffer (100 µL) was added per well. Plates were incubated at 4° C. on orbital shaker for two hours. Plates were spun at 3427× g×10 minutes. Supernatant (80 µL per well) was transferred to its respective well in 96 well V-bottom polypropylene plate. Neutralization Buffer 5× (20 µL per well) was added to V-bottom polypropylene plate containing supernatant. V-bottom polypropylene plates containing crude histone preparation (CHP) were incubated on orbital shaker×five minutes. Crude Histone Preparations were added (2 µL per well) to each respective well into duplicate 96 well ELISA plates containing 100 µL Coating Buffer (1×PBS+BSA 0.05% w/v). Plates were sealed and incubated overnight at 4° C. The following day, plates were washed three times with 300 µL per well 1×PBST. Wells were blocked for two hours with 300 µL per well ELISA Diluent ((PBS (1×) BSA (2% w/v) and Tween20 (0.05% v/v)). Plates were washed three times with 1×PBST. For the Histone H3 detection plate, 100 µL per well were added of anti-Histone-H3 antibody (Abcam, ab1791) diluted 1:10,000 in ELISA Diluent. For H3K27 trimethylation detection plate, 100 µL per well were added of anti-H3K27me3 diluted 1:2000 in ELISA diluent. Plates were incubated for 90 minutes at room temperature. Plates were washed three times with 300 µL 1×PBST per well. For Histone H3 detection, 100 µL of HRP-conjugated anti-rabbit IgG antibody diluted to 1:6000 in ELISA diluent was added per well. For H3K27me3 detection, 100 µL of HRP conjugated anti-rabbit IgG antibody diluted to 1:4000 in ELISA diluent was added per well. Plates were incubated at room temperature for 90 minutes. Plates were washed four times with 1×PBST 300 µL per well. TMB substrate 100 µL was added per well. Histone H3 plates were incubated for five minutes at room temperature. H3K27me3 plates were incubated for 10 minutes at room temperature. The reaction was stopped with sulfuric acid 1N (100 µL per well). Absorbance for each plate was read at 450 nm.

First, the ratio for each well was determined by:

$$\left(\frac{H3K27me3\ OD450\ value}{Histone\ H3\ OD450\ value}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 µM. Percent inhibition was determined and $IC_{50}$ curves were generated using duplicate wells per concentration of compound. $IC_{50}$ values for this assay are presented in Table 8 below.

Percent Inhibition = 100 −

$$\left(\left(\frac{(Individual\ Test\ Sample\ Ratio) - (Background\ Avg\ Ratio)}{(Minimum\ Inhibition\ Ratio) - (Background\ Average\ Ratio)}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, NY, USA. V-bottom polypropylene 384-well plates were purchased from Greiner Bio-One, Monroe, NC, USA. Cell culture 384-well white opaque plates were purchased from Perkin Elmer, Waltham, MA, USA. Cell-Titer Glo® was purchased from Promega Corporation, Madison, WI, USA. SpectraMax M5 plate reader was purchased from Molecular Devices LLC, Sunnyvale, CA, USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 µl of assay medium. A compound source plate was prepared by performing triplicate nine-point 3-fold serial dilutions in DMSO, beginning at 10 mM (final top concentration of compound in the assay was 20 µM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 µl of CellTiter-Glo®® reagent to the cell plates. Luminescence was read in the SpectraMax M5. The concentration inhibiting cell viability by 50% was determined using a 4-parametric fit of the normalized dose response curves.

INCORPORATION BY REFERENCE

The entire disclosure of each of the patent documents and scientific articles referred to herein is incorporated by reference for all purposes.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples above are for purposes of illustration and not limitation of the claims that follow.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A method of treating a human subject comprising administering to the human subject a compound:

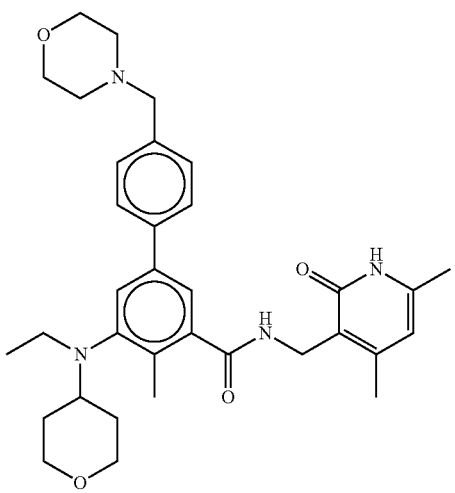

or a pharmaceutically acceptable salt thereof;
wherein the human subject has reduced expression or loss of function of INI1 and epithelioid sarcoma.

2. The method of claim 1, wherein the pharmaceutically acceptable salt is a hydrobromic acid salt.

3. The method of claim 1, wherein the human subject has reduced expression of INI1.

4. The method of claim 2, wherein the human subject has reduced expression of INI1.

5. The method of claim 1, wherein the human subject has loss of function of INI1.

6. The method of claim 2, wherein the human subject has loss of function of INI1.

7. The method of claim 3, wherein reduced expression of INI1 is detected by an immunoassay.

8. The method of claim 4, wherein reduced expression of INI1 is detected by an immunoassay.

9. The method of claim 5, wherein loss of function of INI1 is determined by detecting any alteration in a nucleic acid sequence encoding INI1.

10. The method of claim 6, wherein loss of function of INI1 is determined by detecting any alteration in a nucleic acid sequence encoding INI1.

11. The method of claim 5, wherein loss of function is caused by a loss of function mutation.

12. The method of claim 6, wherein loss of function is caused by a loss of function mutation.

13. The method of claim 9, wherein loss of function is caused by a loss of function mutation.

14. The method of claim 10, wherein loss of function is caused by a loss of function mutation.

* * * * *

SEQUENCE LISTING

<160> NUMBER OF SEQ ID NOS: 14

<210> SEQ ID NO 1
<211> LENGTH: 385
<212> TYPE: PRT
<213> ORGANISM: Homo sapiens

<400> SEQUENCE: 1

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Pro Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270

Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
        355                 360                 365

Asp Arg Asn Thr Arg Arg Met Arg Arg Leu Ala Asn Thr Ala Pro Ala
            370                 375                 380

Trp
385

<210> SEQ ID NO 2
<211> LENGTH: 1717
<212> TYPE: DNA
<213> ORGANISM: Homo sapiens

<400> SEQUENCE: 2

| | | | | | |
|---|---|---|---|---|---|
| aacgccagcg | cctgcgcact | gagggcggcc | tggtcgtcgt | ctgcggcggc | ggcggcggct | 60 |
| gaggagcccg | gctgaggcgc | cagtacccgg | cccggtccgc | atttcgcctt | ccggcttcgg | 120 |
| tttccctcgg | cccagcacgc | cccggccccg | cccagccct | cctgatccct | cgcagcccgg | 180 |
| ctccggccgc | ccgcctctgc | cgccgcaatg | atgatgatgg | cgctgagcaa | gaccttcggg | 240 |
| cagaagcccg | tgaagttcca | gctggaggac | gacggcgagt | tctacatgat | cggctccgag | 300 |
| gtgggaaact | acctccgtat | gttccgaggt | tctctgtaca | agagatacc | ctcactctgg | 360 |
| aggcgactag | ccactgtgga | agagaggaag | aaaatagttg | catcgtcaca | tggtaaaaaa | 420 |
| acaaaaccta | acactaagga | tcacggatac | acgactctag | ccaccagtgt | gaccctgtta | 480 |
| aaagcctcgg | aagtggaaga | gattctggat | ggcaacgatg | agaagtacaa | ggctgtgtcc | 540 |
| atcagcacag | agccccccac | ctacctcagg | gaacagaagg | ccaagaggaa | cagccagtgg | 600 |
| gtacccaccc | tgcccaacag | ctcccaccac | ttagatgccg | tgccatgctc | cacaaccatc | 660 |
| aacaggaacc | gcatgggccg | agacaagaag | agaaccttcc | ccctttgctt | tgatgaccat | 720 |
| gacccagctg | tgatccatga | aacgcatct | cagcccgagg | tgctggtccc | catccggctg | 780 |
| gacatggaga | tcgatgggca | gaagctgcga | gacgccttca | cctggaacat | gaatgagaag | 840 |
| ttgatgacgc | ctgagatgtt | ttcagaaatc | ctctgtgacg | atctggattt | gaacccgctg | 900 |
| acgtttgtgc | cagccatcgc | ctctgccatc | agacagcaga | tcgagtccta | ccccacggac | 960 |
| agcatcctgg | aggaccagtc | agaccagcgc | gtcatcatca | agctgaacat | ccatgtggga | 1020 |
| aacatttccc | tggtggacca | gtttgagtgg | gacatgtcag | agaaggagaa | ctcaccagag | 1080 |
| aagtttgccc | tgaagctgtg | ctcggagctg | gggttgggcg | gggagtttgt | caccaccatc | 1140 |
| gcatacagca | tccggggaca | gctgagctgg | catcagaaga | cctacgcctt | cagcgagaac | 1200 |
| cctctgccca | cagtggagat | tgccatccgg | aacacgggcg | atgcggacca | gtggtgccca | 1260 |
| ctgctggaga | ctctgacaga | cgctgagatg | gagaagaaga | tccgcgacca | ggacaggaac | 1320 |
| acgaggcgga | tgaggcgtct | tgccaacacg | gccccggcct | ggtaaccagc | ccatcagcac | 1380 |
| acggctccca | cggagcatct | cagaagattg | ggccgcctct | cctccatctt | ctggcaagga | 1440 |
| cagaggcgag | gggacagccc | agcgccatcc | tgaggatcgg | gtggggtgg | agtgggggct | 1500 |
| tccaggtggc | ccttcccggc | acacattcca | tttgttgagc | cccagtcctg | cccccaccc | 1560 |
| caccctccct | acccctcccc | agtctctggg | gtcaggaaga | aaccttattt | taggttgtgt | 1620 |
| tttgttttg | tataggagcc | ccaggcaggg | ctagtaacag | ttttaaata | aaaggcaaca | 1680 |
| ggtcatgttc | aatttcttca | acaaaaaaaa | aaaaaaa | | | 1717 |

<210> SEQ ID NO 3
<211> LENGTH: 376
<212> TYPE: PRT
<213> ORGANISM: Homo sapiens

<400> SEQUENCE: 3

```
Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Pro Thr Tyr Leu Arg
            100                 105                 110

Glu Gln Lys Ala Lys Arg Asn Ser Gln Trp Val Pro Thr Leu Pro Asn
            115                 120                 125

Ser Ser His His Leu Asp Ala Val Pro Cys Ser Thr Thr Ile Asn Arg
    130                 135                 140

Asn Arg Met Gly Arg Asp Lys Lys Arg Thr Phe Pro Leu Cys Phe Asp
145                 150                 155                 160

Asp His Asp Pro Ala Val Ile His Glu Asn Ala Ser Gln Pro Glu Val
            165                 170                 175

Leu Val Pro Ile Arg Leu Asp Met Glu Ile Asp Gly Gln Lys Leu Arg
            180                 185                 190

Asp Ala Phe Thr Trp Asn Met Asn Glu Lys Leu Met Thr Pro Glu Met
    195                 200                 205

Phe Ser Glu Ile Leu Cys Asp Asp Leu Asp Leu Asn Pro Leu Thr Phe
210                 215                 220

Val Pro Ala Ile Ala Ser Ala Ile Arg Gln Gln Ile Glu Ser Tyr Pro
225                 230                 235                 240

Thr Asp Ser Ile Leu Glu Asp Gln Ser Asp Gln Arg Val Ile Ile Lys
            245                 250                 255

Leu Asn Ile His Val Gly Asn Ile Ser Leu Val Asp Gln Phe Glu Trp
            260                 265                 270

Asp Met Ser Glu Lys Glu Asn Ser Pro Glu Lys Phe Ala Leu Lys Leu
    275                 280                 285

Cys Ser Glu Leu Gly Leu Gly Gly Glu Phe Val Thr Thr Ile Ala Tyr
290                 295                 300

Ser Ile Arg Gly Gln Leu Ser Trp His Gln Lys Thr Tyr Ala Phe Ser
305                 310                 315                 320

Glu Asn Pro Leu Pro Thr Val Glu Ile Ala Ile Arg Asn Thr Gly Asp
            325                 330                 335

Ala Asp Gln Trp Cys Pro Leu Leu Glu Thr Leu Thr Asp Ala Glu Met
            340                 345                 350

Glu Lys Lys Ile Arg Asp Gln Asp Arg Asn Thr Arg Arg Met Arg Arg
            355                 360                 365

Leu Ala Asn Thr Ala Pro Ala Trp
370                 375
```

<210> SEQ ID NO 4
<211> LENGTH: 1690
<212> TYPE: DNA
<213> ORGANISM: Homo sapiens

<400> SEQUENCE: 4

```
aacgccagcg cctgcgcact gagggcggcc tggtcgtcgt ctgcggcggc ggcggcggct    60
gaggagcccg gctgaggcgc cagtacccgg cccggtccgc atttcgcctt ccggcttcgg   120
tttccctcgg cccagcacgc cccggccccg cccagccct cctgatccct cgcagcccgg   180
ctccggccgc ccgcctctgc cgccgcaatg atgatgatgg cgctgagcaa gaccttcggg   240
cagaagcccg tgaagttcca gctggaggac gacggcgagt ctacatgat cggctccgag   300
gtgggaaact acctccgtat gttccgaggt tctctgtaca agagataccc ctcactctgg   360
aggcgactag ccactgtgga agagaggaag aaaatagttg catcgtcaca tgatcacgga   420
tacacgactc tagccaccag tgtgaccctg ttaaaagcct cggaagtgga agagattctg   480
gatggcaacg atgagaagta caaggctgtg tccatcagca cagagccccc cacctacctc   540
agggaacaga aggccaagag aacagccag tgggtaccca ccctgcccaa cagctcccac   600
cacttagatg ccgtgccatg ctccacaacc atcaacagga accgcatggg ccgagacaag   660
aagagaaacct tccccctttg ctttgatgac catgacccag ctgtgatcca tgagaacgca   720
tctcagcccg aggtgctggt ccccatccgg ctggacatgg agatcgatgg cagaagctg   780
cgagacgcct tcacctggaa catgaatgag aagttgatga cgcctgagat gttttcagaa   840
atcctctgtg acgatctgga tttgaacccg ctgacgtttg tgccagccat cgcctctgcc   900
atcagacagc agatcgagtc ctaccccacg gacagcatcc tggaggacca gtcagaccag   960
cgcgtcatca tcaagctgaa catccatgtg ggaaacattt ccctggtgga ccagtttgag  1020
tgggacatgt cagagaagga gaactcacca gagaagtttg ccctgaagct gtgctcggag  1080
ctggggttgg gcggggagtt tgtcaccacc atcgcataca gcatccgggg acagctgagc  1140
tggcatcaga gacctacgc cttcagcgag aaccctctgc ccacagtgga gattgccatc  1200
cggaacacgg gcgatgcgga ccagtggtgc ccactgctgg agactctgac agacgctgag  1260
atggagaaga gatccgcga ccaggacagg aacacgaggc ggatgaggcg tcttgccaac  1320
acggccccgg cctggtaacc agcccatcag cacacggctc ccacggagca tctcagaaga  1380
ttgggccgcc tctcctccat cttctggcaa ggacagaggc gagggacag cccagcgcca  1440
tcctgaggat cgggtggggg tggagtgggg gcttccaggt ggcccttccc ggcacacatt  1500
ccatttgttg agcccccagtc ctgccccca ccccacccct cctaccccctc cccagtctct  1560
ggggtcagga agaaaccttta ttttaggttg tgttttgttt ttgtatagga gccccaggca  1620
gggctagtaa cagttttttaa ataaaaggca acaggtcatg ttcaatttct tcaacaaaaa  1680
aaaaaaaaaa                                                         1690
```

<210> SEQ ID NO 5
<211> LENGTH: 2492
<212> TYPE: PRT
<213> ORGANISM: Homo sapiens

<400> SEQUENCE: 5

```
Met Thr Ala Glu Pro Met Ser Glu Ser Lys Leu Asn Thr Leu Val Gln
1               5                   10                  15

Lys Leu His Asp Phe Leu Ala His Ser Ser Glu Glu Ser Glu Glu Thr
            20                  25                  30

Ser Ser Pro Pro Arg Leu Ala Met Asn Gln Asn Thr Asp Lys Ile Ser
        35                  40                  45

Gly Ser Gly Ser Asn Ser Asp Met Met Glu Asn Ser Lys Glu Glu Gly
    50                  55                  60
```

-continued

```
Thr Ser Ser Ser Glu Lys Ser Lys Ser Gly Ser Ser Arg Ser Lys
65              70              75              80

Arg Lys Pro Ser Ile Val Thr Lys Tyr Val Glu Ser Asp Asp Glu Lys
            85              90              95

Pro Leu Asp Asp Glu Thr Val Asn Glu Asp Ala Ser Asn Glu Asn Ser
            100             105             110

Glu Asn Asp Ile Thr Met Gln Ser Leu Pro Lys Gly Thr Val Ile Val
            115             120             125

Gln Pro Glu Pro Val Leu Asn Glu Asp Lys Asp Phe Lys Gly Pro
    130             135             140

Glu Phe Arg Ser Arg Ser Lys Met Lys Thr Glu Asn Leu Lys Lys Arg
145             150             155             160

Gly Glu Asp Gly Leu His Gly Ile Val Ser Cys Thr Ala Cys Gly Gln
                165             170             175

Gln Val Asn His Phe Gln Lys Asp Ser Ile Tyr Arg His Pro Ser Leu
            180             185             190

Gln Val Leu Ile Cys Lys Asn Cys Phe Lys Tyr Tyr Met Ser Asp Asp
        195             200             205

Ile Ser Arg Asp Ser Asp Gly Met Asp Glu Gln Cys Arg Trp Cys Ala
    210             215             220

Glu Gly Gly Asn Leu Ile Cys Cys Asp Phe Cys His Asn Ala Phe Cys
225             230             235             240

Lys Lys Cys Ile Leu Arg Asn Leu Gly Arg Lys Glu Leu Ser Thr Ile
            245             250             255

Met Asp Glu Asn Asn Gln Trp Tyr Cys Tyr Ile Cys His Pro Glu Pro
            260             265             270

Leu Leu Asp Leu Val Thr Ala Cys Asn Ser Val Phe Glu Asn Leu Glu
        275             280             285

Gln Leu Leu Gln Gln Asn Lys Lys Ile Lys Val Asp Ser Glu Lys
    290             295             300

Ser Asn Lys Val Tyr Glu His Thr Ser Arg Phe Ser Pro Lys Lys Thr
305             310             315             320

Ser Ser Asn Cys Asn Gly Glu Glu Lys Lys Leu Asp Asp Ser Cys Ser
            325             330             335

Gly Ser Val Thr Tyr Ser Tyr Ser Ala Leu Ile Val Pro Lys Glu Met
            340             345             350

Ile Lys Lys Ala Lys Lys Leu Ile Glu Thr Thr Ala Asn Met Asn Ser
        355             360             365

Ser Tyr Val Lys Phe Leu Lys Gln Ala Thr Asp Asn Ser Glu Ile Ser
    370             375             380

Ser Ala Thr Lys Leu Arg Gln Leu Lys Ala Phe Lys Ser Val Leu Ala
385             390             395             400

Asp Ile Lys Lys Ala His Leu Ala Leu Glu Glu Asp Leu Asn Ser Glu
            405             410             415

Phe Arg Ala Met Asp Ala Val Asn Lys Glu Lys Asn Thr Lys Glu His
            420             425             430

Lys Val Ile Asp Ala Lys Phe Glu Thr Lys Ala Arg Lys Gly Glu Lys
            435             440             445

Pro Cys Ala Leu Glu Lys Lys Asp Ile Ser Lys Ser Glu Ala Lys Leu
    450             455             460

Ser Arg Lys Gln Val Asp Ser Glu His Met His Gln Asn Val Pro Thr
465             470             475             480
```

```
Glu Glu Gln Arg Thr Asn Lys Ser Thr Gly Glu His Lys Lys Ser
                485                 490                 495

Asp Arg Lys Glu Glu Pro Gln Tyr Glu Pro Ala Asn Thr Ser Glu Asp
            500                 505                 510

Leu Asp Met Asp Ile Val Ser Val Pro Ser Ser Val Pro Glu Asp Ile
            515                 520                 525

Phe Glu Asn Leu Glu Thr Ala Met Glu Val Gln Ser Ser Val Asp His
            530                 535                 540

Gln Gly Asp Gly Ser Ser Gly Thr Glu Gln Glu Val Glu Ser Ser Ser
545                 550                 555                 560

Val Lys Leu Asn Ile Ser Ser Lys Asp Asn Arg Gly Gly Ile Lys Ser
                565                 570                 575

Lys Thr Thr Ala Lys Val Thr Lys Glu Leu Tyr Val Lys Leu Thr Pro
            580                 585                 590

Val Ser Leu Ser Asn Ser Pro Ile Lys Gly Ala Asp Cys Gln Glu Val
            595                 600                 605

Pro Gln Asp Lys Asp Gly Tyr Lys Ser Cys Gly Leu Asn Pro Lys Leu
            610                 615                 620

Glu Lys Cys Gly Leu Gly Gln Glu Asn Ser Asp Asn Glu His Leu Val
625                 630                 635                 640

Glu Asn Glu Val Ser Leu Leu Leu Glu Glu Ser Asp Leu Arg Arg Ser
                645                 650                 655

Pro Arg Val Lys Thr Thr Pro Leu Arg Arg Pro Thr Glu Thr Asn Pro
            660                 665                 670

Val Thr Ser Asn Ser Asp Glu Glu Cys Asn Glu Thr Val Lys Glu Lys
            675                 680                 685

Gln Lys Leu Ser Val Pro Val Arg Lys Lys Asp Lys Arg Asn Ser Ser
            690                 695                 700

Asp Ser Ala Ile Asp Asn Pro Lys Pro Asn Lys Leu Pro Lys Ser Lys
705                 710                 715                 720

Gln Ser Glu Thr Val Asp Gln Asn Ser Asp Ser Asp Glu Met Leu Ala
                725                 730                 735

Ile Leu Lys Glu Val Ser Arg Met Ser His Ser Ser Ser Ser Asp Thr
            740                 745                 750

Asp Ile Asn Glu Ile His Thr Asn His Lys Thr Leu Tyr Asp Leu Lys
            755                 760                 765

Thr Gln Ala Gly Lys Asp Asp Lys Gly Lys Arg Lys Arg Lys Ser Ser
            770                 775                 780

Thr Ser Gly Ser Asp Phe Asp Thr Lys Lys Gly Lys Ser Ala Lys Ser
785                 790                 795                 800

Ser Ile Ile Ser Lys Lys Lys Arg Gln Thr Gln Ser Glu Ser Ser Asn
                805                 810                 815

Tyr Asp Ser Glu Leu Glu Lys Glu Ile Lys Ser Met Ser Lys Ile Gly
            820                 825                 830

Ala Ala Arg Thr Thr Lys Lys Arg Ile Pro Asn Thr Lys Asp Phe Asp
            835                 840                 845

Ser Ser Glu Asp Glu Lys His Ser Lys Lys Gly Met Asp Asn Gln Gly
850                 855                 860

His Lys Asn Leu Lys Thr Ser Gln Glu Gly Ser Ser Asp Asp Ala Glu
865                 870                 875                 880

Arg Lys Gln Glu Arg Glu Thr Phe Ser Ser Ala Glu Gly Thr Val Asp
                885                 890                 895

Lys Asp Thr Thr Ile Met Glu Leu Arg Asp Arg Leu Pro Lys Lys Gln
```

-continued

```
                900                 905                 910
Gln Ala Ser Ala Ser Thr Asp Gly Val Asp Lys Leu Ser Gly Lys Glu
            915                 920                 925
Gln Ser Phe Thr Ser Leu Glu Val Arg Lys Val Ala Glu Thr Lys Glu
        930                 935                 940
Lys Ser Lys His Leu Lys Thr Lys Thr Cys Lys Lys Val Gln Asp Gly
945                 950                 955                 960
Leu Ser Asp Ile Ala Glu Lys Phe Leu Lys Lys Asp Gln Ser Asp Glu
                965                 970                 975
Thr Ser Glu Asp Asp Lys Lys Gln Ser Lys Lys Gly Thr Glu Glu Lys
            980                 985                 990
Lys Lys Pro Ser Asp Phe Lys Lys Lys Val Ile Lys Met Glu Gln Gln
        995                 1000                1005
Tyr Glu Ser Ser Ser Asp Gly Thr Glu Lys Leu Pro Glu Arg Glu
    1010                1015                1020
Glu Ile Cys His Phe Pro Lys Gly Ile Lys Gln Ile Lys Asn Gly
    1025                1030                1035
Thr Thr Asp Gly Glu Lys Lys Ser Lys Lys Ile Arg Asp Lys Thr
    1040                1045                1050
Ser Lys Lys Lys Asp Glu Leu Ser Asp Tyr Ala Glu Lys Ser Thr
    1055                1060                1065
Gly Lys Gly Asp Ser Cys Asp Ser Ser Glu Asp Lys Lys Ser Lys
    1070                1075                1080
Asn Gly Ala Tyr Gly Arg Glu Lys Lys Arg Cys Lys Leu Leu Gly
    1085                1090                1095
Lys Ser Ser Arg Lys Arg Gln Asp Cys Ser Ser Ser Asp Thr Glu
    1100                1105                1110
Lys Tyr Ser Met Lys Glu Asp Gly Cys Asn Ser Ser Asp Lys Arg
    1115                1120                1125
Leu Lys Arg Ile Glu Leu Arg Glu Arg Arg Asn Leu Ser Ser Lys
    1130                1135                1140
Arg Asn Thr Lys Glu Ile Gln Ser Gly Ser Ser Ser Asp Ala
    1145                1150                1155
Glu Glu Ser Ser Glu Asp Asn Lys Lys Lys Gln Arg Thr Ser
    1160                1165                1170
Ser Lys Lys Lys Ala Val Ile Val Lys Glu Lys Lys Arg Asn Ser
    1175                1180                1185
Leu Arg Thr Ser Thr Lys Arg Lys Gln Ala Asp Ile Thr Ser Ser
    1190                1195                1200
Ser Ser Ser Asp Ile Glu Asp Asp Gln Asn Ser Ile Gly Glu
    1205                1210                1215
Gly Ser Ser Asp Glu Gln Lys Ile Lys Pro Val Thr Glu Asn Leu
    1220                1225                1230
Val Leu Ser Ser His Thr Gly Phe Cys Gln Ser Ser Gly Asp Glu
    1235                1240                1245
Ala Leu Ser Lys Ser Val Pro Val Thr Val Asp Asp Asp Asp
    1250                1255                1260
Asp Asn Asp Pro Glu Asn Arg Ile Ala Lys Met Leu Leu Glu
    1265                1270                1275
Glu Ile Lys Ala Asn Leu Ser Ser Asp Glu Asp Gly Ser Ser Asp
    1280                1285                1290
Asp Glu Pro Glu Glu Gly Lys Lys Arg Thr Gly Lys Gln Asn Glu
    1295                1300                1305
```

-continued

```
Glu Asn Pro Gly Asp Glu Glu Ala Lys Asn Gln Val Asn Ser Glu
    1310            1315               1320

Ser Asp Ser Asp Ser Glu Glu Ser Lys Lys Pro Arg Tyr Arg His
    1325            1330               1335

Arg Leu Leu Arg His Lys Leu Thr Val Ser Asp Gly Glu Ser Gly
    1340            1345               1350

Glu Glu Lys Lys Thr Lys Pro Lys Glu His Lys Glu Val Lys Gly
    1355            1360               1365

Arg Asn Arg Arg Lys Val Ser Ser Glu Asp Ser Glu Asp Ser Asp
    1370            1375               1380

Phe Gln Glu Ser Gly Val Ser Glu Glu Val Ser Glu Ser Glu Asp
    1385            1390               1395

Glu Gln Arg Pro Arg Thr Arg Ser Ala Lys Lys Ala Glu Leu Glu
    1400            1405               1410

Glu Asn Gln Arg Ser Tyr Lys Gln Lys Lys Arg Arg Arg Ile
    1415            1420               1425

Lys Val Gln Glu Asp Ser Ser Glu Asn Lys Ser Asn Ser Glu
    1430            1435               1440

Glu Glu Glu Glu Glu Lys Glu Glu Glu Glu Glu Glu Glu Glu
    1445            1450               1455

Glu Glu Glu Glu Glu Glu Asp Glu Asn Asp Asp Ser Lys Ser Pro
    1460            1465               1470

Gly Lys Gly Arg Lys Lys Ile Arg Lys Ile Leu Lys Asp Asp Lys
    1475            1480               1485

Leu Arg Thr Glu Thr Gln Asn Ala Leu Lys Glu Glu Glu Glu Arg
    1490            1495               1500

Arg Lys Arg Ile Ala Glu Arg Glu Arg Glu Lys Leu Arg
    1505            1510               1515

Glu Val Ile Glu Ile Glu Asp Ala Ser Pro Thr Lys Cys Pro Ile
    1520            1525               1530

Thr Thr Lys Leu Val Leu Asp Glu Asp Glu Glu Thr Lys Glu Pro
    1535            1540               1545

Leu Val Gln Val His Arg Asn Met Val Ile Lys Leu Lys Pro His
    1550            1555               1560

Gln Val Asp Gly Val Gln Phe Met Trp Asp Cys Cys Cys Glu Ser
    1565            1570               1575

Val Lys Lys Thr Lys Lys Ser Pro Gly Ser Gly Cys Ile Leu Ala
    1580            1585               1590

His Cys Met Gly Leu Gly Lys Thr Leu Gln Val Val Ser Phe Leu
    1595            1600               1605

His Thr Val Leu Leu Cys Asp Lys Leu Asp Phe Ser Thr Ala Leu
    1610            1615               1620

Val Val Cys Pro Leu Asn Thr Ala Leu Asn Trp Met Asn Glu Phe
    1625            1630               1635

Glu Lys Trp Gln Glu Gly Leu Lys Asp Asp Glu Lys Leu Glu Val
    1640            1645               1650

Ser Glu Leu Ala Thr Val Lys Arg Pro Gln Glu Arg Ser Tyr Met
    1655            1660               1665

Leu Gln Arg Trp Gln Glu Asp Gly Gly Val Met Ile Ile Gly Tyr
    1670            1675               1680

Glu Met Tyr Arg Asn Leu Ala Gln Gly Arg Asn Val Lys Ser Arg
    1685            1690               1695
```

```
Lys Leu Lys Glu Ile Phe Asn Lys Ala Leu Val Asp Pro Gly Pro
    1700                1705                1710

Asp Phe Val Val Cys Asp Glu Gly His Ile Leu Lys Asn Glu Ala
    1715                1720                1725

Ser Ala Val Ser Lys Ala Met Asn Ser Ile Arg Ser Arg Arg Arg
    1730                1735                1740

Ile Ile Leu Thr Gly Thr Pro Leu Gln Asn Asn Leu Ile Glu Tyr
    1745                1750                1755

His Cys Met Val Asn Phe Ile Lys Glu Asn Leu Leu Gly Ser Ile
    1760                1765                1770

Lys Glu Phe Arg Asn Arg Phe Ile Asn Pro Ile Gln Asn Gly Gln
    1775                1780                1785

Cys Ala Asp Ser Thr Met Val Asp Val Arg Val Met Lys Lys Arg
    1790                1795                1800

Ala His Ile Leu Tyr Glu Met Leu Ala Gly Cys Val Gln Arg Lys
    1805                1810                1815

Asp Tyr Thr Ala Leu Thr Lys Phe Leu Pro Pro Lys His Glu Tyr
    1820                1825                1830

Val Leu Ala Val Arg Met Thr Ser Ile Gln Cys Lys Leu Tyr Gln
    1835                1840                1845

Tyr Tyr Leu Asp His Leu Thr Gly Val Gly Asn Asn Ser Glu Gly
    1850                1855                1860

Gly Arg Gly Lys Ala Gly Ala Lys Leu Phe Gln Asp Phe Gln Met
    1865                1870                1875

Leu Ser Arg Ile Trp Thr His Pro Trp Cys Leu Gln Leu Asp Tyr
    1880                1885                1890

Ile Ser Lys Glu Asn Lys Gly Tyr Phe Asp Glu Asp Ser Met Asp
    1895                1900                1905

Glu Phe Ile Ala Ser Asp Ser Asp Glu Thr Ser Met Ser Leu Ser
    1910                1915                1920

Ser Asp Asp Tyr Thr Lys Lys Lys Lys Lys Gly Lys Lys Gly Lys
    1925                1930                1935

Lys Asp Ser Ser Ser Ser Gly Ser Gly Ser Asp Asn Asp Val Glu
    1940                1945                1950

Val Ile Lys Val Trp Asn Ser Arg Ser Arg Gly Gly Gly Glu Gly
    1955                1960                1965

Asn Val Asp Glu Thr Gly Asn Asn Pro Ser Val Ser Leu Lys Leu
    1970                1975                1980

Glu Glu Ser Lys Ala Thr Ser Ser Ser Asn Pro Ser Ser Pro Ala
    1985                1990                1995

Pro Asp Trp Tyr Lys Asp Phe Val Thr Asp Ala Asp Ala Glu Val
    2000                2005                2010

Leu Glu His Ser Gly Lys Met Val Leu Leu Phe Glu Ile Leu Arg
    2015                2020                2025

Met Ala Glu Glu Ile Gly Asp Lys Val Leu Val Phe Ser Gln Ser
    2030                2035                2040

Leu Ile Ser Leu Asp Leu Ile Glu Asp Phe Leu Glu Leu Ala Ser
    2045                2050                2055

Arg Glu Lys Thr Glu Asp Lys Asp Lys Pro Leu Ile Tyr Lys Gly
    2060                2065                2070

Glu Gly Lys Trp Leu Arg Asn Ile Asp Tyr Tyr Arg Leu Asp Gly
    2075                2080                2085

Ser Thr Thr Ala Gln Ser Arg Lys Lys Trp Ala Glu Glu Phe Asn
```

```
                2090                2095                2100
Asp  Glu  Thr  Asn  Val  Arg  Gly  Arg  Leu  Phe  Ile  Ile  Ser  Thr  Lys
     2105                2110                2115

Ala  Gly  Ser  Leu  Gly  Ile  Asn  Leu  Val  Ala  Ala  Asn  Arg  Val  Ile
     2120                2125                2130

Ile  Phe  Asp  Ala  Ser  Trp  Asn  Pro  Ser  Tyr  Asp  Ile  Gln  Ser  Ile
     2135                2140                2145

Phe  Arg  Val  Tyr  Arg  Phe  Gly  Gln  Thr  Lys  Pro  Val  Tyr  Val  Tyr
     2150                2155                2160

Arg  Phe  Leu  Ala  Gln  Gly  Thr  Met  Glu  Asp  Lys  Ile  Tyr  Asp  Arg
     2165                2170                2175

Gln  Val  Thr  Lys  Gln  Ser  Leu  Ser  Phe  Arg  Val  Val  Asp  Gln  Gln
     2180                2185                2190

Gln  Val  Glu  Arg  His  Phe  Thr  Met  Asn  Glu  Leu  Thr  Glu  Leu  Tyr
     2195                2200                2205

Thr  Phe  Glu  Pro  Asp  Leu  Leu  Asp  Asp  Pro  Asn  Ser  Glu  Lys  Lys
     2210                2215                2220

Lys  Lys  Arg  Asp  Thr  Pro  Met  Leu  Pro  Lys  Asp  Thr  Ile  Leu  Ala
     2225                2230                2235

Glu  Leu  Leu  Gln  Ile  His  Lys  Glu  His  Ile  Val  Gly  Tyr  His  Glu
     2240                2245                2250

His  Asp  Ser  Leu  Leu  Asp  His  Lys  Glu  Glu  Glu  Leu  Thr  Glu
     2255                2260                2265

Glu  Glu  Arg  Lys  Ala  Ala  Trp  Ala  Glu  Tyr  Glu  Ala  Glu  Lys  Lys
     2270                2275                2280

Gly  Leu  Thr  Met  Arg  Phe  Asn  Ile  Pro  Thr  Gly  Thr  Asn  Leu  Pro
     2285                2290                2295

Pro  Val  Ser  Phe  Asn  Ser  Gln  Thr  Pro  Tyr  Ile  Pro  Phe  Asn  Leu
     2300                2305                2310

Gly  Ala  Leu  Ser  Ala  Met  Ser  Asn  Gln  Gln  Leu  Glu  Asp  Leu  Ile
     2315                2320                2325

Asn  Gln  Gly  Arg  Glu  Lys  Val  Val  Glu  Ala  Thr  Asn  Ser  Val  Thr
     2330                2335                2340

Ala  Val  Arg  Ile  Gln  Pro  Leu  Glu  Asp  Ile  Ile  Ser  Ala  Val  Trp
     2345                2350                2355

Lys  Glu  Asn  Met  Asn  Leu  Ser  Glu  Ala  Gln  Val  Gln  Ala  Leu  Ala
     2360                2365                2370

Leu  Ser  Arg  Gln  Ala  Ser  Gln  Glu  Leu  Asp  Val  Lys  Arg  Arg  Glu
     2375                2380                2385

Ala  Ile  Tyr  Asn  Asp  Val  Leu  Thr  Lys  Gln  Gln  Met  Leu  Ile  Ser
     2390                2395                2400

Cys  Val  Gln  Arg  Ile  Leu  Met  Asn  Arg  Arg  Leu  Gln  Gln  Gln  Tyr
     2405                2410                2415

Asn  Gln  Gln  Gln  Gln  Gln  Met  Thr  Tyr  Gln  Gln  Ala  Thr  Leu
     2420                2425                2430

Gly  His  Leu  Met  Met  Pro  Lys  Pro  Pro  Asn  Leu  Ile  Met  Asn  Pro
     2435                2440                2445

Ser  Asn  Tyr  Gln  Gln  Ile  Asp  Met  Arg  Gly  Met  Tyr  Gln  Pro  Val
     2450                2455                2460

Ala  Gly  Gly  Met  Gln  Pro  Pro  Leu  Gln  Arg  Ala  Pro  Pro  Pro
     2465                2470                2475

Met  Arg  Ser  Lys  Asn  Pro  Gly  Pro  Ser  Gln  Gly  Lys  Ser  Met
     2480                2485                2490
```

```
<210> SEQ ID NO 6
<211> LENGTH: 11202
<212> TYPE: DNA
<213> ORGANISM: Homo sapiens

<400> SEQUENCE: 6
aattctcctg cctgagcctc ggcccaacaa aatggcggcg gcagcggtgt cgctttgttt     60
ccgcggctcc tgcggcggtg gcagtggtag cggcctttga gctgtgggga ggttccagca    120
gcagctacag tgacgactaa gactccagtg catttctatc gtaaccgggc gcggggagc     180 gcagatcggc gcccagcaat cacagaagcc gacaaggcgt tcaagcgaaa acatgaccgc    240
tgagcccatg agtgaaagca agttgaatac attggtgcag aagcttcatg acttccttgc    300
acactcatca gaagaatctg aagaaacaag ttctcctcca cgacttgcaa tgaatcaaaa    360
cacagataaa atcagtggtt ctggaagtaa ctctgatatg atggaaaaca gcaaggaaga    420
gggaactagc tcttcagaaa aatccaagtc ttcaggatcg tcacgatcaa agaggaaacc    480
ttcaattgta acaaagtatg tagaatcaga tgatgaaaaa cctttggatg atgaaactgt    540
aaatgaagat gcgtctaatg aaaattcaga aaatgatatt actatgcaga gcttgccaaa    600
aggtacagtg attgtacagc cagagccagt gctgaatgaa gacaaagatg attttaaagg    660
gcctgaattt agaagcagaa gtaaaatgaa aactgaaaat ctcaaaaaac gcggagaaga    720
tgggcttcat gggattgtga gctgcactgc ttgtggacaa caggtcaatc attttcaaaa    780
agattccatt tatagacacc cttcattgca agttcttatt tgtaagaatt gctttaagta    840
ttacatgagt gatgatatta gccgtgactc agatggaatg gatgaacaat gtaggtggtg    900
tgcggaaggt ggaaacttga tttgttgtga cttttgccat aatgctttct gcaagaaatg    960
cattctacgc aaccttggtc gaaaggagtt gtccacaata atggatgaaa acaaccaatg   1020
gtattgctac atttgtcacc cagagccttt gttggacttg gtcactgcat gtaacagcgt   1080
atttgagaat ttagaacagt tgttgcagca aaataagaag aagataaaag ttgacagtga   1140
aaagagtaat aaagtatatg aacatacatc cagattttct ccaaagaaga ctagttcaaa   1200
ttgtaatgga gaagaaaaga aattagatga ttcctgttct ggctctgtaa cctactctta   1260
ttccgcacta attgtgccca agagatgat taagaaggca aaaaaactga ttgagaccac   1320
agccaacatg aactccagtt atgttaaatt tttaaagcag gcaacagata attcagaaat   1380
cagttctgct acaaaattac gtcagcttaa ggcttttaag tctgtgttgg ctgatattaa   1440
gaaggctcat cttgcattgg aagaagactt aaattccgag tttcgagcga tggatgctgt   1500
aaacaaagag aaaaatacca aagagcataa agtcatagat gctaagtttg aaacaaaagc   1560
acgaaaagga gaaaaccctt gtgctttgga aagaaggat atttcaaagt cagaagctaa   1620
actttcaaga aaacaggtag atagtgagca catgcatcag aatgttccaa cagaggaaca   1680
aagaacaaat aaaagtaccg gtggtgaaca taagaaatct gatagaaaag aagaacctca   1740
atatgaacct gccaacactt ctgaagattt agacatggat attgtgtctg ttccttcctc   1800
agttccagaa gacatttttg agaatcttga gactgctatg gaagttcaga gttcagttga   1860
tcatcaaggg gatggcagca gtggaactga acaagaagtg gagagttcat ctgtaaaatt   1920
aaatatttct tcaaaagaca acagaggagg tattaaatca aaaactacag ctaaagtaac   1980
aaaagaatta tatgttaaac tcactcctgt ttcccttttct aattcccaa ttaaaggtgc   2040 tgattgtcag gaagttccac aagataaaga tggctataaa agttgtggtc tgaacccaa   2100
```

```
gttagagaaa tgtggacttg acaggaaaa cagtgataat gagcatttgg ttgaaaatga    2160
agtttcatta cttttagagg aatctgatct tcgaagatcc ccacgtgtaa agactacacc    2220
cttgaggcga ccgacagaaa ctaaccctgt aacatctaat tcagatgaag aatgtaatga    2280
aacagttaag gagaaacaaa actatcagt tccagtgaga aaaaggata agcgtaattc      2340 ttctgacagt gctatagata atcctaagcc taataaattg ccaaaatcta agcaatcaga    2400
gactgtggat caaaattcag attctgatga aatgctagca atcctcaaag aggtgagcag    2460
gatgagtcac agttcttctt cagatactga tattaatgaa attcatacaa accataagac    2520
tttgtatgat ttaaagactc aggcggggaa agatgataaa ggaaaaagga aacgaaaaag    2580
ttctacatct ggctcagatt ttgatactaa aaagggcaaa tcagctaaga gctctataat    2640
ttctaaaaag aaacgacaaa cccagtctga gtcttctaat tatgactcag aattagaaaa    2700
agagataaag agcatgagta aaattggtgc tgccagaacc accaaaaaaa gaattccaaa    2760
tacaaaagat tttgactctt ctgaagatga gaaacacagc aaaaaaggaa tggataatca    2820
agggcacaaa aatttgaaga cctcacaaga aggatcatct gatgatgctg aaagaaaaca    2880
agagagagag actttctctt cagcagaagg cacagttgat aaagacacga ccatcatgga    2940
attaagagat cgacttccta agaagcagca agcaagtgct tccactgatg gtgtcgataa    3000
gctttctggg aaagagcaga gtttttactt ctttggaagtt agaaaagttg ctgaaactaa    3060
agaaaagagc aagcatctca aaccaaaac atgtaaaaaa gtacaggatg cttatctga    3120 tattgcagag aaattcctaa agaaagacca gagcgatgaa acttctgaag atgataaaaa    3180
gcagagcaaa aagggaactg aagaaaaaaa gaaaccttca gactttaaga aaaaagtaat    3240
taaaatggaa caacagtatg aatcttcatc tgatggcact gaaaagttac ctgagcgaga    3300
agaaatttgt cattttccta agggcataaa acaaattaag aatggaacaa ctgatggaga    3360
aaagaaaagt aaaaaaaataa gagataaaac ttctaaaaag aaggatgaat tatctgatta    3420
tgctgagaag tcaacaggga aaggagatag ttgtgactct tcagaggata aaagagtaa     3480 gaatggagca tatggtagag agaagaaaag gtgcaagttg cttggaaaga gttcaaggaa    3540
gagacaagat tgttcatcat ctgatactga gaaatattcc atgaaagaag atggttgtaa    3600
ctcttctgat aagagactga aagaatagaa attgagggaa agaagaaatt taagttcaaa    3660
gagaaatact aaggaaatac aaagtggctc atcatcatct gatgctgagg aaagttctga    3720
agataataaa aagaagaagc aaagaacttc atctaaaaag aaggcagtca ttgtcaagga    3780 gaaaagaga aactccctaa gaacaagcac taaaaggaag caagctgaca ttacatcctc    3840
atcttcttct gatatagaag atgatgatca gaattctata ggtgagggaa gcagcgatga    3900
acagaaaatt aagcctgtga ctgaaaattt agtgctgtct tcacatactg gattttgcca    3960
atcttcagga gatgaagcct tatctaaatc agtgcctgtc acagtggatg atgatgatga    4020
cgacaatgat cctgagaata gaattgccaa gaagatgctt ttagaagaaa ttaaagccaa    4080
tctttcctct gatgaggatg gatcttcaga tgatgagcca aagaagggaa aaaaagaac    4140 tggaaaacaa aatgaagaaa acccaggaga tgaggaagca aaaaatcaag tcaattctga    4200
atcagattca gattctgaag aatctaagaa gccaagatac agacataggc ttttgcggca    4260
caaattgact gtgagtgacg gagaatctgg agaagaaaaa aagacaaagc ctaaagagca    4320
taaagaagtc aaaggcagaa acagaagaaa ggtgagcagt gaagattcag aagattctga    4380
ttttcaggaa tcaggagtta gtgaagaagt tagtgaatcc gaagatgaac agcggcccag    4440
aacaaggtct gcaaagaaag cagagttgga agaaaatcag cggagctata aacagaaaaa    4500
```

-continued

```
gaaaaggcga cgtattaagg ttcaagaaga ttcatccagt gaaaacaaga gtaattctga      4560
ggaagaagag gaggaaaaag aagaggagga ggaagaggag gaggaggagg aagaggagga      4620
ggaagatgaa aatgatgatt ccaagtctcc tggaaaaggc agaaagaaaa ttcggaagat      4680
tcttaaagat gataaactga gaacagaaac acaaaatgct cttaaggaag aggaagagag      4740
acgaaaacgt attgctgaga gggagcgtga gcgagaaaaa ttgagagagg tgatagaaat      4800
tgaagatgct tcacccacca agtgtccaat aacaaccaag ttggttttag atgaagatga      4860
agaaaccaaa gaacctttag tgcaggttca tagaaatatg gttatcaaat gaaaccccca      4920
tcaagtagat ggtgttcagt ttatgtggga ttgctgctgt gagtctgtga aaaaaacaaa      4980
gaaatctcca ggttcaggat gcattcttgc ccactgtatg ggccttggta agactttaca      5040
ggtggtaagt tttcttcata cagttctttt gtgtgacaaa ctggatttca gcacggcgtt      5100
agtggtttgt cctcttaata ctgctttgaa ttggatgaat gaatttgaga gtggcaaga       5160 gggattaaaa gatgatgaga agcttgaggt ttctgaatta gcaactgtga aacgtcctca      5220
ggagagaagc tacatgctgc agaggtggca agaagatggt ggtgttatga tcataggcta      5280
tgagatgtat agaaatcttg ctcaaggaag gaatgtgaag agtcggaaac ttaaagaaat      5340
atttaacaaa gctttggttg atccaggccc tgattttgtt gtttgtgatg aaggccatat      5400
tctaaaaaat gaagcatctg ctgtttctaa agctatgaat tctatacgat caaggaggag      5460
gattatttta acaggaacac cacttcaaaa taacctaatt gagtatcatt gtatggttaa      5520
ttttatcaag gaaaatttac ttggatccat taaggagttc aggaatagat ttataaatcc      5580
aattcaaaat ggtcagtgtg cagattctac catggtagat gtcagagtga tgaaaaaacg      5640
tgctcacatt ctctatgaga tgttagctgg atgtgttcag aggaaagatt atacagcatt      5700
aacaaaattc ttgcctccaa aacacgaata tgtgttagct gtgagaatga cttctattca      5760
gtgcaagctc tatcagtact acttagatca cttaacaggt gtgggcaata atagtgaagg      5820
tggaagagga aaggcaggtg caaagctttt ccaagatttt cagatgttaa gtagaatatg      5880
gactcatcct tggtgtttgc agctagacta cattagcaaa gaaaataagg gttattttga      5940
tgaagacagt atggatgaat ttatagcctc agattctgat gaaacctcca tgagtttaag      6000
ctccgatgat tatacaaaaa agaagaaaaa agggaaaaag gggaaaaaag atagtagctc      6060
aagtggaagt ggcagtgaca atgatgttga agtgattaag gtctggaatt caagatctcg      6120
gggaggtggt gaaggaaatg tggatgaaac aggaaacaat ccttctgttt ctttaaaact      6180
ggaagaaagt aaagctactt cttcttctaa tccaagcagc ccagctccag actggtacaa      6240
agattttgtt acagatgctg atgctgaggt tttagagcat tctgggaaaa tggtacttct      6300
ctttgaaatt cttcgaatgg cagaggaaat tgggataaaa gtccttgttt tcagccagtc      6360
cctcatatct ctggacttga ttgaagattt tcttgaatta gctagtaggg agaagacaga      6420
agataaagat aaacccctta tttataaagg tgaggggaag tggcttcgaa acattgacta      6480
ttaccgttta gatggttcca ctactgcaca gtcaaggaag aagtgggctg aagaatttaa      6540
tgatgaaact aatgtgagag gacgattatt tatcatttct actaaagcag gatctctagg      6600
aattaatctg gtagctgcta atcgagtaat tatattcgac gcttcttgga atccatctta      6660
tgacatccag agtatattca gagtttatcg ctttggacaa actaagcctg tttatgtata      6720
taggttctta gctcagggaa ccatggaaga taagatttat gatcggcaag taactaagca      6780
gtcactgtct tttcgagttg ttgatcagca gcaggtggag cgtcattta ctatgaatga      6840
```

```
gcttactgaa ctttatactt ttgagccaga cttattagat gaccctaatt cagaaaagaa     6900
gaagaagagg gatactccca tgctgccaaa ggataccata cttgcagagc tccttcagat     6960
acataaagaa cacattgtag gataccatga acatgattct cttttggacc acaaagaaga     7020
agaagagttg actgaagaag aaagaaaagc agcttgggct gagtatgaag cagagaagaa     7080
gggactgacc atgcgtttca acataccaac tgggaccaat ttaccccctg tcagtttcaa     7140
ctctcaaact ccttatattc ctttcaattt gggagccctg tcagcaatga gtaatcaaca     7200
gctggaggac ctcattaatc aaggaagaga aaaagttgta gaagcaacaa acagtgtgac     7260
agcagtgagg attcaacctc ttgaggatat aatttcagct gtatggaagg agaacatgaa     7320
tctctcagag gcccaagtac aggcgttagc attaagtaga caagccagcc aggagcttga     7380
tgttaaacga agagaagcaa tctacaatga tgtattgaca aaacaacaga tgttaatcag     7440
ctgtgttcag cgaatactta tgaacagaag gctccagcag cagtacaatc agcagcaaca     7500
gcaacaaatg acttatcaac aagcaacact gggtcacctc atgatgccaa agcccccaaa     7560
tttgatcatg aatccttcta actaccagca gattgatatg agaggaatgt atcagccagt     7620
ggctggtggt atgcagccac caccattaca gcgtgcacca ccccaatga gaagcaaaaa      7680 tccaggacct cccaaggga aatcaatgtg attttgcact aaaagcttaa tggattgtta     7740
aaatcataga aagatctttt atttttttag gaatcaatga cttaacagaa ctcaactgta     7800
taaatagttt ggtcccctta aatgccaatc ttccatatta gttttacttt tttttttttt     7860 aaataggca taccatttct tcctgacatt tgtcagtgat gttgcctaga atcttcttac      7920
acacgctgag tacagaagat atttcaaatt gttttcagtg aaaacaagtc cttccataat     7980
agtaacaact ccacagattt cctctctaaa tttttatgcc tgcttttagc aaccataaaa     8040
ttgtcataaa attaataaat ttaggaaaga ataaagattt atatattcat tctttacata     8100
taaaaacaca cagctgagtt cttagagttg attcctcaag ttatgaaata cttttgtact     8160
taatccattt cttgattaaa gtgattgaaa tggttttaat gttcttttga ctgaagtctg     8220
aaactgggct cctgctttat tgtctctgtg actgaaagtt agaaactgag ggttatcttt     8280
gacacagaat tgtgtgcaat attcttaaat actactgctc taaaagttgg agaagtcttg     8340
cagttatctt agcattgtat aaacagcctt aagtatagcc taagaagaga attccttttt     8400
cttctttagt ccttctgcca tttttttattt tcagttatat gtgctgaaat aattactggt    8460
aaaatttcag ggttgtggat tatcttccac acatgaattt tctctctcct ggcacgaata     8520
taaagcacat ctcttaactg catggtgcca gtgctaatgc ttcatcctgt tgctggcagt     8580
gggatgtgga cttagaaaat caagttctag cattttagta ggttaacact gaagttgtgg     8640
ttgttaggtt cacaccctgt tttataaaca acatcaaaat ggcagaacca ttgctgactt     8700
taggttcaca tgaggaatgt acttttaaca attcccagta ctatcagtat tgtgaaataa     8760
ttcctctgaa agataagaat cactggcttc tatgcgcttc ttttctctca tcatcatgtt     8820
cttttacccc agtttcctta catttttttta aattgtttca gagtttgttt ttttttttagt    8880 ttagattgtg aggcaattat taaatcaaaa ttaattcatc caatacccct ttactagaag     8940
ttttactaga aaatgtatta cattttattt tttcttaatc cagttctgca aaaatgacct     9000
ataaatttat tcatgtacaa ttttggttac ttgaattgtt aaagaaaaca ttgttttttga    9060 ctatgggagt caactcaaca tggcagaacc attttttgaga tgatgataca acaggtagtg     9120
aaacagctta agaattccaa aaaaaaaaaa aaaaaaaaaa aaagaaaac tgggtttggg       9180 ctttgcttta ggtatcactg gattagaatg agtttaacat tagctaaaac tgctttgagt     9240
```

```
tgtttggatg attaagagat tgccatttt atcttggaag aactagtggt aaaacatcca   9300
agagcactag gattgtgata cagaatttgt gaggtttggt ggatccacgc ccctctcccc   9360
cactttccca tgatgaaata tcactaataa atcctgtata tttagatatt atgctagcca   9420
tgtaatcaga tttatttaat tgggtggggc aggtgtgtat ttactttaga aaaaatgaaa   9480
aagacaagat ttatgagaaa tatttgaagg cagtacactc tggccaactg ttaccagttg   9540
gtatttctac aagttcagaa tatttttaaac ctgatttact agacctggga attttcaaca   9600
tggtctaatt atttactcaa agacatagat gtgaaaattt taggcaacct tctaaatctt   9660
tttcaccatg gatgaaacta taacttaaag aataatactt agaagggtta attggaaatc   9720
agagtttgaa ataaaacttg gaccactttg tatacactct tctcacttga catttttagct  9780 atataatatg tactttgagt ataacatcaa gctttaacaa atatttaaag acaaaaaaat   9840
cacgtcagta aaatactaaa aggctcattt ttatatttgt tttagatgtt taaatagtt    9900 gcaatggatt aaaaatgatg atttaaaatg ttgcttgtaa tacagttttg cctgctaaat   9960
tctccacatt ttgtaacctg ttttatttct ttgggtgtaa agcgtttttg cttagtattg  10020
tgatattgta tatgttttgt cccagttgta tagtaatgtt tcagtccatc atccagcttt  10080
ggctgctgaa atcatacagc tgtgaagact tgcctttgtt tctgttagac tgcttttcag  10140
ttctgtattg agtatcttaa gtactgtaga aaagatgtca cttcttcctt taaggctgtt  10200
ttgtaatata tataaggact ggaattgtgt ttttaaagaa aagcattcaa gtatgacaat  10260
atactatctg tgttttcacc attcaaagtg ctgtttagta gttgaaactt aaactattta  10320
atgtcattta ataaagtgac caaaatgtgt tgtgctcttt attgtatttt cacagctttg  10380
aaaatctgtg cacatactgt ttcatagaaa atgtatagct tttgttgtcc tatataatgg  10440
tggttctttt gcacatttag ttatttaata ttgagaggtc acgaagtttg gttattgaat  10500
ctgttatata ctaaattctg taagggaga tctctcatct caaaaagaat ttacatacca   10560
ggaagtccat gtgtgtttgt gttagtttg gatgtctttg tgtaatccag ccccatttcc   10620
tgtttcccaa cagctgtaac actcatttta agtcaagcag ggctaccaac ccacacttga  10680
tagaaaagct gcttaccatt cagaagcttc cttattacct ggcctccaaa tgagctgaat  10740
attttgtagc cttcccttag ctatgttcat tttccctcca ttatcataaa atcagatcga  10800
tatttatgtg ccccaaacaa aactttaaga gcagttacat tctgtcccag tagcccttgt  10860
ttcctttgag agtagcatgt tgtgaggcta tagagactta ttctaccagt aaaacaggtc  10920
aatcctttta catgtttatt atactaaaaa ttatgttcag ggtatttact actttatttc  10980
accagactca gtctcaagtg acttggctat ctccaaatca gatctaccct tagagaataa  11040
acattttctt accgttattt ttttttcaagt ctataatctg agccagtccc aaaggagtga  11100
tcaagtttca gaaatgcttt catcttcaca acatttttata tatactatta tatggggtga  11160
ataaagtttt aaatccgaaa tataaaaaaa aaaaaaaaa aa                       11202
```

<210> SEQ ID NO 7
<211> LENGTH: 2454
<212> TYPE: PRT
<213> ORGANISM: Homo sapiens

<400> SEQUENCE: 7

Met Thr Ala Glu Pro Met Ser Glu Ser Lys Leu Asn Thr Leu Val Gln
1               5                   10                  15

Lys Leu His Asp Phe Leu Ala His Ser Ser Glu Glu Ser Glu Glu Thr

-continued

```
            20                  25                  30
Ser Ser Pro Arg Leu Ala Met Asn Gln Asn Thr Asp Lys Ile Ser
        35                  40                  45
Gly Ser Gly Ser Asn Ser Asp Met Met Glu Asn Ser Lys Glu Glu Gly
        50                  55                  60
Thr Ser Ser Ser Glu Lys Ser Lys Ser Ser Gly Ser Ser Arg Ser Lys
65                  70                  75                  80
Arg Lys Pro Ser Ile Val Thr Lys Tyr Val Glu Ser Asp Asp Glu Lys
                85                  90                  95
Pro Leu Asp Asp Glu Thr Val Asn Glu Asp Ala Ser Asn Glu Asn Ser
            100                 105                 110
Glu Asn Asp Ile Thr Met Gln Ser Leu Pro Lys Glu Asp Gly Leu His
        115                 120                 125
Gly Ile Val Ser Cys Thr Ala Cys Gly Gln Gln Val Asn His Phe Gln
        130                 135                 140
Lys Asp Ser Ile Tyr Arg His Pro Ser Leu Gln Val Leu Ile Cys Lys
145                 150                 155                 160
Asn Cys Phe Lys Tyr Tyr Met Ser Asp Asp Ile Ser Arg Asp Ser Asp
                165                 170                 175
Gly Met Asp Glu Gln Cys Arg Trp Cys Ala Glu Gly Gly Asn Leu Ile
                180                 185                 190
Cys Cys Asp Phe Cys His Asn Ala Phe Cys Lys Lys Cys Ile Leu Arg
            195                 200                 205
Asn Leu Gly Arg Lys Glu Leu Ser Thr Ile Met Asp Glu Asn Asn Gln
        210                 215                 220
Trp Tyr Cys Tyr Ile Cys His Pro Glu Pro Leu Leu Asp Leu Val Thr
225                 230                 235                 240
Ala Cys Asn Ser Val Phe Glu Asn Leu Glu Gln Leu Leu Gln Gln Asn
                245                 250                 255
Lys Lys Lys Ile Lys Val Asp Ser Glu Lys Ser Asn Lys Val Tyr Glu
            260                 265                 270
His Thr Ser Arg Phe Ser Pro Lys Lys Thr Ser Ser Asn Cys Asn Gly
        275                 280                 285
Glu Glu Lys Lys Leu Asp Asp Ser Cys Ser Gly Ser Val Thr Tyr Ser
        290                 295                 300
Tyr Ser Ala Leu Ile Val Pro Lys Glu Met Ile Lys Lys Ala Lys Lys
305                 310                 315                 320
Leu Ile Glu Thr Thr Ala Asn Met Asn Ser Ser Tyr Val Lys Phe Leu
                325                 330                 335
Lys Gln Ala Thr Asp Asn Ser Glu Ile Ser Ser Ala Thr Lys Leu Arg
            340                 345                 350
Gln Leu Lys Ala Phe Lys Ser Val Leu Ala Asp Ile Lys Lys Ala His
        355                 360                 365
Leu Ala Leu Glu Glu Asp Leu Asn Ser Glu Phe Arg Ala Met Asp Ala
        370                 375                 380
Val Asn Lys Glu Lys Asn Thr Lys Glu His Lys Val Ile Asp Ala Lys
385                 390                 395                 400
Phe Glu Thr Lys Ala Arg Lys Gly Glu Lys Pro Cys Ala Leu Glu Lys
                405                 410                 415
Lys Asp Ile Ser Lys Ser Glu Ala Lys Leu Ser Arg Lys Gln Val Asp
            420                 425                 430
Ser Glu His Met His Gln Asn Val Pro Thr Glu Glu Gln Arg Thr Asn
        435                 440                 445
```

Lys Ser Thr Gly Gly Glu His Lys Lys Ser Asp Arg Lys Glu Glu Pro
    450                 455                 460

Gln Tyr Glu Pro Ala Asn Thr Ser Glu Asp Leu Asp Met Asp Ile Val
465                 470                 475                 480

Ser Val Pro Ser Val Pro Glu Asp Ile Phe Glu Asn Leu Glu Thr
                485                 490                 495

Ala Met Glu Val Gln Ser Ser Val Asp His Gln Gly Asp Gly Ser Ser
            500                 505                 510

Gly Thr Glu Gln Glu Val Glu Ser Ser Ser Val Lys Leu Asn Ile Ser
        515                 520                 525

Ser Lys Asp Asn Arg Gly Gly Ile Lys Ser Lys Thr Thr Ala Lys Val
    530                 535                 540

Thr Lys Glu Leu Tyr Val Lys Leu Thr Pro Val Ser Leu Ser Asn Ser
545                 550                 555                 560

Pro Ile Lys Gly Ala Asp Cys Gln Glu Val Pro Gln Asp Lys Asp Gly
                565                 570                 575

Tyr Lys Ser Cys Gly Leu Asn Pro Lys Leu Glu Lys Cys Gly Leu Gly
            580                 585                 590

Gln Glu Asn Ser Asp Asn Glu His Leu Val Glu Asn Glu Val Ser Leu
        595                 600                 605

Leu Leu Glu Glu Ser Asp Leu Arg Arg Ser Pro Arg Val Lys Thr Thr
    610                 615                 620

Pro Leu Arg Arg Pro Thr Glu Thr Asn Pro Val Thr Ser Asn Ser Asp
625                 630                 635                 640

Glu Glu Cys Asn Glu Thr Val Lys Glu Lys Gln Lys Leu Ser Val Pro
                645                 650                 655

Val Arg Lys Lys Asp Lys Arg Asn Ser Ser Asp Ser Ala Ile Asp Asn
            660                 665                 670

Pro Lys Pro Asn Lys Leu Pro Lys Ser Lys Gln Ser Glu Thr Val Asp
        675                 680                 685

Gln Asn Ser Asp Ser Asp Glu Met Leu Ala Ile Leu Lys Glu Val Ser
    690                 695                 700

Arg Met Ser His Ser Ser Ser Asp Thr Asp Ile Asn Glu Ile His
705                 710                 715                 720

Thr Asn His Lys Thr Leu Tyr Asp Leu Lys Thr Gln Ala Gly Lys Asp
                725                 730                 735

Asp Lys Gly Lys Arg Lys Arg Lys Ser Ser Thr Ser Gly Ser Asp Phe
            740                 745                 750

Asp Thr Lys Lys Gly Lys Ser Ala Lys Ser Ser Ile Ile Ser Lys Lys
        755                 760                 765

Lys Arg Gln Thr Gln Ser Glu Ser Ser Asn Tyr Asp Ser Glu Leu Glu
    770                 775                 780

Lys Glu Ile Lys Ser Met Ser Lys Ile Gly Ala Ala Arg Thr Thr Lys
785                 790                 795                 800

Lys Arg Ile Pro Asn Thr Lys Asp Phe Asp Ser Ser Glu Asp Glu Lys
                805                 810                 815

His Ser Lys Lys Gly Met Asp Asn Gln Gly His Lys Asn Leu Lys Thr
            820                 825                 830

Ser Gln Glu Gly Ser Ser Asp Asp Ala Glu Arg Lys Gln Glu Arg Glu
        835                 840                 845

Thr Phe Ser Ser Ala Glu Gly Thr Val Asp Lys Asp Thr Thr Ile Met
    850                 855                 860

```
Glu Leu Arg Asp Arg Leu Pro Lys Lys Gln Gln Ala Ser Ala Ser Thr
865                 870                 875                 880

Asp Gly Val Asp Lys Leu Ser Gly Lys Glu Gln Ser Phe Thr Ser Leu
                885                 890                 895

Glu Val Arg Lys Val Ala Glu Thr Lys Glu Lys Ser Lys His Leu Lys
            900                 905                 910

Thr Lys Thr Cys Lys Lys Val Gln Asp Gly Leu Ser Asp Ile Ala Glu
        915                 920                 925

Lys Phe Leu Lys Lys Asp Gln Ser Asp Glu Thr Ser Glu Asp Asp Lys
    930                 935                 940

Lys Gln Ser Lys Lys Gly Thr Glu Glu Lys Lys Pro Ser Asp Phe
945                 950                 955                 960

Lys Lys Lys Val Ile Lys Met Glu Gln Gln Tyr Glu Ser Ser Ser Asp
                965                 970                 975

Gly Thr Glu Lys Leu Pro Arg Glu Glu Ile Cys His Phe Pro Lys
                980                 985                 990

Gly Ile Lys Gln Ile Lys Asn Gly Thr Thr Asp Gly Glu Lys Lys Ser
                995                 1000                1005

Lys Lys Ile Arg Asp Lys Thr Ser Lys Lys Lys Asp Glu Leu Ser
        1010                1015                1020

Asp Tyr Ala Glu Lys Ser Thr Gly Lys Gly Asp Ser Cys Asp Ser
        1025                1030                1035

Ser Glu Asp Lys Lys Ser Lys Asn Gly Ala Tyr Gly Arg Glu Lys
        1040                1045                1050

Lys Arg Cys Lys Leu Leu Gly Lys Ser Ser Arg Lys Arg Gln Asp
        1055                1060                1065

Cys Ser Ser Ser Asp Thr Glu Lys Tyr Ser Met Lys Glu Asp Gly
        1070                1075                1080

Cys Asn Ser Ser Asp Lys Arg Leu Lys Arg Ile Glu Leu Arg Glu
        1085                1090                1095

Arg Arg Asn Leu Ser Ser Lys Arg Asn Thr Lys Glu Ile Gln Ser
        1100                1105                1110

Gly Ser Ser Ser Ser Asp Ala Glu Glu Ser Ser Glu Asp Asn Lys
        1115                1120                1125

Lys Lys Lys Gln Arg Thr Ser Ser Lys Lys Ala Val Ile Val
        1130                1135                1140

Lys Glu Lys Lys Arg Asn Ser Leu Arg Thr Ser Lys Arg Lys
        1145                1150                1155

Gln Ala Asp Ile Thr Ser Ser Ser Ser Ser Asp Ile Glu Asp Asp
        1160                1165                1170

Asp Gln Asn Ser Ile Gly Glu Gly Ser Ser Asp Glu Gln Lys Ile
        1175                1180                1185

Lys Pro Val Thr Glu Asn Leu Val Leu Ser Ser His Thr Gly Phe
        1190                1195                1200

Cys Gln Ser Ser Gly Asp Glu Ala Leu Ser Lys Ser Val Pro Val
        1205                1210                1215

Thr Val Asp Asp Asp Asp Asp Asn Asp Pro Glu Asn Arg Ile
        1220                1225                1230

Ala Lys Lys Met Leu Leu Glu Glu Ile Lys Ala Asn Leu Ser Ser
        1235                1240                1245

Asp Glu Asp Gly Ser Ser Asp Asp Glu Pro Glu Glu Gly Lys Lys
        1250                1255                1260

Arg Thr Gly Lys Gln Asn Glu Glu Asn Pro Gly Asp Glu Glu Ala
```

-continued

```
            1265                1270                1275
Lys Asn Gln Val Asn Ser Glu Ser Asp Ser Asp Ser Glu Glu Ser
            1280                1285                1290
Lys Lys Pro Arg Tyr Arg His Arg Leu Leu Arg His Lys Leu Thr
            1295                1300                1305
Val Ser Asp Gly Glu Ser Gly Glu Glu Lys Lys Thr Lys Pro Lys
            1310                1315                1320
Glu His Lys Glu Val Lys Gly Arg Asn Arg Arg Lys Val Ser Ser
            1325                1330                1335
Glu Asp Ser Glu Asp Ser Asp Phe Gln Glu Ser Gly Val Ser Glu
            1340                1345                1350
Glu Val Ser Glu Ser Glu Asp Glu Gln Arg Pro Arg Thr Arg Ser
            1355                1360                1365
Ala Lys Lys Ala Glu Leu Glu Glu Asn Gln Arg Ser Tyr Lys Gln
            1370                1375                1380
Lys Lys Lys Arg Arg Arg Ile Lys Val Gln Glu Asp Ser Ser Ser
            1385                1390                1395
Glu Asn Lys Ser Asn Ser Glu Glu Glu Glu Glu Lys Glu Glu
            1400                1405                1410
Glu Glu Glu Glu Glu Glu Glu Glu Glu Glu Glu Glu Glu Asp Glu
            1415                1420                1425
Asn Asp Asp Ser Lys Ser Pro Gly Lys Gly Arg Lys Lys Ile Arg
            1430                1435                1440
Lys Ile Leu Lys Asp Asp Lys Leu Arg Thr Glu Thr Gln Asn Ala
            1445                1450                1455
Leu Lys Glu Glu Glu Glu Arg Arg Lys Arg Ile Ala Glu Arg Glu
            1460                1465                1470
Arg Glu Arg Glu Lys Leu Arg Glu Val Ile Glu Ile Glu Asp Ala
            1475                1480                1485
Ser Pro Thr Lys Cys Pro Ile Thr Thr Lys Leu Val Leu Asp Glu
            1490                1495                1500
Asp Glu Glu Thr Lys Glu Pro Leu Val Gln Val His Arg Asn Met
            1505                1510                1515
Val Ile Lys Leu Lys Pro His Gln Val Asp Gly Val Gln Phe Met
            1520                1525                1530
Trp Asp Cys Cys Cys Glu Ser Val Lys Lys Thr Lys Lys Ser Pro
            1535                1540                1545
Gly Ser Gly Cys Ile Leu Ala His Cys Met Gly Leu Gly Lys Thr
            1550                1555                1560
Leu Gln Val Val Ser Phe Leu His Thr Val Leu Leu Cys Asp Lys
            1565                1570                1575
Leu Asp Phe Ser Thr Ala Leu Val Val Cys Pro Leu Asn Thr Ala
            1580                1585                1590
Leu Asn Trp Met Asn Glu Phe Glu Lys Trp Gln Glu Gly Leu Lys
            1595                1600                1605
Asp Asp Glu Lys Leu Glu Val Ser Glu Leu Ala Thr Val Lys Arg
            1610                1615                1620
Pro Gln Glu Arg Ser Tyr Met Leu Gln Arg Trp Gln Glu Asp Gly
            1625                1630                1635
Gly Val Met Ile Ile Gly Tyr Glu Met Tyr Arg Asn Leu Ala Gln
            1640                1645                1650
Gly Arg Asn Val Lys Ser Arg Lys Leu Lys Glu Ile Phe Asn Lys
            1655                1660                1665
```

```
Ala Leu Val Asp Pro Gly Pro Asp Phe Val Val Cys Asp Glu Gly
        1670                1675                1680

His Ile Leu Lys Asn Glu Ala Ser Ala Val Ser Lys Ala Met Asn
        1685                1690                1695

Ser Ile Arg Ser Arg Arg Arg Ile Ile Leu Thr Gly Thr Pro Leu
        1700                1705                1710

Gln Asn Asn Leu Ile Glu Tyr His Cys Met Val Asn Phe Ile Lys
        1715                1720                1725

Glu Asn Leu Leu Gly Ser Ile Lys Glu Phe Arg Asn Arg Phe Ile
        1730                1735                1740

Asn Pro Ile Gln Asn Gly Gln Cys Ala Asp Ser Thr Met Val Asp
        1745                1750                1755

Val Arg Val Met Lys Lys Arg Ala His Ile Leu Tyr Glu Met Leu
        1760                1765                1770

Ala Gly Cys Val Gln Arg Lys Asp Tyr Thr Ala Leu Thr Lys Phe
        1775                1780                1785

Leu Pro Pro Lys His Glu Tyr Val Leu Ala Val Arg Met Thr Ser
        1790                1795                1800

Ile Gln Cys Lys Leu Tyr Gln Tyr Tyr Leu Asp His Leu Thr Gly
        1805                1810                1815

Val Gly Asn Asn Ser Glu Gly Gly Arg Gly Lys Ala Gly Ala Lys
        1820                1825                1830

Leu Phe Gln Asp Phe Gln Met Leu Ser Arg Ile Trp Thr His Pro
        1835                1840                1845

Trp Cys Leu Gln Leu Asp Tyr Ile Ser Lys Glu Asn Lys Gly Tyr
        1850                1855                1860

Phe Asp Glu Asp Ser Met Asp Glu Phe Ile Ala Ser Asp Ser Asp
        1865                1870                1875

Glu Thr Ser Met Ser Leu Ser Ser Asp Asp Tyr Thr Lys Lys Lys
        1880                1885                1890

Lys Lys Gly Lys Lys Gly Lys Lys Asp Ser Ser Ser Ser Gly Ser
        1895                1900                1905

Gly Ser Asp Asn Asp Val Glu Val Ile Lys Val Trp Asn Ser Arg
        1910                1915                1920

Ser Arg Gly Gly Gly Glu Gly Asn Val Asp Glu Thr Gly Asn Asn
        1925                1930                1935

Pro Ser Val Ser Leu Lys Leu Glu Glu Ser Lys Ala Thr Ser Ser
        1940                1945                1950

Ser Asn Pro Ser Ser Pro Ala Pro Asp Trp Tyr Lys Asp Phe Val
        1955                1960                1965

Thr Asp Ala Asp Ala Glu Val Leu Glu His Ser Gly Lys Met Val
        1970                1975                1980

Leu Leu Phe Glu Ile Leu Arg Met Ala Glu Glu Ile Gly Asp Lys
        1985                1990                1995

Val Leu Val Phe Ser Gln Ser Leu Ile Ser Leu Asp Leu Ile Glu
        2000                2005                2010

Asp Phe Leu Glu Leu Ala Ser Arg Glu Lys Thr Glu Asp Lys Asp
        2015                2020                2025

Lys Pro Leu Ile Tyr Lys Gly Glu Gly Lys Trp Leu Arg Asn Ile
        2030                2035                2040

Asp Tyr Tyr Arg Leu Asp Gly Ser Thr Thr Ala Gln Ser Arg Lys
        2045                2050                2055
```

```
Lys Trp Ala Glu Glu Phe Asn Asp Glu Thr Asn Val Arg Gly Arg
2060                2065                2070

Leu Phe Ile Ile Ser Thr Lys Ala Gly Ser Leu Gly Ile Asn Leu
2075                2080                2085

Val Ala Ala Asn Arg Val Ile Ile Phe Asp Ala Ser Trp Asn Pro
2090                2095                2100

Ser Tyr Asp Ile Gln Ser Ile Phe Arg Val Tyr Arg Phe Gly Gln
2105                2110                2115

Thr Lys Pro Val Tyr Val Arg Phe Leu Ala Gln Gly Thr Met
2120                2125                2130

Glu Asp Lys Ile Tyr Asp Arg Gln Val Thr Lys Gln Ser Leu Ser
2135                2140                2145

Phe Arg Val Val Asp Gln Gln Val Glu Arg His Phe Thr Met
2150                2155                2160

Asn Glu Leu Thr Glu Leu Tyr Thr Phe Glu Pro Asp Leu Leu Asp
2165                2170                2175

Asp Pro Asn Ser Glu Lys Lys Lys Lys Arg Asp Thr Pro Met Leu
2180                2185                2190

Pro Lys Asp Thr Ile Leu Ala Glu Leu Leu Gln Ile His Lys Glu
2195                2200                2205

His Ile Val Gly Tyr His Glu His Asp Ser Leu Leu Asp His Lys
2210                2215                2220

Glu Glu Glu Glu Leu Thr Glu Glu Arg Lys Ala Ala Trp Ala
2225                2230                2235

Glu Tyr Glu Ala Glu Lys Lys Gly Leu Thr Met Arg Phe Asn Ile
2240                2245                2250

Pro Thr Gly Thr Asn Leu Pro Pro Val Ser Phe Asn Ser Gln Thr
2255                2260                2265

Pro Tyr Ile Pro Phe Asn Leu Gly Ala Leu Ser Ala Met Ser Asn
2270                2275                2280

Gln Gln Leu Glu Asp Leu Ile Asn Gln Gly Arg Glu Lys Val Val
2285                2290                2295

Glu Ala Thr Asn Ser Val Thr Ala Val Arg Ile Gln Pro Leu Glu
2300                2305                2310

Asp Ile Ile Ser Ala Val Trp Lys Glu Asn Met Asn Leu Ser Glu
2315                2320                2325

Ala Gln Val Gln Ala Leu Ala Leu Ser Arg Gln Ala Ser Gln Glu
2330                2335                2340

Leu Asp Val Lys Arg Arg Glu Ala Ile Tyr Asn Asp Val Leu Thr
2345                2350                2355

Lys Gln Gln Met Leu Ile Ser Cys Val Gln Arg Ile Leu Met Asn
2360                2365                2370

Arg Arg Leu Gln Gln Gln Tyr Asn Gln Gln Gln Gln Gln Met
2375                2380                2385

Thr Tyr Gln Gln Ala Thr Leu Gly His Leu Met Met Pro Lys Pro
2390                2395                2400

Pro Asn Leu Ile Met Asn Pro Ser Asn Tyr Gln Gln Ile Asp Met
2405                2410                2415

Arg Gly Met Tyr Gln Pro Val Ala Gly Gly Met Gln Pro Pro Pro
2420                2425                2430

Leu Gln Arg Ala Pro Pro Pro Met Arg Ser Lys Asn Pro Gly Pro
2435                2440                2445

Ser Gln Gly Lys Ser Met
```

2450

<210> SEQ ID NO 8
<211> LENGTH: 11088
<212> TYPE: DNA
<213> ORGANISM: Homo sapiens

<400> SEQUENCE: 8

| | | | | | |
|---|---|---|---|---|---|
| aattctcctg | cctgagcctc | ggcccaacaa | aatggcggcg | gcagcggtgt | cgctttgttt | 60 |
| ccgcggctcc | tgcggcggtg | gcagtggtag | cggcctttga | gctgtgggga | ggttccagca | 120 |
| gcagctacag | tgacgactaa | gactccagtg | catttctatc | gtaaccgggc | gcggggagc | 180 |
| gcagatcggc | gcccagcaat | cacagaagcc | gacaaggcgt | tcaagcgaaa | acatgaccgc | 240 |
| tgagcccatg | agtgaaagca | agttaatac | attggtgcag | aagcttcatg | acttccttgc | 300 |
| acactcatca | gaagaatctg | aagaaacaag | ttctcctcca | cgacttgcaa | tgaatcaaaa | 360 |
| cacagataaa | atcagtggtt | ctggaagtaa | ctctgatatg | atggaaaaca | gcaaggaaga | 420 |
| gggaactagc | tcttcagaaa | aatccaagtc | ttcaggatcg | tcacgatcaa | agaggaaacc | 480 |
| ttcaattgta | acaaagtatg | tagaatcaga | tgatgaaaaa | cctttggatg | atgaaactgt | 540 |
| aaatgaagat | gcgtctaatg | aaaattcaga | aaatgatatt | actatgcaga | gcttgccaaa | 600 |
| agaagatggg | cttcatggga | ttgtgagctg | cactgcttgt | ggacaacagg | tcaatcattt | 660 |
| tcaaaaagat | tccatttata | cacccttc | attgcaagtt | cttatttgta | agaattgctt | 720 |
| taagtattac | atgagtgatg | atattagccg | tgactcagat | ggaatggatg | aacaatgtag | 780 |
| gtggtgtgcg | gaaggtggaa | acttgatttg | ttgtgacttt | tgccataatg | ctttctgcaa | 840 |
| gaaatgcatt | ctacgcaacc | ttggtcgaaa | ggagttgtcc | acaataatgg | atgaaaacaa | 900 |
| ccaatggtat | tgctacactt | gtcacccaga | gcctttgttg | gacttggtca | ctgcatgtaa | 960 |
| cagcgtattt | gagaatttag | aacagttgtt | gcagcaaaat | aagaagaaga | taaaagttga | 1020 |
| cagtgaaaag | agtaataaag | tatatgaaca | tacatccaga | ttttctccaa | agaagactag | 1080 |
| ttcaaattgt | aatggagaag | aaaagaaatt | agatgattcc | tgttctggct | ctgtaaccta | 1140 |
| ctcttattcc | gcactaattg | tgcccaaaga | gatgattaag | aaggcaaaaa | aactgattga | 1200 |
| gaccacagcc | aacatgaact | ccagttatgt | taaatttta | aagcaggcaa | cagataattc | 1260 |
| agaaatcagt | tctgctacaa | aattacgtca | gcttaaggct | tttaagtctg | tgttggctga | 1320 |
| tattaagaag | gctcatcttg | cattggaaga | agacttaaat | tccgagtttc | gagcgatgga | 1380 |
| tgctgtaaac | aaagagaaaa | ataccaaaga | gcataaagtc | atagatgcta | agtttgaaac | 1440 |
| aaaagcacga | aaaggagaaa | aaccttgtgc | tttggaaaag | aaggatattt | caaagtcaga | 1500 |
| agctaaactt | tcaagaaaac | aggtagatag | tgagcacatg | catcagaatg | ttccaacaga | 1560 |
| ggaacaaaga | acaaataaaa | gtaccggtgg | tgaacataag | aaatctgata | gaaaagaaga | 1620 |
| acctcaatat | gaacctgcca | acacttctga | agatttagac | atggatattg | tgtctgttcc | 1680 |
| ttcctcagtt | ccagaagaca | ttttttgagaa | tcttgagact | gctatggaag | ttcagagttc | 1740 |
| agttgatcat | caaggggatg | gcagcagtgg | aactgaacaa | gaagtggaga | gttcatctgt | 1800 |
| aaaattaaat | atttcttcaa | aagacaacag | aggaggtatt | aaatcaaaaa | ctacagctaa | 1860 |
| agtaacaaaa | gaattatatg | ttaaactcac | tcctgtttcc | ctttctaatt | ccccaattaa | 1920 |
| aggtgctgat | tgtcaggaag | ttccacaaga | taaagatggc | tataaaagtt | gtggtctgaa | 1980 |
| ccccaagtta | gagaaatgtg | gacttggaca | ggaaaacagt | gataatgagc | atttggttga | 2040 |
| aaatgaagtt | tcattacttt | tagaggaatc | tgatcttcga | agatccccac | gtgtaaagac | 2100 |

```
tacacccttg aggcgaccga cagaaactaa ccctgtaaca tctaattcag atgaagaatg   2160
taatgaaaca gttaaggaga aacaaaaact atcagttcca gtgagaaaaa aggataagcg   2220
taattcttct gacagtgcta tagataatcc taagcctaat aaattgccaa aatctaagca   2280
atcagagact gtggatcaaa attcagattc tgatgaaatg ctagcaatcc tcaaagaggt   2340
gagcaggatg agtcacagtt cttcttcaga tactgatatt aatgaaattc atacaaacca   2400
taagactttg tatgatttaa agactcaggc ggggaaagat gataaggaa aaggaaacg    2460 aaaaagttct acatctggct cagattttga tactaaaaag ggcaaatcag ctaagagctc   2520
tataatttct aaaagaaac gacaaaccca gtctgagtct tctaattatg actcagaatt    2580
agaaaaagag ataaagagca tgagtaaaat tggtgctgcc agaaccacca aaaaagaat    2640 tccaaataca aaagattttg actcttctga agatgagaaa cacagcaaaa aaggaatgga   2700
taatcaaggg cacaaaaatt tgaagacctc acaagaagga tcatctgatg atgctgaaag   2760
aaaacaagag agagagactt tctcttcagc agaaggcaca gttgataaag acacgaccat   2820
catggaatta agagatcgac ttcctaagaa gcagcaagca agtgcttcca ctgatggtgt   2880
cgataagctt tctgggaaag agcagagttt tacttctttg gaagttagaa agttgctga    2940 aactaaagaa aagagcaagc atctcaaaac caaaacatgt aaaaaagtac aggatggctt   3000
atctgatatt gcagagaaat tcctaaagaa agaccagagc gatgaaactt ctgaagatga   3060
taaaaagcag agcaaaaagg gaactgaaga aaaaagaaa ccttcagact ttaagaaaaa    3120
agtaattaaa atggaacaac agtatgaatc ttcatctgat ggcactgaaa agttacctga   3180
gcgagaagaa atttgtcatt ttcctaaggg cataaaacaa attaagaatg aacaactga    3240 tggagaaaag aaaagtaaaa aataagagaa taaaacttct aaaaagaagg atgaattatc   3300
tgattatgct gagaagtcaa cagggaaagg agatagttgt gactcttcag aggataaaaa   3360
gagtaagaat ggagcatatg gtagagagaa gaaaaggtgc aagttgcttg gaaagagttc   3420
aaggaagaga caagattgtt catcatctga tactgagaaa tattccatga agaagatgg    3480 ttgtaactct tctgataaga gactgaaaag aatagaattg agggaaagaa gaaatttaag   3540
ttcaaagaga atactaaagg aaatacaaag tggctcatca tcatctgatg ctgaggaaag   3600
ttctgaagat aataaaaaga agaagcaaag aacttcatct aaaaagaagg cagtcattgt   3660
caaggagaaa aagagaaact ccctaagaac aagcactaaa aggaagcaag ctgacattac   3720
atcctcatct tcttctgata tagaagatga tgatcagaat tctataggtg agggaagcag   3780
cgatgaacag aaaattaagc ctgtgactga aaatttagtg ctgtcttcac atactggatt   3840
ttgccaatct tcaggagatg aagccttatc taaatcagtg cctgtcacag tggatgatga   3900
tgatgacgac aatgatcctg agaatagaat tgccaagaag atgcttttag aagaaattaa   3960
agccaatctt tcctctgatg aggatggatc ttcagatgat gagccagaag aagggaaaaa   4020
aagaactgga aaacaaaatg aagaaaaccc aggagatgag gaagcaaaaa atcaagtcaa   4080
ttctgaatca gattcagatt ctgaagaatc taagaagcca agatacagac ataggctttt   4140
gcggcacaaa ttgactgtga gtgacggaga atctggagaa gaaaaaagaa caaagcctaa   4200
agagcataaa gaagtcaaag gcagaaacag aagaaaggtg agcagtgaag attcagaaga   4260
ttctgatttt caggaatcag gagttagtga agaagttagt gaatccgaag atgaacagcg   4320
gcccagaaca aggtctgcaa agaaagcaga gttggaagaa aatcagcgga gctataaaca   4380
gaaaaagaaa aggcgacgta ttaaggttca agaagattca tccagtgaaa acaagagtaa   4440
```

```
ttctgaggaa gaagaggagg aaaaagaaga ggaggaggaa gaggaggagg aggaggaaga    4500
ggaggaggaa gatgaaaatg atgattccaa gtctcctgga aaaggcagaa agaaaattcg    4560
gaagattctt aaagatgata aactgagaac agaaacacaa aatgctctta aggaagagga    4620
agagagacga aaacgtattg ctgagaggga gcgtgagcga gaaaaattga gagaggtgat    4680
agaaattgaa gatgcttcac ccaccaagtg tccaataaca accaagttgg ttttagatga    4740
agatgaagaa accaaagaac ctttagtgca ggttcataga aatatggtta tcaaattgaa    4800
accccatcaa gtagatggtg ttcagtttat gtgggattgc tgctgtgagt ctgtgaaaaa    4860
aacaaagaaa tctccaggtt caggatgcat tcttgcccac tgtatgggcc ttggtaagac    4920
tttacaggtg gtaagttttc ttcatacagt tcttttgtgt gacaaactgg atttcagcac    4980
ggcgttagtg gtttgtcctc ttaatactgc tttgaattgg atgaatgaat ttgaagagtg    5040
gcaagaggga ttaaagatgg atgagaagct tgaggtttct gaattagcaa ctgtgaaacg    5100
tcctcaggag agaagctaca tgctgcagag gtggcaagaa gatggtggtg ttatgatcat    5160
aggctatgag atgtatagaa atcttgctca aggaaggaat gtgaagagtc ggaaacttaa    5220
agaaatattt aacaaagctt tggttgatcc aggccctgat tttgttgttt gtgatgaagg    5280
ccatattcta aaaaatgaag catctgctgt ttctaaagct atgaattcta tacgatcaag    5340
gaggaggatt atttttaacag gaacaccact tcaaaataac ctaattgagt atcattgtat    5400
ggttaatttt atcaaggaaa atttacttgg atccattaag gagttcagga atagatttat    5460
aaatccaatt caaaatggtc agtgtgcaga ttctaccatg gtagatgtca gagtgatgaa    5520
aaaacgtgct cacattctct atgagatgtt agctggatgt gttcagagga aagattatac    5580
agcattaaca aaattcttgc ctccaaaaca cgaatatgtg ttagctgtga gaatgacttc    5640
tattcagtgc aagctctatc agtactactt agatcactta acaggtgtgg gcaataatag    5700
tgaaggtgga agaggaaagg caggtgcaaa gcttttccaa gattttcaga tgttaagtag    5760
aatatggact catccttggt gtttgcagct agactacatt agcaaagaaa ataagggtta    5820
ttttgatgaa gacagtatgg atgaatttat agcctcagat tctgatgaaa cctccatgag    5880
tttaagctcc gatgattata caaaaaagaa gaaaaaaggg aaaaagggga aaaaagatag    5940
tagctcaagt ggaagtggca gtgacaatga tgttgaagtg attaaggtct ggaattcaag    6000
atctcgggga ggtggtgaag gaaatgtgga tgaaacagga aacaatcctt ctgtttcttt    6060
aaaactggaa gaaagtaaag ctacttcttc ttctaatcca agcagcccag ctccagactg    6120
gtacaaagat tttgttacag atgctgatgc tgaggtttta gagcattctg ggaaaatggt    6180
acttctcttt gaaattcttc gaatggcaga ggaaattggg gataaagtcc ttgttttcag    6240
ccagtccctc atatctctgg acttgattga agattttctt gaattagcta gtagggagaa    6300
gacagaagat aaagataaac cccttattta taaaggtgag gggaagtggc ttcgaaacat    6360
tgactattac cgtttagatg gttccactac tgcacagtca aggaagaagt gggctgaaga    6420
atttaatgat gaaactaatg tgagaggacg attatttatc atttctacta aagcaggatc    6480
tctaggaatt aatctggtag ctgctaatcg agtaattata ttcgacgctt cttggaatcc    6540
atcttatgac atccagagta tattcagagt ttatcgcttt ggacaaacta agcctgttta    6600
tgtatatagg ttcttagctc agggaaccat ggaagataag atttatgatc ggcaagtaac    6660
taagcagtca ctgtcttttc gagttgttga tcagcagcag gtggagcgtc attttactat    6720
gaatgagctt actgaacttt atacttttga gccagactta ttagatgacc ctaattcaga    6780
aaagaagaag aagagggata ctcccatgct gccaaaggat accatacttg cagagctcct    6840
```

```
tcagatacat aaagaacaca ttgtaggata ccatgaacat gattctcttt tggaccacaa    6900
agaagaagaa gagttgactg aagaagaaag aaaagcagct tgggctgagt atgaagcaga    6960
gaagaaggga ctgaccatgc gtttcaacat accaactggg accaatttac ccctgtcag     7020 tttcaactct caaactcctt atattccttt caatttggga gccctgtcag caatgagtaa    7080
tcaacagctg gaggacctca ttaatcaagg aagagaaaaa gttgtagaag caacaaacag    7140
tgtgacagca gtgaggattc aacctcttga ggatataatt tcagctgtat ggaaggagaa    7200
catgaatctc tcagaggccc aagtacaggc gttagcatta agtagacaag ccagccagga    7260
gcttgatgtt aaacgaagag aagcaatcta caatgatgta ttgacaaaac aacagatgtt    7320
aatcagctgt gttcagcgaa tacttatgaa cagaaggctc cagcagcagt acaatcagca    7380
gcaacagcaa caaatgactt atcaacaagc aacactgggt cacctcatga tgccaaagcc    7440
cccaaatttg atcatgaatc cttctaacta ccagcagatt gatatgagag gaatgtatca    7500
gccagtggct ggtggtatgc agccaccacc attacagcgt gcaccacccc caatgagaag    7560
caaaaatcca ggaccttccc aagggaaatc aatgtgattt tgcactaaaa gcttaatgga    7620
ttgttaaaat catagaaaga tcttttattt ttttaggaat caatgactta acagaactca    7680
actgtataaa tagtttggtc cccttaaatg ccaatcttcc atattagttt tacttttttt    7740
ttttttaaat agggcatacc atttcttcct gacatttgtc agtgatgttg cctagaatct    7800
tcttacacac gctgagtaca aagatatttt caaattgttt tcagtgaaaa caagtccttc    7860
cataatagta acaactccac agatttcctc tctaaatttt tatgcctgct tttagcaacc    7920
ataaaattgt cataaaatta ataaatttag gaaagaataa agatttatat attcattctt    7980
tacatataaa aacacacagc tgagttctta gagttgattc ctcaagttat gaaatacttt    8040
tgtacttaat ccatttcttg attaaagtga ttgaaatggt tttaatgttc ttttgactga    8100
agtctgaaac tgggctcctg ctttattgtc tctgtgactg aaagttagaa actgagggtt    8160
atctttgaca cagaattgtg tgcaatattc ttaaatacta ctgctctaaa agttggagaa    8220
gtcttgcagt tatcttagca ttgtataaac agccttaagt atagcctaag aagagaattc    8280 cttttctcc tttagtcctt ctgccatttt ttattttcag ttatatgtgc tgaaataatt    8340
actggtaaaa tttcagggtt gtggattatc ttccacacat gaattttctc tctcctggca    8400
cgaatataaa gcacatctct taactgcatg gtgccagtgc taatgcttca tcctgttgct    8460
ggcagtggga tgtggactta gaaaatcaag ttctagcatt ttagtaggtt aacactgaag    8520
ttgtggttgt taggttcaca ccctgtttta taaacaacat caaaatggca gaaccattgc    8580
tgactttagg ttcacatgag gaatgtactt ttaacaattc ccagtactat cagtattgtg    8640
aaataattcc tctgaaagat aagaatcact ggcttctatg cgcttctttt ctctcatcat    8700
catgttcttt tacccccagtt tccttacatt ttttttaaatt gtttcagagt tgttttttt    8760 tttagtttag attgtgaggc aattattaaa tcaaaattaa ttcatccaat accccttttac    8820 tagaagtttt actagaaaat gtattacatt ttatttttc ttaatccagt tctgcaaaaa    8880
tgacctataa atttattcat gtacaatttt ggttacttga attgttaaag aaaacattgt    8940
ttttgactat gggagtcaac tcaacatggc agaaccattt tgagatgat gatacaacag    9000 gtagtgaaac agcttaagaa ttccaaaaaa aaaaaaaaa aaaaaaaaaa gaaaactggg    9060
tttgggcttt gctttaggta tcactggatt agaatgagtt taacattagc taaaactgct    9120
ttgagttgtt tggatgatta agagattgcc attttatct tggaagaact agtggtaaaa    9180
```

| | | |
|---|---|---|
| catccaagag cactaggatt gtgatacaga atttgtgagg tttggtggat ccacgcccct | 9240 |
| ctcccccact ttcccatgat gaaatatcac taataaatcc tgtatattta gatattatgc | 9300 |
| tagccatgta atcagattta tttaattggg tggggcaggt gtgtatttac tttagaaaaa | 9360 |
| atgaaaaaga caagatttat gagaaatatt tgaaggcagt acactctggc caactgttac | 9420 |
| cagttggtat ttctacaagt tcagaatatt ttaaacctga tttactagac ctgggaattt | 9480 |
| tcaacatggt ctaattattt actcaaagac atagatgtga aaattttagg caaccttcta | 9540 |
| aatcttttc accatggatg aaactataac ttaaagaata atacttagaa gggttaattg | 9600 |
| gaaatcagag tttgaaataa aacttggacc actttgtata cactcttctc acttgacatt | 9660 |
| ttagctatat aatatgtact ttgagtataa catcaagctt taacaaatat ttaaagacaa | 9720 |
| aaaaatcacg tcagtaaaat actaaaaggc tcatttttat atttgtttta gatgttttaa | 9780 |
| atagttgcaa tggattaaaa atgatgattt aaaatgttgc ttgtaataca gttttgcctg | 9840 |
| ctaaattctc cacattttgt aacctgtttt atttctttgg gtgtaaagcg ttttgctta | 9900 |
| gtattgtgat attgtatatg ttttgtccca gttgtatagt aatgtttcag tccatcatcc | 9960 |
| agctttggct gctgaaatca tacagctgtg aagacttgcc tttgtttctg ttagactgct | 10020 |
| tttcagttct gtattgagta tcttaagtac tgtagaaaag atgtcacttc ttccttttaag | 10080 |
| gctgttttgt aatatatata aggactggaa ttgtgttttt aaagaaaagc attcaagtat | 10140 |
| gacaatatac tatctgtgtt ttcaccattc aaagtgctgt ttagtagttg aaacttaaac | 10200 |
| tatttaatgt catttaataa agtgaccaaa atgtgttgtg ctctttattg tattttcaca | 10260 |
| gctttgaaaa tctgtgcaca tactgttcca tagaaaatgt atagcttttg ttgtcctata | 10320 |
| taatggtggt tcttttgcac atttagttat ttaatattga gaggtcacga agtttggtta | 10380 |
| ttgaatctgt tatatactaa attctgtaaa gggagatctc tcatctcaaa agaatttac | 10440 |
| ataccaggaa gtccatgtgt gtttgtgtta gttttggatg tctttgtgta atccagcccc | 10500 |
| atttcctgtt tcccaacagc tgtaacactc attttaagtc aagcagggct accaacccac | 10560 |
| acttgataga aaagctgctt accattcaga agcttcctta ttacctggcc tccaaatgag | 10620 |
| ctgaatattt tgtagccttc ccttagctat gttcattttc cctccattat cataaaatca | 10680 |
| gatcgatatt tatgtgcccc aaacaaaact ttaagagcag ttacattctg tcccagtagc | 10740 |
| ccttgtttcc tttgagagta gcatgttgtg aggctataga gacttattct accagtaaaa | 10800 |
| caggtcaatc cttttacatg tttattatac taaaaattat gttcagggta tttactactt | 10860 |
| tatttcacca gactcagtct caagtgactt ggctatctcc aaatcagatc tacccttaga | 10920 |
| gaataaacat ttttctaccg ttattttttt tcaagtctat aatctgagcc agtcccaaag | 10980 |
| gagtgatcaa gtttcagaaa tgctttcatc ttcacaacat tttatatata ctattatatg | 11040 |
| gggtgaataa agttttaaat ccgaaatata aaaaaaaaa aaaaaaa | 11088 |

<210> SEQ ID NO 9
<211> LENGTH: 2285
<212> TYPE: PRT
<213> ORGANISM: Homo sapiens

<400> SEQUENCE: 9

Met Ala Ala Gln Val Ala Pro Ala Ala Ala Ser Ser Leu Gly Asn Pro
1               5                   10                  15

Pro Pro Pro Pro Pro Ser Glu Leu Lys Lys Ala Glu Gln Gln Gln Arg
            20                  25                  30

Glu Glu Ala Gly Gly Glu Ala Ala Ala Ala Ala Ala Ala Glu Arg Gly

```
                35                  40                  45
Glu Met Lys Ala Ala Ala Gly Gln Glu Ser Glu Gly Pro Ala Val Gly
 50                  55                  60

Pro Pro Gln Pro Leu Gly Lys Glu Leu Gln Asp Gly Ala Glu Ser Asn
 65                  70                  75                  80

Gly Gly Gly Gly Gly Gly Ala Gly Ser Gly Gly Pro Gly Ala
                 85                  90                  95

Glu Pro Asp Leu Lys Asn Ser Asn Gly Asn Ala Gly Pro Arg Pro Ala
                100                 105                 110

Leu Asn Asn Asn Leu Thr Glu Pro Pro Gly Gly Gly Gly Gly Gly Ser
                115                 120                 125

Ser Asp Gly Val Gly Ala Pro Pro His Ser Ala Ala Ala Ala Leu Pro
                130                 135                 140

Pro Pro Ala Tyr Gly Phe Gly Gln Pro Tyr Gly Arg Ser Pro Ser Ala
145                 150                 155                 160

Val Ala Ala Ala Ala Ala Val Phe His Gln Gln His Gly Gly Gln
                    165                 170                 175

Gln Ser Pro Gly Leu Ala Ala Leu Gln Ser Gly Gly Gly Gly Gly Leu
                180                 185                 190

Glu Pro Tyr Ala Gly Pro Gln Gln Asn Ser His Asp His Gly Phe Pro
                195                 200                 205

Asn His Gln Tyr Asn Ser Tyr Tyr Pro Asn Arg Ser Ala Tyr Pro Pro
210                 215                 220

Pro Ala Pro Ala Tyr Ala Leu Ser Ser Pro Arg Gly Gly Thr Pro Gly
225                 230                 235                 240

Ser Gly Ala Ala Ala Ala Gly Ser Lys Pro Pro Ser Ser Ser
                    245                 250                 255

Ala Ser Ala Ser Ser Ser Ser Ser Phe Ala Gln Gln Arg Phe Gly
                260                 265                 270

Ala Met Gly Gly Gly Gly Pro Ser Ala Ala Gly Gly Thr Pro Gln
                275                 280                 285

Pro Thr Ala Thr Pro Thr Leu Asn Gln Leu Leu Thr Ser Pro Ser Ser
    290                 295                 300

Ala Arg Gly Tyr Gln Gly Tyr Pro Gly Gly Asp Tyr Ser Gly Gly Pro
305                 310                 315                 320

Gln Asp Gly Gly Ala Gly Lys Gly Pro Ala Asp Met Ala Ser Gln Cys
                325                 330                 335

Trp Gly Ala Ala Ala Ala Ala Ala Ala Ala Ala Ser Gly Gly
                340                 345                 350

Ala Gln Gln Arg Ser His His Ala Pro Met Ser Pro Gly Ser Ser Gly
                355                 360                 365

Gly Gly Gly Gln Pro Leu Ala Arg Thr Pro Gln Pro Ser Ser Pro Met
    370                 375                 380

Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gly His Gly
                    405                 410                 415

Tyr Pro Gly Gln Pro Tyr Gly Ser Gln Thr Pro Gln Arg Tyr Pro Met
                420                 425                 430

Thr Met Gln Gly Arg Ala Gln Ser Ala Met Gly Gly Leu Ser Tyr Thr
                435                 440                 445

Gln Gln Ile Pro Pro Tyr Gly Gln Gly Pro Ser Gly Tyr Gly Gln
                450                 455                 460
```

```
Gln Gly Gln Thr Pro Tyr Tyr Asn Gln Gln Ser Pro His Pro Gln Gln
465                 470                 475                 480

Gln Gln Pro Pro Tyr Ser Gln Gln Pro Pro Ser Gln Thr Pro His Ala
            485                 490                 495

Gln Pro Ser Tyr Gln Gln Gln Pro Gln Ser Gln Pro Pro Gln Leu Gln
        500                 505                 510

Ser Ser Gln Pro Pro Tyr Ser Gln Gln Pro Ser Gln Pro Pro His Gln
            515                 520                 525

Gln Ser Pro Ala Pro Tyr Pro Ser Gln Gln Ser Thr Thr Gln Gln His
    530                 535                 540

Pro Gln Ser Gln Pro Pro Tyr Ser Gln Pro Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Thr Ala Tyr
            580                 585                 590

Ser Gln Gln Arg Phe Pro Pro Gln Glu Leu Ser Gln Asp Ser Phe
        595                 600                 605

Gly Ser Gln Ala Ser Ser Ala Pro Ser Met Thr Ser Ser Lys Gly Gly
    610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
        675                 680                 685

Leu Pro Gly Ile Arg Gly Pro Ser Pro Ser Pro Val Gly Ser Pro Ala
690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
        755                 760                 765

Ser Ala Leu Ser Pro Arg Gln Pro Ser Gly Gly Gln Ile His Thr Gly
770                 775                 780

Met Gly Ser Tyr Gln Gln Asn Ser Met Gly Ser Tyr Gly Pro Gln Gly
785                 790                 795                 800

Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830

Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
    850                 855                 860

Asn Arg Pro Tyr Gly Pro Asn Met Ala Asn Met Pro Pro Gln Val Gly
865                 870                 875                 880
```

```
Ser Gly Met Cys Pro Pro Gly Gly Met Asn Arg Lys Thr Gln Glu
            885                 890                 895

Thr Ala Val Ala Met His Val Ala Ala Asn Ser Ile Gln Asn Arg Pro
        900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
        930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
                965                 970                 975

Pro Ala Thr Lys Met Asn Asn Lys Ala Asp Gly Thr Pro Lys Thr Glu
                980                 985                 990

Ser Lys Ser Lys Lys Ser Ser Ser Thr Thr Thr Asn Glu Lys Ile
            995                 1000                1005

Thr Lys Leu Tyr Glu Leu Gly Gly Pro Glu Arg Lys Met Trp
    1010            1015            1020

Val Asp Arg Tyr Leu Ala Phe Thr Glu Glu Lys Ala Met Gly Met
    1025            1030            1035

Thr Asn Leu Pro Ala Val Gly Arg Lys Pro Leu Asp Leu Tyr Arg
    1040            1045            1050

Leu Tyr Val Ser Val Lys Glu Ile Gly Gly Leu Thr Gln Val Asn
    1055            1060            1065

Lys Asn Lys Lys Trp Arg Glu Leu Ala Thr Asn Leu Asn Val Gly
    1070            1075            1080

Thr Ser Ser Ser Ala Ala Ser Leu Lys Lys Gln Tyr Ile Gln
    1085            1090            1095

Cys Leu Tyr Ala Phe Glu Cys Lys Ile Glu Arg Gly Glu Asp Pro
    1100            1105            1110

Pro Pro Asp Ile Phe Ala Ala Ala Asp Ser Lys Lys Ser Gln Pro
    1115            1120            1125

Lys Ile Gln Pro Pro Ser Pro Ala Gly Ser Gly Ser Met Gln Gly
    1130            1135            1140

Pro Gln Thr Pro Gln Ser Thr Ser Ser Ser Met Ala Glu Gly Gly
    1145            1150            1155

Asp Leu Lys Pro Pro Thr Pro Ala Ser Thr Pro His Ser Gln Ile
    1160            1165            1170

Pro Pro Leu Pro Gly Met Ser Arg Ser Asn Ser Val Gly Ile Gln
    1175            1180            1185

Asp Ala Phe Asn Asp Gly Ser Asp Ser Thr Phe Gln Lys Arg Asn
    1190            1195            1200

Ser Met Thr Pro Asn Pro Gly Tyr Gln Pro Ser Met Asn Thr Ser
    1205            1210            1215

Asp Met Met Gly Arg Met Ser Tyr Glu Pro Asn Lys Asp Pro Tyr
    1220            1225            1230

Gly Ser Met Arg Lys Ala Pro Gly Ser Asp Pro Phe Met Ser Ser
    1235            1240            1245

Gly Gln Gly Pro Asn Gly Gly Met Gly Asp Pro Tyr Ser Arg Ala
    1250            1255            1260

Ala Gly Pro Gly Leu Gly Asn Val Ala Met Gly Pro Arg Gln His
    1265            1270            1275

Tyr Pro Tyr Gly Gly Pro Tyr Asp Arg Val Arg Thr Glu Pro Gly
```

```
              1280                1285                1290
Ile Gly Pro Glu Gly Asn Met Ser Thr Gly Ala Pro Gln Pro Asn
              1295                1300                1305
Leu Met Pro Ser Asn Pro Asp Ser Gly Met Tyr Ser Pro Ser Arg
              1310                1315                1320
Tyr Pro Pro Gln Gln Gln Gln Gln Gln Gln Arg His Asp Ser
              1325                1330                1335
Tyr Gly Asn Gln Phe Ser Thr Gln Gly Thr Pro Ser Gly Ser Pro
              1340                1345                1350
Phe Pro Ser Gln Gln Thr Thr Met Tyr Gln Gln Gln Gln Asn
              1355                1360                1365
Tyr Lys Arg Pro Met Asp Gly Thr Tyr Gly Pro Pro Ala Lys Arg
              1370                1375                1380
His Glu Gly Glu Met Tyr Ser Val Pro Tyr Ser Thr Gly Gln Gly
              1385                1390                1395
Gln Pro Gln Gln Gln Gln Leu Pro Pro Ala Gln Pro Gln Pro Ala
              1400                1405                1410
Ser Gln Gln Gln Ala Ala Gln Pro Ser Pro Gln Gln Asp Val Tyr
              1415                1420                1425
Asn Gln Tyr Gly Asn Ala Tyr Pro Ala Thr Ala Thr Ala Ala Thr
              1430                1435                1440
Glu Arg Arg Pro Ala Gly Gly Pro Gln Asn Gln Phe Pro Phe Gln
              1445                1450                1455
Phe Gly Arg Asp Arg Val Ser Ala Pro Pro Gly Thr Asn Ala Gln
              1460                1465                1470
Gln Asn Met Pro Pro Gln Met Met Gly Gly Pro Ile Gln Ala Ser
              1475                1480                1485
Ala Glu Val Ala Gln Gln Gly Thr Met Trp Gln Gly Arg Asn Asp
              1490                1495                1500
Met Thr Tyr Asn Tyr Ala Asn Arg Gln Ser Thr Gly Ser Ala Pro
              1505                1510                1515
Gln Gly Pro Ala Tyr His Gly Val Asn Arg Thr Asp Glu Met Leu
              1520                1525                1530
His Thr Asp Gln Arg Ala Asn His Glu Gly Ser Trp Pro Ser His
              1535                1540                1545
Gly Thr Arg Gln Pro Pro Tyr Gly Pro Ser Ala Pro Val Pro Pro
              1550                1555                1560
Met Thr Arg Pro Pro Pro Ser Asn Tyr Gln Pro Pro Pro Ser Met
              1565                1570                1575
Gln Asn His Ile Pro Gln Val Ser Ser Pro Ala Pro Leu Pro Arg
              1580                1585                1590
Pro Met Glu Asn Arg Thr Ser Pro Ser Lys Ser Pro Phe Leu His
              1595                1600                1605
Ser Gly Met Lys Met Gln Lys Ala Gly Pro Pro Val Pro Ala Ser
              1610                1615                1620
His Ile Ala Pro Ala Pro Val Gln Pro Pro Met Ile Arg Arg Asp
              1625                1630                1635
Ile Thr Phe Pro Pro Gly Ser Val Glu Ala Thr Gln Pro Val Leu
              1640                1645                1650
Lys Gln Arg Arg Arg Leu Thr Met Lys Asp Ile Gly Thr Pro Glu
              1655                1660                1665
Ala Trp Arg Val Met Met Ser Leu Lys Ser Gly Leu Leu Ala Glu
              1670                1675                1680
```

```
Ser Thr Trp Ala Leu Asp Thr Ile Asn Ile Leu Leu Tyr Asp Asp
1685                1690                1695

Asn Ser Ile Met Thr Phe Asn Leu Ser Gln Leu Pro Gly Leu Leu
1700                1705                1710

Glu Leu Leu Val Glu Tyr Phe Arg Arg Cys Leu Ile Glu Ile Phe
1715                1720                1725

Gly Ile Leu Lys Glu Tyr Glu Val Gly Asp Pro Gly Gln Arg Thr
1730                1735                1740

Leu Leu Asp Pro Gly Arg Phe Ser Lys Val Ser Ser Pro Ala Pro
1745                1750                1755

Met Glu Gly Gly Glu Glu Glu Glu Leu Leu Gly Pro Lys Leu
1760                1765                1770

Glu Glu Glu Glu Glu Glu Val Val Glu Asn Asp Glu Glu Ile
1775                1780                1785

Ala Phe Ser Gly Lys Asp Lys Pro Ala Ser Glu Asn Ser Glu Glu
1790                1795                1800

Lys Leu Ile Ser Lys Phe Asp Lys Leu Pro Val Lys Ile Val Gln
1805                1810                1815

Lys Asn Asp Pro Phe Val Val Asp Cys Ser Asp Lys Leu Gly Arg
1820                1825                1830

Val Gln Glu Phe Asp Ser Gly Leu Leu His Trp Arg Ile Gly Gly
1835                1840                1845

Gly Asp Thr Thr Glu His Ile Gln Thr His Phe Glu Ser Lys Thr
1850                1855                1860

Glu Leu Leu Pro Ser Arg Pro His Ala Pro Cys Pro Pro Ala Pro
1865                1870                1875

Arg Lys His Val Thr Thr Ala Glu Gly Thr Pro Gly Thr Thr Asp
1880                1885                1890

Gln Glu Gly Pro Pro Pro Asp Gly Pro Pro Glu Lys Arg Ile Thr
1895                1900                1905

Ala Thr Met Asp Asp Met Leu Ser Thr Arg Ser Ser Thr Leu Thr
1910                1915                1920

Glu Asp Gly Ala Lys Ser Ser Glu Ala Ile Lys Glu Ser Ser Lys
1925                1930                1935

Phe Pro Phe Gly Ile Ser Pro Ala Gln Ser His Arg Asn Ile Lys
1940                1945                1950

Ile Leu Glu Asp Glu Pro His Ser Lys Asp Glu Thr Pro Leu Cys
1955                1960                1965

Thr Leu Leu Asp Trp Gln Asp Ser Leu Ala Lys Arg Cys Val Cys
1970                1975                1980

Val Ser Asn Thr Ile Arg Ser Leu Ser Phe Val Pro Gly Asn Asp
1985                1990                1995

Phe Glu Met Ser Lys His Pro Gly Leu Leu Ile Leu Gly Lys
2000                2005                2010

Leu Ile Leu Leu His His Lys His Pro Glu Arg Lys Gln Ala Pro
2015                2020                2025

Leu Thr Tyr Glu Lys Glu Glu Gln Asp Gln Gly Val Ser Cys
2030                2035                2040

Asn Lys Val Glu Trp Trp Trp Asp Cys Leu Glu Met Leu Arg Glu
2045                2050                2055

Asn Thr Leu Val Thr Leu Ala Asn Ile Ser Gly Gln Leu Asp Leu
2060                2065                2070
```

```
Ser Pro Tyr Pro Glu Ser Ile Cys Leu Pro Val Leu Asp Gly Leu
    2075                2080                2085
Leu His Trp Ala Val Cys Pro Ser Ala Glu Ala Gln Asp Pro Phe
    2090                2095                2100
Ser Thr Leu Gly Pro Asn Ala Val Leu Ser Pro Gln Arg Leu Val
    2105                2110                2115
Leu Glu Thr Leu Ser Lys Leu Ser Ile Gln Asp Asn Asn Val Asp
    2120                2125                2130
Leu Ile Leu Ala Thr Pro Pro Phe Ser Arg Leu Glu Lys Leu Tyr
    2135                2140                2145
Ser Thr Met Val Arg Phe Leu Ser Asp Arg Lys Asn Pro Val Cys
    2150                2155                2160
Arg Glu Met Ala Val Val Leu Leu Ala Asn Leu Ala Gln Gly Asp
    2165                2170                2175
Ser Leu Ala Ala Arg Ala Ile Ala Val Gln Lys Gly Ser Ile Gly
    2180                2185                2190
Asn Leu Leu Gly Phe Leu Glu Asp Ser Leu Ala Ala Thr Gln Phe
    2195                2200                2205
Gln Gln Ser Gln Ala Ser Leu Leu His Met Gln Asn Pro Pro Phe
    2210                2215                2220
Glu Pro Thr Ser Val Asp Met Met Arg Arg Ala Ala Arg Ala Leu
    2225                2230                2235
Leu Ala Leu Ala Lys Val Asp Glu Asn His Ser Glu Phe Thr Leu
    2240                2245                2250
Tyr Glu Ser Arg Leu Leu Asp Ile Ser Val Ser Pro Leu Met Asn
    2255                2260                2265
Ser Leu Val Ser Gln Val Ile Cys Asp Val Leu Phe Leu Ile Gly
    2270                2275                2280
Gln Ser
    2285

<210> SEQ ID NO 10
<211> LENGTH: 8585
<212> TYPE: DNA
<213> ORGANISM: Homo sapiens

<400> SEQUENCE: 10
cagaaagcgg agagtcacag cggggccagg ccctggggag cggagcctcc accgcccccc      60
tcattcccag gcaagggctt gggggggaatg agccgggaga gccgggtccc gagcctacag    120
agccgggagc agctgagccg ccggcgcctc ggccgccgcc gccgcctcct cctcctccgc    180
cgccgccagc ccggagcctg agccggcggg gcggggggga gaggagcgag cgcagcgcag    240
cagcggagcc ccgcgaggcc cgcccggcg ggtggggagg gcagcccggg ggactgggcc      300
ccggggcggg gtgggagggg gggagaagac gaagacaggg ccgggtctct ccgcggacga    360
gacagcgggg atcatggccg cgcaggtcgc cccgccgcc gccagcagcc tgggcaaccc      420
gccgccgccg ccgccctcgg agctgaagaa agccgagcag cagcagcggg aggaggcggg    480
gggcgaggcg gcggcggcgg cagcggccga gcgcggggaa atgaaggcag ccgccgggca    540
ggaaagcgag ggccccgccg tgggccgcc gcagccgctg ggaaaggagc tgcaggacgg      600
ggccgagagc aatggggggtg cggcggcgcg cggagccggc agcggcggcg ggcccggcgc    660
ggagccggac ctgaagaact cgaacgggaa cgcgggccct aggcccgccc tgaacaataa    720
cctcacggag ccgcccggcg gcggcggtgg cggcagcagc gatggggtgg gggcgcctcc    780
```

```
tcactcagcc gcggccgcct tgccgccccc agcctacggc ttcgggcaac cctacggccg      840
gagcccgtct gccgtcgccg ccgccgcggc cgccgtcttc caccaacaac atggcggaca      900
acaaagccct ggcctggcag cgctgcagag cggcggcggc gggggcctgg agccctacgc      960
ggggccccag cagaactctc acgaccacgg cttccccaac caccagtaca actcctacta     1020
ccccaaccgc agcgcctacc ccccgccccgc cccggcctac gcgctgagct ccccgagagg    1080
tggcactccg ggctcggcg cggcggcggc tgccggctcc aagccgcctc cctcctccag      1140
cgcctccgcc tcctcgtcgt cttcgtcctt cgctcagcag cgcttcgggg ccatgggggg      1200
aggcggcccc tccgcggccg gcggggggaac tccccagccc accgccaccc ccaccctcaa    1260
ccaactgctc acgtcgccca gctcggcccg gggctaccag ggctaccccg ggggcgacta     1320
cagtggcggg ccccaggacg ggggcgccgg caagggcccg gcggacatgg cctcgcagtg     1380 ttgggggct gcggcggcgg cagctgcggc ggcggccgcc tcgggagggg cccaacaaag      1440
gagccaccac gcgcccatga gccccgggag cagcggcggc gggggcagc cgctcgcccg      1500 gaccccctcag ccatccagtc caatggatca gatgggcaag atgagacctc agccatatgg    1560
cgggactaac cctatactcgc agcaacaggg acctccgtca ggaccgcagc aaggacatgg    1620
gtacccaggg cagccatacg ggtcccagac cccgcagcgg tacccgatga ccatgcaggg    1680
ccgggcgcag agtgccatgg gcggcctctc ttatacacag cagattcctc cttatggaca     1740
acaaggcccc agcgggtatg gtcaacaggg ccagactcca tattacaacc agcaaagtcc    1800
tcaccctcag cagcagcagc caccctactc ccagcaacca ccgtcccaga cccctcatgc    1860
ccaaccttcg tatcagcagc agccacagtc tcaaccacca cagctccagt cctctcagcc    1920
tccatactcc cagcagccat cccagcctcc acatcagcag tccccggctc catacccctc    1980
ccagcagtcg acgacacagc agcacccccca gagccagccc ccctactcac agccacaggc   2040
tcagtctcct taccagcagc agcaacctca gcagccagca ccctcgacgc tctcccagca    2100
ggctgcgtat cctcagcccc agtctcagca gtcccagcaa actgcctatt ccagcagcg      2160 cttccctcca ccgcaggagc tatctcaaga ttcatttggg tctcaggcat cctcagcccc     2220
ctcaatgacc tccagtaagg gagggcaaga agatatgaac ctgagccttc agtcaagacc     2280
ctccagcttg cctgatctat ctggttcaat agatgacctc cccatgggga cagaaggagc     2340
tctgagtcct ggagtgagca catcagggat ttccagcagc caaggagagc agagtaatcc    2400
agctcagtct cctttctctc ctcataccctc ccctcacctg cctggcatcc gaggcccttc   2460 cccgtccccct gttggctctc ccgccagtgt tgctcagtct cgctcaggac cactctcgcc    2520
tgctgcagtg ccaggcaacc agatgccacc tcggccaccc agtggccagt cggacagcat    2580
catgcatcct tccatgaacc aatcaagcat tgcccaagat cgaggttata tgcagaggaa    2640
cccccagatg ccccagtaca gttccccccca gcccggctca gccttatctc cgcgtcagcc   2700
ttccggagga cagatacaca caggcatggg ctcctaccag cagaactcca tggggagcta    2760 tggtcccag ggggtcagt atggcccaca aggtggctac cccaggcagc caaactataa     2820
tgccttgccc aatgccaact accccagtgc aggcatggct ggaggcataa accccatggg   2880
tgccggaggt caaatgcatg gacagcctgg catcccacct tatggcacac tccctccagg    2940
gaggatgagt cacgcctcca tgggcaaccg gccttatggc cctaacatgg ccaatatgcc    3000
acctcaggtt gggtcaggga tgtgtccccc accagggggc atgaaccgga aacccaaga    3060 aactgctgtc gccatgcatg ttgctgccaa ctctatccaa aacaggccgc caggctaccc    3120
caatatgaat caagggggca tgatgggaac tggacctcct tatggacaag ggattaatag    3180
```

```
tatggctggc atgatcaacc ctcagggacc cccatattcc atgggtggaa ccatggccaa    3240
caattctgca gggatggcag ccagcccaga gatgatgggc cttggggatg taaagttaac    3300
tccagccacc aaaatgaaca acaaggcaga tgggacaccc aagacagaat ccaaatccaa    3360
gaaatccagt tcttctacta caaccaatga gaagatcacc aagttgtatg agctgggtgg    3420
tgagcctgag aggaagatgt gggtggaccg ttatctggcc ttcactgagg agaaggccat    3480
gggcatgaca aatctgcctg ctgtgggtag gaaacctctg gacctctatc gcctctatgt    3540
gtctgtgaag gagattggtg gattgactca ggtcaacaag aacaaaaaat ggcgggaact    3600
tgcaaccaac ctcaatgtgg gcacatcaag cagtgctgcc agctccttga aaaagcagta    3660
tatccagtgt ctctatgcct ttgaatgcaa gattgaacgg ggagaagacc ctcccccaga    3720
catctttgca gctgctgatt ccaagaagtc ccagcccaag atccagcctc cctctcctgc    3780
gggatcagga tctatgcagg ggccccagac tccccagtca accagcagtt ccatggcaga    3840
aggaggagac ttaaagccac caactccagc atccacacca cacagtcaga tcccccatt    3900 gccaggcatg agcaggagca attcagttgg gatccaggat gcctttaatg atggaagtga    3960
ctccacattc cagaagcgga attccatgac tccaaaccct gggtatcagc ccagtatgaa    4020
tacctctgac atgatggggc gcatgtccta tgagccaaat aaggatcctt atggcagcat    4080
gaggaaagct ccagggagtg atcccttcat gtcctcaggg cagggcccca acggcgggat    4140
gggtgacccc tacagtcgtg ctgccggccc tgggctagga aatgtggcga tgggaccacg    4200
acagcactat ccctatggag gtccttatga cagagtgagg acggagcctg aataggggcc    4260
tgagggaaac atgagcactg gggcccccaca gccgaatctc atgccttcca cccagactc    4320 ggggatgtat tctcctagcc gctaccccc gcagcagcag cagcagcagc agcaacgaca    4380
tgattcctat ggcaatcagt tctccaccca aggcaccct tctggcagcc ccttccccag    4440
ccagcagact acaatgtatc aacagcaaca gcagaattac aagcggccaa tggatggcac    4500
atatggccct cctgccaagc ggcacgaagg ggagatgtac agcgtgccat acagcactgg    4560
gcaggggcag cctcagcagc agcagttgcc cccagcccag ccccagcctg ccagccagca    4620
acaagctgcc cagccttccc ctcagcaaga tgtatacaac cagtatggca atgcctatcc    4680
tgccactgcc acagctgcta ctgagcgccg accagcaggc ggcccccaga accaatttcc    4740
attccagttt ggccgagacc gtgtctctgc acccccctggc accaatgccc agcaaaacat    4800
gccaccacaa atgatgggcg cccccataca ggcatcagct gaggttgctc agcaaggcac    4860
catgtggcag gggcgtaatg acatgaccta taattatgcc aacaggcaga gcacgggctc    4920
tgccccccag ggccccgcct atcatggcgt gaaccgaaca gatgaaatgc tgcacacaga    4980
tcagagggcc aaccacgaag gctcgtggcc ttcccatggc acacgccagc cccatatgg    5040 tccctctgcc cctgtgcccc ccatgacaag gcccccctcca tctaactacc agccccacc    5100 aagcatgcag aatcacattc ctcaggtatc cagccctgct cccctgcccc ggccaatgga    5160
gaaccgcacc tctcctagca agtctccatt cctgcactct gggatgaaaa tgcagaaggc    5220
aggtccccca gtacctgcct cgcacatagc acctgcccct gtgcagcccc ccatgattcg    5280
gcgggatatc accttcccac ctggctctgt tgaagccaca cagcctgtgt tgaagcagag    5340
gaggcggctc acaatgaaag acattggaac cccggaggca tggcgggtaa tgatgtccct    5400
caagtctggt ctcctggcag agagcacatg ggcattagat accatcaaca tcctgctgta    5460
tgatgacaac agcatcatga ccttcaacct cagtcagctc ccagggttgc tagagctcct    5520
```

```
tgtagaatat tttccgacgat gcctgattga gatctttggc attttaaagg agtatgaggt   5580
gggtgaccca ggacagagaa cgctactgga tcctgggagg ttcagcaagg tgtctagtcc   5640
agctcccatg gagggtgggg aagaagaaga agaacttcta ggtcctaaac tagaagagga   5700
agaagaagag gaagtagttg aaaatgatga ggagatagcc ttttcaggca aggacaagcc   5760
agcttcagag aatagtgagg agaagctgat cagtaagttt gacaagcttc cagtaaagat   5820
cgtacagaag aatgatccat tgtggtggga ctgctcagat aagcttgggc gtgtgcagga   5880
gtttgacagt ggcctgctgc actggcggat tggtgggggg gacaccactg agcatatcca   5940
gacccacttc gagagcaaga cagagctgct gccttccggg cctcacgcac cctgcccacc   6000
agcccctcgg aagcatgtga acagcaga gggtacacca gggacaacag accaggaggg   6060
gcccccacct gatggacctc cagaaaaacg gatcacagcc actatggatg acatgttgtc   6120
tactcggtct agcaccttga ccgaggatgg agctaagagt tcagaggcca tcaaggagag   6180
cagcaagttt ccatttggca ttagcccagc acagagccac cggaacatca agatcctaga   6240
ggacgaaccc cacagtaagg atgagacccc actgtgtacc cttctggact ggcaggattc   6300
tcttgccaag cgctgcgtct gtgtgtccaa taccattcga agcctgtcat ttgtgccagg   6360
caatgacttt gagatgtcca acacccagg ctgctgctc atcctgggca agctgatcct   6420
gctgcaccac aagcacccag aacggaagca ggcaccacta acttatgaaa aggaggagga   6480
acaggaccaa ggggtgagct gcaacaaagt ggagtggtgg tgggactgct ggagatgct   6540 ccgggaaaac accttggtta cactcgccaa catctcgggg cagttggacc tatctccata   6600 cccccgagagc atttgcctgc ctgtcctgga cggactccta cactgggcag tttgcccttc   6660
agctgaagcc caggaccct ttccacccct gggccccaat gccgtccttt cccgcagag   6720 actggtcttg gaaaccctca gcaaactcag catccaggac aacaatgtgg acctgattct   6780
ggccacaccc cccttcagcc gcctggagaa gttgtatagc actatggtgc gcttcctcag   6840
tgaccgaaag aacccggtgt gccgggagat ggctgtggta ctgctggcca acctggctca   6900
gggggacagc ctggcagctc gtgccattgc agtgcagaag ggcagtatcg caacctcct   6960 gggcttccta gaggacagcc ttgccgccac acagttccag cagagccagg ccagcctcct   7020
ccacatgcag aacccaccct ttgagccaac tagtgtggac atgatgcggc gggctgcccg   7080
cgcgctgctt gccttggcca aggtggacga gaaccactca gagttttactc tgtacgaatc   7140 acggctgttg acatctcgg tatcaccgtt gatgaactca ttggtttcac aagtcatttg   7200
tgatgtactg tttttgattg gccagtcatg acagccgtgg acacctccc ccccccgtgt   7260 gtgtgtgcgt gtgtggagaa cttagaaact gactgttgcc ctttatttat gcaaaaccac   7320
ctcagaatcc agtttaccct gtgctgtcca gcttctccct tgggaaaaag tctctccttg   7380
ttctctctcc tccttccacc tccccctccct ccatcacctc acgcctttct gttccttgtc   7440
ctcaccttac tccctcagg accctaccc cccctctttg aaaagacaaa gctctgccta   7500
catagaagac ttttttttatt ttaaccaaag ttactgttgt ttacagtgag tttggggaaa   7560 aaaaaataaaa taaaaatggc tttcccagtc cttgcatcaa cgggatgcca catttcataa   7620
ctgtttttaa tggtaaaaaa aaaaaaaaaa aatacaaaaa aaaattctga aggacaaaaa   7680
aggtgactgc tgaactgtgt gtggtttatt gttgtacatt cacaatcttg caggagccaa   7740
gaagttcgca gttgtgaaca gaccctgttc actggagagg cctgtgcagt agagtgtaga   7800
ccctttcatg tactgtactg tacacctgat actgtaaaca tactgtaata ataatgtctc   7860
acatggaaac agaaaacgct gggtcagcag caagctgtag ttttttaaaaa tgttttttagt   7920
```

```
taaacgttga ggagaaaaaa aaaaaaggct tttcccccaa agtatcatgt gtgaacctac    7980
aacaccctga cctctttctc tcctccttga ttgtatgaat aaccctgaga tcacctctta    8040
gaactggttt taacctttag ctgcagcggc tacgctgcca cgtgtgtata tatatgacgt    8100
tgtacattgc atatacccct ggatccccac agtttggtcc tcctcccagc tacccctta    8160
tagtatgacg agttaacaag ttggtgacct gcacaaagcg agacacagct atttaatctc    8220
ttgccagata tcgcccctct tggtgcgatg ctgtacaggt ctctgtaaaa agtccttgct    8280
gtctcagcag ccaatcaact tatagtttat tttttctgg gttttgttt tgttttgttt     8340
tctttctaat cgaggtgtga aaaagttcta ggttcagttg aagttctgat gaagaaacac    8400
aattgagatt ttttcagtga taaaatctgc atatttgtat ttcaacaatg tagctaaaac    8460
ttgatgtaaa ttcctccttt ttttcctttt tggcttaat gaatatcatt tattcagtat     8520
gaaatcttta tactatatgt tccacgtgtt aagaataaat gtacattaaa tcttggtaag    8580
acttt                                                                 8585

<210> SEQ ID NO 11
<211> LENGTH: 2068
<212> TYPE: PRT
<213> ORGANISM: Homo sapiens

<400> SEQUENCE: 11

Met Ala Ala Gln Val Ala Pro Ala Ala Ser Ser Leu Gly Asn Pro
 1               5                  10                  15

Pro Pro Pro Pro Pro Ser Glu Leu Lys Lys Ala Glu Gln Gln Arg
                20                  25                  30

Glu Glu Ala Gly Gly Glu Ala Ala Ala Ala Ala Glu Arg Gly
            35                  40                  45

Glu Met Lys Ala Ala Ala Gly Gln Glu Ser Glu Gly Pro Ala Val Gly
     50                  55                  60

Pro Pro Gln Pro Leu Gly Lys Glu Leu Gln Asp Gly Ala Glu Ser Asn
 65                  70                  75                  80

Gly Gly Gly Gly Gly Gly Gly Ala Gly Ser Gly Gly Pro Gly Ala
                85                  90                  95

Glu Pro Asp Leu Lys Asn Ser Asn Gly Asn Ala Gly Pro Arg Pro Ala
                100                 105                 110

Leu Asn Asn Asn Leu Thr Glu Pro Pro Gly Gly Gly Gly Gly Gly Ser
            115                 120                 125

Ser Asp Gly Val Gly Ala Pro Pro His Ser Ala Ala Ala Ala Leu Pro
        130                 135                 140

Pro Pro Ala Tyr Gly Phe Gly Gln Pro Tyr Gly Arg Ser Pro Ser Ala
145                 150                 155                 160

Val Ala Ala Ala Ala Ala Val Phe His Gln Gln His Gly Gly Gln
                165                 170                 175

Gln Ser Pro Gly Leu Ala Ala Leu Gln Ser Gly Gly Gly Gly Leu
            180                 185                 190

Glu Pro Tyr Ala Gly Pro Gln Gln Asn Ser His Asp His Gly Phe Pro
        195                 200                 205

Asn His Gln Tyr Asn Ser Tyr Tyr Pro Asn Arg Ser Ala Tyr Pro Pro
    210                 215                 220

Pro Ala Pro Ala Tyr Ala Leu Ser Ser Pro Arg Gly Gly Thr Pro Gly
225                 230                 235                 240

Ser Gly Ala Ala Ala Ala Ala Gly Ser Lys Pro Pro Pro Ser Ser Ser
```

```
                245                 250                 255
Ala Ser Ala Ser Ser Ser Ser Ser Phe Ala Gln Gln Arg Phe Gly
            260                 265                 270
Ala Met Gly Gly Gly Pro Ser Ala Gly Gly Thr Pro Gln
        275                 280             285
Pro Thr Ala Thr Pro Thr Leu Asn Gln Leu Leu Thr Ser Pro Ser Ser
    290                 295                 300
Ala Arg Gly Tyr Gln Gly Tyr Pro Gly Gly Asp Tyr Ser Gly Gly Pro
305                 310                 315                 320
Gln Asp Gly Gly Ala Gly Lys Gly Pro Ala Asp Met Ala Ser Gln Cys
                325                 330                 335
Trp Gly Ala Ala Ala Ala Ala Ala Ala Ala Ala Ala Ser Gly Gly
            340                 345                 350
Ala Gln Gln Arg Ser His His Ala Pro Met Ser Pro Gly Ser Ser Gly
                355                 360                 365
Gly Gly Gly Gln Pro Leu Ala Arg Thr Pro Gln Pro Ser Ser Pro Met
    370                 375                 380
Asp Gln Met Gly Lys Met Arg Pro Gln Pro Tyr Gly Gly Thr Asn Pro
385                 390                 395                 400
Tyr Ser Gln Gln Gln Gly Pro Pro Ser Gly Pro Gln Gln Gly His Gly
                    405                 410                 415
Tyr Pro Gly Gln Pro Tyr Gly Ser Gln Thr Pro Gln Arg Tyr Pro Met
            420                 425                 430
Thr Met Gln Gly Arg Ala Gln Ser Ala Met Gly Gly Leu Ser Tyr Thr
            435                 440                 445
Gln Gln Ile Pro Pro Tyr Gly Gln Gln Gly Pro Ser Gly Tyr Gly Gln
    450                 455                 460
Gln Gly Gln Thr Pro Tyr Tyr Asn Gln Gln Ser Pro His Pro Gln Gln
465                 470                 475                 480
Gln Gln Pro Pro Tyr Ser Gln Pro Pro Ser Gln Thr Pro His Ala
                485                 490                 495
Gln Pro Ser Tyr Gln Gln Pro Gln Ser Gln Pro Gln Leu Gln
            500                 505                 510
Ser Ser Gln Pro Pro Tyr Ser Gln Gln Pro Ser Gln Pro Pro His Gln
        515                 520                 525
Gln Ser Pro Ala Pro Tyr Pro Ser Gln Ser Thr Thr Gln Gln His
    530                 535                 540
Pro Gln Ser Gln Pro Pro Tyr Ser Gln Pro Gln Ala Gln Ser Pro Tyr
545                 550                 555                 560
Gln Gln Gln Gln Pro Gln Gln Pro Ala Pro Ser Thr Leu Ser Gln Gln
            565                 570                 575
Ala Ala Tyr Pro Gln Pro Gln Ser Gln Ser Gln Gln Thr Ala Tyr
            580                 585                 590
Ser Gln Gln Arg Phe Pro Pro Pro Gln Glu Leu Ser Gln Asp Ser Phe
    595                 600                 605
Gly Ser Gln Ala Ser Ser Ala Pro Ser Met Thr Ser Ser Lys Gly Gly
610                 615                 620
Gln Glu Asp Met Asn Leu Ser Leu Gln Ser Arg Pro Ser Ser Leu Pro
625                 630                 635                 640
Asp Leu Ser Gly Ser Ile Asp Asp Leu Pro Met Gly Thr Glu Gly Ala
                645                 650                 655
Leu Ser Pro Gly Val Ser Thr Ser Gly Ile Ser Ser Ser Gln Gly Glu
            660                 665                 670
```

```
Gln Ser Asn Pro Ala Gln Ser Pro Phe Ser Pro His Thr Ser Pro His
        675                 680                 685

Leu Pro Gly Ile Arg Gly Pro Ser Pro Val Gly Ser Pro Ala
690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
        755                 760                 765

Ser Ala Leu Ser Pro Arg Gln Pro Ser Gly Gln Ile His Thr Gly
770                 775                 780

Met Gly Ser Tyr Gln Gln Asn Ser Met Gly Ser Tyr Gly Pro Gln Gly
785                 790                 795                 800

Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830

Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
850                 855                 860

Asn Arg Pro Tyr Gly Pro Asn Met Ala Asn Met Pro Pro Gln Val Gly
865                 870                 875                 880

Ser Gly Met Cys Pro Pro Pro Gly Gly Met Asn Arg Lys Thr Gln Glu
                885                 890                 895

Thr Ala Val Ala Met His Val Ala Ala Asn Ser Ile Gln Asn Arg Pro
            900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
                965                 970                 975

Pro Ala Thr Lys Met Asn Asn Lys Ala Asp Gly Thr Pro Lys Thr Glu
            980                 985                 990

Ser Lys Ser Lys Ser Ser Ser Ser Thr Thr Asn Glu Lys Ile
        995                 1000                1005

Thr Lys Leu Tyr Glu Leu Gly Gly Glu Pro Glu Arg Lys Met Trp
    1010                1015                1020

Val Asp Arg Tyr Leu Ala Phe Thr Glu Glu Lys Ala Met Gly Met
    1025                1030                1035

Thr Asn Leu Pro Ala Val Gly Arg Lys Pro Leu Asp Leu Tyr Arg
    1040                1045                1050

Leu Tyr Val Ser Val Lys Glu Ile Gly Gly Leu Thr Gln Val Asn
    1055                1060                1065

Lys Asn Lys Lys Trp Arg Glu Leu Ala Thr Asn Leu Asn Val Gly
    1070                1075                1080
```

```
Thr Ser Ser Ser Ala Ala Ser Ser Leu Lys Lys Gln Tyr Ile Gln
1085                1090                1095

Cys Leu Tyr Ala Phe Glu Cys Lys Ile Glu Arg Gly Glu Asp Pro
    1100                1105                1110

Pro Pro Asp Ile Phe Ala Ala Ala Asp Ser Lys Lys Ser Gln Pro
    1115                1120                1125

Lys Ile Gln Pro Pro Ser Pro Ala Gly Ser Gly Ser Met Gln Gly
    1130                1135                1140

Pro Gln Thr Pro Gln Ser Thr Ser Ser Ser Met Ala Glu Gly Gly
    1145                1150                1155

Asp Leu Lys Pro Pro Thr Pro Ala Ser Thr Pro His Ser Gln Ile
    1160                1165                1170

Pro Pro Leu Pro Gly Met Ser Arg Ser Asn Ser Val Gly Ile Gln
    1175                1180                1185

Asp Ala Phe Asn Asp Gly Ser Asp Ser Thr Phe Gln Lys Arg Asn
    1190                1195                1200

Ser Met Thr Pro Asn Pro Gly Tyr Gln Pro Ser Met Asn Thr Ser
    1205                1210                1215

Asp Met Met Gly Arg Met Ser Tyr Glu Pro Asn Lys Asp Pro Tyr
    1220                1225                1230

Gly Ser Met Arg Lys Ala Pro Gly Ser Asp Pro Phe Met Ser Ser
    1235                1240                1245

Gly Gln Gly Pro Asn Gly Gly Met Gly Asp Pro Tyr Ser Arg Ala
    1250                1255                1260

Ala Gly Pro Gly Leu Gly Asn Val Ala Met Gly Pro Arg Gln His
    1265                1270                1275

Tyr Pro Tyr Gly Gly Pro Tyr Asp Arg Val Arg Thr Glu Pro Gly
    1280                1285                1290

Ile Gly Pro Glu Gly Asn Met Ser Thr Gly Ala Pro Gln Pro Asn
    1295                1300                1305

Leu Met Pro Ser Asn Pro Asp Ser Gly Met Tyr Ser Pro Ser Arg
    1310                1315                1320

Tyr Pro Pro Gln Gln Gln Gln Gln Gln Gln Arg His Asp Ser
    1325                1330                1335

Tyr Gly Asn Gln Phe Ser Thr Gln Gly Thr Pro Ser Gly Ser Pro
    1340                1345                1350

Phe Pro Ser Gln Gln Thr Thr Met Tyr Gln Gln Gln Gln Gln Val
    1355                1360                1365

Ser Ser Pro Ala Pro Leu Pro Arg Pro Met Glu Asn Arg Thr Ser
    1370                1375                1380

Pro Ser Lys Ser Pro Phe Leu His Ser Gly Met Lys Met Gln Lys
    1385                1390                1395

Ala Gly Pro Pro Val Pro Ala Ser His Ile Ala Pro Ala Pro Val
    1400                1405                1410

Gln Pro Pro Met Ile Arg Arg Asp Ile Thr Phe Pro Pro Gly Ser
    1415                1420                1425

Val Glu Ala Thr Gln Pro Val Leu Lys Gln Arg Arg Arg Leu Thr
    1430                1435                1440

Met Lys Asp Ile Gly Thr Pro Glu Ala Trp Arg Val Met Met Ser
    1445                1450                1455

Leu Lys Ser Gly Leu Leu Ala Glu Ser Thr Trp Ala Leu Asp Thr
    1460                1465                1470

Ile Asn Ile Leu Leu Tyr Asp Asp Asn Ser Ile Met Thr Phe Asn
```

```
            1475                1480                1485

Leu Ser Gln Leu Pro Gly Leu Leu Glu Leu Leu Val Glu Tyr Phe
    1490                1495                1500

Arg Arg Cys Leu Ile Glu Ile Phe Gly Ile Leu Lys Glu Tyr Glu
    1505                1510                1515

Val Gly Asp Pro Gly Gln Arg Thr Leu Leu Asp Pro Gly Arg Phe
    1520                1525                1530

Ser Lys Val Ser Ser Pro Ala Pro Met Glu Gly Gly Glu Glu Glu
    1535                1540                1545

Glu Glu Leu Leu Gly Pro Lys Leu Glu Glu Glu Glu Glu Glu Glu
    1550                1555                1560

Val Val Glu Asn Asp Glu Glu Ile Ala Phe Ser Gly Lys Asp Lys
    1565                1570                1575

Pro Ala Ser Glu Asn Ser Glu Glu Lys Leu Ile Ser Lys Phe Asp
    1580                1585                1590

Lys Leu Pro Val Lys Ile Val Gln Lys Asn Asp Pro Phe Val Val
    1595                1600                1605

Asp Cys Ser Asp Lys Leu Gly Arg Val Gln Glu Phe Asp Ser Gly
    1610                1615                1620

Leu Leu His Trp Arg Ile Gly Gly Gly Asp Thr Thr Glu His Ile
    1625                1630                1635

Gln Thr His Phe Glu Ser Lys Thr Glu Leu Leu Pro Ser Arg Pro
    1640                1645                1650

His Ala Pro Cys Pro Pro Ala Pro Arg Lys His Val Thr Thr Ala
    1655                1660                1665

Glu Gly Thr Pro Gly Thr Thr Asp Gln Glu Gly Pro Pro Pro Asp
    1670                1675                1680

Gly Pro Pro Glu Lys Arg Ile Thr Ala Thr Met Asp Asp Met Leu
    1685                1690                1695

Ser Thr Arg Ser Ser Thr Leu Thr Glu Asp Gly Ala Lys Ser Ser
    1700                1705                1710

Glu Ala Ile Lys Glu Ser Ser Lys Phe Pro Phe Gly Ile Ser Pro
    1715                1720                1725

Ala Gln Ser His Arg Asn Ile Lys Ile Leu Glu Asp Glu Pro His
    1730                1735                1740

Ser Lys Asp Glu Thr Pro Leu Cys Thr Leu Leu Asp Trp Gln Asp
    1745                1750                1755

Ser Leu Ala Lys Arg Cys Val Cys Val Ser Asn Thr Ile Arg Ser
    1760                1765                1770

Leu Ser Phe Val Pro Gly Asn Asp Phe Glu Met Ser Lys His Pro
    1775                1780                1785

Gly Leu Leu Leu Ile Leu Gly Lys Leu Ile Leu Leu His His Lys
    1790                1795                1800

His Pro Glu Arg Lys Gln Ala Pro Leu Thr Tyr Glu Lys Glu Glu
    1805                1810                1815

Glu Gln Asp Gln Gly Val Ser Cys Asn Lys Val Glu Trp Trp Trp
    1820                1825                1830

Asp Cys Leu Glu Met Leu Arg Glu Asn Thr Leu Val Thr Leu Ala
    1835                1840                1845

Asn Ile Ser Gly Gln Leu Asp Leu Ser Pro Tyr Pro Glu Ser Ile
    1850                1855                1860

Cys Leu Pro Val Leu Asp Gly Leu Leu His Trp Ala Val Cys Pro
    1865                1870                1875
```

-continued

| | | | | | | | | | | |
|---|---|---|---|---|---|---|---|---|---|---|
| Ser | Ala | Glu | Ala | Gln | Asp | Pro | Phe | Ser | Thr | Leu | Gly | Pro | Asn | Ala |
| | 1880 | | | | 1885 | | | | 1890 | |

Ser Ala Glu Ala Gln Asp Pro Phe Ser Thr Leu Gly Pro Asn Ala
        1880                1885                1890

Val Leu Ser Pro Gln Arg Leu Val Leu Glu Thr Leu Ser Lys Leu
        1895                1900                1905

Ser Ile Gln Asp Asn Asn Val Asp Leu Ile Leu Ala Thr Pro Pro
        1910                1915                1920

Phe Ser Arg Leu Glu Lys Leu Tyr Ser Thr Met Val Arg Phe Leu
        1925                1930                1935

Ser Asp Arg Lys Asn Pro Val Cys Arg Glu Met Ala Val Val Leu
        1940                1945                1950

Leu Ala Asn Leu Ala Gln Gly Asp Ser Leu Ala Ala Arg Ala Ile
        1955                1960                1965

Ala Val Gln Lys Gly Ser Ile Gly Asn Leu Leu Gly Phe Leu Glu
        1970                1975                1980

Asp Ser Leu Ala Ala Thr Gln Phe Gln Gln Ser Gln Ala Ser Leu
        1985                1990                1995

Leu His Met Gln Asn Pro Pro Phe Glu Pro Thr Ser Val Asp Met
        2000                2005                2010

Met Arg Arg Ala Ala Arg Ala Leu Leu Ala Leu Ala Lys Val Asp
        2015                2020                2025

Glu Asn His Ser Glu Phe Thr Leu Tyr Glu Ser Arg Leu Leu Asp
        2030                2035                2040

Ile Ser Val Ser Pro Leu Met Asn Ser Leu Val Ser Gln Val Ile
        2045                2050                2055

Cys Asp Val Leu Phe Leu Ile Gly Gln Ser
        2060                2065

<210> SEQ ID NO 12
<211> LENGTH: 7934
<212> TYPE: DNA
<213> ORGANISM: Homo sapiens

<400> SEQUENCE: 12

```
cagaaagcgg agagtcacag cggggccagg ccctggggag cggagcctcc accgccccccc      60
tcattcccag gcaagggctt ggggggaatg agccgggaga gccgggtccc gagcctacag     120
agccgggagc agctgagccg ccggcgcctc ggccgccgcc gccgcctcct cctcctccgc     180
cgccgccagc ccggagcctg agccggcggg gcgggggggga gaggagcgag cgcagcgcag     240
cagcggagcc ccgcgaggcc cgcccggcg ggtggggagg gcagcccggg ggactgggcc     300
ccggggcggg gtgggagggg gggagaagac gaagacaggg ccgggtctct ccgcggacga     360
gacagcgggg atcatggccg cgcaggtcgc ccccgccgcc gccagcagcc tgggcaaccc     420
gccgccgccg ccgccctcgg agctgaagaa agccgagcag cagcagcggg aggaggcggg     480
gggcgaggcg gcggcggcgg cagcggccga gcgcggggaa atgaaggcag ccgccgggca     540
ggaaagcgag ggccccgccg tgggccgcc gcagccgctg ggaaaggagc tgcaggacgg     600
ggccgagagc aatggggggtg gcggcggcgg cggagccggc agcggcggcg ggcccggcgc     660
ggagccggac ctgaagaact cgaacgggaa cgcgggccct aggcccgccc tgaacaataa     720
cctcacggag ccgcccggcg gcggcggtgg cggcagcagc gatggggtgg gggcgcctcc     780
tcactcagcc gcggccgcct tgccgccccc agcctacggc ttcgggcaac cctacggccg     840
gagcccgtct gccgtcgccg ccgccgcggc cgccgtcttc caccaacaac atggcggaca     900
acaaagccct ggcctggcag cgctgcagag cggcggcggc gggggcctgg agccctacgc     960
```

-continued

```
ggggccccag cagaactctc acgaccacgg cttccccaac caccagtaca actcctacta    1020
ccccaaccgc agcgcctacc ccccgcccgc cccggcctac gcgctgagct ccccgagagg    1080
tggcactccg ggctccggcg cggcggcggc tgccggctcc aagccgcctc cctcctccag    1140
cgcctccgcc tcctcgtcgt cttcgtcctt cgctcagcag cgcttcgggg ccatgggggg    1200
aggcggcccc tccgcggccg gcgggggaac tccccagccc accgccaccc ccaccctcaa    1260
ccaactgctc acgtcgccca gctcggcccg ggctaccag ggctaccccg ggggcgacta    1320
cagtggcggg ccccaggacg ggggcgccgg caagggcccg gcggacatgg cctcgcagtg    1380 ttgggggggct gcgcggcgg cagctgcggc ggcggccgcc tcgggagggg cccaacaaag    1440
gagccaccac gcgcccatga gcccgggag cagcggcggc gggggcagc cgctcgcccg    1500 gaccctcag ccatccagtc caatggatca gatgggcaag atgagacctc agccatatgg    1560
cgggactaac ccatactcgc agcaacaggg acctccgtca ggaccgcagc aaggacatgg    1620
gtacccaggg cagccatacg ggtcccgac cccgcagcgg tacccgatga ccatgcaggg    1680
ccgggcgcag agtgccatgg gcggcctctc ttatacacag cagattcctc cttatggaca    1740
acaaggcccc agcgggtatg gtcaacaggg ccagactcca tattacaacc agcaaagtcc    1800
tcaccctcag cagcagcagc caccctactc ccagcaacca ccgtcccaga cccctcatgc    1860
ccaaccttcg tatcagcagc agccacagtc tcaaccacca cagctccagt cctctcagcc    1920
tccatactcc cagcagccat cccagcctcc acatcagcag tccccggctc catacccctc    1980
ccagcagtcg acgacacagc agcacccca gagccagccc cctactcac agccacaggc    2040 tcagtctcct taccagcagc agcaacctca gcagccagca ccctcgacgc tctcccagca    2100
ggctgcgtat cctcagcccc agtctcagca gtcccagcaa actgcctatt ccagcagcg    2160 cttccctcca ccgcaggagc tatctcaaga ttcatttggg tctcaggcat cctcagcccc    2220
ctcaatgacc tccagtaagg gagggcaaga agatatgaac ctgagccttc agtcaagacc    2280
ctccagcttg cctgatctat ctggttcaat agatgacctc cccatgggga cagaaggagc    2340
tctgagtcct ggagtgagca catcagggat ttccagcagc caaggagagc agagtaatcc    2400
agctcagtct cctttctctc ctcatacctc ccctcacctg cctggcatcc gaggcccttc    2460
cccgtcccct gttggctctc ccgccagtgt tgctcagtct cgctcaggac cactctcgcc    2520
tgctgcagtg ccaggcaacc agatgccacc tcggccaccc agtggccagt cggacagcat    2580
catgcatcct tccatgaacc aatcaagcat tgcccaagat cgaggttata tgcagaggaa    2640
cccccagatg ccccagtaca gttccccca gcccggctca gccttatctc cgcgtcagcc    2700
ttccggagga cagatacaca caggcatggg ctcctaccag cagaactcca tggggagcta    2760
tggtccccag gggggtcagt atgggccaca aggtggctac cccaggcagc caaactataa    2820
tgccttgccc aatgccaact acccccagtgc aggcatggct ggaggcataa accccatggg    2880
tgccggaggt caaatgcatg gacagcctgg catcccacct tatggcacac tccctccagg    2940
gaggatgagt cacgcctcca tggcaaccg gccttatggc cctaacatgg caatatgcc    3000 acctcaggtt gggtcaggga tgtgtccccc accagggggc atgaaccgga aacccaaga    3060 aactgctgtc gccatgcatg ttgctgccaa ctctatccaa aacaggccgc caggctaccc    3120
caatatgaat caagggggca tgatgggaac tggacctcct tatggacaag ggattaatag    3180
tatggctgga atgatcaacc ctcagggacc cccatattcc atgggtggaa ccatggccaa    3240
caattctgca gggatggcag ccagcccaga gatgatgggc cttggggatg taaagttaac    3300
```

```
tccagccacc aaaatgaaca acaaggcaga tgggacaccc aagacagaat ccaaatccaa   3360
gaaatccagt tcttctacta caaccaatga gaagatcacc aagttgtatg agctgggtgg   3420
tgagcctgag aggaagatgt gggtggaccg ttatctggcc ttcactgagg agaaggccat   3480
gggcatgaca aatctgcctg ctgtgggtag gaaacctctg gacctctatc gcctctatgt   3540
gtctgtgaag gagattggtg gattgactca ggtcaacaag aacaaaaaat ggcgggaact   3600
tgcaaccaac ctcaatgtgg gcacatcaag cagtgctgcc agctccttga aaaagcagta   3660
tatccagtgt ctctatgcct ttgaatgcaa gattgaacgg ggagaagacc ctcccccaga   3720
catctttgca gctgctgatt ccaagaagtc ccagcccaag atccagcctc cctctcctgc   3780
gggatcagga tctatgcagg ggccccagac tccccagtca accagcagtt ccatggcaga   3840
aggaggagac ttaaagccac caactccagc atccacacca cacagtcaga tcccccatt   3900 gccaggcatg agcaggagca attcagttgg gatccaggat gcctttaatg atggaagtga   3960
ctccacattc cagaagcgga attccatgac tccaaaccct gggtatcagc ccagtatgaa   4020
tacctctgac atgatggggc gcatgtccta tgagccaaat aaggatcctt atggcagcat   4080
gaggaaagct ccagggagtg atcccttcat gtcctcaggg cagggcccca acggcgggat   4140
gggtgacccc tacagtcgtg ctgccggccc tgggctagga aatgtggcga tgggaccacg   4200
acagcactat ccctatggag gtccttatga cagagtgagg acggagcctg gaatagggcc   4260
tgagggaaac atgagcactg ggccccaca gccgaatctc atgccttcca cccagactc   4320 ggggatgtat tctcctagcc gctacccccc gcagcagcag cagcagcagc agcaacgaca   4380
tgattcctat ggcaatcagt tctccaccca aggcaccct tctggcagcc ccttccccag   4440
ccagcagact acaatgtatc aacagcaaca gcaggtatcc agccctgctc ccctgccccg   4500
gccaatggag aaccgcacct ctcctagcaa gtctccattc ctgcactctg ggatgaaaat   4560
gcagaaggca ggtcccccag tacctgcctc gcacatagca cctgcccctg tgcagccccc   4620
catgattcgg cgggatatca ccttcccacc tggctctgtt gaagccacac agcctgtgtt   4680
gaagcagagg aggcggctca caatgaaaga cattggaacc ccggaggcat ggcgggtaat   4740
gatgtccctc aagtctggtc tcctggcaga gagcacatgg gcattagata ccatcaacat   4800
cctgctgtat gatgacaaca gcatcatgac cttcaacctc agtcagctcc cagggttgct   4860
agagctcctt gtagaatatt ccgacgatg cctgattgag atctttggca ttttaaagga   4920
gtatgaggtg ggtgacccag acagagaac gctactggat cctgggaggt tcagcaaggt   4980
gtctagtcca gctcccatgg agggtgggga agaagaagaa gaacttctag gtcctaaact   5040
agaagaggaa gaagaagagg aagtagttga aaatgatgag gagatagcct tttcaggcaa   5100
ggacaagcca gcttcagaga atagtgagga gaagctgatc agtaagtttg acaagcttcc   5160
agtaaagatc gtacagaaga atgatccatt tgtggtggac tgctcagata gcttgggcg   5220 tgtgcaggag tttgacagtg gcctgctgca ctggcggatt ggtggggggg acaccactga   5280
gcatatccag acccacttcg agagcaagac agagctgctg ccttcccggc ctcacgcacc   5340
ctgcccacca gcccctcgga agcatgtgac aacagcagag ggtacaccag ggacaacaga   5400
ccaggagggg cccccacctg atggacctcc agaaaaacgg atcacagcca ctatggatga   5460
catgttgtct actcggtcta gcaccttgac cgaggatgga gctaagagtt cagaggccat   5520
caaggagagc agcaagtttc catttggcat tagcccagca cagagccacc ggaacatcaa   5580
gatcctagag gacgaacccc acagtaagga tgagacccca ctgtgtaccc ttctggactg   5640
gcaggattct cttgccaagc gctgcgtctg tgtgtccaat accattcgaa gcctgtcatt   5700
```

```
tgtgccaggc aatgactttg agatgtccaa acacccaggg ctgctgctca tcctgggcaa    5760
gctgatcctg ctgcaccaca agcacccaga acggaagcag gcaccactaa cttatgaaaa    5820
ggaggaggaa caggaccaag gggtgagctg caacaaagtg gagtggtggt gggactgctt    5880
ggagatgctc cggaaaaaca ccttggttac actcgccaac atctcggggc agttggacct    5940
atctccatac cccgagagca tttgcctgcc tgtcctggac ggactcctac actgggcagt    6000
ttgcccttca gctgaagccc aggacccctt ttccaccctg gccccaatg ccgtcctttc     6060 cccgcagaga ctggtcttgg aaaccctcag caaactcagc atccaggaca caatgtgga    6120 cctgattctg gccacacccc ccttcagccg cctggagaag ttgtatagca ctatggtgcg    6180
cttcctcagt gaccgaaaga acccggtgtg ccgggagatg gctgtggtac tgctggccaa    6240
cctggctcag ggggacagcc tggcagctcg tgccattgca gtgcagaagg gcagtatcgg    6300
caacctcctg ggcttcctag aggacagcct tgccgccaca cagttccagc agagccaggc    6360
cagcctcctc cacatgcaga acccaccctt tgagccaact agtgtggaca tgatgcggcg    6420
ggctgcccgc gcgctgcttg ccttggccaa ggtggacgag aaccactcag agtttactct    6480
gtacgaatca cggctgttgg acatctcggt atcaccgttg atgaactcat tggtttcaca    6540
agtcatttgt gatgtactgt ttttgattgg ccagtcatga cagccgtggg cacctcccc     6600 cccccgtgtg tgtgtgcgtg tgtggagaac ttagaaactg actgttgccc tttatttatg    6660
caaaaccacc tcagaatcca gtttaccctg tgctgtccag cttctcctt gggaaaaagt     6720 ctctcctgtt tctctctcct ccttccacct ccctccctc catcacctca cgcctttctg      6780
ttccttgtcc tcaccttact ccctcagga ccctacccca ccctctttga aaagacaaag     6840
ctctgcctac atagaagact tttttattt taaccaaagt tactgttgtt tacagtgagt     6900
ttggggaaaa aaaataaaat aaaatggct ttcccagtcc ttgcatcaac gggatgccac     6960
atttcataac tgttttaat ggtaaaaaaa aaaaaaaaa atacaaaaaa aaattctgaa      7020
ggacaaaaaa ggtgactgct gaactgtgtg tggtttattg ttgtacattc acaatcttgc    7080
aggagccaag aagttcgcag ttgtgaacag accctgttca ctggagaggc ctgtgcagta    7140
gagtgtagac cctttcatgt actgtactgt acacctgata ctgtaaacat actgtaataa    7200
taatgtctca catggaaaca gaaaacgctg ggtcagcagc aagctgtagt tttaaaaat    7260 gttttagtt aaacgttgag gagaaaaaaa aaaaggctt tccccccaaa gtatcatgtg      7320
tgaacctaca acaccctgac ctctttctct cctccttgat tgtatgaata accctgagat    7380
cacctcttag aactggtttt aacctttagc tgcagcggct acgctgccac gtgtgtatat    7440
atatgacgtt gtacattgca catacccttg gatccccaca gtttggtcct cctcccagct    7500
acccctttat agtatgacga gttaacaagt tggtgacctg cacaaagcga gacacagcta    7560
tttaatctct tgccagatat cgcccctctt ggtgcgatgc tgtacaggtc tctgtaaaaa    7620
gtccttgctg tctcagcagc caatcaactt atagtttatt ttttctggg tttttgtttt     7680 gttttgtttt ctttctaatc gaggtgtgaa aaagttctag gttcagttga agttctgatg    7740
aagaaacaca attgagattt tttcagtgat aaaatctgca tatttgtatt tcaacaatgt    7800
agctaaaact tgatgtaaat tcctccttt tttccttttt tggcttaatg aatatcatttt     7860 attcagtatg aaatctttat actatatgtt ccacgtgtta agaataaatg tacattaaat    7920
cttggtaaga cttt                                                       7934

<210> SEQ ID NO 13
```

```
<211> LENGTH: 26
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (26)..(26)
<223> OTHER INFORMATION: wherein the Lys is attached to a biotin and an
      amide

<400> SEQUENCE: 13

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 14
<211> LENGTH: 26
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (7)..(7)
<223> OTHER INFORMATION: wherein the Lys is trimethylated
<220> FEATURE:
<221> NAME/KEY: MISC_FEATURE
<222> LOCATION: (26)..(26)
<223> OTHER INFORMATION: wherein the Lys is attached to a biotin and an
      amide

<400> SEQUENCE: 14

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

UNITED STATES PATENT AND TRADEMARK OFFICE
CERTIFICATE OF CORRECTION

PATENT NO. : 12,162,865 B2
APPLICATION NO. : 17/689704
DATED : December 10, 2024
INVENTOR(S) : Knutson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this
Third Day of June, 2025

Coke Morgan Stewart
*Acting Director of the United States Patent and Trademark Office*